United States Patent
Barf et al.

(10) Patent No.: US 7,618,961 B2
(45) Date of Patent: Nov. 17, 2009

(54) INHIBITORS OF 11-BETA-HYDROXY STEROID DEHYDROGENASE TYPE 1

(75) Inventors: Tjeerd Barf, Uppsala (SE); Rikard Emond, Saltsjöbaden (SE); Guido Kurz, Stockholm (SE); Jerk Vallgårda, Uppsala (SE); Marianne Nilsson, Rimbo (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 10/296,553

(22) PCT Filed: May 22, 2001

(86) PCT No.: PCT/SE01/01155

§ 371 (c)(1),
(2), (4) Date: Feb. 18, 2003

(87) PCT Pub. No.: WO01/90090

PCT Pub. Date: Nov. 29, 2001

(65) Prior Publication Data

US 2004/0224996 A1    Nov. 11, 2004

(30) Foreign Application Priority Data

May 22, 2000    (SE) .................................. 0001899

(51) Int. Cl.
| | | |
|---|---|---|
| A61K 31/535 | (2006.01) | |
| A61K 31/497 | (2006.01) | |
| A61K 31/47 | (2006.01) | |
| A61K 31/445 | (2006.01) | |
| A61K 31/425 | (2006.01) | |
| C07D 413/12 | (2006.01) | |
| C07D 413/14 | (2006.01) | |
| C07D 413/06 | (2006.01) | |
| C07D 453/04 | (2006.01) | |
| C07D 277/38 | (2006.01) | |

(52) U.S. Cl. ............... 514/232.2; 514/235.8; 514/236.8; 514/254.02; 514/314; 514/326; 514/365; 544/121; 544/129; 544/133; 544/359; 544/367; 546/135; 546/187; 548/185; 548/187; 548/184

(58) Field of Classification Search ................. 548/194, 548/197, 184, 185, 187; 514/370, 236.8, 514/232.2, 235.8, 254.02, 314, 326, 356; 544/133, 121, 129, 359, 367; 546/135, 187

See application file for complete search history.

(56) References Cited

U.S. PATENT DOCUMENTS

| | | | |
|---|---|---|---|
| 2,362,087 A | 11/1944 | Newbery | |
| 2,611,770 A | 9/1952 | Smith, Jr. | |
| 4,254,260 A | 3/1981 | Takaya et al. | |
| 5,403,857 A | 4/1995 | Edwards et al. | |
| 5,594,021 A | 1/1997 | Chan et al. | |
| 5,783,597 A | 7/1998 | Beers et al. | |
| 5,856,347 A | 1/1999 | Hashiguchi et al. | |
| 5,962,490 A | 10/1999 | Chan et al. | |
| 6,030,991 A | 2/2000 | Chan et al. | |
| 7,030,135 B2 | 4/2006 | Nilsson et al. | |
| 2003/0130258 A1 | 7/2003 | Kurz et al. | |
| 2003/0130279 A1 | 7/2003 | Kurz et al. | |
| 2003/0130318 A1 | 7/2003 | Barf et al. | |
| 2003/0166689 A1 | 9/2003 | Kurz et al. | |
| 2003/0176476 A1 | 9/2003 | Barf et al. | |
| 2003/0199501 A1 | 10/2003 | Nilsson et al. | |
| 2004/0224996 A1 | 11/2004 | Barf et al. | |

FOREIGN PATENT DOCUMENTS

| | | |
|---|---|---|
| CA | 2210613 | 1/1998 |
| CA | 2466490 | 5/2003 |
| EP | 0 749 964 A1 | 12/1996 |
| EP | 0 790 057 A1 | 8/1997 |
| EP | 0 819 681 A2 | 1/1998 |
| EP | 1 069 114 A2 | 1/2001 |
| FR | 94.123 | 5/1969 |
| FR | 2 384 498 A1 | 10/1978 |
| GB | 620654 * | 7/1940 |
| GB | 822947 | 11/1959 |
| GB | 6610324 | 1/1969 |
| JP | 2001483 A | 1/1990 |
| JP | 03173876 A2 | 7/1991 |
| JP | 6-87841 | 3/1994 |
| NL | 6610324 | 1/1967 |
| WO | WO 96/04912 A1 | 2/1996 |

(Continued)

OTHER PUBLICATIONS

Database CAS Online on STN, Chem. Abstr., Accession No. 1941:32570, Dansk Tidsskrift for Farmaci (1941), 15, 41-77, abstract only.*

Huff, Joel R., "HIV Protease: A Novel Chemotherapeutic Target for AIDS," *Journal of Medicinal Chemistry*, vol. 34, No. 8, Aug. 1991, pp. 2305-2314.

Röver, S., et al., "Synthesis and Biochemical Evaluation of N-(4-Phenylthiazol-2-yl)benzenesulfonamides as High-Affinity Inhibitors of Kynurenine 3-Hydroxylase", J. Med. Chem., 40, pp. 4378-4385 (1997).

(Continued)

*Primary Examiner*—Rebecca L Anderson
(74) *Attorney, Agent, or Firm*—Foley & Lardner LLP

(57) ABSTRACT

The present invention relates to compounds with the formula (II) and also to pharmaceutical compositions comprising the compounds, to processes for their preparation, as well as to the use of the compounds in medicine and for the preparation of a medicament which acts on the human 11-β-hydroxy-steroid dehydrogenase type 1 enzyme.

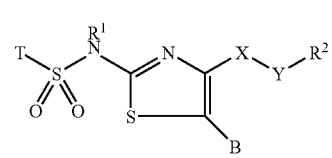

(II)

3 Claims, No Drawings

FOREIGN PATENT DOCUMENTS

| WO | WO 96/38179 A1 | 12/1996 |
|---|---|---|
| WO | WO 97/07789 A1 | 3/1997 |
| WO | WO 98/16520 | 4/1998 |
| WO | WO 98/27081 | 6/1998 |
| WO | WO 98/36770 A1 | 8/1998 |
| WO | WO 99/02502 | 1/1999 |
| WO | WO 99/28306 A1 | 6/1999 |
| WO | WO 99/65884 | 12/1999 |
| WO | WO 00/02851 A1 | 1/2000 |
| WO | WO 01/01971 A1 | 1/2001 |
| WO | WO 01/52833 A1 | 7/2001 |
| WO | WO 01/54691 A1 | 8/2001 |
| WO | WO 01/90090 A1 | 11/2001 |
| WO | WO 01/90091 A1 | 11/2001 |
| WO | WO 02/28353 A2 | 4/2002 |
| WO | WO 03/011258 A1 | 2/2003 |

OTHER PUBLICATIONS

Anton-Fox et al., "Pharmacological Studies of the Two New Hypoglycaemic Compounds 4-(3-Methyl-5-oxo-2-pyrazolin-1-hl)benzoic Acid and 1-(Mesitylen-2-sulfonyl)-1H-1,2,4-triazole," Arzneim.-Forsch./Drug Res 1994, 44(11), No. 7, pp. 821-826.

Merck & Co. Inc., USA, 1999, Monograph No. 4488, "Glybuzole," CAS Registry No. 1492-02-0.

Merck & Co., Inc., USA, 1999, Monograph No. 9084, "Sulfamethizole," CAS Registry No. 144-82-1.

Beuchet, Eur. J. Med. Chem., 34(9), p. 773 (1999).

Desai et al., "Sulfonamides. II. Preparation of N1-hetrocyclic substituted sulfonamides from alpha-naphthylamine and evaluation of their antibacterial properties", J. Indian Chem. Soc. 46(2):115-118, (1969). CAPLUS accession No. 1969:412872, document No. 71:12872.

Desai et al., "Sulfonamides. IV. Some N-6-heterocyclic sulfonamides from 2-paphthylamine as possible antibacterial agents", J. Indian Chem. Soc. 46(2): 411-414, 1969. Caplus accession No. 1969:449825, document No. 71:49825.

Gagiu et al., "Mitodepressive substances. 6.4-[(Haloacetyl)amino]-N1-$-benzenesulfonamides", Pharmazie 27(3):166, 1972. CAPLUS accession No. 1972:428762, document No. 77:28762.

DiCarlo et al., "Pentobarbital action on the binding capability of methylenoxytetracycline sulfaethylthiazole, and cyancobalamin with serum macromolecules", Atti Soc. Ital. Sci. Vet. 20:278-82, 1966, CAPLUS accession No. 1967:4020611, document No. 67:2061.

Chaurasia et al., "Synthesis of some new 2-sulphanilamidothiazoles as potential fungicides", Agric. Biol. Chem. 45(5): 1129-34, 1981. CAPLUS accession No. 1981-480840, document No. 95-80840.

Chemcats, "5-Thiazolecarboxylic acid, 4-methyl-2-(((4-methylphenyl)sulfonyl)amino)-, ethyl ester," Phrma Library Collection, (May 14, 2001). Chemcats Accession No. 2001:20962, Order No. NS46076, CAS Registry No. 313230-18-1.

Chemcats, "5-Thiazolecarboxylic acid, 2-(((4-chlorophenyl) sulfonyl)amino)-4-methyl-, ethyl ester," Pharma Library Collection, (May 14, 2001). Chemicals Accession No. 2001:19109, Order No. NS41693, CAS Registry No. 312915-26-7.

Chemcats, "5-Thiazolecarboxylic acid, 4-methyl-2-(((3-nitrophenyl)sulfonyl)amino)-, ethyl ester," ChemDiv. Inc. Product Library, (Apr. 26, 2001). Chemcats Accession No. 2001:786400, Order No. 0947-0103. CAS Registry No. 313237-92-2.

Chemcats, "5-Thiazolecarboxylic acid, 4-methyl-2-((phenylsulfonyl)amino)-, ethyl ester," Pharma Library Collection, (May 14, 2001). Chemcats Accession No. 2001:2446055, Order No. NS44365, CAS Registry No. 313237-91-1.

Chemcats, "5-Thiazolecarboxylic acid, 4-methyl-2-((2-naphthalenylsulfonyl)amino)-, ethyl ester," Pharma Library Collection, (May 14, 2001). Chemcats Accession No. 2001:19110, Order No. NS41694, CAS Registry No. 312915-27-8.

Chemcats, "5-Thiazolecarboxylic acid, 4-methyl-2-((4-methylphenyl)sulfonyl)amino)-, ethyl ester," Compounds for Screening, (Jul. 1, 2001). Chemcats Accession No. 2001:1499370, Order No. AG-690/36005052, CAS Registry No. 313230-18-1.

Chemcats, "5-Thiazolecarboxylic acid, 2-(((2-chlorophenyl)sulfonyl)amino)-4-methyl-ethyl ester," Interbioscreen Compound Library, (Feb. 11, 2002). Chemcats Accession No. 2002:175108, Order No. STOCK2S-28380, CAS Registry No. 378764-18-2.

Chemcats, "5-Thiazolecarboxamide, 4-methyl-N-phenyl-2-((phenylsulfonyl)amino)-," Interbioscreen Compound Library, (Feb. 11, 2002). Chemcats Accession No. 2002:174900, Order No. STOCK2S-27987, CAS Registry No. 378768-75-3.

Chemcats, "5-Thiazolecarboxamide, 2-(((2,5-dimethylphenyl)sulfonyl)amino)-4-methyl-N-phenyl-," Interbioscreen Compound Library, (Feb. 11, 2002). Chemcats Accession No. 2002:310940, Order No. STOCK2S-37273, CAS Registry No. 380584-86-1.

Chemcats, "5-Thiazolecarboxamide, 4-methyl-2-(((4-methylphenyl)sulvonyl)amino)-N-phenyl-," Interbioscreen Compound Library, (Feb. 11, 2002). Chemcats Accession No. 2002:310143, Order No. STOCK2S-35716, CAS Registry No. 380590-91-0.

Chemcats, "5-Thiazolecarboxylic acid, 2-(((2,5-dimethylphenyl)sulfonyl)amino)-4-methyl-, ethyl ester," Interbioscreen Compound Library, (Feb. 11, 2002). Chemcats Accession No. 2002:312516, Order No. STOCK2S-40385, CAS Registry No. 380878-60-4.

Hökfelt, Bernt "Hypoglycemic Activity in Relation to Chemical Structure of Potential Oral Antidiabetic Substances, I. 1-Sulfonyl-3-alkylureas," Journal of Medicinal and Pharmaceutical Chemistry, 5(1):231-257 (Jan. 6, 1962) ©American Chemical Society.

Sonlno et al., "Ketoconazole treatment in Cushing's syndrome: experience in 34 patients," Clinical Endocrinology 35:347-352 (1991) ©Blackwell Scientific Publications Ltd.

Verhelst et al., "Use of ketoconazole in the treatment of a virilizing adrenocortical carcinoma," Acta Endocrinologica 121:229-234 (1989) ©Acta Endocrinologica (Copenhagen).

"Analgesic tetrahydrothiazolo[5,4-c]pyridines, Fr. Addn., Addn to FR. 1498465 (1969)," corresponding to FR 6013, (Jul. 1, 1969).

Hisamitsu Pharmaceutical Co: "Preparation of 2-(substituted amino)thiazole derivatives as esterase inhibitors," CAPLUS Accession No. 1995:818696, Document No. 123:228174 (1995).

Hisamitsu Pharmaceutical Co: "Preparation of 2-aminothiazole derivatives as esterase inhibitors," CAPLUS Accession No. 1995:867676, Document No. 123:256699 (1995).

Susan Budavari et al., "The Merck Index, An Encyclopedia of Chemical, Drugs, and Biologicals, Twelfth Edition,", No. 9115, pp. 1529 (1996).

Friedrich Boberg et al., "Reaction of thioxo compounds with N-chloramidines. VI. Reaction of thioquinolone, dihydrothiazolethione and dihydroisothiazole thione with sodium N-chlorobenzenesulfonamides," CAPLUS Accession no. 1996:420288, Document No. 125:195596 (1996).

Chemcats Accession No. 1998:584450, Maybridge, Apr. 3, 2000, (1998).

Chemcats Accession No. 1998:584451, Maybridge, Apr. 3, 2000, (1998).

Hisamitsu Pharmaceutical Co: "Preparation of 2-(substituted amino)thiazole derivatives as esterase inhibitors," CAPLUS Accession No. 1995:818696, Document No. 123:228174 (1995).

Asahi Chemical Ind: "Therapeutics for Alzheimer's disease containing N-(5-nitro-2-thiazolyl)benzenesulfonamides," CAPLUS Accession No. 1996:111694, Document No. 124:165271 (1996).

Hisamitsu Pharmaceutical Co: "Preparation of diphenylthiazoles as pharmaceuticals," CAPLUS Accession No. 1991:680016, Document No. 115:280016, (1991).

Zaki El-Hewehi et al., "Sulfonic acid derivatives: preparation and applicability as mothproofing agents," Chemical Abstracts, vol. 58, The Abstract No. 5671, J. Prakt.Chem., pp. 297-336 (1962).

AsInEx Compound Collection, "5-Thiazolecarboxylic acid, 4-methy1-2-(((4-methylphenyl)sulfonyl)amino)-, ethyl ester," CHEMCATS Accession No. 2001:67657, (2001).

Pharma Library Collection, "5-Thiazolecarboxylic acid, 2-(((4-chlorophenyl)sulfonyl)amino)-4-methyl-, ethyl ester," CHEMCATS Accession No. 2001:19109, (2001).

ChemDiv, Inc. Product Library, Apr. 26, 2001, "5-Thiazolecarboxylic acid, 4-methyl-2-(((4-methylphenyl)sulfonyl)amino-), ethyl ester," CHEMCATS Accession No. 2001:444469, (2001).

V.V. Berezhinskaya, "hypoglycemic activity in relation to chem. Structure of potential oral antidiabetic substances—(I) 1-sulfonyl-3-alkylureas, (II) analogs of 1-sulfonyl-3-alkylureas, (III) 2-benzene-sulfonamido-5-alkyl-1,3,4-thiadiazole and-oxadiazoles," CAOLD Accession No. CA57:3567g (1962).

Hans Wojahn, "Bromination of sulfapyrimidine and sulfathiazole compounds. II.," Chemical Abstracts, vol. 51, The Abstract No. 6646d, Arch. Pharm., pp. 288, 321-336 (1955).

V.A. Krasovskii et al., "Alkylation of aminothiazoles. VII. Alkylation of 2-aminothiazole and 4-methyl-2-aminothiazole by tert-butyl alcohol," CAPLUS Accession No. 1969:115051, Document No. 70:115051, (1969).

J.D. McColl et al., "Effect of Some Sulfonylurea Deriviatives in Experimental Ulcer Formation in the Rat," Chemical Abstracts, vol. 59, The Abstract No. 3231, Arch. Intern. Pharmacodyn, pp. 181-189 (1963).

Gaile E. Gudriniece et al., "Heterocyclic compounds based on diketones. II. 2'-Amino-5,5-dimethyl-1-cyclohexanone(2,3:4',5')thiazole. I.," Chemical Abstracts, vol. 59, The Abstract No. 6380 (1962).

Anton-Fos et al., "Pharmacological Studies of the Two New Hypoglycaemic Compounds 4-(3-Methyl-5-oxo-2-pyrazolin-1-yl)benzoic Acid and 1-(Mesitylen-2-sulfonyl)-1H-1,2,4-triazole," Arzneim.-Forsch./Drug Res 44(11), No. 7, 1994, pp. 821-826.

Merck & Co. Inc., USA, 1999, Monograph No. 4488, "Glybuzole," CAS Registry No. 1492-02-0.

Merck & Co. Inc., USA, 1999, Monograph No. 9084, "Sulfamethizole," CAS Registry No. 144-82-1.

Kim, C.H et al., J. Endocrinol, vol. 162, pp. 371-379 (1999).

C.G. Bellows et al., Bone, vol. 23, pp. 119-125 (1998).

M.S. Cooper et al., Bone, vol. 27, pp. 375-381 (2000).

Analgesic tetrahydrothiazolo[5,4-c]pyridines, Fr. Addn., Addn to Fr. 1498465, (1969).

Bym et al., Solid-State Chemistry of Drugs, Second Edition, 1999, pp. 233-247.

Hultquist et al., "N-Heterocyclic Benzensulfonamides," Journal of the American Chemical Society, 1951, pp. 2558-2566, vol. 73.

Sprague et al., "Carboxy Derivatives of Sulfonamidothiazoles," Journal of the American Chemical Society, 1946, pp. 266-269, vol. 68.

Search Report from Corresponding Canadian Patent Application No. 2,408,783.

Search Report for Corresponding Canadian Patent Application No. 2,408,142.

Notice of References Cited in Office Action received in the corresponding U.S. Appl. No. 11/511,224, dated Dec. 4, 2008. (1 pg.).

* cited by examiner

INHIBITORS OF 11-BETA-HYDROXY STEROID DEHYDROGENASE TYPE 1

CROSS REFERENCE TO RELATED APPLICATIONS

The present application is a national phase application under 35 U.S.C. Section 371 filed from International Patent Application PCT/SE01/01155, filed 22 May 2001, which claims priority to Swedish patent application Serial. No. 0001899-4, filed 22 May 2000. The contents of these applications are incorporated herein by reference in their entirety.

TECHNICAL FIELD

The present invention relates to novel compounds, to pharmaceutical compositions comprising the compounds, to processes for their preparation, as well as to the use of the compounds in medicine and for the preparation of a medicament which acts on the human 11-β-hydroxysteroid dehydrogenase type 1 enzyme (11βHSD1).

BACKGROUND ART

1. Glucorticoids, Diabetes and Hepatic Glucose Production

It has been known for more than half a century that glucocorticoids have a central role in diabetes, e.g. the removal of the pituitary or the adrenal gland from a diabetic animal alleviates the most severe symptoms of diabetes and lowers the concentration of glucose in the blood (Long, C. D. and F. D. W. Leukins (1936) J. Exp. Med. 63: 465-490; Houssay, B. A. (1942) Endocrinology 30: 884-892). It is also well established that glucocorticoids enable the effect of glucagon on the liver.

The role of 11βHSD1 as an important regulator of local glucocorticoid effect and thus of hepatic glucose production is well substantiated (see e.g. Jamieson et al. (2000) J. Endocrinol. 165: p. 685-692). The hepatic insulin sensitivity was improved in healthy human volunteers treated with the non-specific 11βHSD1 inhibitor carbenoxolone (Walker, B. R et al. (1995) J. Clin. Endocrinol. Metab. 80: 3155-3159). Furthermore, the expected mechanism has been established by different experiments with mice and rats. These studies showed that the mRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6Pase) catalyzing the last common step of gluconeogenesis and glycogenolysis. Finally, the blood glucose level and hepatic glucose production is reduced in mice having the 11βHSD1 gene knocked-out. Data from this model also confirm that inhibition of 11βHSD1 will not cause hypoglycemia, as predicted since the basal levels of PEPCK and G6 Pase are regulated independently of glucocorticoids (Kotelevtsev, Y. et al., (1997) Proc. Natl. Acad. Sci. USA 94: 14924-14929).

2. Possible Reduction of Obesity and Obesity Related Cardiovascular Risk Factors Obesity is an important factor in syndrome X as well as in the majority (>80%) of type 2 diabetic, and omental fat appears to be of central importance. Abdominal obesity is closely associated with glucose intolerance, hyperinsulinemia, hypertriglyceridemia, and other factors of the so-called syndrome X (e.g. raised blood pressure, decreased levels of HDL and increased levels of VLDL) (Montague & O'Rahilly, Diabetes 49: 883-888, 2000). Inhibition of the enzyme in pre-adipocytes (stromal cells) has been shown to decrease the rate of differentiation into adipocytes. This is predicted to result in diminished expansion (possibly reduction) of the omental fat depot, i.e. reduced central obesity (Bujalska, I. J., S. Kumar, and P. M. Stewart (1997) Lancet 349: 1210-1213).

Inhibition of 11βHSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097-4105). Furthermore, there is a clear correlation between glucocorticoid "activity" and cardiovascular risk factore suggesting that a reduction of the glucocorticoid effects would be beneficial (Walker, B. R. et al. (1998) Hypertension 31: 891-895; Fraser, RP et al. (1999) Hypertension 33: 1364-1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 1378-1383).

3. Possible Beneficial Effect on the Pancreas

Inhibition of 11βHSD1 in isolated murine pancreatic β-cells improves the glucose-stimulated insulin secretion (Davani, B. et al. (2000) J. Biol. Chem. 2000 Nov. 10; 275 (45): 34841-4). Glucocorticoids were previously known to reduce pancreatic insulin release in vivo (Billaudel, B. and B. C. J. Sutter (1979) Horm. Metab. Res. 11: 555-560). Thus, inhibition of 11βHSD1 is predicted to yield other beneficial effects for diabetes treatment, besides effects on liver and fat.

4. Possible Beneficial Effects on Cognition and Dementia

Stress and glucocorticoids influence cognitive function (de Quervain, D. J.-F., B. Roozendaal, and J. L. McGaugh (1998) Nature 394: 787-790). The enzyme 11βHSD1 controls the level of glucocorticoid action in the brain and thus contributes to neurotoxicity (Rajan, V., C. R. W. Edwards, and J. R. Seckl, J. (1996) Neuroscience 16: 65-70; Seckl, J. R., Front. (2000) Neuroendocrinol. 18: 49-99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced anxiety (Tronche, F. et al. (1999) Nature Genetics 23: 99-103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite (previous section).

5. Possible Use of Immuno-modulation Using 11βHSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillièr's Clin. Endocrinol. Metab. 13: 576-581). The balance between the cell-mediated response and humoral responses is modulated by glucocorticoids. A high glucocorticoid activity, such as at a state of stress, is associated with a humoral response. Thus, inhibition of the enzyme 11βHSD1 has been suggested as a means of shifting the response towards a cell-based reaction.

In certain disease states, including tuberculosis, lepra and psoriasis the immune reaction is normally biased towards a humoral response when in fact the appropriate response would be cell based. Temporal inhibition of 11βHSD1, local or systemic, might be used to push the immune system into the appropriate response (Mason, D. (1991) Immunology Today 12: 57-60; Rook et al., supra).

An analogous use of 11βHSD1 inhibition, in this case temporal, would be to booster the immune response in association with immunization to ensure that a cell based response would be obtained, when desired.

6. Reduction of Intraocular Pressure

Recent data suggest that the levels of the glucocorticoid target receptors and the 11βHSD enzymes determines the susceptibility to glaucoma (Stokes, J. et al. (2000) Invest. Ophthalmol. 41: 1629-1638). Further, inhibition of 11βHSD1 was recently presented as a novel approach to lower the intraocular pressure (Walker E. A. et al, poster P3-698 at the Endocrine society meeting Jun. 12-15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epithalamium of the cornea (the site of aqueous production), to ciliary muscle and to the sphincter and dilator muscles of the iris. In contrast, the distant isoenzyme 11βHSD2 is highly expressed in the non-pigmented ciliary epithelium and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

7. Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., S. L. Cheng, and G. S. Kim (1999) J. Endocrinol. 162: 371-379). The negative effect on bone nodule formation could be blocked by the non-specific inhibitor carbenoxolone suggesting an important role of 11βHSD1 in the glucocorticoid effect (Bellows, C. G., A. Ciaccia, and J. N. M. Heersche, (1998) Bone 23: 119-125). Other data suggest a role of 11βHSD1 in providing sufficiently high levels of active glucocorticoid in osteoclasts, and thus in augmenting bone resorption (Cooper, M. S. et al. (2000) Bone 27: 375-381). Taken together, these different data suggest that inhibition of 11βHSD1 may have beneficial effects against osteoporosis by more than one mechanism working in parallel.

WO 99/65884 discloses carbon substituted aminothiazole inhibitors of cyclin dependent kinases. These compounds may e.g. be used against cancer, inflammation and arthritis. U.S. Pat. No. 5,856,347 discloses an antibacterial preparation or bactericide comprising 2-aminothiazole derivative and/or salt thereof. Further, U.S. Pat. No. 5,403,857 discloses benzenesulfonamide derivatives having 5-lipoxygenase inhibitory activity. Additionally, tetrahydrothiazolo[5,4-c]pyridines are disclosed in: Analgesic tetrahydrothiazolo[5,4-c]pyridines. Fr. Addn. (1969), 18 pp, Addn. to Fr. 1498465. CODEN: FAXXA3; FR 94123 19690704 CAN 72:100685 AN 1970:100685 CAPLUS and 4,5,6,7-Tetrahydrothiazolo[5,4-c]pyridines. Neth. Appl. (1967), 39 pp. CODEN: NAXXAN NL 6610324 19670124 CAN 68:49593, AN 1968: 49593 CAPLUS.

However, none of the above disclosures discloses the compounds according to the present invention, or their use for the treatment of diabetes, obesity, glaucoma, osteoporosis, cognitive disorders, immune disorders, and depression.

Consequently, there is a need of new compounds that are useful in the treatment of diabetes, obesity, glaucoma, osteoporosis, cognitive disorders, immune disorders, and depression.

DISCLOSURE OF THE INVENTION

The compounds according to the present invention solves the above problems and embraces a novel class of compounds which has been developed and which inhibit the human 11-β-hydroxysteroid dehydrogenase type 1 enzyme (11-β-HSD$_1$), and may therefore be of use in the treating disorders such as diabetes, obesity, glaucoma, osteoporosis, cognitive disorders and immune disorders.

One object of the present invention is a compound of the formula (II)

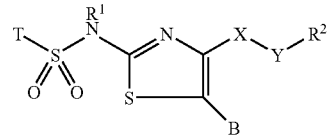

wherein

T is an aryl ring or heteroaryl ring or aryl-C$_2$-alkenyl ring, optionally independently substituted by [R]$_n$, wherein n is an integer 0-5, and R is hydrogen, aryl, heteroaryl, a heterocyclic ring, optionally halogenated C$_{1-6}$-alkyl, optionally halogenated C$_{1-6}$-alkoxy, C$_{1-6}$-alkylsulfonyl, carboxy, cyano, nitro, halogen, amine which is optionally mono- or di-substituted, amide which is optionally mono- or di-substituted, aryloxy, arylsulfonyl, arylamino, wherein aryl, heteroaryl and aryloxy residues and heterocyclic rings can further be optionally substituted in one or more positions independently of each other by C$_{1-6}$-acyl, C$_{1-6}$-alkylthio, cyano, nitro, hydrogen, halogen, optionally halogenated C$_{1-6}$-alkyl, optionally halogenated C$_{1-6}$-alkoxy, amide which is optionally mono- or di-substituted, (benzoylamino)methyl, carboxy, 2-thienylmethylamino or ({[4-(2-ethoxy-2-oxoethyl)-1,3-thiazol-2-yl]amino}carbonyl);

with the proviso that when R$^1$ is H, X is CH$_2$, Y is CO, R$^2$ is EtO and B is H, then T is not 2,4-dichloro-5-methylphenyl, 4-chlorophenyl, 4-chloro-2,5-dimethylphenyl, 2,4-difluorophenyl, 3-nitrophenyl and phenyl;

optionally also when R$^1$ is H, X is CH$_2$, Y is CO, R$^2$ is OH and B is H, then T is not 4-aminophenyl; and optionally also when R$^1$ is H, X is CH$_2$, Y is CO, R$^2$ is MeO and B is H, then T is not 4-acetylaminophenyl;

R$^1$ is hydrogen or C$_{1-6}$-alkyl;

X is CH$_2$ or CO;

Y is CH$_2$, CO or a single bond;

B is hydrogen, C$_{1-6}$-alkyl or dimethylaminomethyl;

R$^2$ is selected from C$_{1-6}$-alkyl, azido, arylthio, heteroarylthio, halogen, hydroxymethyl, 2-hydroxyethylaminomethyl, methylsulfonyloxymethyl, 3-oxo-4-morpholinolinylmethylene, C$_{1-6}$-alkoxycarbonyl, 5-methyl-1,3,4-oxadiazol-2-yl;

NR$^3$R$^4$, wherein R$^3$ and R$^4$ are each independently selected from hydrogen, C$_{1-6}$-alkyl, optionally halogenated C$_{1-6}$-alkylsulfonyl, C$_{1-6}$-alkoxy, 2-methoxyethyl, 2-hydroxyethyl, 1-methylimidazolylsulfonyl, C$_{1-6}$-acyl, cyclohexylmethyl, cyclopropanecarbonyl, aryl, optionally halogenated arylsulfonyl, furylcarbonyl, tetrahydro-2- furanylmethyl, N-carbethoxypiperidyl, or $C_{1-6}$-alkyl substituted with one or more aryl or heteroaryl, or $NR^3R^4$ represent together heterocyclic systems which can be imidazole, piperidine, pyrrolidine, piperazine, morpholine, oxazepine, oxazole, thiomorpholine, 1,1-dioxidothiomorpholine, 2-(3,4-dihydro-2(1H)isoquinolinyl), (1S,4S)-2-oxa-5-azabicyclo[2.2.1]hept-5-yl, which heterocyclic systems can be optionally substituted by $C_{1-6}$-alkyl, $C_{1-6}$-acyl, hydroxy, oxo, t-butoxycarbonyl;

$OCONR^3R^4$, wherein $R^3$ and $R^4$ are each independently selected from hydrogen, $C_{1-6}$-alkyl or form together morpholinyl;

$R^5O$, wherein $R^5$ is hydrogen, optionally halogenated $C_{1-6}$-alkyl, aryl, heteroaryl, $C_{1-6}$-acyl, $C_{1-6}$-alkylsulfonyl, arylcarbonyl, heteroarylcarbonyl, 2-carbomethoxyphenyl;

or a salt, hydrate or solvate thereof.

It is preferred that:

T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; (E)-2-phenylethenyl; 8-quinolinyl;

thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with one or more of acetylamino, 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, methyl, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or with the proviso that when $R^1$ is H, X is $CH_2$, Y is CO, $R^2$ is EtO and B is H, then T is not 2,4-dichloro-5-methylphenyl, 4-chlorophenyl, 4-chloro-2,5-dimethylphenyl, 2,4-difluorophenyl, 3-nitrophenyl and phenyl;

optionally also when $R^1$ is H, X is $CH_2$, Y is CO, $R^2$ is OH and B is H, then T is not 4-aminophenyl; and optionally also when $R^1$ is H, X is $CH_2$, Y is CO, $R^2$ is MeO and B is H, then T is not 4-acetylaminophenyl;

$R^1$ is hydrogen or methyl;

X is $CH_2$ or CO;

Y is $CH_2$, CO or a single bond;

B is hydrogen, methyl or dimethylaminomethyl;

$R^2$ is selected from n-propyl, azido, bromo, chloro, 2-pyridinylsulfanyl, 3-oxo-4-morpholinolinylmethylene, ethoxycarbonyl, 5-methyl-1,3,4-oxadiazol-2-yl, hydroxymethyl, 2-hydroxyethylaminomethyl, methylsulfonyloxymethyl;

$NR^3R^4$, wherein $R^3$ and $R^4$ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, propyl, tetrahydro-2-furanylmethyl, trifluoromethylsulfonyl, N-carbethoxypiperidyl; or $NR^3R^4$ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-azabicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

$OCONR^3R^4$, wherein $R^3$ and $R^4$ are each independently selected from ethyl, hydrogen or form together morpholinyl;

$R^5O$, wherein $R^5$ is acetyl, benzoyl, benzyl, ethyl, 2-fluoroethyl, 2-furylcarbonyl, hydrogen, isobutyryl, isopropyl, methyl, 2-carbomethoxyphenyl, methylsulfonyl, phenyl, propionyl, 3-pyridinyl, 2,2,2-trifluoroethyl.

When T is a substituted phenyl group, it is preferred that the phenyl ring is substituted as follows:

a) either T is phenyl, wherein the phenyl is substituted with one or more of acetylamino, 3-acetylaminophenyl, 3-acetylphenyl, benzeneamino, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), 5-fluoro-2-methoxyphenyl, 2-furyl, iodo, isopropyl, methanesulfonyl, methoxy, methyl, 3,4-methylenedioxyphenyl, 4-methyl-1-piperazinyl, 4-methyl-1-piperidinyl, 4-methylsulfanylphenyl, 5-methyl-2-thienyl, 4-morpholinyl, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or b) T is phenyl substituted with chloro in at least one of the positions 3, 5 or 6 and with one or more of acetylamino, 3-acetylaminophenyl, 3-acetylphenyl, benzeneamino, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), 5-fluoro-2-methoxyphenyl, 2-furyl, iodo, isopropyl, methanesulfonyl, methoxy, methyl, 3,4-methylenedioxyphenyl, 4-methyl-1-piperazinyl, 4-methyl-1-piperidinyl, 4-methylsulfanylphenyl, 5-methyl-2-thienyl, 4-morpholinyl, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or c) T is phenyl substituted with chloro in position 2 and with one or more of acetylamino, 3-acetylaminophenyl, 3-acetylphenyl, benzeneamino, 2-benzofuryl, benzylamino, 3,5-bis(trifluoromethyl)phenyl, bromo, butoxy, carboxy, 4-carboxyphenyl, 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), 5-fluoro-2-methoxyphenyl, 2-furyl, iodo, isopropyl, methanesulfonyl, methoxy, methyl, 3,4-methylenedioxyphenyl, 4-methyl-1-piperazinyl, 4-methyl-1-piperidinyl, 4-methylsulfanylphenyl, 5-methyl-2-thienyl, 4-morpholinyl, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or d) T is phenyl substituted with one or three fluorine and optionally one or more bromo and methyl.

The following compounds are especially preferred:

Ethyl 2-(2-(((4-methylphenyl)sulfonyl)amino)-1,3-thiazol-4-yl)acetate,
Ethyl 2-(2-{[(2,5-dichloro-3-thienyl)sulfonyl]amino}-1,3-thiazol-4-yl)acetate,
Ethyl (2-{[(2-chlorophenyl)sulfonyl]amino}-1,3-thiazol-4-yl)acetate,
Ethyl 2-(2-{[(3-chloro-2-methylphenyl)sulfonyl]amino}-1,3-thiazol-4-yl)acetate,
Ethyl 2-{2-[([1,1'-biphenyl]-4-ylsulfonyl)amino]-1,3-thiazol-4-yl}acetate,
Ethyl 2-(2-{[(3-bromophenyl)sulfonyl]amino}-1,3-thiazol-4-yl)acetate,
Ethyl (2-{[(4-nitrophenyl)sulfonyl]amino}-1,3-thiazol-4-yl)acetate,
Ethyl (2-{[(4-methoxyphenyl)sulfonyl]amino}-1,3-thiazol-4-yl)acetate,
Ethyl (2-{[(3-methylphenyl)sulfonyl]amino}-1,3-thiazol-4-yl)acetate,
Ethyl (2-{[(3-chlorophenyl)sulfonyl]amino}-1,3-thiazol-4-yl)acetate,
Ethyl (2-{[(4-fluorophenyl)sulfonyl]amino}-1,3-thiazol-4-yl)acetate,
Ethyl (2-{[(3-fluorophenyl)sulfonyl]amino}-1,3-thiazol-4-yl)acetate,
Ethyl (2-{[(4-isopropylphenyl)sulfonyl]amino}-1,3-thiazol-4-yl)acetate,
Ethyl [2-({[3-({[4-(2-ethoxy-2-oxoethyl)-1,3-thiazol-2-yl]amino}carbonyl)phenyl]sulfonyl}amino)-1,3-thiazol-4-yl]acetate,
Ethyl [2-({[4-({[4-(2-ethoxy-2-oxoethyl)-1,3-thiazol-2-yl]amino}carbonyl)phenyl]sulfonyl}amino)-1,3-thiazol-4-yl]acetate,
Ethyl (2-{[(2-methylphenyl)sulfonyl]amino}-1,3-thiazol-4-yl)acetate,
Ethyl [2-({[2-(trifluoromethyl)phenyl]sulfonyl}amino)-1,3-thiazol-4-yl]acetate,
Ethyl [2-({[3-(trifluoromethyl)phenyl]sulfonyl}amino)-1,3-thiazol-4-yl]acetate,
Ethyl [2-({[4-(trifluoromethyl)phenyl]sulfonyl}amino)-1,3-thiazol-4-yl]acetate,
Ethyl 2-(2-{[(4-bromophenyl)sulfonyl]amino}-1,3-thiazol-4-yl)acetate,
Ethyl (2-{[(2-nitrophenyl)sulfonyl]amino}-1,3-thiazol-4-yl)acetate,
Ethyl (2-{[(2,4-dichloro-6-methylphenyl)sulfonyl]amino}-1,3-thiazol-4-yl)acetate,
Ethyl (2-{[(2,4,6-trichlorophenyl)sulfonyl]amino}-1,3-thiazol-4-yl)acetate,
Ethyl (2-{[(2,4-dichlorophenyl)sulfonyl]amino}-1,3-thiazol-4-yl)acetate,
Ethyl (2-{[(5-fluoro-2-methylphenyl)sulfonyl]amino}-1,3-thiazol-4-yl)acetate,
Ethyl (2-{[(4-propylphenyl)sulfonyl]amino}-1,3-thiazol-4-yl)acetate,
Ethyl (2-{[(2-methoxy-4-methylphenyl)sulfonyl]amino}-1,3-thiazol-4-yl)acetate,
Ethyl (2-{[(3,5-dichlorophenyl)sulfonyl]amino)-1,3-thiazol-4-yl)acetate,
Ethyl [2-({[4-(3-chloro-2-cyanophenoxy)phenyl]sulfonyl}amino)-1,3-thiazol-4-yl]acetate,
Ethyl (2-{[(3,4-dichlorophenyl)sulfonyl]amino}-1,3-thiazol-4-yl)acetate,
Ethyl (2-{[(4-butoxyphenyl)sulfonyl]amino}-1,3-thiazol-4-yl)acetate,
Ethyl (2-{[(4-chloro-2-methylphenyl)sulfonyl]amino}-1,3-thiazol-4-yl)acetate,
Ethyl [2-({[4-(acetylamino)phenyl]sulfonyl}amino)-1,3-thiazol-4-yl]acetate,
Ethyl {2-[(8-quinolinylsulfonyl)amino]-1,3-thiazol-4-yl}acetate,
Ethyl (2-{[(3,4-dimethoxyphenyl)sulfonyl]amino}-1,3-thiazol-4-yl)acetate,
Ethyl (2-{[(4-iodophenyl)sulfonyl]amiino}-1,3-thiazol-4-yl)acetate,
Ethyl (2-{[(3-chloro-4-methylphenyl)sulfonyl]amino}-1,3-thiazol-4-yl)acetate,
Ethyl [2-({[5-(dimethylamino)-1-naphthyl]sulfonyl}amino)-1,3-thiazol-4-yl]acetate,
Ethyl (2-{[(1-methyl-1H-imidazol-4-yl)sulfonyl]amino}-1,3-thiazol-4-yl)acetate,
Ethyl (2-{[(5-bromo-2-methoxyphenyl)sulfonyl]amino}-1,3-thiazol-4-yl)acetate,
Ethyl (2-{[(2,5-dimethoxyphenyl)sulfonyl]amino}-1,3-thiazol-4-yl)acetate,
Ethyl {2-[(2-naphthylsulfonyl)amino]-1,3-thiazol-4-yl}acetate,
Ethyl {2-[(mesitylsulfonyl)amino]-1,3-thiazol-4-yl}acetate,
Ethyl (2-{[(3-bromo-5-chloro-2-thienyl)sulfonyl]amino}-1,3-thiazol-4-yl)acetate,
Ethyl {2-[({5-[(benzoylamino)methyl]-2-thienyl}sulfonyl)amino]-1,3-thiazol-4-yl}acetate,
Ethyl {2-[({5-[1-methyl-5-(trifluoromethyl)-1H-pyrazol-3-yl]-2-thienyl}sulfonyl)amino]-1,3-thiazol-4-yl}acetate,
Ethyl (2-{[(4-cyanophenyl)sulfonyl]amino}-1,3-thiazol-4-yl)acetate,
Ethyl {2-[({5-[2-(methylsulfanyl)-4-pyrimidinyl]-2-thienyl}sulfonyl)amino]-1,3-thiazol-4-yl}acetate,
Ethyl (2-{[(3-cyanophenyl)sulfonyl]amino}-1,3-thiazol-4-yl)acetate,
Ethyl (2-{[(2,4,5-trichlorophenyl)sulfonyl]amino}-1,3-thiazol-4-yl)acetate,
Ethyl [2-({[(E)-2-phenylethenyl]sulfonyl}amino)-1,3-thiazol-4-yl]acetate,
Ethyl (2-{[(2,3,4-trichlorophenyl)sulfonyl]amino}-1,3-thiazol-4-yl)acetate,
Ethyl (2-{[(4-bromo-2,5-difluorophenyl)sulfonyl]amino}-1,3-thiazol-4-yl)acetate,
Ethyl [2-({[4-(trifluoromethoxy)phenyl]sulfonyl}amino)-1,3-thiazol-4-yl]acetate,
Ethyl (2-{[(2,3-dichlorophenyl)sulfonyl]amino}-1,3-thiazol-4-yl)acetate,
Ethyl (2-{[(2-bromophenyl)sulfonyl]amino}-1,3-thiazol-4-yl)acetate,
Ethyl (2-{[(4,5-dichloro-2-thienyl)sulfonyl]amino}-1,3-thiazol-4-yl)acetate,
Ethyl [2-({[4-(phenylsulfonyl)-2-thienyl]sulfonyl}amino)-1,3-thiazol-4-yl]acetate,
Ethyl [2-({[5-(phenylsulfonyl)-2-thienyl]sulfonyl}amino)-1,3-thiazol-4-yl]acetate,
Ethyl (2-{[(2,6-dichlorophenyl)sulfonyl]amino}-1,3-thiazol-4-yl)acetate,
Ethyl (2-{[(2-cyanophenyl)sulfonyl]amino}-1,3-thiazol-4-yl)acetate,
Ethyl [2-({[4-(acetylamino)-3-chlorophenyl]sulfonyl}amino)-1,3-thiazol-4-yl]acetate,
Ethyl (2-{[(5-chloro-1,3-dimethyl-1H-pyrazol-4-yl)sulfonyl]amino}-1,3-thiazol-4-yl)acetate,
Ethyl (2-{[(3-methoxyphenyl)sulfonyl]amino}-1,3-thiazol-4-yl)acetate, Ethyl (2-{[(4-bromo-5-chloro-2-thienyl)sulfonyl]amino}-1,3-thiazol-4-yl)acetate,
Ethyl 2-{2-[(1-naphthylsulfonyl)amino]-1,3-thiazol-4-yl}acetate,
Ethyl (2-{[(2,5-dichlorophenyl)sulfonyl]amino}-1,3-thiazol-4-yl]acetate,
Ethyl [2-({[4-(methylsulfonyl)phenyl]sulfonyl}amino)-1,3-thiazol-4-yl]acetate,
Ethyl [2-({[2-(methylsulfonyl)phenyl]sulfonyl}amino)-1,3-thiazol-4-yl]acetate,
Ethyl (2-{[(4-bromo-2-fluorophenyl)sulfonyl]amino}-1,3-thiazol-4-yl)acetate,
Ethyl (2-{[(2,3,4-trifluorophenyl)sulfonyl]amino}-1,3-thiazol-4-yl)acetate,
Ethyl (2-{[(7-chloro-2,1,3-benzoxadiazol-4-yl)sulfonyl]amino}-1,3-thiazol-4-yl)acetate,
Ethyl (2-{[(2,4,6-trifluorophenyl)sulfonyl]amino}-1,3-thiazol-4-yl)acetate,
2-Chloro-5-({[4-(2-ethoxy-2-oxoethyl)-1,3-thiazol-2-yl]amino}sulfonyl)-4-fluorobenzoic acid,
Ethyl (2-{[(5-chloro-2-thienyl)sulfonyl]amino}-1,3-thiazol-4-yl)acetate,
Ethyl (2-{[(2-chloro-4-fluorophenyl)sulfonyl]amino}-1,3-thiazol-4-yl)acetate,
Ethyl [2-({[5-(3-isoxazolyl)-2-thienyl]sulfonyl}amino)-1,3-thiazol-4-yl]acetate,
Ethyl (2-{[(4-bromo-2-methylphenyl)sulfonyl]amino}-1,3-thiazol-4-yl)acetate,
Ethyl (2-{[(4-phenoxyphenyl)sulfonyl]amino}-1,3-thiazol-4-yl)acetate,
Ethyl (2-{[(4-chloro-2,6-dimethylphenyl)sulfonyl]amino}-1,3-thiazol-4-yl)acetate,
Ethyl [2-({[2-methyl-4-(trifluoromethoxy)phenyl]sulfonyl}amino)-1,3-thiazol-4-yl]acetate,
Ethyl [2-({[2,4-bis(trifluoromethyl)phenyl]sulfonyl}amino)-1,3-thiazol-4-yl]acetate,
Ethyl 2-{2-[[(3-chloro-2-methylphenyl)sulfonyl](methyl)amino]-1,3-thiazol-4-yl}acetate,
Ethyl oxo(2-{[(4-propylphenyl)sulfonyl]amino}-1,3-thiazol-4-yl)acetate,
Ethyl (2-{[(3-chloro-2-methylphenyl)sulfonyl]amino}-1,3-thiazol-4-yl)(oxo)acetate,
Ethyl oxo(2-{[(2,4,6-trichlorophenyl)sulfonyl]amino}-1,3-thiazol-4-yl)acetate,
Ethyl {2-[([1,1'-biphenyl]-4-ylsulfonyl)amino]-1,3-thiazol-4-yl}(oxo)acetate,
Ethyl (2-{[(2,4-dichloro-6-methylphenyl)sulfonyl]amino}-1,3-thiazol-4-yl)(oxo)acetate,
2-(2-{[(4-Methylphenyl)sulfonyl]amino}-1,3-thiazol-4-yl)acetic acid,
2-(2-{[(2,5-Dichloro-3-thienyl)sulfonyl]amino}-1,3-thiazol-4-yl)acetic acid,
(2-{[(2-Chlorophenyl)sulfonyl]amino}-1,3-thiazol-4-yl)acetic acid,
2-(2-{[(3-Chloro-2-methylphenyl)sulfonyl]amino}-1,3-thiazol-4-yl)acetic acid,
Isopropyl 2-(2-{[(3-chloro-2-methylphenyl)sulfonyl]amino}-1,3-thiazol-4-yl)acetate,
Phenyl 2-(2-{[(3-chloro-2-methylphenyl)sulfonyl]amino}-1,3-thiazol-4-yl)acetate,
Methyl (2-{[(3-chloro-2-methylphenyl)sulfonyl]amino}-1,3-thiazol-4-yl)acetate,
Methyl {2-[([1,1'-biphenyl]-4-ylsulfonyl)amino]-5-methyl-1,3-thiazol-4-yl}acetate,
Methyl (2-{[(4-chlorophenyl)sulfonyl]amino}-5-methyl-1,3-thiazol-4-yl)acetate,
Methyl (2-{[(3-chloro-2-methylphenyl)sulfonyl]amino}-5-methyl-1,3-thiazol-4-yl)acetate,
Methyl [2-({[4-(3-chloro-2-cyanophenoxy)phenyl]sulfonyl}amino)-5-methyl-1,3-thiazol-4-yl]acetate,
Methyl (5-methyl-2-{[(4-propylphenyl)sulfonyl]amino}-1,3-thiazol-4-yl)acetate,
Methyl (5-methyl-2-{[(2,4,6-trichlorophenyl)sulfonyl]amino}-1,3-thiazol-4-yl)acetate,
Methyl (2-{[(2,4-dichloro-6-methylphenyl)sulfonyl]amino}-5-methyl-1,3-thiazol-4-yl)acetate,
N-(2-Methoxyethyl)-2-(2-{[(4-methylphenyl)sulfonyl]amino}-1,3-thiazol-4-yl)acetamide,
2-(2-{[(2,5-Dichloro-3-thienyl)sulfonyl]amino}-1,3-thiazol-4-yl)-N-methylacetamide,
N-(1,3-Benzodioxol-5-ylmethyl)-2-{2-[(1-naphthylsulfonyl)amino]-1,3-thiazol-4-yl}acetamide,
N-(2-Furylmethyl)-2-{2-[(1-naphthylsulfonyl)amino]-1,3-thiazol-4-yl}acetamide,
2-(2-{[(2,4-Difluorophenyl)sulfonyl]amino}-1,3-thiazol-4-yl)-N-ethylacetamide,
N-Isopropyl-2-{2-[(1-naphthylsulfonyl)amino]-1,3-thiazol-4-yl}acetamide,
N-[2-(1H-Indol-3-yl)ethyl]-2-{2-[(1-naphthylsulfonyl)amino]-1,3-thiazol-4-yl}acetamide,
N-(Cyclohexylmethyl)-2-{2-[(phenylsulfonyl)amino]-1,3-thiazol-4-yl}acetamide,
2-(2-{[(3-Chloro-2-methylphenyl)sulfonyl]amino})-1,3-thiazol-4-yl)-N-methylacetamide,
2-(2-{([(3-Chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N-phenylacetamide,
2-(2-{[(4-Chlorophenyl)sulfonyl]amino}-1,3-thiazol-4-yl)-N-(2-furylmethyl)acetamide,
N-Benzhydryl-2-(2-{[(4-chlorophenyl)sulfonyl]amino}-1,3-thiazol-4-yl)acetamide,
2-(2-{[(4-Chlorophenyl)sulfonyl]amino}-1,3-thiazol-4-yl)-N-(tetrahydro-2-furanylmethyl)acetamide,
Ethyl 4-{[2-(2-{[(4-chlorophenyl)sulfonyl]amino}-1,3-thiazol-4-yl)acetyl]amino}-1-piperidinecarboxylate,
N-Benzhydryl-2-(2-{[(3-chloro-2-methylphenyl)sulfonyl]aniino}-1,3-thiazol-4-yl)acetamide,
2-(2-{[(4-Chlorophenyl)sulfonyl]amino}-1,3-thiazol-4-yl)-N-phenylacetamide,
2-(2-{[(3-Chloro-2-methylphenyl)sulfonyl]amino}-1,3-thiazol-4-yl)acetamide,
2-(2-{[(3-Chloro-2-methylphenyl)sulfonyl]amino})-1,3-thiazol-4-yl)-N,N-diethylacetamide,
2-{2-[([1,1'-Biphenyl]-4-ylsulfonyl)amino]-1,3-thiazol-4-yl}-N,N-diethylacetamide,
N,N-diethyl-2-(2-{[(4-propylphenyl)sulfonyl]amino}-1,3-thiazol-4-yl)acetamide,
2-(2-{[(2,4-Dichloro-6-methylphenyl)sulfonyl]amino}-1,3-thiazol-4-yl)-N,N-diethylacetamide,
N,N-diethyl-2-(2-{[(2,4,6-trichlorophenyl)sulfonyl]amino}-1,3-thiazol-4-yl)acetamide,
2-{2-[([1,1'-Biphenyl]-4-ylsulfonyl)amino]-1,3-thiazol-4-yl}-N,N-diisopropylacetamide,
N,N-diisopropyl-2-(2-{[(4-propylphenyl)sulfonyl]amino}-1,3-thiazol-4-yl)acetamide,
2-(2-{[(2,4-Dichloro-6-methylphenyl)sulfonyl]amino}-1,3-thiazol-4-yl)-N,N-diisopropylacetamide,
N,N-diisopropyl-2-(2-{[(2,4,6-trichlorophenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diisopropylacetamide, 2-(2-{[(3-Chloro-2-methylphenyl)sulfonyl]amino})-1,3-thiazol-4-yl)-N,N-dipropylacetamide,
N-benzyl-2-(2-{[(3-chloro-2-methylphenyl)sulfonyl]amino}-1,3-thiazol-4-yl)-N-methylacetamide,
N-benzyl-2-(2-{[(3-chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N,N-dimethylacetamide,
2-(2-{[(3-chloro-2-methylphenyl)sulfonyl]amino}-1,3-thiazol-4-yl)-N-cyclohexyl-N-methylacetamide,
3-Chloro-N-{4-[2-(3,4-dihydro-2(1H)-isoquinolinyl)-2-oxoethyl]-1,3-thiazol-2-yl}-2-methylbenzenesulfonamide,
2-(2-{[(3-Chloro-2-methylphenyl)sulfonyl]amino}-1,3-thiazol-4-yl)-N-methyl-N-phenylacetamide,
2-(2-{[(3-Chloro-2-methylphenyl)sulfonyl]amino}-1,3-thiazol-4-yl)-N-isopropyl-N-methylacetamide,
2-{2-[([1,1'-Biphenyl]-4-ylsulfonyl)amino]-1,3-thiazol-4-yl}-N-isopropyl-N-methylacetamide,
N-ethyl-N-methyl-2-(2-{[(2,4,6-trichlorophenyl)sulfonyl]amino}-1,3-thiazol-4-yl)acetamide,
2-(2-{[(2,4-Dichloro-6-methylphenyl)sulfonyl]amino}-1,3-thiazol-4-yl)-N-ethyl-N-methylacetamide,
N-ethyl-N-methyl-2-(2-{[(4-propylphenyl)sulfonyl]amino})-1,3-thiazol-4-yl)acetamide,
2-{2-[([1,1'-Biphenyl]-4-ylsulfonyl)amino]-1,3-thiazol-4-yl}-N-ethyl-N-methylacetamide,
2-(2-{[(3-Chloro-2-methylphenyl)sulfonyl]amino}-1,3-thiazol-4-yl)-N-ethyl-N-methylacetamide,
2-(2-{[(3-Chloro-2-methylphenyl)sulfonyl]amino}-1,3-thiazol-4-yl)-N-methyl-N-[(1S)-1-phenylethyl]acetamide,
3-Chloro-2-methyl-N-{4-[2-oxo-2-(1-pyrrolidinyl)ethyl]-1,3-thiazol-2-yl}benzenesulfonamide,
3-Chloro-2-methyl-N-{4-[2-oxo-2-(1-piperidinyl)ethyl]-1,3-thiazol-2-yl}benzenesulfonamide,
N-{4-[2-oxo-2-(1-piperidinyl)ethyl]-1,3-thiazol-2-yl}[1,1'-biphenyl]-4-sulfonamide,
N-{4-[2-oxo-2-(1-piperidinyl)ethyl]-1,3-thiazol-2-yl}-4-propylbenzenesulfonamide,
2,4-Dichloro-6-methyl-N-{4-[2-oxo-2-(1-piperidinyl)ethyl]-1,3-thiazol-2-yl}benzenesulfonamide,
2,4,6-Trichloro-N-{4-[2-oxo-2-(1-piperidinyl)ethyl]-1,3-thiazol-2-yl}benzenesulfonamide,
3-Chloro-2-methyl-N-{4-[2-(4-morpholinyl)-2-oxoethyl]-1,3-thiazol-2-yl}benzenesulfonamide,
2,4,6-Trichloro-N-{4-[2-(4-morpholinyl)-2-oxoethyl]-1,3-thiazol-2-yl}benzenesulfonamide,
2,4-Dichloro-6-methyl-N-{4-[2-(4-morpholinyl)₂-oxoethyl]-1,3-thiazol-2-yl}benzenesulfonamide,
N-{4-[2-(4-morpholinyl)-2-oxoethyl]-1,3-thiazol-2-yl}[1,1'-biphenyl]-4-sulfonamide,
N-{4-[2-(4-morpholinyl)-2-oxoethyl]-1,3-thiazol-2-yl}-4-propylbenzenesulfonamide,
2,4-Dichloro-N-{4-[2-(4-morpholinyl)-2-oxoethyl]-1,3-thiazol-2-yl}benzenesulfonamide,
4-Chloro-2,6-dimethyl-N-{4-[2-(4-morpholinyl)-2-oxoethyl]-1,3-thiazol-2-yl}benzenesulfonamide,
N-{4-[2-(4-morpholinyl)-2-oxoethyl]-1,3-thiazol-2-yl}-4-phenoxybenzenesulfonamide,
2-Methyl-N-{4-[2-(4-morpholinyl)-2-oxoethyl]-1,3-thiazol-2-yl}-4-(trifluoromethoxy)benzenesulfonamide,
N-{4-[2-(4-morpholinyl)-2-oxoethyl]-1,3-thiazol-2-yl}-2,4-bis(trifluoromethyl)benzenesulfonamide,
4-Bromo-2-methyl-N-{4-[2-(4-morpholinyl)-2-oxoethyl]-1,3-thiazol-2-yl}benzenesulfonamide,
4-(2-Furyl)-N-{4-[2-4-morpholinyl)-2-oxoethyl]-1,3-thiazol-2-yl}benzenesulfonamide,
3'-Fluoro-6'-methoxy-N-{4-[2-(4-morpholinyl)-2-oxoethyl]-1,3-thiazol-2-yl}[1,1'-biphenyl]-4-sulfonamide,
4-(5-Methyl-2-thienyl)-N-{4-[2-(4-morpholinyl)-2-oxoethyl]-1,3-thiazol-2-yl}benzenesulfonamide,
3'-Acetyl-N-{4-[2-(4-morpholinyl)-2-oxoethyl]-1,3-thiazol-2-yl}[1,1-biphenyl]-4-sulfonamide,
N-{4-[2-(4-Morpholinyl)-2-oxoethyl]-1,3-thiazol-2-yl}-4'-(trifluoromethoxy)[1,1'-biphenyl]-4-sulfonamide,
3',4'-Dichloro-N-{4-[2-(4-morpholinyl)-2-oxoethyl]-1,3-thiazol-2-yl}[1,1'-biphenyl]-4-sulfonamide,
4-(1,3-Benzodioxol-5-yl)-N-{4-[2-(4-morpholinyl)-2-oxoethyl]-1,3-thiazol-2-yl}benzenesulfonamide,
4-(5-chloro-2-thienyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(4-pyridinyl)benzenesulfonamide,
N-{4'-[({4-[2-(4-morpholinyl)-2-oxoethyl]-1,3-thiazol-2-yl}amino)sulfonyl][1,1'-biphenyl]-3-yl}acetamide,
N-{4-[2-(4-Morpholinyl)-2-oxoethyl]-1,3-thiazol-2-yl}-4-(3-thienyl)benzenesulfonamide,
N-{4-[2-(4-Morpholinyl)-2-oxoethyl]-1,3-thiazol-2-yl}-4-(2-thienyl)benzenesulfonamide,
4'-[({4-[2-(4-Morpholinyl)-2-oxoethyl]-1,3-thiazol-2-yl}amino)sulfonyl][1,1'-biphenyl]-4-carboxylic acid,
4'-(Methylsulfanyl)-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3',5'-bis(trifluoromethyl)[1,1'-biphenyl]-4-sulfonamide,
4'-Chloro-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3'-nitro[1,1'-biphenyl]-4-sulfonamide,
4-(1-Benzofuran-2-yl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(1-pyrrolidinyl)benzenesulfonamide,
4-(4-Methyl-1-piperidinyl)-N-{4-[2-(4-morpholinyl)-2-oxoethyl]-1,3-thiazol-2-yl}benzenesulfonamide,
4-Anilino-N-{4-[2-(4-morpholinyl)-2-oxoethyl]-1,3-thiazol-2-yl}benzenesulfonamide,
4-(Benzylamino)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(2-thienylmethyl)amino]benzenesulfonamide,
4-(4-Morpholinyl)-N-{4-[2-(4-morpholinyl)-2-oxoethyl]-1,3-thiazol-2-yl}benzenesulfonamide,
4-(4-Methyl-1-piperazinyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(3-pyridinylmethyl)amino]benzenesulfonamide,
2,4-Dichloro-6-methyl-N-{5-methyl-4-[2-(4-morpholinyl)-2-oxoethyl]-1,3-thiazol-2-yl}benzenesulfonamide,
N-{5-methyl-4-[2-(4-morpholinyl)-2-oxoethyl]-1-3-thiazol-2-yl}[1,1'-biphenyl]-4-sulfonamide,
2,4,6-trichloro-N-{5-methyl-4-[2-(4-morpholinyl)-2-oxoethyl]-1,3-thiazol-2-yl}benzenesulfonamide,
3-chloro-2-methyl-N-{5-methyl-4-[2-(4-morpholinyl)-2-oxoethyl]-1,3-thiazol-2-yl}benzenesulfonamide,
3-Chloro-N-(4-{2-[(2R,6S)-2,6-dimethylmorpholinyl]-2-oxoethyl}-1,3-thiazol-2-yl)-2-methylbenzenesulfonamide,
3-Chloro-2-methyl-N-(4-{2-[(1S,4S)-2-oxa-5-azabicyclo[2.2.1]hept-5-yl]-2-oxoethyl}-1,3-thiazol-2-yl)benzenesulfonamide, 3-Chloro-2-methyl-N-{4-[2-oxo-2-(4-thiomorpholinyl)ethyl]-1,3-thiazol-2-yl}benzenesulfonamide,
N-{4-[2-oxo-2-(4-thiomorpholinyl)ethyl]-1,3-thiazol-2-yl}[1,1'-biphenyl]-4-sulfonamide,
N-{4-[2-oxo-2-(4-thiomorpholinyl)ethyl]-1,3-thiazol-2-yl}-4-propylbenzenesulfonamide,
2,4-Dichloro-6-methyl-N-{4-[2-oxo-2-(4-thiomorpholinyl)ethyl]-1,3-thiazol-2-yl}benzenesulfonamide,
2,4,6-Trichloro-N-{4-[2-oxo-2-(4-thiomorpholinyl)ethyl]-1,3-thiazol-2-yl}benzenesulfonamide,
N-{4-[2-(1,1-dioxido-4-thiomorpholinyl)-2-oxoethyl]-1,3-thiazol-2-yl}-4-propylbenzenesulfonamide,
Tert-butyl 4-[(2-{[(3-chloro-2-methylphenyl)sulfonyl]amino}-1,3-thiazol-4-yl)acetyl]-1-piperazinecarboxylate,
N-{4-[2-(4-Acetyl-1-piperazinyl)-2-oxoethyl]-1,3-thiazol-2-yl}-3-chloro-2-methylbenzenesulfonamide,
3-Chloro-2-methyl-N-{4-[2-(4-methyl-1-piperazinyl)-2-oxoethyl]-1,3-thiazol-2-yl}benzenesulfonamide trifluoroacetate,
3-Chloro-2-methyl-N-{4-[2-oxo-2-(1-piperazinyl)ethyl]-1,3-thiazol-2-yl}benzenesulfonamide trifluoroacetate,
2-Methyl-N-{4-[2-(4-methyl-1-piperazinyl)-2-oxoethyl]-1,3-thiazol-2-yl}-4-(trifluoromethoxy)benzenesulfonamide,
2,4-Dichloro-6-methyl-N-{4-[2-(4-methyl-1-piperazinyl)-2-oxoethyl]-1,3-thiazol-2-yl}benzenesulfonamide,
2,4-Dichloro-N-{4-[2-(4-methyl-1-piperazinyl)-2-oxoethyl]-1,3-thiazol-2-yl}benzenesulfonamide,
3-chloro-N-(4-{2-[(2R)-2,4-dimethylpiperazinyl]-2-oxoethyl}-1,3-thiazol-2-yl)-2-methylbenzenesulfonamide,
2-(2-{[(3-Chloro-2-methylphenyl)sulfonyl]amino}-1,3-thiazol-4-yl)-N-methoxy-N-methylacetamide,
3-Chloro-2-methyl-N-[4-(2-oxopentyl)-1,3-thiazol-2-yl]benzenesulfonamide,
4-Chloro-N-[4-(2-hydroxyethyl)-1,3-thiazol-2-yl]benzenesulfonamide,
3-Chloro-N-[4-(2-hydroxyethyl)-1,3-thiazol-2-yl]-2-methylbenzenesulfonamide,
3-Chloro-N-[4-(3-hydroxypropyl)-1,3-thiazol-2-yl]-2-methylbenzenesulfonamide,
3-Chloro-N-[4-(2-ethoxyethyl-1,3-thiazol-2-yl]-2-methylbenzenesulfonamide,
3-Chloro-N-[4-(2-isopropoxyethyl)-1,3-thiazol-2-yl]-2-methylbenzenesulfonamide,
N-{4-[2-(benzyloxy)ethyl]-1,3-thiazol-2-yl}-3-chloro-2-methylbenzenesulfonamide,
3-Chloro-N-[4-(2-methoxyethyl)-1,3-thiazol-2-yl]-2-methylbenzenesulfonamide,
3-Chloro-N-{4-[2-(2-fluoroethoxy)ethyl]-1,3-thiazol-2-yl}-2-methylbenzenesulfonamide,
3-Chloro-2-methyl-N-{4-[2-(2,2,2-trifluoroethoxy)ethyl]-1,3-thiazol-2-yl}benzenesulfonamide,
3-Chloro-2-methyl-N-{4-[2-(2-pyridinylsulfanyl)ethyl]-1,3-thiazol-2-yl}benzenesulfonamide,
3-Chloro-2-methyl-N-{4-[2-(3-pyridinyloxy)ethyl]-1,3-thiazol-2-yl}benzenesulfonamide,
Methyl 2-[2-(2-{[(3-chloro-2-methylphenyl)sulfonyl]amino}-1,3-thiazol-4-yl)ethoxy]benzoate,
3-Chloro-N-[5-[(dimethylamino)methyl]-4-(2-ethoxyethyl)-1,3-thiazol-2-yl]-2-methylbenzenesulfonamide,
2-(2-{[(3-Chloro-2-methylphenyl)sulfonyl]amino}-1,3-thiazol-4-yl)ethyl methanesulfonate,
3-(2-{[(3-chloro-2-methylphenyl)sulfonyl]amino}-1,3-thiazol-4-yl)propyl methanesulfonate,
2-(2-{[(3-Chloro-2-methylphenyl)sulfonyl]amino}-1,3-thiazol-4-yl)ethyl acetate,
2-(2-{[(3-Chloro-2-methylphenyl)sulfonyl]amino}-1,3-thiazol-4-yl)ethyl propionate,
2-(2-{[(3-Chloro-2-methylphenyl)sulfonyl]amino}-1,3-thiazol-4-yl)ethyl 2-methylpropanoate,
2-(2-{[(3-Chloro-2-methylphenyl)sulfonyl]amino}-1,3-thiazol-4-yl)ethyl 2-furoate,
2-(2-{[(3-chloro-2-methylphenyl)sulfonyl]amino}-1,3-thiazol-4-yl)ethyl benzoate,
2-(2-{[(3-Chloro-2-methylphenyl)sulfonyl]amino}-1,3-thiazol-4-yl)ethyl 4-morpholinecarboxylate,
2-(2-{[(3-Chloro-2-methylphenyl)sulfonyl]amino}-1,3-thiazol-4-yl)ethyl diethylcarbamate,
2-(2-{[(3-Chloro-2-methylphenyl)sulfonyl]amino}-1,3-thiazol-4-yl)ethyl ethylcarbamate,
N-[4-(2-azidoethyl)-1,3-thiazol-2-yl]-3-chloro-2-methylbenzenesulfonamide,
N-[4-(2-aminoethyl)-1,3-thiazol-2-yl]-3-chloro-2-methylbenzenesulfonamide,
3-Chloro-2-methyl-N-{4-[2-(methylamino)ethyl]-1,3-thiazol-2-yl}benzenesulfonamide,
4-Chloro-N-{4-[2-(diethylamino)ethyl]-1,3-thiazol-2-yl}benzenesulfonamide hydrochloride,
3-Chloro-N-{4-[2-(diethylamino)ethyl]-1,3-thiazol-2-yl}-2-methylbenzenesulfonamide hydrochloride,
3-Chloro-N-{4-[2-(1H-imidazol-1-yl)ethyl]-1,3-thiazol-2-yl}-2-methylbenzenesulfonamide dihydrate,
3-Chloro-2-methyl-N-{4-[2-(4-methyl-1-piperazinyl)ethyl]-1,3-thiazol-2-yl}benzenesulfonamide dihydrochloride,
3-Chloro-2-methyl-N-{4-[2-(4-morpholinyl)ethyl]-1,3-thiazol-2-yl}benzenesulfonamide hydrochloride,
3-Chloro-2-methyl-N-[4-(4-morpholinylmethyl)-1,3-thiazol-2-yl]benzenesulfonamide hydrochloride,
2,4,6-Trichloro-N-{4-[2-(4-morpholinyl)ethyl]-1,3-thiazol-2-yl}benzenesulfonamide hydrochloride,
2,4-Dichloro-N-{4-[2-(4-morpholinyl)ethyl]-1,3-thiazol-2-yl}benzenesulfonamide hydrochloride,
2,4-Dichloro-6-methyl-N-{4-[2-(4-morpholinyl)ethyl]-1,3-thiazol-2-yl}benzenesulfonamide hydrochloride,
N-{4-[2-(4-Morpholinyl)ethyl]-1,3-thiazol-2-yl}-4-propylbenzenesulfonamide hydrochloride,
3-Chloro-N-{4-[2-(ethylamino)ethyl]-1,3-thiazol-2-yl}-2-methylbenzenesulfonamide,
3-Chloro-N-(4-{2-[(2-hydroxyethyl)amino]ethyl}-1,3-thiazol-2-yl)-2-methylbenzenesulfonamide,
3-Chloro-N-(4-{3-[(2-hydroxyethyl)amino]propyl}-1,3-thiazol-2-yl)-2-methylbenzenesulfonamide hydrochloride hydrate,
N-[2-(2-{[(3-chloro-2-methylphenyl)sulfonyl]amino}-1,3-thiazol-4-yl)ethyl]-N-ethylacetamide,
3-Chloro-2-methyl-N-{4-[2-(3-oxo-4-morpholinyl)ethyl]-1,3-thiazol-2-yl}benzenesulfonamide,
3-Chloro-N-{4-[2-(2-hydroxy-3-oxo-4-morpholinyl)ethyl]-1,3-thiazol-2-yl}-2-methylbenzenesulfonamide,
2,4-Dichloro-N-{4-[2-(3-oxo-4-morpholinyl)ethyl]-1,3-thiazol-2-yl}benzenesulfonamide,
2,4-Dichloro-6-methyl-N-{4-[2-(3-oxo-4-morpholinyl)ethyl]-1,3-thiazol-2-yl}benzenesulfonamide,
2,4,6-Trichloro-N-{4-[2-(3-oxo-4-morpholinyl)ethyl]-1,3-thiazol-2-yl}benzenesulfonamide,
4,5-Dichloro-N-{4-[2-(3-oxo-4-morpholinyl)ethyl]-1,3-thiazol-2-yl}-2-thiophenesulfonamide,
N-{4-[2-(3-Oxo-4-morpholinyl)ethyl]-1,3-thiazol-2-yl}-4-phenoxybenzenesulfonamide,
3-Fluoro-N-{4-[2-(3-oxo-4-morpholinyl)ethyl]-1,3-thiazol-2-yl}benzenesulfonamide,
N-{4-[2-(3-Oxo-4-morpholinyl)ethyl]-1,3-thiazol-2-yl}-5-(2-pyridinyl)-2-thiophenesulfonamide, N-{2-Chloro-4-[({4-[2-(3-oxo-4-morpholinyl)ethyl]-1,3-thiazol-2-yl}amino)sulfonyl]phenyl}acetamide, 3-Chloro-2-methyl-N-{4-[(3-oxo-4-morpholinyl)methyl]-1,3-thiazol-2-yl}benzenesulfonamide, 3-Chloro-2-meihyl-N-{4-[3-(3-oxo-4-morpholinyl)propyl]-1,3-thiazol-2-yl}benzenesulfonamide, 3-Chloro-N,2-dimethyl-N-{4-[2-(3-oxo-4-morpholinyl)ethyl]-1,3-thiazol-2-yl}benzenesulfonamide, 3-Chloro-2-methyl-N-{4-[2-(2-methyl-3-oxo-4-morpholinyl)ethyl]-1,3-thiazol-2-yl}benzenesulfonamide, N-[2-(2-{[(3-Chloro-2-methylphenyl)sulfonyl]amino}-1,33-thiazol-4-yl)ethyl]acetamide, 3-Chloro-2-methyl-N-{4-[2-(3-oxo-1,4-oxazepan-4-yl)ethyl]-1,3-thiazol-2-yl}benzenesulfonamide, 3-Chloro-2-methyl-N-{4-[2-(2-oxo-1-pyrrolidinyl)ethyl]-1,3-thiazol-2-yl}benzenesulfonamide, 3-Chloro-2-methyl-N-{4-[2-(2-oxo-1-imidazolidinyl)ethyl]-1,3-thiazol-2-yl}benzenesulfonamide, 3-Chloro-2-methyl-N-{4-[2-(2-oxo-1,3-oxazolidin-3-yl)ethyl]-1,3-thiazol-2-yl}benzenesulfonamide, N-[2-(2-{[(3-Chloro-2-methylphenyl)sulfonyl]amino}-1,3-thiazol-4-yl)ethyl]-N-(2-hydroxyethyl)-2-furamide, N-[2-(2-{[(3-chloro-2-methylphenyl)sulfonyl]amino}-1,3-thiazol-4-yl)ethyl]-N-methylcyclopropanecarboxamide, 3-Chloro-2-methyl-N-{4-[2-(4-methyl-2-oxo-1-piperazinyl)ethyl]-1,3-thiazol-2-yl}benzenesulfonamide hydrochloride, 3-Chloro-2-methyl-N-(4-{2-[(methylsulfonyl)amino]ethyl}-1,3-thiazol-2-yl)benzenesulfonamide, 3-Chloro-2-methyl-N-(4-{2-[methyl(methylsulfonyl)amino]ethyl}-1,3-thiazol-2-yl)benzenesulfonamide, 3-Chloro-2-methyl-N-[4-(2 {[(trifluoromethyl)sulfonyl]amino}ethyl)-1,3-thiazol-2-yl]benzenesulfonamide, 3-Chloro-2-methyl-N-[4-(2-{methyl[(trifluoromethyl)sulfonyl]amino}ethyl)-1,3-thiazol-2-yl]benzenesulfonamide, N-[2-(2-{[(3-Chloro-2-methylphenyl)sulfonyl]amino}-1,3-thiazol-4-yl)ethyl]-1-methyl-1H-imidazole-4-sulfonamide, 3-Chloro-N-(4-{2-[[(3-chloro-2-methylphenyl)sulfonyl](methyl)amino]ethyl}-1,3-thiazol-2-yl)-2-methylbenzenesulfonamide, N-[4-(2-bromoethyl)-1,3-thiazol-2-yl]-3-chloro-2-methylbenzenesulfonamide, 3-Chloro-N-[4-(2-chloroethyl)-1,3-thiazol-2-yl]-2-methylbenzenesulfonamide, 3-Chloro-2-methyl-N-{4-[(5-methyl-1,3,4-oxadiazol-2-yl)methyl]-1,3-thiazol-2-yl}benzenesulfonamide, Ethyl 3-(2-{[(3-chloro-2-methylphenyl)sulfonyl]amino}-1,3-thiazol-4-yl)propanoate.

Another object of the present invention is a compound as described above for medical use.

Another object of the present invention is a process for the preparation of a compound as described above comprising at least one of the following steps:

a) sulfonamide coupling by reacting a 2-aminothiazole with a sulfonylchloride in the presence of a base, b) sulfonamide coupling by reacting a 2-aminothiazole derivative with a sulfonylchloride in the presence of a base, c) saponification by treatment of a carboxylic acid ester with aqueous hydroxide, d) amide coupling by reacting a carboxylic acid ester with an amine, e) amide coupling by reacting a carboxylic acid with an amine in the presence of EDCI, f) amide coupling by reacting a carboxylic acid with an amine in the presence of EDCI, HOAT or HOBT, g) amide coupling by reacting a carboxylic acid ester with an amine in the presence of aluminium chloride, h) formation of a thiazole ring by reacting an optionally substituted thiourea with an α-haloketone, i) formation of a thiazole ring by reacting a thiourea with a ketone, j) acylation of an alcohol by reacting with an acid chloride in the presence of a base, k) carbamoylation of an alcohol by reacting with 4-nitrophenylchloroformate and then with a primary or secondary amine, l) palladium coupling of a halo compound with a boronic acid, m) palladium coupling of a halo compound with an amine with 18-crown-6, n) palladium coupling of a halo compound with an amine without 18-crown-6.

Another object of the present invention is a method for the treatment or prevention of diabetes, syndrome X, obesity, glaucoma, hyperlipidemia, hyperglycemia, hyperinsulinemia, osteoporosis, tuberculosis, dementia, depression, virus diseases and inflammatory disorders, said method comprising administering to a mammal, including man, in need of such treatment an effective amount of a compound of the formula (II)

wherein

T is an aryl ring or heteroaryl ring or aryl-$C_2$-alkenyl ring, optionally independently substituted by $[R]_n$, wherein n is an integer 0-5, and R is hydrogen, aryl, heteroaryl, a heterocyclic ring, optionally halogenated $C_{1-6}$alkyl, optionally halogenated $C_{1-6}$-alkoxy, $C_{1-6}$-alkylsulfonyl, carboxy, cyano, nitro, halogen, amine which is optionally mono- or di-substituted, amide which is optionally mono- or di-substituted, aryloxy, arylsulfonyl, arylamino, wherein aryl, heteroaryl and aryloxy residues and heterocyclic rings can further be optionally substituted in one or more positions independently of each other by $C_{1-6}$-acyl, $C_{1-6}$-alkylthio, cyano, nitro, hydrogen, halogen, optionally halogenated $C_{1-6}$-alkyl, optionally halogenated $C_{1-6}$-alkoxy, amide which is optionally mono- or di-substituted, (benzoylamino)methyl, carboxy, 2-thienylmethylamino or ({[4-(2-ethoxy-2-oxoethyl)-1,3-thiazol-2-yl]amino}carbonyl);

$R^1$ is hydrogen or $C_{1-6}$-alkyl;

X is $CH_2$ or CO;

Y is $CH_2$, CO or a single bond;

B is hydrogen, $C_{1-6}$-alkyl or dimethylaminomethyl;

$R^2$ is selected from $C_{1-6}$-alkyl, azido, arylthio, heteroarylthio, halogen, hydroxymethyl, 2-hydroxyethylaminomethyl, methylsulfonyloxymethyl, 3-oxo-4-morpholinolinylmethylene, $C_{1-6}$-alkoxycarbonyl, 5-methyl-1,3,4-oxadiazol-2-yl;

$NR^3R^4$, wherein $R^3$ and $R^4$ are each independently selected from hydrogen, $C_{1-6}$-alkyl, optionally halogenated $C_{1-6}$-alkylsulfonyl, $C_{1-6}$-alkoxy, 2-methoxyethyl, 2-hydroxyethyl, 1-methylimidazolylsulfonyl, $C_{1-6}$-acyl, cyclohexylmethyl, cyclopropanecarbonyl, aryl, optionally halogenated arylsulfonyl, furylcarbonyl, tetrahydro-2-furanylmethyl, N-carbethoxypiperidyl or $C_{1-6}$-alkyl substituted with one or more aryl or heteroaryl, or $NR^3R^4$ represent together heterocyclic systems which can be imidazole, piperidine, pyrrolidine, piperazine, morpholine, oxazepine, oxazole, thiomorpholine, 1,1-dioxidothiomorpholine, 2-(3,4-dihydro-2(1H)isoquinolinyl), (1S,4S)-2-oxa-5-azabicyclo[2.2.1]hept-5-yl, which heterocyclic systems can be optionally substituted by $C_{1-6}$-alkyl, $C_{1-4}$-acyl, hydroxy, oxo, t-butoxycarbonyl;

OCONR³R⁴, wherein R³ and R⁴ are each independently selected from hydrogen, $C_{1-6}$-alkyl or form together morpholinyl;

R⁵O, wherein R⁵ is hydrogen, optionally halogenated $C_{1-6}$-alkyl, aryl, heteroaryl, $C_{1-6}$-acyl, $C_{1-6}$-alkylsulfonyl, arylcarbonyl, heteroarylcarbonyl, 2-carbomethoxyphenyl;

or a salt, hydrate or solvate thereof.

These compounds may also be used in the manufacture of a medicament for the prevention, management or treatment of diabetes, syndrome X, obesity, glaucoma, hyperlipidemia, hyperglycemia, hyperinsulinemia, osteoporosis, tuberculosis, dementia, depression, virus diseases and inflammatory disorders.

It is preferred that:

T is selected from 5-chloro-1,3-dimethyl-1H-pyrazol-4-yl; 4-chloro-2,3,1-benzoxadiazolyl; 5-(dimethylamino)-1-naphthyl; 1-methylimidazol-4-yl; 1-naphthyl; 2-naphthyl; (E)-2-phenylethenyl; 8-quinolinyl;

thienyl substituted with one or more of (benzoylamino)methyl, bromo, chloro, 3-isoxazolyl, 2-(methylsulfanyl)-4-pyrimidinyl, 1-methyl-5-(trifluoromethyl)pyrazol-3-yl, phenylsulfonyl, pyridyl;

phenyl substituted with one or more of acetylamino, 3-acetylaminophenyl, 3-acetylphenyl, benzeneamino, 1,3-benzodioxol-5-yl, 2-benzofuryl, benzylamino, 3,5-bis(trifluoromethyl)phenyl, bromo, butoxy, carboxy, chloro, 4-carboxyphenyl 3-chloro-2-cyanophenoxy, 4-chlorophenyl, 5-chloro-2-thienyl, cyano, 3,4-dichlorophenyl, ({[4-(2-ethoxy-2-oxoethyl)-1,3-thiazol-2-yl]amino}carbonyl), fluoro, 5-fluoro-2-methoxyphenyl, 2-furyl, hydrogen, iodo, isopropyl, methanesulfonyl, methoxy, methyl, 4-methyl-1-piperazinyl, 4-methyl-1-piperidinyl, 4-methylsulfanylphenyl, 5-methyl-2-thienyl, 4-morpholinyl, nitro, 3-nitrophenyl, phenoxy, phenyl, n-propyl, 4-pyridyl, 3-pyridylmethylamino, 1-pyrrolidinyl, 2-thienyl, 3-thienyl, 2-thienylmethylamino, trifluoromethoxy, 4-trifluoromethoxyphenyl, trifluoromethyl; or R¹ is hydrogen or methyl;

X is $CH_2$ or CO;

Y is $CH_2$, CO or a single bond;

B is hydrogen, methyl or dimethylaminomethyl;

R² is selected from n-propyl, azido, bromo, chloro, 2-pyridinylsulfanyl, 3-oxo-4-morpholinylmethylene, ethoxycarbonyl, 5-methyl-1,3,4-oxadiazol-2-yl, hydroxymethyl, 2-hydroxyethylaminomethyl, methylsulfonyloxymethyl;

NR³R⁴, wherein R³ and R⁴ are each independently selected from acetyl, benzhydryl, 1,3-benzodioxol-5-ylmethyl, benzyl, 3-chloro-2-methylphenylsulfonyl, cyclohexyl, cyclohexylmethyl, cyclopropanecarbonyl, ethyl, 2-furylcarbonyl, 2-furylmethyl, hydrogen, 2-hydroxyethyl, 2-(1H-indol-3-yl)ethyl, isopropyl, methoxy, 2-methoxyethyl, methyl, 4-(1-methylimidazolyl)sulfonyl, methylsulfonyl, phenyl, (1S)-phenylethyl, n-propyl, tetrahydro-2-furanylmethyl, trifluoromethylsulfonyl, N-carbethoxypiperidyl; or NR³R⁴ represent together 4-acetylpiperazinyl, 4-t-butoxycarbonylpiperazinyl, 2-(3,4-dihydro-2(1H)isoquinolinyl), (2R,6S)-2,6-dimethylmorpholinyl, (2R)-2,4-dimethyl-1-piperazinyl, 2-hydroxy-3-oxomorpholinyl, imidazolyl, 2-methyl-3-oxomorpholinyl, 4-methyl-2-oxopiperazinyl, 4-methylpiperazinyl, morpholinyl, (1S,4S)-2-oxa-5-azabicyclo[2.2.1]hept-5-yl, 2-oxoimidazolinyl, 3-oxomorpholinyl, 3-oxo-1,4-oxazepinyl, 2-oxooxazolinyl, piperazinyl; piperidinyl; pyrrolidinyl; pyrrolidonyl, thiomorpholinyl; 1,1-dioxido-thiomorpholinyl;

OCONR³R⁴, wherein R³ and R⁴ are each independently selected from ethyl, hydrogen or form together morpholinyl;

R⁵O, wherein R⁵ is acetyl, benzoyl, benzyl ethyl, 2-fluoroethyl, 2-furylcarbonyl, hydrogen, isobutyryl, isopropyl, methyl, 2-carbomethoxyphenyl, methylsulfonyl, phenyl, propionyl, 3-pyridinyl, 2,2,2-trifluoroethyl.

The following compounds are especially preferred:

Ethyl (2-{[(2,4-dichloro-5-methylphenyl)sulfonyl]amino}-1,3-thiazol-4-yl)acetate, Ethyl 2-(2-[[(4-chlorophenyl)sulfonyl]amino]-1,3-thiazole-4-yl)acetate, Ethyl 2-(2-{[(4-chloro-2,5-dimethylphenyl)sulfonyl]amino}-1,3-thiazol-4-yl)acetate, Ethyl 2-(2-{[(2,4-difluorophenyl)sulfonyl]amino}-1,3-thiazol-4-yl)acetate, Ethyl 2-(2-(((4-methylphenyl)sulfonyl)amino)-1,3-thiazol-4-yl)acetate, Ethyl 2-(2-{[(2,5-dichloro-3-thienyl)sulfonyl]amino}-1,3-thiazol-4-yl)acetate, Ethyl (2-{[(2-chlorophenyl)sulfonyl]amino}-1,3-thiazol-4-yl) acetate, Ethyl 2-(2-{[(3-chloro-2-methylphenyl)sulfonyl]amino}-1,3-thiazol-4-yl)acetate, Ethyl 2-{2-[([1,1'-biphenyl]-4-ylsulfonyl)amino]-1,3-thiazol-4-yl}acetate, Ethyl 2-(2-{[(3-bromophenyl)sulfonyl]amino}-1,3-thiazol-4-yl)acetate, Ethyl (2-{[(4-nitrophenyl)sulfonyl]amino}-1,3-thiazol-4-yl) acetate, Ethyl (2-{[(4-methoxyphenyl)sulfonyl]amino}-1,3-thiazol-4-yl)acetate, Ethyl (2-{[(3-nitrophenyl)sulfonyl]amino}-1,3-thiazol-4-yl) acetate, Ethyl (2-{[(3-methylphenyl)sulfonyl]amino}-1,3-thiazol-4-yl)acetate, Ethyl (2-{[(3-chlorophenyl)sulfonyl]amino}-1,3-thiazol-4-yl)acetate, Ethyl (2-{[(4-fluorophenyl)sulfonyl]amino}-1,3-thiazol-4-yl)acetate, Ethyl (2-{[(3-fluorophenyl)sulfonyl]amino}-1,3-thiazol-4-yl)acetate, Ethyl {2-[(phenylsulfonyl)amino]-1,3-thiazol-4-yl}acetate, Ethyl (2-{[(4-isopropylphenyl)sulfonyl]amino}-1,3-thiazol-4-yl)acetate, Ethyl [2-({[3-({[4-(2-ethoxy-2-oxoethyl)-1,3-thiazol-2-yl]amino}carbonyl)phenyl]sulfonyl}amino)-1,3-thiazol-4-yl]acetate, Ethyl [2-({[4-({[4-(2-ethoxy-2-oxoethyl)-1,3-thiazol-2-yl]amino}carbonyl)phenyl]sulfonyl}amino)-1,3-thiazol-4-yl]acetate, Ethyl (2-{[(2-methylphenyl)sulfonyl]amino}-1,3-thiazol-4-yl)acetate, Ethyl [2-({[2-(trifluoromethyl)phenyl]sulfonyl}amino)-1,3-thiazol-4-yl]acetate, Ethyl [2-({[3-(trifluoromethyl)phenyl]sulfonyl}amino)-1,3-thiazol-4-yl]acetate, Ethyl [2-({[4-(trifluoromethyl)phenyl]sulfonyl}amino)-1,3-thiazol-4-yl]acetate, Ethyl 2-(2-{[(4-bromophenyl)sulfonyl]amino}-1,3-thiazol-4-yl)acetate, Ethyl (2-{[(2-nitrophenyl)sulfonyl]amino}-1,3-thiazol-4-yl) acetate, Ethyl (2-{[(2,4-dichloro-6-methylphenyl)sulfonyl]ami-o}-1,3-thiazol-4-yl)acetate, Ethyl (2-{[(2,4,6-trichlorophenyl)sulfonyl]amino}-1,3-thiazol-4-yl)acetate, Ethyl (2-{[(2,4-dichlorophenyl)sulfonyl]amino}-1,3-thiazol-4-yl)acetate,
Ethyl (2-{[(5-fluoro-2-methylphenyl)sulfonyl]amino}-1,3-thiazol-4-yl)acetate,
Ethyl (2-{[(4-propylphenyl)sulfonyl]amino}-1,3-thiazol-4-yl)acetate,
Ethyl (2-{[(2-methoxy-4-methylphenyl)sulfonyl]amino}-1,3-thiazol-4-yl)acetate,
Ethyl (2-{[(3,5-dichlorophenyl)sulfonyl]amino}-1,3-thiazol-4-yl)acetate,
Ethyl [2-({[4-(3-chloro-2-cyanophenoxy)phenyl]sulfonyl}amino)-1,3-thiazol-4-yl]acetate,
Ethyl (2-{[(3,4-dichlorophenyl)sulfonyl]amino}-1,3-thiazol-4-yl)acetate,
Ethyl (2-{[(4-butoxyphenyl)sulfonyl]amino}-1,3-thiazol-4-yl)acetate,
Ethyl (2-{[(4-chloro-2-methylphenyl)sulfonyl]amino}-1,3-thiazol-4-yl)acetate,
Ethyl [2-({[4-(acetylamino)phenyl]sulfonyl}amino)-1,3-thiazol-4-yl]acetate,
Ethyl {2-[(8-quinolinylsulfonyl)amino]-1,3-thiazol-4-yl}acetate,
Ethyl (2-{[(3,4-dimethoxyphenyl)sulfonyl]amino}-1,3-thiazol-4-yl)acetate,
Ethyl (2-{[(4-iodophenyl)sulfonyl]amino}-1,3-thiazol-4-yl)acetate,
Ethyl (2-{[(3-chloro-4-methylphenyl)sulfonyl]amino}-1,3-thiazol-4-yl)acetate,
Ethyl [2-({[5-(dimethylamino)-1-naphthyl]sulfonyl}amino)-1,3-thiazol-4-yl]acetate,
Ethyl (2-{[(1-methyl-1H-imidazol-4-yl)sulfonyl]amino}-1,3-thiazol-4-yl)acetate,
Ethyl (2-{[(5-bromo-2-methoxyphenyl)sulfonyl]amino}-1,3-thiazol-4-yl)acetate,
Ethyl (2-{[(2,5-dimethoxyphenyl)sulfonyl]amino}-1,3-thiazol-4-yl)acetate,
Ethyl {2-[(2-naphthylsulfonyl)amino]-1,3-thiazol-4-yl}acetate,
Ethyl {2-[(mesitylsulfonyl)amino]-1,3-thiazol-4-yl}acetate,
Ethyl (2-{[(3-bromo-5-chloro-2-thienyl)sulfonyl]amino}-1,3-thiazol-4-yl)acetate,
Ethyl {2-[({5-[(benzoylamino)methyl]-2-thienyl}sulfonyl)amino]-1,3-thiazol-4-yl}acetate,
Ethyl {2-[({5-[1-methyl-5-(trifluoromethyl)-1H-pyrazol-3-yl]-2-thienyl}sulfonyl)amino]-1,3-thiazol-4-yl}acetate,
Ethyl (2-{[(4-cyanophenyl)sulfonyl]amino}-1,3-thiazol-4-yl)acetate,
Ethyl {2-[({5-[2-(methylsulfanyl)-4-pyrimidinyl]-2-thienyl}sulfonyl)amino]-1,3-thiazol-4-yl}acetate,
Ethyl (2-{[(3-cyanophenyl)sulfonyl]amino}-1,3-thiazol-4-yl)acetate,
Ethyl (2-{[(2,4,5-trichlorophenyl)sulfonyl]amino}-1,3-thiazol-4-yl)acetate,
Ethyl [2-({[(E)-2-phenylethenyl]sulfonyl}amino)-1,3-thiazol-4-yl]acetate,
Ethyl (2-{[(2,3,4-trichlorophenyl)sulfonyl]amino}-1,3-thiazol-4-yl)acetate,
Ethyl (2-{[(4-bromo-2,5-difluorophenyl)sulfonyl]amino}-1,3-thiazol-4-yl)acetate,
Ethyl [2-({[4-(trifluoromethoxy)phenyl]sulfonyl}amino)-1,3-thiazol-4-yl]acetate,
Ethyl (2-{[(2,3-dichlorophenyl)sulfonyl]amino}-1,3-thiazol-4-yl)acetate,
Ethyl (2-{[(2-bromophenyl)sulfonyl]amino}-1,3-thiazol-4-yl)acetate,
Ethyl (2-{[(4,5-dichloro-2-thienyl)sulfonyl]amino}-1,3-thiazol-4-yl)acetate,
Ethyl [2-({[4-(phenylsulfonyl)-2-thienyl]sulfonyl}amino)-1,3-thiazol-4-yl]acetate,
Ethyl [2-({[5-(phenylsulfonyl)-2-thienyl]sulfonyl}amino)-1,3-thiazol-4-yl]acetate,
Ethyl (2-{[(2,6-dichlorophenyl)sulfonyl]amino}-1,3-thiazol-4-yl)acetate,
Ethyl (2-{[(2-cyanophenyl)sulfonyl]amino}-1,3-thiazol-4-yl)acetate,
Ethyl [2-({[4-(acetylamino)-3-chlorophenyl]sulfonyl}amino)-1,3-thiazol-4-yl]acetate,
Ethyl (2-{[(5-chloro-1,3-dimethyl 1H-pyrazol-4-yl)sulfonyl]amino}-1,3-thiazol-4-yl)acetate,
Ethyl (2-{[(3-methoxyphenyl)sulfonyl]amino}-1,3-thiazol-4-yl)acetate,
Ethyl (2-{[(4-bromo-5-chloro-2-thienyl)sulfonyl]amino}-1,3-thiazol-4-yl)acetate,
Ethyl 2-{2-[(1-naphthylsulfonyl)amino]-1,3-thiazol-4-yl}acetate,
Ethyl (2-{[(2,5-dichlorophenyl)sulfonyl]amino}-1,3-thiazol-4-yl)acetate,
Ethyl [2-({[4-(methylsulfonyl)phenyl]sulfonyl}amino)-1,3-thiazol-4-yl]acetate,
Ethyl [2-({[2-(methylsulfonyl)phenyl]sulfonyl}amino)-1,3-thiazol-4-yl]acetate,
Ethyl (2-{[(4-bromo-2-fluorophenyl)sulfonyl]amino}-1,3-thiazol-4-yl)acetate,
Ethyl (2-{[(2,3,4-trifluorophenyl)sulfonyl]amino}-1,3-thiazol-4-yl)acetate,
Ethyl (2-{[(7-chloro-2,1,3-benzoxadiazol-4-yl)sulfonyl]amino}-1,3-thiazol-4-yl)acetate,
Ethyl (2-{[(2,4,6-trifluorophenyl)sulfonyl]amino}-1,3-thiazol-4-yl)acetate,
2-Chloro-5-({[4-(2-ethoxy-2-oxoethyl)-1,3-thiazol-2-yl]amino}sulfonyl)-4-fluorobenzoic acid,
Ethyl (2-{[(5-chloro-2-thienyl)sulfonyl]amino}-1,3-thiazol-4-yl)acetate,
Ethyl (2-{[(2-chloro-4-fluorophenyl)sulfonyl]amino}-1,3-thiazol-4-yl)acetate,
Ethyl [2-({[5-(3-isoxazolyl)-2-thienyl]sulfonyl}amino)-1,3-thiazol-4-yl]acetate,
Ethyl (2-{[(4-bromo-2-methylphenyl)sulfonyl]amino-} 1,3-thiazol-4-yl)acetate,
Ethyl (2-{[(4-phenoxyphenyl)sulfonyl]amino}-1,3-thiazol-4-yl)acetate,
Ethyl (2-{[(4-chloro-2,6-dimethylphenyl)sulfonyl]amino}1,3-thiazol-4-yl)acetate,
Ethyl [2-({[2-methyl-4-(trifluoromethoxy)phenyl]sulfonyl}amino)-1,3-thiazol-4-yl]acetate,
Ethyl [2-({[2,4-bis(trifluoromethyl)phenyl]sulfonyl}amino)-1,3-thiazol-4-yl]acetate,
Ethyl 2-{2-[[(3-chloro-2-methylphenyl)sulfonyl](methyl)amino]-1,3-thiazol-4-yl}acetate,
Ethyl oxo(2-{[(4-propylphenyl)sulfonyl]amino}-1,3-thiazol-4-yl)acetate,
Ethyl (2-{[(3-chloro-2-methylphenyl)sulfonyl]amino}-1,3-thiazol-4-yl)(oxo)acetate,
Ethyl oxo(2-{[(2,4,6-trichlorophenyl)sulfonyl]amino}-1,3-thiazol-4-yl)acetate,
Ethyl {2-[([1,1'-biphenyl]-4-ylsulfonyl)amino]-1,3-thiazol-4-yl}(oxo)acetate,
Ethyl (2-{[(2,4-dichloro-6-methylphenyl)sulfonyl]amino}-1,3-thiazol-4-yl)(oxo)acetate,
2-(2-{[(4-Methylphenyl)sulfonyl]amino}-1,3-thiazol-4-yl)acetic acid,
2-(2-{[(2,5-Dichloro-3-thienyl)sulfonyl]amino}-1,3-thiazol-4-yl)acetic acid, (2-{[(2-Chlorophenyl)sulfonyl]amino}-1,3-thiazol-4-yl) acetic acid,
2-(2-{[(3-Chloro-2-methylphenyl)sulfonyl]amino}-1,3-thiazol-4-yl)acetic acid,
Isopropyl 2-(2-{[(3-chloro-2-methylphenyl)sulfonyl]amino}-1,3-thiazol-4-yl)acetate,
Phenyl 2-(2-{[(3-chloro-2-methylphenyl)sulfonyl]amino}-1,3-thiazol-4-yl)acetate,
Methyl (2-{[(3-chloro-2-methylphenyl)sulfonyl]amino}-1,3-thiazol-4-yl)acetate,
Methyl {2-[([1,1'-biphenyl]-4-ylsulfonyl)amino]-5-methyl-1,3-thiazol-4-yl}acetate,
Methyl (2-{[(4-chlorophenyl)sulfonyl]amino}-5-methyl-1,3-thiazol-4-yl)acetate,
Methyl (2-{[(3-chloro-2-methylphenyl)sulfonyl]amino}-5-methyl-1,3-thiazol-4-yl)acetate,
Methyl [2-({[4-(3-chloro-2-cyanophenoxy)phenyl]sulfonyl}amino)-5-methyl-1,3-thiazol-4-yl]acetate,
Methyl (5-methyl-2-{[(4-propylphenyl)sulfonyl]amino}-1,3-thiazol-4-yl)acetate,
Methyl (5-methyl-2-{[(2,4,6-trichlorophenyl)sulfonyl]amino}-1,3-thiazol-4-yl)acetate,
Methyl (2-{[(2,4-dichloro-6-methylphenyl)sulfonyl]amino}-5-methyl-1,3-thiazol-4-yl)acetate,
N-(2-Methoxyethyl)-2-(2-{[(4-methylphenyl)sulfonyl]amino}-1,3-thiazol-4-yl)acetamide,
2-(2-{[(2,5-Dichloro-3-thienyl)sulfonyl]amino}-1,3-thiazol-4-yl)-N-methylacetamide,
N-(1,3-Benzodioxol-5-ylmethyl)-2-{2-[(1-naphthylsulfonyl)amino]-1,3-thiazol-4-yl}acetamide,
N-(2-Furylmethyl)-2-{2-[(1-naphthylsulfonyl)amino]-1,3-thiazol-4-yl}acetamide,
2-(2-{[(2,4-Difluorophenyl)sulfonyl]amino}-1,3-thiazol-4-yl)-N-ethylacetamide,
N-Isopropyl-2-{2-[(1-naphthylsulfonyl)amino]-1,3-thiazol-4-yl}acetamide,
N-[2-(1H-Indol-3-yl)ethyl]-2 {2-[(1-naphthylsulfonyl)amino]-1,3-thiazol-4-yl}acetamide,
N-(Cyclohexylmethyl)-2-{2-[(phenylsulfonyl)amino]-1,3-thiazol-4-yl}acetamide,
2-(2-{[(3-Chloro-2-methylphenyl)sulfonyl]amnmo}-1,3-thiazol-4-yl)-N-methylacetamide,
2-(2-{[(3-Chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N-phenylacetamide,
2-(2-{[(4-Chlorophenyl)sulfonyl]amino}-1,3-thiazol-4-yl)-N-(2-furylmethyl)acetamide,
N-Benzhydryl-2-(2-{[(4-chlorophenyl)sulfonyl]amino}-1,3-thiazol-4-yl)acetamide,
2-(2-{[(4-Chlorophenyl)sulfonyl]amino}-1,3-thiazol-4-yl)-N-(tetrahydro-2-furanylmethyl)acetamide,
Ethyl 4-{[2-(2-{[(4-chlorophenyl)sulfonyl]amino}-1,3-thiazol-4-yl)acetyl]amino}-1-piperidinecarboxylate,
N-Benzhydryl-2-(2-{[(3-chloro-2-methylphenyl)sulfonyl]amino}-1,3-thiazol-4-yl)acetamide,
2-(2-{[(4-Chlorophenyl)sulfonyl]amino}-1,3-thiazol-4-yl)-N-phenylacetamide,
2-(2-{[(3-Chloro-2-methylphenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diethylacetamide,
2-{2-[([1,1'-Biphenyl]-4-ylsulfonyl)amino]-1,3-thiazol-4-yl}-N,N-diethylacetamide,
N,N-diethyl-2-(2-{[(4-propylphenyl)sulfonyl]amino}-1,3-thiazol-4-yl)acetamide,
2-(2-{[(2,4-Dichloro-6-methylphenyl)sulfonyl]amino}-1,3-thiazol-4-yl)-N,N-diethylacetamide,
N,N-diethyl-2-(2-{[(2,4,6-trichlorophenyl)sulfonyl]amino}-1,3-thiazol-4-yl)acetamide,
2-{2-[([1,1'-Biphenyl]-4-ylsulfonyl)amino]-1,3-thiazol-4-yl}-N,N-diisopropylacetamide,
N,N-diisopropyl-2-(2-{[(4-propylphenyl)sulfonyl]amino}-1,3-thiazol-4-yl)acetamide,
2-(2-{[(2,4-Dichloro-6-methylphenyl)sulfonyl]amino}-1,3-thiazol-4-yl)-N,N-diisopropylacetamide,
N,N-diisopropyl-2-(2-{[(2,4,6-trichlorophenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diisopropylacetamide,
2-(2-{[(3-Chloro-2-methylphenyl)sulfonyl]amino}-1,3-thiazol-4-yl)-N,N-dipropylacetamide,
N-benzyl-2-(2-{[(3-chloro-2-methylphenyl)sulfonyl]amino}-1,3-thiazol-4-yl)-N-methylacetamide,
N-benzyl-2-(2-{[(3-chloro-2-methylphenyl)sulfonyl]amino}-1,3-thiazol-4-yl)-N-ethylacetamide,
2-(2-{[(3-Chloro-2-methylphenyl)sulfonyl]amino})-1,3-thiazol-4-yl)-N,N-dimethylacetamide,
2-(2-{[(3-chloro-2-methylphenyl)sulfonyl]amino}-1,3-thiazol-4-yl)-N-cyclohexyl-N-methylacetamide,
3-Chloro-N-{4-[2-(3,4-dihydro-2(1H)-isoquinolinyl)-2-oxoethyl]-1,3-thiazol-2-yl}-2-methylbenzenesulfonamide,
2-(2-{[(3-Chloro-2-methylphenyl)sulfonyl]amino}-1,3-thiazol-4-yl)-N-methyl-N-phenylacetamide,
2-(2-{[(3-Chloro-2-methylphenyl)sulfonyl]amino}-1,3-thiazol-4-yl)-N-isopropyl-N-methylacetamide,
2-{2-[([1,1'-Biphenyl]-4-ylsulfonyl)amino]-1,3-thiazol-4-yl}-N-isopropyl-N-methylacetamide,
N-ethyl-N-methyl-2-(2-{[(2,4,6-trichlorophenyl)sulfonyl]amino}-1,3-thiazol-4-yl)acetamide,
2-(2-{[(2,4-Dichloro-6-methylphenyl)sulfonyl]amino}-1,3-thiazol-4-yl)-N-ethyl-N-methylacetamide,
N-ethyl-N-methyl-2-(2-{[(4-propylphenyl)sulfonyl]amino}-1,3-thiazol-4-yl)acetamide,
2-{2-[([1,1'-Biphenyl]-4-ylsulfonyl)amino]-1,3-thiazol-4-yl}-N-ethyl-N-methylacetamide,
2-(2-{[(3-Chloro-2-methylphenyl)sulfonyl]amino})-1,3-thiazol-4-yl)-N-ethyl-N-methylacetamide,
2-(2-{[(3-Chloro-2-methylphenyl)sulfonyl]amino}-1,3-thiazol-4-yl)-N-methyl-N-[(1S)-1-phenylethyl]acetamide,
3-Chloro-2-methyl-N-{4-[2-oxo-2-(1-pyrrolidinyl)ethyl]-1,3-thiazol-2-yl}benzenesulfonamide,
3-Chloro-2-methyl-N-{4-[2-oxo-2-(1-piperidinyl)ethyl]-1,3-thiazol-2-yl}benzenesulfonamide,
N-{4-[2-oxo-2-(1-piperidinyl)ethyl]-1,3-thiazol-2-yl}[1,1'-biphenyl]-4-sulfonamide,
N-{4-[2-oxo-2-(1-piperidinyl)ethyl]-1,3-thiazol-2-yl}-4-propylbenzenesulfonamide,
2,4-Dichloro-6-methyl-N-{4-[2-oxo-2-(1-piperidinyl)ethyl]-1,3-thiazol-2-yl}benzenesulfonamide,
2,4,6-Trichloro-N-{4-[2-oxo-2-(1-piperidinyl)ethyl]-1,3-thiazol-2-yl}benzenesulfonamide,
3-Chloro-2-methyl-N-{4-[2-(4-morpholinyl)-2-oxoethyl]-1,3-thiazol-2-yl}benzenesulfonamide,
2,4,6-Trichloro-N-{4-[2-(4-morpholinyl)-2-oxoethyl]-1,3-thiazol-2-yl}benzenesulfonamide,
2,4-Dichloro-6-methyl-N-{4-[2-(4-morpholinyl)-2-oxoethyl]-1,3-thiazol-2-yl}benzenesulfonamide,
N-{4-[2-(4-morpholinyl)-2-oxoethyl]-1,3-thiazol-2-yl}[1,1'-biphenyl]-4-sulfonamide, N-{4-[2-(4-morpholinyl)-2-oxoethyl]-1,3-thiazol-2-yl}-4-propylbenzenesulfonamide,
2,4-Dichloro-N-{4-[2-(4-morpholinyl)-2-oxoethyl]-1,3-thiazol-2-yl}benzenesulfonamide,
4-Chloro-2,6-dimethyl-N-{4-[2-(4-morpholinyl)-2-okoethyl]-1,3-thiazol-2-yl}benzenesulfonamide,
N-{4-[2-(4-morpholinyl)-2-oxoethyl]-1,3-thiazol-2-yl}-4-phenoxybenzenesulfonamide,
2-Methyl-N-{4-[2-(4-morpholinyl)-2-oxoethyl]-1,3-thiazol-2-yl}-4-(trifluoromethoxy)benzenesulfonamide,
N-{4-[2-(4-morpholinyl)-2-oxoethyl]-1,3-thiazol-2-yl}-2,4-bis(trifluoromethyl)benzenesulfonamide,
4-Bromo-2-methyl-N-{4-[2-(4-morpholinyl)-2-oxoethyl]-1,3-thiazol-2-yl}benzenesulfonamide,
4-(2-Furyl)-N-{4-[2-(4-morpholinyl)-2-oxoethyl]-1,3-thiazol-2-yl}benzenesulfonamide,
3'-Fluoro-6'-methoxy-N-{4-[2-(4-morpholinyl)-2-oxoethyl]-1,3-thiazol-2-yl}[1,1'-biphenyl]-4-sulfonamide,
4-(5-Methyl-2-thienyl)-N-{4-[2-(4-morpholinyl)-2-oxoethyl]-1,3-thiazol-2-yl}benzenesulfonamide,
3'-Acetyl-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-4'-(trifluoromethoxy)[1,1'-biphenyl]-4-sulfonamide,
3',4'-Dichloro-N-{4-[2-(4-morpholinyl)-2-oxoethyl]-1,3-thiazol-2-yl}[1,1'-biphenyl]-4-sulfonamide,
4-(1,3-Benzodioxol-5-yl)-N-({4-[2-(4-morpholinyl)-2-oxoethyl]-1,3-thiazol-2-yl}benzenesulfonamide,
4-(5-chloro-2-thienyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(4-pyridinyl)benzenesulfonamide,
N-{4'-[({4-[2-(4-morpholinyl)-2-oxoethyl]-1,3-thiazol-2-yl}amino)sulfonyl][1,1'-biphenyl]-3-yl}acetamide,
N-{4-[2-(4-Morpholinyl)-2-oxoethyl]-1,3-thiazol-2-yl}-4-(3-thienyl)benzenesulfonamide,
N-{4-[2-(4-Morpholinyl)-2-oxoethyl]-1,3-thiazol-2-yl}-4-(2-thienyl)benzenesulfonamide,
4'-[({4-[2-(4-Morpholinyl)-2-oxoethyl]-1,3-thiazol-2-yl}amino)sulfonyl][1,1'-biphenyl]-4-carboxylic acid,
4'-(Methylsulfanyl)-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3',5'-bis(trifluoromethyl)[1,1'-biphenyl]-4-sulfonamide,
4'-Chloro-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3'-nitro[1,1'-biphenyl]-4-sulfonamide,
4-(1-Benzofuran-2-yl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(1-pyrrolidinyl)benzenesulfonamide,
4-(4-Methyl-1-piperidinyl)-N-{4-[2-(4-morpholinyl)-2-oxoethyl]-1,3-thiazol-2-yl}benzenesulfonamide,
4-Anilino-N-{4-[2-(4-morpholinyl)-2-oxoethyl]-1,3-thiazol-2-yl}benzenesulfonamide,
4-(Benzylamino)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(2-thienylmethyl)amino]benzenesulfonamide,
4-(4-Morpholinyl)-N-{4-[2-(4-morpholinyl)-2-oxoethyl]-1,3-thiazol-2-yl}benzenesulfonamide,
4-(4-Methyl-1-piperazinyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(3-pyridinylmethyl)amino]benzenesulfonamide,
2,4-Dichloro-6-methyl-N-{5-methyl-4-[2-(4-morpholinyl)-2-oxoethyl]-1,3-thiazol-2-yl}benzenesulfonamide,
N-{5-methyl-4-[2-(4-morpholinyl)-2-oxoethyl]-1,3-thiazol-2-yl}[1,1'-biphenyl]-4-sulfonamide,
2,4,6-trichloro-N-{5-methyl-4-[2-(4-morpholinyl)-2-oxoethyl]-1,3-thiazol-2-yl}benzenesulfonamide,
3-chloro-2-methyl-N-{5-methyl-4-[2-(4-morpholinyl)-2-oxoethyl]-1,3-thiazol-2-yl}benzene sulfonamide,
3-Chloro-N-(4-{2-[(2R,6S)-2,6-dimethylmorpholinyl]-2-oxoethyl}-1,3-thiazol-2-yl)-2-methylbenzenesulfonamide,
3-Chloro-2-methyl-N-(4-{2-[(1S,4S)-2-oxa-5-azabicyclo[2.2.1]hept-5-yl]-2-oxoethyl}-1,3-thiazol-2-yl)benzenesulfonamide,
3-Chloro-2-methyl-N-{4-[2-oxo-2-(4-thiomorpholinyl)ethyl]-1,3-thiazol-2-yl}benzenesulfonamide,
N-{4-[2-oxo-2-(4-thiomorpholinyl)ethyl]-1,3-thiazol-2-yl)}[1,1'-biphenyl]-4-sulfonamide,
N-{4-[2-oxo-2-(4-thiomorpholinyl)ethyl]-1,3-thiazol-2-yl}-4-propylbenzenesulfonamide,
2,4-Dichloro-6-methyl-N-{4-[2-oxo-2-(4-thiomorpholinyl)ethyl]-1,3-thiazol-2-yl}benzenesulfonamide,
2,4,6-Trichloro-N-{4-[2-oxo-2-(4-thiomorpholinyl)ethyl]-1,3-thiazol-2-yl}benzenesulfonamide,
N-{4-[2-(1,1-dioxido-4-thiomorpholinyl)-2-oxoethyl]-1,3-thiazol-2-yl}-4-propylbenzenesulfonamide,
Tert-butyl 4-[(2-{[(3-chloro-2-methylphenyl)sulfonyl]amino}-1,3-thiazol-4-yl)acetyl]-1-piperazinecarboxylate,
N-{4-[2-(4-Acetyl-1-piperazinyl)-2-oxoethyl]-1,3-thiazol-2-yl}-3-chloro-2-methylbenzenesulfonamide,
3-Chloro-2-methyl-N-{4-[2-(4-methyl-1-piperazinyl)-2-oxoethyl]-1,3-thiazol-2-yl}benzenesulfonamide trifluoroacetate,
3-Chloro-2-methyl-N-{4-[2-oxo-2-(1-piperazinyl)ethyl]-1,3-thiazol-2-yl}benzenesulfonamide trifluoroacetate,
2-Methyl-N-{4-[2-(4-methyl-1-piperazinyl)-2-oxoethyl]-1,3-thiazol-2-yl}-4-(trifluoromethoxy)benzenesulfonamide,
2,4-Dichloro-6-methyl-N-{4-[2-(4-methyl-1-piperazinyl)-2-oxoethyl]-1,3-thiazol-2-yl}benzenesulfonamide,
2,4-Dichloro-N-{4-[2-(4-methyl-1-piperazinyl)-2-oxoethyl]-1,3-thiazol-2-yl}benzenesulfonamide,
3-chloro-N-(4-{2-[(2R)-2,4-dimethylpiperazinyl]-2-oxoethyl}-1,3-thiazol-2-yl)-2-methylbenzenesulfonamide,
2-(2-{[(3-Chloro-2-methylphenyl)sulfonyl]amino}-1,3-thiazol-4-yl)-N-methoxy-N-methylacetamide,
3-Chloro-2-methyl-N-[4-(2-oxopentyl)-1,3-thiazol-2-yl]benzenesulfonamide,
4-Chloro-N-[4-(2-hydroxyethyl)-1,3-thiazol-2-yl]benzenesulfonamide,
3-Chloro-N-[4-(2-hydroxyethyl)-1,3-thiazol-2-yl]-2-methylbenzenesulfonamide,
3-Chloro-N-[4-(3-hydroxypropyl)-1,3-thiazol-2-yl]-2-methylbenzenesulfonamide,
3-Chloro-N-[4-(2-ethoxyethyl)-1,3-thiazol-2-yl]-2-methylbenzenesulfonamide,
3-Chloro-N-[4-(2-isopropoxyethyl)-1,3-thiazol-2-yl]-2-methylbenzenesulfonamide,
N-{4-[2-(benzyloxy)ethyl]-1,3-thiazol-2-yl}-3-chloro-2-methylbenzenesulfonamide,
3-Chloro-N-[4-(2-methoxyethyl)-1,3-thiazol-2-yl]-2-methylbenzenesulfonamide,
3-Chloro-N-{4-[2-(2-fluoroethoxy)ethyl]-1,3-thiazol-2-yl}-2-methylbenzenesulfonamide,
3-Chloro-2-methyl-N-{4-[2-(2,2,2-trifluoroethoxy)ethyl]-1,3-thiazol-2-yl}benzenesulfonamide, 3-Chloro-2-methyl-N-{4-[2-(2-pyridinylsulfanyl)ethyl]-1,3-thiazol-2-yl}benzenesulfonamide,
3-Chloro-2-methyl-N-{4-[2-(3-pyridinyloxy)ethyl]-1,3-thiazol-2-yl}benzenesulfonamide,
Methyl 2-[2-(2-[{(3-chloro-2-methylphenyl)sulfonyl]amino}-1,3-thiazol-4-yl)ethoxy]benzoate,
3-Chloro-N-[5-[(dimethylamino)methyl]-4-(2-ethoxy-ethyl)-1,3-thiazol-2-yl]-2-methylbenzenesulfonamide,
2-(2-{[(3-Chloro-2-methylphenyl)sulfonyl]amino}-1,3-thiazol-4-yl)ethyl methanesulfonate,
3-(2-{[(3-chloro-2-methylphenyl)sulfonyl]amino}-1,3-thiazol-4-yl)propyl methanesulfonate,
2-(2-{[(3-Chloro-2-methylphenyl)sulfonyl]amino}-1,3-thiazol-4-yl)ethyl acetate,
2-(2-{[(3-Chloro-2-methylphenyl)sulfonyl]amino}-1,3-thiazol-4-yl)ethyl propionate,
2-(2-{[(3-Chloro-2-methylphenyl)sulfonyl]amino}-1,3-thiazol-4-yl)ethyl 2-methylpropanoate,
2-(2-{[(3-Chloro-2-methylphenyl)sulfonyl]amino}-1,3-thiazol-4-yl)ethyl 2-furoate,
2-(2-{[(3-chloro-2-methylphenyl)sulfonyl]amino}-1,3-thiazol-4-yl)ethyl benzoate,
2-(2-{[(3-Chloro-2-methylphenyl)sulfonyl]amino}-1,3-thiazol-4-yl)ethyl 4-morpholinecarboxylate,
2-(2-{[(3-Chloro-2-methylphenyl)sulfonyl]amino}-1,3-thiazol-4-yl)ethyl diethylcarbamate,
2-(2-{[(3-Chloro-2-methylphenyl)sulfonyl]amino}-1,3-thiazol-4-yl)ethyl ethylcarbamate,
N-[4-(2-azidoethyl)-1,3-thiazol-2-yl]-3-chloro-2-methyl-benzenesulfonamide,
N-[4-(2-aminoethyl 1,3-thiazol-2-yl]-3-chloro-2-methyl-benzenesulfonamide,
3-Chloro-2-methyl-N-{4-[2-(methylamino)ethyl]-1,3-thiazol-2-yl}benzenesulfonamide,
4-Chloro-N-{4-[2-(diethylamino)ethyl]-1,3-thiazol-2-yl}benzenesulfonamide hydrochloride,
3-Chloro-N-{4-[2-(diethylamino)ethyl]-1,3-thiazol-2-yl}-2-methylbenzenesulfonamide hydrochloride,
3-Chloro-N-{4-[2-(1H-imidazol-1-yl)ethyl]-1,3-thiazol-2-yl}-2-methylbenzenesulfonamide dihydrate,
3-Chloro-2-methyl-N-{4-[2-(4-methyl-1-piperazinyl)ethyl]-1,3-thiazol-2-yl}benzenesulfonamide dihydrochloride,
3-Chloro-2-methyl-N-{4-[2-(4-morpholinyl)ethyl]-1,3-thiazol-2-yl}benzenesulfonamide hydrochloride,
3-Chloro-2-methyl-N-[4-(4-morpholinylmethyl)-1,3-thiazol-2-yl]benzenesulfonamide hydrochloride,
2,4,6-Trichloro-N-{4-[2-(4-morpholinyl)ethyl]-1,3-thiazol-2-yl}benzenesulfonamide hydrochloride,
2,4-Dichloro-N-{4-[2-(4-morpholinyl)ethyl]-1,3-thiazol-2-yl}benzenesulfonamide hydrochloride,
2,4-Dichloro-6-methyl-N-{4-[2-(4-morpholinyl)ethyl]-1,3-thiazol-2-yl}benzenesulfonamide hydrochloride,
N-{4-[2-(4-Morpholinyl)ethyl]1,3-thiazol-2-yl}-4-propyl-benzenesulfonamide hydrochloride,
3-Chloro-N-{4-[2-(ethylamino)ethyl]-1,3-thiazol-2-yl}-2-methylbenzenesulfonamide,
3-Chloro-N-(4-{2-[(2-hydroxyethyl)amino]ethyl}-1,3-thiazol-2-yl)-2-methylbenzenesulfonamide,
3-Chloro-N-(4-{3-[(2-hydroxyethyl)amino]propyl}-1,3-thiazol-2-yl)-2-methylbenzenesulfonamide hydrochloride hydrate,
N-[2-(2-{[(3-chloro-2-methylphenyl)sulfonyl]amino}-1,3-thiazol-4-yl)ethyl]-N-ethylacetamide,
3-Chloro-2-methyl-N-{4-[2-(3-oxo-4-morpholinyl)ethyl]-1,3-thiazol-2-yl}benzenesulfonamide,
3-Chloro-N-{4-[2-(2-hydroxy-3-oxo-4-morpholinyl)ethyl]-1,3-thiazol-2-yl}-2-methylbenzenesulfonamide,
2,4-Dichloro-N-{4-[2-(3-oxo-4-morpholinyl)ethyl]-1,3-thiazol-2-yl}benzenesulfonamide,
2,4-Dichloro-6-methyl-N-{4-[2-(3-oxo-4-morpholinyl)ethyl]-1,3-thiazol-2-yl}benzenesulfonamide,
2,4,6-Trichloro-N-{4-[2-(3-oxo-4-morpholinyl)ethyl]-1,3-thiazol-2-yl}benzenesulfonamide,
4,5-Dichloto-N-{4-[2-(3-oxo-4-morpholinyl)ethyl]-1,3-thiazol-2-yl}-2-thiophenesulfonamide,
N-{4-[2-(3-Oxo-4-morpholinyl)ethyl]-1,3-thiazol-2-yl}-4-phenoxybenzenesulfonamide,
3-Fluoro-N-{4-[2-(3-oxo-4-morpholinyl)ethyl]-1,3-thiazol-2-yl}benzenesulfonamide,
N-{4-[2-(3-Oxo-4-morpholinyl)ethyl]-1,3-thiazol-2-yl}-5-(2-pyridinyl)-2-thiophenesulfonamide,
N-{2-Chloro-4-[({4-[2-(3-oxo-4-morpholinyl)ethyl]-1,3-thiazol-2-yl}amino)sulfonyl]phenyl}acetamide,
3-Chloro-2-methyl-N-{4-[(3-oxo-4-morpholinyl)methyl]-1,3-thiazol-2-yl}benzenesulfonamide,
3-Chloro-2-methyl-N-{4-[3-(3-oxo-4-morpholinyl)propyl]-1,3-thiazol-2-yl}benzenesulfonamide,
3-Chloro-N,2-dimethyl-N-{4-[2-(3-oxo-4-morpholinyl)ethyl]-1,3-thiazol-2-yl}benzenesulfonamide,
3-Chloro-2-methyl-N-{4-[2-(2-methyl-3-oxo-4-morpholinyl)ethyl]-1,3-thiazol-2-yl}benzenesulfonamide,
N-[2-(2-{[(3-Chloro-2-methylphenyl)sulfonyl]amino}-1,3-thiazol-4-yl)ethyl]acetamide,
3-Chloro-2-methyl-N-{4-[2-(3-oxo-1,4-oxazepan-4-yl)ethyl]-1,3-thiazol-2-yl}benzenesulfonamide,
3-Chloro-2-methyl-N-{4-[2-(2-oxo-1-pyrrolidinyl)ethyl]-1,3-thiazol-2-yl}benzenesulfonamide,
3-Chloro-2-methyl-N-{4-[2-(2-oxo-1-imidazolidinyl)ethyl]-1,3-thiazol-2-yl}benzenesulfonamide,
3-Chloro-2-methyl-N-{4-[2-(2-oxo-1,3-oxazolidin-3-yl)ethyl]-1,3-thiazol-2-yl}benzenesulfonamide,
N-[2-(2-{[(3-Chloro-2-methylphenyl)sulfonyl]amino}-1,3-thiazol-4-yl)ethyl]-N-(2-hydroxyethyl)-2-furamide,
N-[2-(2-{[(3-chloro-2-methylphenyl)sulfony]amino}-1,3-thiazol-4-yl)ethyl]-N-methylcyclopropanecarboxamide,
3-Chloro-2-methyl-N-{4-[2-(4-methyl-2-oxo-1-piperazinyl)ethyl]-1,3-thiazol-2-yl}benzenesulfonamide hydrochloride,
3-Chloro-2-methyl-N-(4-{2-[(methylsulfonyl)amino]ethyl}-1,3-thiazol-2-yl)benzenesulfonamide,
3-Chloro-2-methyl-N-(4-{2-[methyl(methylsulfonyl)amino]ethyl}-1,3-thiazol-2-yl)benzenesulfonamide,
3-Chloro-2-methyl-N-[4-(2-{[(trifluoromethyl)sulfonyl]amino}ethyl)-1,3-thiazol-2-yl]benzenesulfonamide,
3-Chloro-2-methyl-N-[4-(2-{methyl[(trifluoromethyl)sulfonyl]amino}ethyl)-1,3-thiazol-2-yl]benzenesulfonamide,
N-[2-(2-{[(3-Chloro-2-methylphenyl)sulfonyl]amino}-1,3-thiazol-4-yl)ethyl]-1-methyl-1H-imidazole-4-sulfonamide,
3-Chloro-N-(4-{2-[[(3-chloro-2-methylphenyl)sulfonyl](methyl)amino]ethyl}-1,3-thiazol-2-yl)-2-methylbenzenesulfonamide,
N-[4-(2-bromoethyl)-1,3-thiazol-2-yl]-3-chloro-2-methyl-benzenesulfonamide,
3-Chloro-N-[4-(2-chloroethyl)-1,3-thiazol-2-yl]-2-methyl-benzenesulfonamide,
3-Chloro-2-methyl-N-{4-[(5-methyl-1,3,4-oxadiazol-2-yl)methyl]-1,3-thiazol-2-yl}benzenesulfonamide,
Ethyl 3-(2-{[(3-chloro-2-methylphenyl)sulfonyl]amino}-1,3-thiazol-4-yl)propanoate.

Another object of the present invention is a pharmaceutical composition comprising at least one compound of the formula (II) as defined above, and a pharmaceutically acceptable carrier.

The compounds according to the present invention may be used in several indications which involve 11-β-hydroxysteroid dehydrogenase type 1 enzyme. Thus the compounds according to the present invention may be used against dementia (see WO97/07789), osteoporosis (see Canalis E 1996, Mechanisms of glucocorticoid action in bone: implications to glucocorticoid-induced osteoporosis, Journal of Clinical Endocrinology and Metabolism, 81, 3441-3447) and may also be used disorders in the immune system (see Franchimont et al, "Inhibition of Th1 immune response by glucocorticoids: dexamethasone selectively inhibits IL-12-induced Stat 4 phosphorylation in T lymphocytes", The journal of Immunology 2000, Feb. 15, vol 164 (4), pages 1768-74) and also in the above listed indications.

The various terms used, separately and in combinations, in the above definition of the compounds having the formula (II) will be explained.

The term "aryl" in the present description is intended to include aromatic rings (monocyclic or bicyclic) having from 6 to 10 ring carbon atoms, such as phenyl (Ph) and naphthyl, which optionally may be substituted by $C_{1-6}$-alkyl. Examples of substituted aryl groups are benzyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, quinoline, quinoxaline, isoquinoline, phthalazine, cinnoline, quinazoline, indole, isoindole, indoline, isoindoline, benzothiophene, benzofuran, isobenzofuran, benzoxazole, 2,1,3-benzoxadiazole, benzothiazole, 2,1,3-benzothiazole, 2,1,3-benzoselenadiazole, benzimidazole, indazole, benzodioxane, indane, 1,2,3,4-tetrahydroquinoline, 3,4-dihydro-2H-1,4-benzoxazine, 1,5-naphthyridine, 1,8-naphthyridine, acridine, fenazine and xanthene.

The term "heterocyclic" in the present description is intended to include unsaturated as well as partially and fully saturated mono-, bi- and tricyclic rings having from 4 to 14, preferably 4 to 10 ring atoms, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine and 1,4-oxazepane.

$C_{1-6}$-alkyl in the compound of formula (II) according to the present application, which may be straight, branched or cyclic, is preferably $C_{1-4}$-alkyl. Exemplary alkyl groups include methyl, ethyl, n-propyl, isopropyl, n-butyl, sec-butyl, tert-butyl, pentyl, isopentyl, hexyl, isohexyl, and cyclohexyl.

$C_{1-6}$-alkoxy, in the compound of formula (II) according to the present application may be straight or branched, is preferably $C_{1-4}$-alkoxy. Exemplary alkoxy groups include methoxy, ethoxy, propoxy, isopropoxy, butoxy, sec-butoxy, tert-butoxy, pentyloxy, isopentyloxy, hexyloxy, and isohexyloxy.

$C_{1-6}$-acyl, in the compound of formula (II) according to the present application may be saturated or unsaturated and is preferably $C_{1-4}$-acyl. Exemplary acyl groups include formyl, acetyl, propionyl, butyryl, isobutyryl, valeryl, isovaleryl, butenoyl (e.g. 3-butenoyl), hexenoyl (e.g. 5-hexenoyl).

The term "halogen" in the present description is intended to include fluorine, chlorine, bromine and iodine.

The term "sulfanyl" in the present description means a thio group.

With the expression mono- or di-substituted is meant in the present description that the functionalities in question may be substituted with independently H, $C_{1-6}$-acyl, $C_{1-6}$-alkenyl, $C_{1-6}$-(cyclo)alkyl, aryl, pyridylmethyl, or heterocyclic rings e.g. azetidine, pyrrolidine, piperidine, piperazine, morpholine and thiomorpholine, which heterocyclic rings optionally may be substituted with $C_{1-6}$-alkyl.

The term "prodrug forms" in the present description means a pharmacologically acceptable derivative, such as an ester or an amide, which derivative is biotransformed in the body to form the active drug (see Goodman and Gilman's, The Pharmacological basis of Therapeutics, $8^{th}$ ed., McGraw-Hill, Int. Ed. 1992, "Biotransformation of Drugs, p. 13-15).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean in the present description salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like.

Pharmaceutical compositions according to the present invention contain a pharmaceutically acceptable carrier together with at least one of the compounds comprising the formula (II) as described herein above, dissolved or dispersed therein as an active, antimicrobial, ingredient. In a preferred embodiment, the therapeutic composition is not immunogenic when administered to a human patient for therapeutic purposes, unless that purpose is to induce an immune response.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient may be mixed with excipients, which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition may contain minor amounts of auxiliary substances such as wetting or emulsifying agents, pH buffering agents and the like which enhance the effectiveness of the active ingredient. Adjuvants may also be present in the composition.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerine, vegetable oils such as cottonseed oil, organic esters such as ethyl oleate, and water-oil emulsions.

The pharmaceutical composition according to one of the preferred embodiments of the present invention comprising compounds comprising the formula (II), may include pharmaceutically acceptable salts of that component therein as set out above. Pharmaceutically acceptable salts include the acid addition salts (formed with the free amino groups of the polypeptide) that are formed with inorganic acids such as, for example, hydrochloric or phosphoric acids, or such organic acids as acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

The preparations according to the preferred embodiments may be administered orally, topically, intraperitoneally, intraarticularly, intracranially, intradermally, intramuscularly, intraocularly, intrathecally, intravenously, subcutaneously. Other routes which are known for the skilled person in the art are thinkable.

The orally administrable compositions according to the present invention may be in the form of tablets, capsules, powders, granules, lozenges, liquid or gel preparations, such as oral, topical or sterile parenteral solutions or suspensions. Tablets and capsules for oral administration may be in unit dose presentation form and may contain conventional excipients such as binding agents, for example syrup, acacia, gelatin, sorbitol, traganath or polyvinyl-pyrrolidone; fillers e.g. lactose, sugar, maize-starch, calcium phosphate, sorbitol or glycine; tabletting lubricant e.g. magnesium stearate, talc, polyethylene glycol or silica; disintegrants e.g. potato starch, or acceptable wetting agents such as sodium lauryl sulfate. The tablets may be coated according to methods well known in normal pharmaceutical practice. Oral liquid preparations may be in the form of e.g. aqueous or oily suspensions, solutions, emulsions, syrups or elixirs or may be presented as a dry product for reconstitution with water or other suitable vehicle before use. Such liquid preparations may contain conventional additives such as suspending agents, e.g. sorbitol, syrup, methyl cellulose, glucose syrup, gelatin hydrogenated edible fats; emulsifying agents e.g. lecithin, sorbitan monooleate or acacia, non-aqueous vehicles (which may include edible oils), e.g. almond oil, fractionated coconut oil, oily esters such as glycerine, propylene glycol, or ethyl alcohol; preservatives e.g. methyl or propyl p-hydroxybenzoate or sorbic acid, and if desired conventional flavouring or colouring agents.

A pharmaceutical composition according to the present invention, may comprise typically an amount of at least 0.1 weight percent of compound comprising the formula (II) per weight of total therapeutic composition. A weight percent is a ratio by weight of total composition. Thus, for example, 0.1 weight percent is 0.1 grams of compound comprising the formula (II) per 100 grams of total composition. A suitable daily oral dose for a mammal, preferably a human being, may vary widely depending on the condition of the patient. However a dose of compound comprising the formula (II) of about 0.1 to 300 mg/kg body weight may be appropriate.

The compositions according to the present invention may also be used veterinarily and thus they may comprise a veterinarily acceptable excipient or carrier.

The compounds of the present invention in labelled form, e.g. isotopically labelled, may be used as a diagnostic agent.

The compounds of the formula (II) above may be prepared by, or in analogy with, conventional methods, and especially according to or in analogy with the following methods. Further, the pharmacology in-vitro was studied using the following reagents and methods.

All publications mentioned herein are hereby incorporated by reference. By the expression "comprising" we understand including but not limited to. Thus, other non-mentioned substances, additives or carriers may be present.

The invention will now be described in reference to the following Figures and Examples. These Figures and Examples are not to be regarded as limiting the scope of the present invention, but shall only serve in an illustrative manner.

EXPERIMENTAL METHODS

Scintillation Proximity Assay

[1, 2(n)-$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β-HSD$_1$) was expressed in Pichia pastoris. 18-β-glycyrrhetinic acid (GA) was obtained from Sigma. The serial dilutions of the compounds were performed on a Tecan Genesis RSP 150.

Compounds to be tested were dissolved in DMSO (1 mM) and diluted in 50 mM Tris-HCl, pH 7.2 containing 1 mM EDTA.

The multiplication of plates was done on a WallacQuadra. The amount of the product [$^3$H]-cortisol, bound to the beads was determined in a Packard, Top Count microplate liquid scintillation counter.

The 11-β-HSD$_1$ enzyme assay was carried out in 96 well microtiter plates (Packard, Optiplate) in a total well volume of 220 μL and contained 30 mM Tris-HCl, pH 7.2 with 1 mM EDTA, a substrate mixture tritiated Cortisone/NADPH (175 nM/181 μM), G-6-P (1 mM) and inhibitors in serial dilutions (9 to 0.15 μM). Reactions were initiated by the addition of human 11-β-HSD$_1$, either as Pichia pastoris cell homogenate or microsomes prepared from Pichia pastoris (the final amount of enzyme used was varied between 0.057 to 0.11 mg/mL). Following mixing, the plates were shaken for 30 to 45 minutes at room temperature. The reactions were terminated with 10 μL 1 mM GA stop solution. Monoclonal mouse antibody was then added (10 μL of 4 μM) followed by 100 μL of SPA beads (suspended according to the manufacturers instructions). Appropriate controls were set up by omitting the 11-β-HSD$_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter.

The calculation of the K$_i$ values for the inhibitors was performed by use of Activity Base. The K$_i$ value is calculated from IC$_{50}$ and the K$_m$ value is calculated using the Cheng Prushoff equation (with reversible inhibition that follows the Michaelis-Menten equation): K$_i$=IC$_{50}$(1+[S]/K$_m$) [Cheng, Y. C.; Prushoff, W. H. Biochem. Pharmacol. 1973, 22, 3099-3108]. The IC$_{50}$ is measured experimentally in an assay wherein the decrease of the turnover of cortisone to cortisol is dependent on the inhibition potential of each substance. The Ki values of the compounds of the present invention for the 11-β-HSD1 enzyme lie typically between about 10 nM and about 10 µM. Illustrative of the invention, the following Ki values have been determined in the human 11-β-HSD1 enzyme assay (see Table 1):

TABLE 1

Ki values determined in the human 11-β-HSD1 enzyme assay.

| Compound of Example | $K_i$ (nM) |
|---|---|
| 1A | 32 |
| 149A | 51 |
| 151A | 21 |
| 179A | 14 |
| 181A | 53 |
| 189A | 299 |
| 204A | 91 |

COMPOUND PREPARATION

General:

For preparative straight phase HPLC purification a Phenomenex column (250×21.1 mm, 10 µm) was used on a Gilson system eluting with ethanol in chloroform (gradient from 0-10% in 10 min) with a flow of 20 mL/min. Column chromatography was performed on silica using Silica gel 60 (230-400 mesh), Merck. Melting points were determined on a Gallenkamp apparatus. Elemental analyses were recorded using a Vario EL instrument. HPLC analyses were performed using a Hypersil Elite column (150×4.6 mm, 3µ) with a flow of 3 mL/min on a Waters 600E system with monitoring at 254 nm. Reverse phase preparative HPLC was carried out on a 100×21.2 mm, 5µ Hypersil Elite column eluting with a gradient of 5% ACN in 95% water to 95% ACN in 5% water (0.2% TFA buffer) over 10 mins at a flow rate of 20 mL/min with the UV detector set at 254 nm. Thin layer chromatography was carried out using pre-coated silica gel F-254 plates (thickness 0.25 mm). Electrospray MS spectra were obtained on a Micromass platform LCMS spectrometer. Crude, worked up compounds were purified by flash column chromatography using pre packed silica SPE columns (10 g silica) on an Isco Foxy 200 Combiflash system, and a gradient of 16.67% ethyl acetate in hexane increasing incrementally to 100% ethyl acetate.

List of Abbreviations
DCM=dichloromethane
DIEA=N,N-diisopropylethylamine
DMAP=4-dimethylaminopyridine
DME=ethyleneglycol dimethyl ether
DMF=dimethylformamide
DMSO=dimethyl sulfoxide
EDCI=1-(3-dimethylaminopropyl)-3-ethylcarbodiimide hydrochloride
EDTA=ethylenediaminetetraacetic acid
HCOOH=formic acid
HOAT=1-hydroxy-7-azabenzotriazole
HOBT=1-hydroxybenzotriazole hydrate
MTBE=tert-butyl methyl ether
TEA=triethylamine
THF=tetrahydrofuran Sulfonamide Couplings:

Method A:

1 Eq of the 2-aminothiazole was dissolved in pyridine (0.5 M solution). The sulfonyl chloride (1.2 eq) was added and the reaction mixture was stirred at ambient temperature under nitrogen atmosphere for 15 h. The reaction mixture was poured into aqueous HCl (1 M). If the product precipitated it was collected on a filter and washed with aqueous HCl (1 M) and recrystallised from ethanol. In case an oil was obtained, the crude was extracted with DCM and worked up and purified using standard procedures.

Method B:

A solution of the 2-aminothiazole derivative (1 eq), triethylamine (2 eq) and DMAP (1 eq) in DMF (1 M) and DCM (0.225 M) was dispensed into a reaction vial. The sulfonyl chloride (1.2 eq) was dissolved in DCM (0.33 M) and added. The reaction mixtures were kept at room temperature over night. The mixture was then added to petroleum ether (10 times reaction volume). After some hours in refrigerator the supernatants were decanted and (a portion of) the residual materials were dissolved in DMSO-methanol-acetic acid (300 µL+500 µL+50 µL) and purified by preparative LCMS (acetonitrile-water gradients). The purest fractions were collected and lyophilized. Alternatively, the crude was isolated using extractive work-up and purified using standard procedures.

Saponifications:

Method C:

1 Eq of the ester was suspended in 95% ethanol (0.1 M) and treated with KOH (aqueous, 6 eq). Water was added until a clear solution was achieved. The reaction mixture was stirred for 2-3 h at ambient temperature. The solvent was removed under reduced pressure and the crude was redissolved in water. Addition of conc. HCl until pH 2 gave a precipitate which was collected on a filter and washed with cold water and dried.

Amide Couplings:

Method D:

The carboxylic acid ester was dissolved (0.05 M) in a large excess of the amine in 40 or 70% water-solution. The reaction mixture was stirred at ambient temperature over night. The solvent was removed under reduced pressure and the crude product was purified by flash column chromatography on silica gel eluting with methanol (0→6%) in DCM.

Method E:

The carboxylic acid was suspended in DCM (0.05M) followed by the addition of EDCI (1.1 eq), triethylamine (3 eq), DMAP (0.5 eq) and the amine of choice (1.2 eq). DMF was added when the starting materials did not dissolve properly. The reaction mixture was stirred at ambient temperature over night. The organic phase was washed with aqueous HCl (1 M), dried over sodium sulfate, filtered and evaporated in vacuo. The crude product amide was purified by flash column chromatography on silica gel, eluting with methanol (1→3→6%) in DCM or ethyl acetate.

Method F:

The carboxylic acid was suspended in DCM (0.1 M) and cooled to 0° C. under nitrogen (g) atmosphere. EDCI (1 eq), HOAT (1 eq) or HOBT (1 eq) was added, followed by TEA (2.2 eq). After 10 min, the amine of choice (1.2 eq) was added and the reaction mixture was allowed to warm to ambient temperature. After 5 h, the DCM phase was washed with aqueous HCl (1 M) and worked up and purified as described in METHOD E.

Method G:

Under $N_2$-atmosphere, aluminium chloride (1 eq) was suspended in DCM (0.1 M) and treated with the amine of choice (4 eq) at ambient temperature. After 10 min, the alkyl ester (1 eq) was added and the reaction mixture was stirred until starting material had been consumed (TLC). Quenching with saturated aqueous sodium hydrogen carbonate or aqueous HCl (1 M) and extractive workup with ethyl acetate gave the crude products which were then purified by flash chromatography on silica gel eluting with DCM/methanol mixtures.

Formation of Thiazole Ring:

Method H:

To a solution or suspension of an optionally substituted thiourea in ethanol (0.5 M), 1 equivalent of α-haloketone was added at room temperature. The reaction mixture was stirred in a sealed tube at 95° C. for 4 h, cooled, concentrated, redissolved in ethyl acetate, washed with saturated aqueous sodium hydrogen carbonate, dried over sodium sulfate and chromatographed on silica gel using petroleum-ether and ethyl acetate as eluents.

Method I:

To a 0.5 M solution of ketone (1 eq) and thiourea (2 eq) in ethanol at 60° C., 1 eq of iodine was added in one portion. The reaction tube was sealed and the reaction mixture was stirred at 100° C. for 16 hours. After evaporation of the solvent the residue was taken up in DCM, washed with saturated aqueous sodium hydrogen carbonate, dried with magnesium sulfate. Products were purified by chromatography on silica gel using a gradient of petroleum-ether/ethyl acetate from 8:1 to 2:1 for elution.

Acylations:

Method J:

To a solution of the alcohol in dry pyridine (0.3 M), 1.1 eq of acid chloride was added at 0° C. The reaction mixture was stirred at room temperature for 6 h, concentrated, co-evaporated with acetonitrile, re-dissolved in DCM, washed with aqueous HCl (0.5 M), dried with sodium sulfate and chromatographed on silica gel using petroleum-ether and ethyl acetate as eluents.

Carbamates:

Method K:

To a solution of the alcohol in dry pyridine (0.3 M), 1.5 eq of 4-nitrophenyl chloroformate (0.5 M in dry pyridine) was added at 0° C. After the reaction mixture was stirred at room temperature for 12 h, 5 eq of primary or secondary amine were added at 0° C. The solution was stirred at room temperature for 3 h, concentrated, co-evaporated with acetonitrile, re-dissolved in DCM, washed with aqueous HCl (0.5 M) and saturated aqueous sodium bicarbonate, dried with sodium sulfate and chromatographed on silica gel using DCM and methanol as eluents.

Palladium Couplings:

Method L:

Intermediate 18 (50 mg, 0.10 mmol) and the boronic acid (0.15 mmol) were weighed into reaction tubes together with palladium(II)acetate (2 mg). Dioxane (1.0 mL) was added followed by aqueous potassium carbonate (100 μL, 2 M). The mixtures were stirred at 80° C. until the starting material was consumed (2-20 hours). The solvents were evaporated and the materials were dissolved in acetic acid-acetonitrile (400 μL-600 μL) and purified by preparative HPLC using acetonitrile-water gradients containing 0.1% acetic acid. After HPLC analysis the purest fractions were collected and lyophilized.

Method M:

Intermediate 18 (50 mg, 0.10 mmol), 18-crown-6 (37 mg, 0.14 mmol), (R)-(+)-2,2'-bis(diphenylphosphino)1,1'-binaphthyl (3.7 mg, 6 μmol), tris(dibenzylidene-acetone)dipalladium(0) (1.8 mg, 2 μml), sodium tert.butoxide (13.5 mg, 0.14 mmol) and the amines (0.15 mmol) were weighed into reaction tubes under nitrogen atmosphere. Dry dioxane (800 μL) was added and the mixtures were stirred at 80° C. until the starting material was consumed (2-3 hours). The solvent was evaporated and the materials were purified by preparative LCMS using acetonitrile-water gradients containing 0.1% acetic acid. After HPLC analysis the purest fractions were collected and lyophilized.

Method N:

Intermediate 18 (50 mg, 0.10 mmol), (R)-(+)-2,2'-bis(diphenylphosphino)1,1'-binaphthyl (3.7 mg, 6 μmol), tris(dibenzylideneacetone)dipalladium(0) (1.8 mg, 2 μmol) and sodium tert.butoxide (29 mg, 0.30 mmol) were weighed into reaction tubes under nitrogen atmosphere. The amines (1.0 mmol) were dissolved in dry toluene (300 μL) and added. The reaction mixtures were stirred at 80° C. over night. The materials were purified by preparative LCMS using acetonitrile-water gradients containing 0.1% acetic acid. After HPLC analysis the purest fractions were collected and lyophilized.

Sulfonyl Chlorides

Arylsulfonyl chlorides (for EXAMPLE 40, 77M-77Q, 154A-158A) that were not commercially available were prepared from the aniline derivatives according to literature procedures (see for instance: Hoffman, R. V. (1981) Org. Synth. 60: 121).

INTERMEDIATES

Intermediate 1

Ethyl {2-[(tert-butoxycarbonyl)amino]-1,3-thiazol-4-yl}acetate

Ethyl 2-amino-4-thiazolylacetate (25.0 g, 134 mmol) was suspended in 75 g of tert-butanol. DMAP (1.6 g, 10 mol %) was added at 40° C. Boc-anhydride (32.0 g, 147 mmol) was added during 30 min. The suspension was stirred for 2.5 h (after 2 h gas evolution ceased), the mixture was diluted with a large amount of water and extracted with a toluene-heptane (30/60) mixture. The organic phase was washed with a sodium hydrogensulfate solution, dried with magnesium sulfate and the solvent was evaporated. The residue was crystallised from methanol (50 mL) and of water (15 mL), cooled to 0° C. and filtered off giving 23.4 g of a white crystals. A second crop of 3.6 g was obtained from the mother liquor (27.0 g, 71%): MS-EI$^+$ m/z 286; Anal. Calcd. (found) for $C_{12}H_{18}N_2O_4S$: C, 50.3 (50.5)%; H, 6.3 (6.2)%; N, 9.8 (9.7)%; S, 11.2 (11.2).

Intermediate 2 tert-Butyl 4-(2-hydroxyethyl)-1,3-thiazol-2-ylcarbamate

Intermediate 1 (28.6 g, 100 mmol) was dissolved in dry DME (200 mL) and heated to 50° C. Lithium borohydride (1.76 g, 81 mmol) was added cautiously and the solution was heated to 80° C. (reflux). After 2 h, the solution was cooled and acetic acid (15 mL) was added cautiously followed by a sodium chloride solution. The organic phase was separated and the water solution is extracted three times with ethyl acetate. The organic phases are combined and the solvent is evaporated. To destroy the formed boron complex of the product alcohol, the residue is dissolved in ethanol (100 mL)

and ethanolamine (6.1 g) and refluxed for 30 min. The solvent is evaporated and the residue is re-dissolved in toluene and washed with sodium hydrogensulfate solution, with sodium chloride solution, with sodium bicarbonate solution, with brine and finally dried with magnesium sulfate. Filtration and removal of the solvent gives a colorless oil in a nearly quantitative yield: MS-EI+ m/z 244.

Intermediate 3 tert-Butyl 4-{2-[(2-hydroxyethyl)amino]ethyl}-1,3-thiazol-2-ylcarbamate oxalate

INTERMEDIATE 2 (27.5 g, 98 mmol) was dissolved in toluene (150 mL) and cooled below 5° C. TEA (15.0 g, 147 mmol) and mesyl chloride (12.4 g, 125 mmol) were added dropwise at <5° C. After 30 min, ice-water was added and the organic phase was washed with sodium hydrogen sulfate solution, water and sodium hydrogen carbonate solution, after which it was dried with magnesium sulfate and the solvent evaporated [$^1$H NMR (CDCl$_3$) δ 1.50 (s, 9H), 2.87 (s, 3H), 3.13 (t, 2H), 4.43 (t, 2H), 5.26 (s, 1H), 6.62 (s, 1H)]. The residue was dissolved in ethanolamine (60.4 g, 98 mmol) and kept at 60° C. for 2 h. The ethanolamine was distilled off at 60° C. and 0.5 torr. Water was added to the residue which was extracted with ethyl acetate. The organic phase was washed with water, dried with sodium sulfate and concentrated to dryness. The residual oil was dissolved in ethanol (100 mL), heated to 50° C., and treated with oxalic acid (9.0 g) in warm ethanol. After cooling the product crystallised from solution. Ethyl acetate (50 mL) was added and the product was collected on a filter and washed with ethyl acetate. This procedure gave 27.8 g (74%) of white crystals. Anal. Calcd. (found) for $C_{12}H_{21}N_3O_3S$: C, 44.6 (44.1)%; H, 6.1 (5.8)%; N, 11.1 (11.1)%; S, 8.5 (8.4).

Intermediate 4 tert-Butyl 4-{2-[(chloroacetyl)(2-hydroxyethyl)amino]ethyl}-1,3-thiazol-2-ylcarbamate INTERMEDIATE 3 (37.7 g, 100 mmol) was dissolved in THF (50 mL) and water (100 mL). To that, a solution of calcium chloride dihydrate (16.7 g, 110 mmol) in water (15 mL) was added while the pH was kept near neutral with addition of a sodium hydroxide solution. The solution was cooled below 10° C. and chloroacetyl chloride was added while the pH was kept at 7-9 with addition of a sodium hydroxide solution. The reaction was finished (TLC) when less then 2 equivalents of chloroacetyl chloride had been added. Water and sodium hydrogen sulfate were added and the crude product was extracted with ethyl acetate. The organic phase was washed with water and the solvent evaporated. The residue was dissolved in toluene and the solution was washed with sodium hydrogen carbonate solution, with brine, treated with activated carbon and dried with magnesium sulfate. After evaporation of the solvent 38.5 g (96%) of an oil remained: $^1$H NMR (CDCl$_3$) δ 1.50 (s, 9H), 2.84 (t, 2H), 3.36 (t, 2H), 3.56 (t, 2H), 3.61 (t, 2H), 4.28 (br s, 2H), 6.73 (s, 1H).

Intermediate 5 tert-Butyl 4-[2-(3-oxo-4-morpholinyl)ethyl]-1,3-thiazol-2-ylcarbamate

A solution of INTERMEDIATE 4 (8.2 g, 22.5 mmol) in THF (30 mL) was added to aqueous potassium hydroxide (3.6 g, 0.6 mol in 3.6 mL water) while keeping the temperature at 20-25° C. with an ice bath. After 20 min, acetic acid was added and the THF was evaporated, the residue was extracted with toluene and washed with sodium hydrogen sulfate and sodium hydrogen carbonate solution. The organic phase was dried with magnesium sulfate and the solvent evaporated. The product which crystallised in the flask was recrystallised from MTBE yielding 4.2 g (57%) of a white solid: $^1$H NMR (CDCl$_3$) δ 1.52 (s, 9H), 2.96 (t, 2H), 3.18 (t, 2H), 3.66 (t, 2H), 3.75 (t, 2H), 4.12 (s, 2H), 6.57 (s, 1H).

Intermediate 6

4-[2-(2-Amino-1,3-thiazol-4-yl)ethyl]-3-morpholinone

The title compound was prepared by stirring INTERMEDIATE 5 (145 mg, 0.44 mmol) in DCM and trifluoroacetic acid (1:1; 5 mL) for 40 min. After removal of the solvent and drying in vacuum at 50° C. for 18 h, 105 mg of material was isolated. Part of this material (55 mg) was dissolved in DCM (7 mL) and washed with aqueous sodium hydroxide (2 M, 1.5 mL), dried over magnesium sulfate and the solvent was removed. A white solid was isolated (27 mg, 95% pure by HPLC): $^1$H NMR (CDCl$_3$) δ 8.70 (s, 1H), 6.27 (s, 1H), 3.95 (s, 2H), 3.90 (t, 2H), 3.75 (t, 2H), 3.43 (t, 2H), 2.9 (t, 2H); LCMS (pos) m/z 228.2.

Intermediate 7 tert-Butyl (3R)-3-methyl-1-piperazinecarboxylate

R-(−)-2-Methylpiperazine (1.00 g, 10 mmol) was dissolved in 50% aqueous methanol (5 mL). Acetic acid (0.57 mL, 10 mmol) was added and the solution was cooled in ice. Di-tert-butyldicarbonate (2.18 g, 10 mmol) dissolved in methanol (5 mL) was added slowly. The mixture was allowed to reach room temperature and left for 0.5 h after the gas evolution had ceased. The mixture was concentrated in vacuum and a small amount (0.1 g) of precipitate was filtered off. Aqueous potassium carbonate (10 mL, 1 M) was added to the filtrate and the solution was extracted with ethyl acetate (2×20 mL). The organic phase was washed with brine, dried (Magnesium sulfate), filtered and evaporated to give 1.68 g (84%) product as a white solid: $^1$H NMR (CDCl$_3$) δ 3.88 (bs, 2H), 2.89 (m, 1H), 2.4-2.8 (m, 3H), 2.3 (m, 1H), 1.62 (1H), 1.41 (s, 9H), 1.0 (d, 3H).

Intermediate 8

2-(2-Amino-1,3-thiazol-4-yl)-N-ethyl-N-methylacetamide

This compound was prepared from 2-amino-4-thiazoleacetic acid (3.48 g, 22 mmol), EDCI (4.37 g, 22.8 mmol), DMAP (270 mg, 2.2 mmol) and N-ethylmethylamine (1.99 mL, 23.2 mmol) in DMF (30 mL). The resulting solution was left overnight at room temperature. DMF was removed in vacuo and the residue purified by flash chromatography on silica gel using 2% and 5% methanol/ethyl acetate as eluent. This procedure yielded 2.09 g (40%) of the title compound:

¹H NMR (CDCl₃) δ 6.28, 6.30 (1H), 5.06 (bs, 1H), 3.60, 3.61 (2H), 3.41 (m, 2H), 3.0, 2.92 (s, 3H), 1.11 (q, 3H). MS EI m/z 200.2.

Intermediate 9

2-(2-Amino-1,3-thiazol-4-yl)-N-isopropyl-N-methylacetamide

This compound was prepared as described for INTERMEDIATE 8, using N-methyl-N-isopropylamine. Yield 0.87 g, 19%: ¹H NMR (CDCl₃) δ6.24 (s, 1H), 4.88, 4.20 (m, 1H), 3.64, 3.58 (s, 2H), 2.82, 2.77 (s, 3H), 1.08 (t, 6H). MS-ES (pos) m/z 214.2.

Intermediate 10

4-[2-(4-Morpholinyl)-2-oxoethyl]-1,3-thiazol-2-amine

This compound was prepared as described for INTERMEDIATE 8, using morpholine. DMF was distilled off in vacuum and methanol (10 mL) was added to the residue. The mixture was centrifugated and the supernatant separated. The solid was stirred with methanol (20 mL) and diethyl ether (20 mL). The mixture was centrifugated and the solid dried in vacuum. Yield 3.19 g, 64%: ¹H NMR (CDCl₃) δ 6.28 (s, 1H), 5.19 (bs, 3H), 3.5-3.7 (m, 10H). MS-ES (pos) m/z 228.0.

Intermediate 11

2-(2-Amino-1,3-thiazol-4-yl)-N,N-diethylacetamide

This compound was prepared as described for INTERMEDIATE 8, using N,N-diethylamine. DMF was distilled off and the residue was recrystallized from methanol. Yield 1.87 g, 40%: ¹H NMR (DMSO) δ6.85 (bs, 2H), 6.17 (s, 1H), 3.41 (s, 2H), 3.34 (q, 2H), 3.23 (q, 2H), 1.04 (t, 3H), 0.92 (t, 3H). MS-ES (pos) m/z 214.2.

Intermediate 12

4-[2-Oxo-2-(4-thiomorpholinyl)ethyl]-1,3-thiazol-2-amine

This compound was prepared as described for INTERMEDIATE 8, using thiomorpholine. Yield 2.57 g, 48%: ¹H NMR (CDCl₃) δ 6.28 (s, 1H), 5.25 (bs), 3.7-3-95 (m, 4H), 2.4-2.65 (m, 4H). MS-ES (pos) m/z 244.2.

Intermediate 13

4-[2-Oxo-2-(1-piperidinyl)ethyl]-1,3-thiazol-2-amine

This compound was prepared as described for INTERMEDIATE 8, using piperidine. Yield 3.47 g, 70%. ¹H NMR (CDCl₃) δ 6.26 (s, 1H), 5.25 (bs, 2H), 3.62 (s, 2H), 3.55 (t, 2H), 3.42 (m, 2H), 1.4-1.66 (6H). MS-ES (pos) m/z 226.2.

Intermediate 14

2-(2-Amino-1,3-thiazol-4-yl)-N,N-diisopropylacetamide

This compound was prepared as described for INTERMEDIATE 8, using N,N-diisopropylamine. Yield 1.40 g, 26%: ¹H NMR (CDCl₃) δ 6.25 (s, 1H), 5.20 (bs, 2H), 4.01 (m, 1H), 3.58 (s, 2H), 3.39 (m, 1H), 1.39 (d, 6H), 1.11 (d, 6H). MS-EI⁺ m/z 241.

Intermediate 15

2-(2-Amino-1,3-thiazol-4-yl)-N,N-dipropylacetamide

This compound was prepared as described for INTERMEDIATE 8, using N,N-dipropylamine. Yield 346 mg, 65%: ¹H NMR (CDCl₃) δ 6.29 (s, 1H), 5.16 (bs, 2H), 3.61 (s, 2H), 3.25 (m, 4H), 1.56 (m, 4H), 0.88 (m, 6H). MS-ES (pos) m/z 242.0.

Intermediate 16

5-methyl-4-[2-(4-morpholinyl)-2-oxoethyl]-1,3-thiazol-2-ylamine

A suspension of alumiumchloride (0.86 g, 6.44 mmol) in DCM (50 mL) was treated dropwise with morpholine (4.7 mL, 53.7 mmol) giving a colorless solution. Methyl (2-amino-5-methyl-1,3-thiazol-4-yl)acetate (1.0 g, 5.37 mmol) was added (orange solution) and after 1 h, the reaction mixture was quenched with aqueous citric acid (3%, 10 mL) and basified with saturated aqueous sodium bicarbonate. Extraction with DCM (3×50 mL), drying (sodium sulfate) of the combined organic layers and evaporation of the volatiles gave 0.70 g of a yellow foam. Purification of the solid by flash column chromatography on silicagel eluting with DCM/methanol (10/1 v/v) gave 545 mg (42%) of an ivory solid: Anal. Calcd. (found) for C₁₀H₁₅N₃O₂S: C, 49.7 (49.5)%; H, 6.3 (6.3)%; N, 17.4 (17.3)%; S, 13.3 (13.3).

Intermediate 17

4-[2-(4-morpholinyl)ethyl]-1,3-thiazol-2-amine

To INTERMEDIATE 2 (2.12 g, 8.68 mmol) dissolved in pyridine (20 mL) was added methane sulfonyl chloride (1.49 g, 13.02 mmol) at 0° C. The mixture was stirred at 0° C. for 4 h and was then poured into a mixture of ice (37 g) and conc. HCl (29 mL). Extraction with ethyl acetate followed by evaporation of the solvent gave 2.83 g crude mesylate. The crude product was dissolved in ethanol (15 mL) and morpholine (3.02 g, 34.71 mmol) was added. After 3 h at reflux, all mesylate was converted to amine and the Boc-group was removed by adding conc. HCl (10 mL). The deprotection was going on for 6 h at 50° C. and the solvent was evaporated. The crude material was purified by reversed phase flash chromatography on LiChroprep RP-18. The product was gradient eluted with (acetonitrile in H₂O/0.4% conc. HCl). Pure fractions were pooled and the solvent volume was reduced by evaporation to approximately 50%. 11 M NaOH was added until the product solidified. The solid was filtered off and washed by water giving (1.04 g, 4.89 mmol, 56%): ¹H NMR (CD₃OD) δ 2.50 (m, 4H), 2.53 (m, 4H), 3.54 (t, 4H), 6.19 (s, 1H); MS (Ionspray, [M+H]⁺) m/z 213. Anal. Calcd. (found) for C₉H₁₅N₃OS: C, 50.7 (50.5)%; H, 7.1 (7.3)%; N, 19.7 (19.8)%.

Intermediate 18

4-Iodo-N-{4-[2-(4-morpholinyl)-2-oxoethyl]-1,3-thiazol-2-yl}benzenesulfonamide

The title compound was prepared essentially according to METHOD B from INTERMEDIATE 10 and pipsyl chloride.

The product was purified by dissolving the impurities in hot ethanol. Yield 6.39 g, 59%: $^1$H NMR (DMSO) δ 7.91 (d, 2H), 7.55 (d, 2H), 6.52 (s, 1H), 3.64 (s, 2H), 3.4-3.6 (m). MS-ES (neg) m/z 492.3.

Intermediate 19

4-(Chloromethyl)-1,3-thiazol-2-ylamine hydrochloride

A solution of 1,3-dichloroacetone (25.4 g, 200 mmol) in acetone (100 mL) was stirred while a solution of thiourea (15.2 g, 200 mmol) in acetone (500 mL) was dropped in at a fairly rapid rate. A clear oil began to separate when the addition was about one quarter complete. The mixture stood over night during which time the oil solidified to a mass of white crystals. After decantation of the acetone, the solid was stirred with EtOH (200 mL). Insoluble material was filtered off and to the solution was petroleumether added. The product separated as an oil which solidified (18 g, 49%): MS (Ionspray, [M+H]$^+$) m/z 148. Anal. Calcd. (found) for $C_4H_5ClN_2S.1$ HCl: C, 26.0 (26.0)%; H, 3.3 (3.2)%; N, 15.1 (15.1)%.

Intermediate 20

2-{[(2-Amino-1,3-thiazol-4-yl)methyl]amino}ethanol dihydrochloride

INTERMEDIATE 19 (1.00 g, 5.40 mmol) was added to 2-ethanolamine (8.28 g, 135 mmol) in portions and the mixture was stirred at room temperature over night. Most of the ethanolamine was evaporated on rotavapor at 100° C. and the residue was flash chromatographed on RP silica gel eluting with 5% acetonitrile in $H_2O$/1% conc. HCl giving 790 mg (59%) of an oil. $^1$H NMR (DMSO) δ 2.62 (t, 2H), 3.46 (t, 2H), 6.28 (s, 1H), 6.81 (br s, 1H); MS (Ionspray, [M+H]$^+$) m/z 174.

Intermediate 21

4-[(2-Amino-1,3-thiazol-4-yl)methyl]-3-morpholinone

To a solution of INTERMEDIATE 20 (350 mg, 1.42 mmol) in $H_2O$ (3 mL)/THF (1.5 mL) was chloroacetyl chloride (400 mg, 3.55 mmol) in THF (3 mL) dropwise added under a period of 20 min. The temperature was kept at 8° C. and aqueous KOH (2 M) was added continuously to adjust the pH to around 6-8. Aqueous KOH (6 M, 1.2 mL, 7.2 mmol) was added and the mixture was stirred at room temperature for 20 min. The pH was adjusted to 8 and the mixture was extracted with ethyl acetate. The organic phase was separated and the solvent was evaporated giving a solid. The solid was boiled in ethyl acetate and was then filtered off (160 mg, 53%): $^1$H NMR (DMSO) δ 3.32 (t, 2H), 3.81 (t, 2H), 4.03 (s, 2H), 4.32 (s, 2H), 6.31 (s, 1H), 6.81 (brs, 1H); MS (Ionspray, [M+H]$^+$) m/z 213. Anal. Calcd. (found) for $C_8H_{11}N_3O_2S$: C, 45.1 (44.9)%; H, 5.2 (5.4)%; N, 19.7 (19.1)%.

Intermediate 22

Tert-butyl 4-[2-(3-oxo-1,4-oxazepan-4-yl)ethyl]-1,3-thiazol-2-ylcarbamate

The title compound was essentially prepared according to the synthetic route outlined for INTERMEDIATE 5, starting from INTERMEDIATE 2 and using 3-amino-1-propanol instead of 2-aminoethanol. The product was obtained as an oil (0.133 g, 86%) after the last step: $^1$H NMR (DMSO-d$_6$) δ 11.37 (s, 1H), 6.78 (s, 1H); 4.08 (s, 2H), 3.72 (t, 2H), 3.55 (t, 2H), 3.42 (m, 2H), 2.72 (t, 2H), 1.72 (m, 2H), 1.47 (s, 9H); HRMS calcd (found) for $C_{15}H_{23}N_3O_4S$ m/z 341.1409 (341.1399).

Intermediate 23

Methyl 2-[2-(2-amino-1,3-thiazol-4-yl)ethoxy]benzoate

Ethyl 2-aminothiazole-4-acetate (931 mg, 5.0 mmol) was dissolved in DCM (10 mL) and TEA (0.765 mL, 5.5 mmol). Trityl chloride (1.53 g, 5.5 mmol) was added in portions. The mixture was left overnight at room temp and filtered. The filtrate was evaporated and the product purified by flash-chromatography on silica gel using 20% ethyl acetate/toluene as eluent: $^1$H NMR (CDCl$_3$) δ 7.2-7.4 (m), 6.6 (s, 1H), 6.15 (s, 1H), 4.2 (q, 2H), 3.5 (s, 2H), 1.3 (t, 3H). A solution of the tritylated ethylester (5 mmol) in THF (18 mL) was added to lithium aluminiumborohydride (1.00 g, 26 mmol) in THF (100 mL) under cooling in ice. The mixture was stirred overnight at room temperature and then cooled in ice. Aqueous sodium hydroxide (10%, 15 mL) was added carefully. The solution was separated from the precipitate. The precipitate was washed with THF and ethyl acetate. The combined solutions were evaporated and the residue dissolved in ethyl acetate (80 mL) and washed with brine. Evaporation and chromatography on silica gel with 20% and 50% ethyl acetate in toluene gave 1.22 g product, 63% yield: $^1$H NMR (CDCl$_3$) δ 7.2-7.4 (m), 6.4 (s, 1H), 6.0 (s, 1H), 3.75 (t, 2H), 2.7 (t 2H). This material (386 mg, 1.0 mmol), methyl salicylate (183 mg, 1.2 mmol) and triphenylphosphine (314 mg, 1.2 mmol) were dissolved in THF (5 mL). N,N,N',N'-tetramethylazo-dicarboxamide (206 mg, 1.2 mmol) was added and the solution was left overnight. The mixture was filtered and the filtrate was purified by flash-chromatography on silica gel using toluene and ethyl acetate/toluene as eluent. Yield 418 mg, 80%: $^1$H NMR (CDCl$_3$) δ 7.74 (d, 1H), 7.4 (m, 1H), 7.18-7.38 (m), 6.95 (m, 2H), 6.5 (s, 1H), 6.15 (s, 1H), 4.2 (q, 2H), 3.8 (s, 3H), 3.0 (t, 2H). MS-ES (pos) m/z 521.2. Methyl 2-{2-[2-(tritylamino)-1,3-thiazol-4-yl]ethoxy}benzoate (343 mg, 0.656 mmol) was mixed with methanol: conc. HCl 9:1 (50 mL) and heated to 60° C. for 24 h. The mixture was concentrated to 10 mL, filtered and the filtrate was made alkaline with aqueous sodium carbonate (1 M). The solution was extracted with chloroform. Evaporation gave a product that was purified by flash-chromatography on silica gel using 0-2% methanol/DCM as eluent. Yield 128 mg, 70% (partially crystalline): $^1$H NMR (CDCl$_3$) δ 7.75 (d, 1H), 7.42 (t, 1H), 6.96 (m, 2H), 6.35 (s, 1H), 4.29 (t, 2H), 3.85 (s, 3H), 3.05 (t, 2H). MS-ES (pos) m/z 279.3.

KNOWN EXAMPLES

The compounds of these Examples are all commercially available and could e g be purchased from Kalamazoo.

1A Ethyl (2-{[(2,4-dichloro-5-methylphenyl)sulfonyl]amino}-1,3-thiazol-4-yl)acetate
2A Ethyl (2-{[(4-chlorophenyl)sulfonyl]amino}-1,3-thiazol-4-yl)acetate
3A Ethyl (2-{[(4-chloro-2,5-dimethylphenyl)sulfonyl]amino)}-1,3-thiazol-4-yl)acetate
4A Ethyl (2-{[(2,4-difluorophenyl)sulfonyl]amino}-1,3-thiazol-4-yl)acetate
15A Ethyl (2-{[(3-nitrophenyl)sulfonyl]amino}-1,3-thiazol-4-yl)acetate 20A Ethyl {2-[(phenylsulfonyl)amino]-1,3-thiazol-4-yl}acetate

NOVEL EXAMPLES

The following specific compounds were synthesized. The commercially available compounds thus only form embodiments, as indicated earlier in the description, as pharmaceutical preparations and use of said compounds as set out in the appended set of claims.

EXAMPLE 5A

Ethyl 2-(2-(((4-methylphenyl)sulfonyl)amino)-1,3-thiazol-4-yl)acetate

The title compound was prepared from ethyl 2-amino-4-thiazolylacetate and 4-methylbenzenesulfonyl chloride according to METHOD A, giving 0.36 g (66%) of a pink solid; mp 173° C.; MS (Ionspray, [M+H]$^+$) m/z 341.

EXAMPLE 6A

Ethyl 2-(2-{[(2,5-dichloro-3-thienyl)sulfonyl]amino}-1,3-thiazol-4-yl)acetate

The title compound was prepared from ethyl 2-amino-4-thiazolylacetate and 2,5-dichloro-3-thienyl)sulfonyl chloride according to METHOD A, giving 0.44 g (70%) of a red solid: MS (Ionspray, [M+H]$^+$) m/z 400; Anal. Calcd (found) for $C_{11}H_{10}Cl_2N_2O_4S_3$.0.7 HCl: C, 31.0 (31.0)%, H, 2.2 (2.2)%, N, 6.6 (6.8)%.

EXAMPLE 7A

Ethyl (2-{[(2-chlorophenyl)sulfonyl]amino}-1,3-thiazol-4-yl)acetate

The tide compound was prepared from ethyl 2-amino-4-thiazolylacetate and 2-chlorobenzenesulfonyl chloride according to METHOD A, giving 0.65 g (22%) of a pink solid after recrystallization from methanol: MS (Ionspray, [M+H]$^+$) m/z 361; Anal. Calcd (found) for $C_{13}H_{13}ClN_2O_4S_2$: C, 43.3 (43.2)%, H, 3.6 (3.5)%, N, 7.8 (7.6)%.

EXAMPLE 8A

Ethyl 2-(2-{[(3-chloro-2-methylphenyl)sulfonyl]amino}-1,3-thiazol-4-yl)acetate

The title compound was prepared from ethyl 2-amino-4-thiazolylacetate and 3-chloro-2-methylbenzenesulfonyl chloride according to METHOD A at 30° C., using a Quest 210 apparatus. This procedure gave 2.05 g (34%) of an off-white solid: mp 154° C.; MS (Ionspray, [M+H]$^+$) m/z 375; Anal. Calcd (found) for $C_{14}H_{15}ClN_2O_4S_2$: C, 44.9 (45.0)%, H, 4.0 (3.7)%, N, 7.5 (7.1)%.

EXAMPLE 10A

Ethyl 2-{2-[([1,1'-biphenyl]-4-ylsulfonyl)amino]-1,3-thiazol-4-yl}acetate

The title compound was prepared from ethyl 2-amino-4-thiazolylacetate and 1,1'-biphenylsulfonyl chloride according to METHOD A, using a Quest 210 apparatus and at 30° C., giving 0.99 g (23%) of an off-white solid: mp 182° C.; MS (Ionspray, [M+H]$^+$) m/z 403; Anal. Calcd (found) for $C_{19}H_{18}N_2O_4S_2$.0.1 $H_2O$: C, 56.4 (56.6)%, H, 4.5 (4.3)%, N, 6.9 (6.3)%.

EXAMPLE 12A

Ethyl 2-(2-{[(3-bromophenyl)sulfonyl]amino}-1,3-thiazol-4-yl)acetate

The title compound was prepared from ethyl 2-amino-4-thiazolylacetate and 3-bromobenzenesulfonyl chloride according to METHOD A, using a Quest 210 apparatus and at 30° C., giving 1.16 g (27%) of an off-white solid: mp 155° C.; MS (Ionspray, [M+H]$^+$) m/z 405; Anal. Calcd (found) for $C_{13}H_{13}BrN_2O_4S_2$: C, 38.5 (38.4)%, H, 3.2 (3.0)%, N, 6.9 (6.6)%.

EXAMPLE 13A

Ethyl (2-{[(4-nitrophenyl)sulfonyl]amino}-1,3-thiazol-4-yl)acetate

The title compound was prepared from ethyl 2-amino-4-thiazolylacetate and 4-nitrobenzenesulfonyl chloride according to METHOD A, giving 8.66 g (46%) of product: MS (Ionspray, [M+H]$^+$) m/z 372; Anal. Calcd. (found) for $C_{13}H_{13}N_3O_6S_2$: C, 42.0 (42.5)%; H, 3.5 (3.3)%; N, 11.3 (11.4)%.

EXAMPLE 14A

Ethyl (2-{[(4-methoxyphenyl)sulfonyl]amino}-1,3-thiazol-4-yl)acetate

The title compound was prepared from ethyl 2-amino-4-thiazolylacetate and 4-methoxybenzenesulfonyl chloride according to METHOD A, giving 9.83 g (55%) of pure material: MS (Ionspray, [M+H]$^+$) m/z 356; Anal. Calcd. (found) for $C_{14}H_{16}N_2O_5S_2$: C, 47.2 (47.1)%; H, 4.5 (4.5)%; N, 7.9 (7.8)%.

EXAMPLE 16A

Ethyl (2-{[(3-methylphenyl)sulfonyl]amino}-1,3-thiazol-4-yl)acetate

The title compound was prepared from ethyl 2-amino-4-thiazolylacetate and 3-methylbenzenesulfonyl chloride according to METHOD A, giving 0.51 g (75%) of a pink powder: MS (electrospray, [M−H]$^−$) m/z 339.2.

EXAMPLE 17A

Ethyl (2-{[(3-chlorophenyl)sulfonyl]amino}-1,3-thiazol-4-yl)acetate

The title compound was prepared from ethyl 2-amino-4-thiazolylacetate and 3-chlorobenzenesulfonyl chloride according to METHOD A, giving 0.47 g (65%) of a pink powder: MS (electrospray, [M−H]$^−$) m/z 359.1.

EXAMPLE 18A

Ethyl (2-{[(4-fluorophenyl)sulfonyl]amino}-1,3-thiazol-4-yl)acetate

The title compound was prepared from ethyl 2-amino-4-thiazolylacetate and 4-fluorobenzenesulfonyl chloride according to METHOD A, giving 0.29 g (42%) of a pink powder: MS (electrospray, [M−H]$^−$) m/z 343.1

EXAMPLE 19A

Ethyl (2-{[(3-fluorophenyl)sulfonyl]amino}-1,3-thiazol-4-yl)acetate

The title compound was prepared from ethyl 2-amino-4-thiazolylacetate and 3-fluorobenzenesulfonyl chloride according to METHOD A, giving 0.55 g (80%) of a pink powder: MS (electrospray, [M−H]⁻) m/z 343.1

EXAMPLE 21A

Ethyl (2-{[(4-isopropylphenyl)sulfonyl]amino}-1,3-thiazol-4-yl)acetate

The title compound was prepared from ethyl 2-amino-4-thiazolylacetate and 4-isopropylbenzenesulfonyl chloride according to METHOD A, giving 0.57 g (78%) of a pink powder: MS (electrospray, [M−H]⁻) m/z 367.2.

EXAMPLE 22A

Ethyl [2-({[3-({[4-(2-ethoxy-2-oxoethyl)-1,3-thiazol-2-yl]amino}carbonyl)phenyl]sulfonyl}amino)-1,3-thiazol-4-yl]acetate Synthetic METHOD A was undertaken using ethyl-2-amino-4-thiazoleacetate (0.37 g, 2 mmol), 3-carboxylphenylsulphonyl chloride (0.49 g, 2.2 mmol), and pyridine (10 mL). Purification gave the title compound as a cream powder (52 mg, 7%): MS (electrospray, [M−H]⁻) m/z 537.2.

EXAMPLE 23A

Ethyl [2-({[4-({[4-(2-ethoxy-2-oxoethyl)-1,3-thiazol-2-yl]amino}carbonyl)phenyl]sulfonyl}amino)-1,3-thiazol-4-yl]acetate Synthetic METHOD A was undertaken using ethyl-2-amino-4-thiazoleacetate (0.37 g, 2 mmol), 4-carboxylphenylsulphonyl chloride (0.49 g, 2.2 mmol), and pyridine (10 mL). Purification gave the title compound as a cream powder (44 mg, 6%): MS (electrospray, [M−H]⁻) m/z 537.2.

EXAMPLE 24A

Ethyl (2-{[(2-methylphenyl)sulfonyl]amino}-1,3-thiazol-4-yl)acetate

The title compound was prepared from ethyl 2-amino-4-thiazolylacetate and 2-methylbenzenesulfonyl chloride according to METHOD A, giving 0.22 g (32%) of a pink powder: $^1$H NMR (CDCl$_3$) δ: 1.3 (3H, t), 2.5 (3H, s), 3.9 (2H, s), 4.2 (2H, q), 6.4 (1H, s), 7.8-7.2 (3H, m), 8.1 (1H, t).

EXAMPLE 25A

Ethyl [2-({[2-(trifluoromethyl)phenyl]sulfonyl}amino)-1,3-thiazol-4-yl]acetate

The title compound was prepared from ethyl 2-amino-4-thiazolylacetate and 2-trifluoromethylbenzenesulfonyl chloride according to METHOD A, giving 0.13 g (31%) of a red solid after recrystallization from acetone/ether/petroleum ether: mp 171° C.; MS (Ionspray, [M+H]⁺) m/z 395; Anal. Calcd (found) for C$_{14}$H$_{13}$F$_3$N$_2$O$_4$S$_2$: C, 42.6 (43.0)%, H, 3.3 (2.9)%, N, 7.1 (6.9)%.

EXAMPLE 26A

Ethyl [2-({[3-(trifluoromethyl)phenyl]sulfonyl}amino)-1,3-thiazol-4-yl]acetate

The title compound was prepared from ethyl 2-amino-4-thiazolylacetate and 3-trifluoromethylbenzenesulfonyl chloride according to METHOD A, giving 0.26 g (62%) of an orange solid after recrystallization from acetone/ether/petroleum ether: mp 145° C.; MS (Ionspray, [M+H]⁺) m/z 395; Anal. Calcd (found) for C$_{14}$H$_{13}$F$_3$N$_2$O$_4$S$_2$: C, 42.6 (42.8)%, H, 3.3 (2.9)%, N, 7.1 (6.9)%

EXAMPLE 27A

Ethyl [2-({[4-(trifluoromethyl)phenyl]sulfonyl}amino)-1,3-thiazol-4-yl]acetate

The title compound was prepared from ethyl 2-amino-4-thiazolylacetate and 4-trifluoromethylbenzenesulfonyl chloride according to METHOD A, giving 0.14 g (33%) of an off-white solid after recrystallization from acetone/ether/petroleum ether: mp 174° C.; MS (Ionspray, [M+H]⁺) m/z 395; Anal. Calcd (found) for C$_{14}$H$_{13}$F$_3$N$_2$O$_4$S$_2$: C, 42.6 (42.4)%, H, 3.3 (2.8)%, N, 7.1 (6.8)%

EXAMPLE 28A

Ethyl 2-(2-{[(4-bromophenyl)sulfonyl]amino}-1,3-thiazol-4-yl)acetate

The title compound was prepared from ethyl 2-amino-4-thiazolylacetate and 4-bromobenzenesulfonyl chloride according to METHOD A, giving 0.14 g (31%) of a pink solid after recrystallization from acetone/ether/petroleum ether: mp 183° C.; MS (Ionspray, [M+H]⁺) m/z 405; Anal. Calcd (found) for C$_{13}$H$_{13}$BrN$_2$O$_4$S$_2$: C, 38.5 (38.5)%, H, 3.2 (3.0)%, N, 6.9 (6.6)%

EXAMPLE 29A

Ethyl (2-{[(2-nitrophenyl)sulfonyl]amino}-1,3-thiazol-4-yl)acetate

The title compound was prepared from ethyl 2-amino-4-thiazolylacetate and 2-nitrobenzenesulfonyl chloride as described in the synthetic METHOD B. The reaction mixture was applied on a Hydromatrix column pre-treated with aqueous HCl (0.5 mL, 2 M) and the eluted with DCM. After concentration the material was purified by preparative LCMS and lyophilized to give a white solid (26.6 mg) with purity >90%: $^1$H-NMR (DMSO-d$_6$) δ 11.40 (s, NH), 8.24 (m, 1H), 7.65 (m, 3H), 6.39 (s, 1H), 4.21 (dd, J=7.2 Hz, J=14.4 Hz, 2H), 3.73 (s, 2H), 1.28 (t, J=7.2 Hz, 3H); HRMS Calcd (found) for C$_{13}$H$_{13}$N$_3$O$_6$S$_2$ m/z 371.0246 (371.0248).

EXAMPLE 30A

Ethyl (2-{[(2,4-dichloro-6-methylphenyl)sulfonyl]amino}-1,3-thiazol-4-yl)acetate The title compound was prepared from ethyl 2-amino-4-thiazolylacetate and 2,4-dichloro-6-methylbenzenesulfonyl chloride as described in the synthetic METHOD B to give a white solid (34.6 mg) with purity >90%: LCMS (pos) m/z 409.0, 411.0; HRMS m/z 407.9753 (calc. of monoisotopic mass for C$_{14}$H$_{14}$Cl$_2$N$_2$O$_4$S$_2$ gives 407.9772).

EXAMPLE 31A

Ethyl (2-{[(2,4,6-trichlorophenyl)sulfonyl]amino}-1,3-thiazol-4-yl)acetate

The title compound was prepared from ethyl 2-amino-4-thiazolylacetate and 2,4,6-trichlorobenzenesulfonyl chloride as described in the synthetic METHOD B to give a white solid (32.0 mg) with purity >90%: LCMS (pos) m/z 431.0; HRMS m/z 427.9238 (calc. of monoisotopic mass for $C_{13}H_{11}Cl_3N_2O_4S_2$ gives 427.9226).

EXAMPLE 32A

Ethyl (2-{[(2,4-dichlorophenyl)sulfonyl]amino}-1,3-thiazol-4-yl)acetate

The title compound was prepared from ethyl 2-amino-4-thiazolylacetate and 2,4-dichlorobenzenesulfonyl chloride as described in the synthetic METHOD B to give a white solid (45.8 mg) with purity >90%. MS (pos) m/z 395.2, 397.2.

EXAMPLE 33A

Ethyl (2-{[(5-fluoro-2-methylphenyl)sulfonyl]amino}-1,3-thiazol-4-yl)acetate

The title compound was prepared from ethyl 2-amino-4-thiazolylacetate and 5-fluoro-2-methylbenzenesulfonyl chloride as described in the synthetic METHOD B to give a white solid (32.7 mg) with purity >90%. LCMS (pos) m/z 359.2.

EXAMPLE 34A

Ethyl (2-{[(4-propylphenyl)sulfonyl]amino}-1,3-thiazol-4-yl)acetate

The title compound was prepared from ethyl 2-amino-4-thiazolylacetate and 4-n-propylbenzenesulfonyl chloride as described in the synthetic METHOD B to give a white solid (16.0 mg) with purity >90%. LCMS (pos) m/z 369.0.

EXAMPLE 35A

Ethyl (2-{[(2-methoxy-4-methylphenyl)sulfonyl]amino}-1,3-thiazol-4-yl)acetate

The title compound was prepared from ethyl 2-amino-4-thiazolylacetate and 2-methoxy-4-methylbenzenesulfonyl chloride as described in the synthetic METHOD B to give a white solid (2.3 mg) with purity >90%. LCMS (pos) m/z 371.2.

EXAMPLE 36A

Ethyl (2-{[(3,5-dichlorophenyl)sulfonyl]amino}-1,3-thiazol-4-yl)acetate

The title compound was prepared from ethyl 2-amino-4-thiazolylacetate and 3,5-dichlorobenzenesulfonyl chloride as described in the synthetic METHOD B to give a white solid (42.2 mg) with purity >90%. LCMS (pos) m/z 395.0, 397.0.

EXAMPLE 37A

Ethyl [2-({[4-(3-chloro-2-cyanophenoxy)phenyl]sulfonyl}amino)-1,3-thiazol-4-yl]acetate The title compound was prepared from ethyl 2-amino-4-thiazolylacetate and 4-(3-chloro-2-cyanophenoxy)benzenesulfonyl chloride as described in the synthetic METHOD B to give a white solid (41.4 mg) with purity >90%. LCMS (pos) m/z 478.0.

EXAMPLE 38A

Ethyl (2-{[(3,4-dichlorophenyl)sulfonyl]amino}-1,3-thiazol-4-yl)acetate

The tide compound was prepared from ethyl 2-amino-4-thiazolylacetate and 3,4-dichlorobenzenesulfonyl chloride as described in the synthetic METHOD B to give a white solid (50.1 mg) with purity >90%. LCMS (pos) m/z 395.0, 397.0.

EXAMPLE 39A

Ethyl (2-{[(4-butoxyphenyl)sulfonyl]amino}-1,3-thiazol-4-yl)acetate

The title compound was prepared from ethyl 2-amino-4-thiazolylacetate and 4-n-butoxybenzenesulfonyl chloride as described in the synthetic METHOD B to give a white solid (11.8 mg) with purity >90%. LCMS (pos) m/z 399.2.

EXAMPLE 40A

Ethyl (2-{[(4-chloro-2-methylphenyl)sulfonyl]amino}-1,3-thiazol-4-yl)acetate

The title compound was prepared from ethyl 2-amino-4-thiazolylacetate and 4-chloro-2-methylbenzenesulfonyl chloride as described in the synthetic METHOD B to give a white-yellow solid (9.4 mg) with purity >90%. LCMS (pos) m/z 375.2.

EXAMPLE 41A

Ethyl [2-({[4-(acetylamino)phenyl]sulfonyl}amino)-1,3-thiazol-4-yl]acetate

The title compound was prepared from ethyl 2-amino-4-thiazolylacetate and 4-acetamidobenzenesulfonyl chloride as described in the synthetic METHOD B to give a white solid (5.6 mg) with purity >90%. LCMS (pos) m/z 384.2.

EXAMPLE 42A

Ethyl {2-[(8-quinolinylsulfonyl)amino]-1,3-thiazol-4-yl}acetate

The title compound was prepared from ethyl 2-amino-4-thiazolylacetate and 8-quinolinesulfonyl chloride as described in the synthetic METHOD B to give a white-yellow solid (9.2 mg) with purity >80%. LCMS (pos) m/z 378.2.

EXAMPLE 43A

Ethyl (2-{[(3,4-dimethoxyphenyl)sulfonyl]amino}-1,3-thiazol-4-yl)acetate

The title compound was prepared from ethyl 2-amino-4-thiazolylacetate and 3,4-dimethoxybenzenesulfonyl chloride as described in the synthetic METHOD B to give a white solid (19.3 mg) with purity >90%. LCMS (pos) m/z 387.2.

EXAMPLE 44A

Ethyl (2-{[(4-iodophenyl)sulfonyl]amino}-1,3-thia-zol-4-yl)acetate

The title compound was prepared from ethyl 2-amino-4-thiazolylacetate and pipsyl chloride as described in the synthetic METHOD B to give a white solid (47.0 mg) with purity >90%. LCMS (pos) m/z 453.0.

EXAMPLE 45A

Ethyl (2-{[(3-chloro-4-methylphenyl)sulfonyl] amino}-1,3-thiazol-4-yl)acetate

The title compound was prepared from ethyl 2-amino-4-thiazolylacetate and 3-chloro-4-methylbenzenesulfonyl chloride as described in the synthetic METHOD B to give a white solid (51.7 mg) with purity >90%. LCMS (pos) m/z 375.2.

EXAMPLE 46A

Ethyl [2-({[5-(dimethylamino)-1-naphthyl] sulfonyl}amino)-1,3-thiazol-4-yl]acetate The title compound was prepared from ethyl 2-amino-4-thiazolylacetate and dansyl chloride as described in the synthetic METHOD B to give a yellow solid (10.0 mg) with purity >90%. LCMS (pos) m/z 420.2.

EXAMPLE 47A

Ethyl (2-{[(1-methyl-1H-imidazol-4-yl)sulfonyl] amino}-1,3-thiazol-4-yl)acetate

The title compound was prepared from ethyl 2-amino-4-thiazolylacetate and 1-methylimidazole-4-sulfonyl chloride as described in the synthetic METHOD B to give a white solid (3.2 mg) with purity >90%. LCMS (pos) m/z 331.0.

EXAMPLE 48A

Ethyl (2-{[(5-bromo-2-methoxyphenyl)sulfonyl] amino}-1,3-thiazol-4-yl)acetate

The title compound was prepared from ethyl 2-amino-4-thiazolylacetate and 5-bromo-2-methoxybenzenesulfonyl chloride as described in the synthetic METHOD B to give a white solid (14.4 mg) with purity >90%. LCMS (pos) m/z 437.0.

EXAMPLE 49A

Ethyl (2-{[(2,5-dimethoxyphenyl)sulfonyl]amino}-1, 3-thiazol-4-yl)acetate

The title compound was prepared from ethyl 2-amino-4-thiazolylacetate and 2,5-dimethoxybenzenesulfonyl chloride as described in the synthetic METHOD B to give a white solid (17.0 mg) with purity >80%. LCMS (pos) m/z 387.2.

EXAMPLE 50A

Ethyl {2-[(2-naphthylsulfonyl)amino]-1,3-thiazol-4-yl}acetate

The title compound was prepared from ethyl 2-amino-4-thiazolylacetate and 2-naphthalenesulfonyl chloride as described in the synthetic METHOD B to give a white solid (41.2 mg) with purity >90%. LCMS (pos) m/z 377.2.

EXAMPLE 51A

Ethyl {2-[(mesitylsulfonyl)amino]-1,3-thiazol-4-yl}acetate

The title compound was prepared from ethyl 2-amino-4-thiazolylacetate and 2-mesitylenesulfonyl chloride as described in the synthetic METHOD B to give a white-yellow solid (7.5 mg) with purity >90%. LCMS (pos) m/z 369.0.

EXAMPLE 52A

Ethyl (2-{[(3-bromo-5-chloro-2-thienyl)sulfonyl] amino}-1,3-thiazol-4-yl)acetate The title compound was prepared from ethyl 2-amino-4-thiazolylacetate and 3-bromo-5-chlorothiophene-2-sulfonyl chloride as described in the synthetic METHOD B to give a yellow solid (29.0 mg) with purity >90%. MS (pos) m/z 445.0, 447.0.

EXAMPLE 53A

Ethyl {2-[({5-[(benzoylamino)methyl]-2-thienyl}sulfonyl)amino]-1,3-thiazol-4-yl}acetate The title compound was prepared from ethyl 2-amino-4-thiazolylacetate and 5-[(benzoylamino)methyl]thiophene-2-sulfonyl chloride as described in the synthetic METHOD B to give a white solid (8.6 mg) with purity >70%. MS (pos) m/z 466.2.

EXAMPLE 54A

Ethyl {2-[({5-[1-methyl-5-(trifluoromethyl)-1H-pyrazol-3-yl]-2-thienyl}sulfonyl)amino]-1,3-thiazol-4-yl}acetate The title compound was prepared from ethyl 2-amino-4-thiazolylacetate and 2-[1-methyl-5-(trifluoromethyl)pyrazol-3-yl]-thiophene-5-sulfonyl chloride as described in the synthetic METHOD B giving a yellow solid with a purity of 93%. MS (electrospray, [M+H]$^+$) m/z 481.0.

EXAMPLE 55A

Ethyl (2-{1[(4-cyanophenyl)sulfonyl]amino}-1,3-thiazol-4-yl)acetate

The title compound was prepared from ethyl 2-amino-4-thiazolylacetate and 4-cyanobenzenesulfonyl chloride as described in the synthetic METHOD B to give a white solid (16.9 mg) with purity >90%. MS (pos) m/z 352.2.

EXAMPLE 56A

Ethyl {2-[({5-[2-(methylsulfanyl)-4-pyrimidinyl]-2-thienyl}sulfonyl)amino]-1,3-thiazol-4-yl}acetate The title compound was prepared from ethyl 2-amino-4-thiazolylacetate and 5-[2-(methylthio)pyrimidin-4-yl] thiophene-2-sulfonyl chloride as described in the synthetic METHOD B to give a white solid (34.5 mg) with purity >90%. MS (pos) m/z 475.3.

EXAMPLE 57A

Ethyl (2-{[(3-cyanophenyl)sulfonyl]amino}-1,3-thiazol-4-yl)acetate

The title compound was prepared from ethyl 2-amino-4-thiazolylacetate and 3-cyanobenzenesulfonyl chloride as described in the synthetic METHOD B to give a white solid (39.4 mg) with purity >90%. MS (pos) m/z 352.3.

EXAMPLE 59A

Ethyl (2-{[(2,4,5-trichlorophenyl)sulfonyl]amino}-1,3-thiazol-4-yl)acetate

The title compound was prepared from ethyl 2-amino-4-thiazolylacetate and 2,4,5-trichlorobenzenesulfonyl chloride as described in the synthetic METHOD B to give a white solid (51.0 mg) with purity >90%. MS (pos) m/z 429.0. 431.0.

EXAMPLE 60A

Ethyl [2-({[(E)-2-phenylethenyl]sulfonyl}amino)-1,3-thiazol-4-yl]acetate

The title compound was prepared from ethyl 2-amino-4-thiazolylacetate and beta-styrenesulfonyl chloride as described in the synthetic METHOD B to give a white solid (21.3 mg) with purity >90%. MS (pos) m/z 353.1.

EXAMPLE 61A

Ethyl (2-{[(2,3,4-trichlorophenyl)sulfonyl]amino}-1,3-thiazol-4-yl)acetate

The title compound was prepared from ethyl 2-amino-4-thiazolylacetate and 2,3,4-trichlorobenzenesulfonyl chloride as described in the synthetic METHOD B to give a white solid (51.9 mg) with purity >90%. MS (pos) m/z 429.0, 431.0, 433.0.

EXAMPLE 63A

Ethyl (2-{[(4-bromo-2,5-difluorophenyl)sulfonyl]amino}-1,3-thiazol-4-yl)acetate

The title compound was prepared from ethyl 2-amino-4-thiazolylacetate and 4-bromo-2,5-difluorobenzenesulfonyl chloride as described in the synthetic METHOD B to give a white solid (21.9 mg) with purity >90%. MS (pos) m/z 441.0, 443.0.

EXAMPLE 64A

Ethyl [2-({[4-(trifluoromethoxy)phenyl]sulfonyl}amino)-1,3-thiazol-4-yl]acetate

The title compound was prepared from ethyl 2-amino-4-thiazolylacetate and 4-(trifluoromethoxy)benzenesulfonyl chloride as described in the synthetic METHOD B to give a white solid (29.1 mg) with purity >90%. MS (pos) m/z 411.1.

EXAMPLE 65A

Ethyl (2-{[(2,3-dichlorophenyl)sulfonyl]amino}-1,3-thiazol-4-yl)acetate

The title compound was prepared from ethyl 2-amino-4-thiazolylacetate and 2,3-dichlorobenzenesulfonyl chloride as described in the synthetic METHOD B to give a white solid (25.0 mg) with purity >90%. MS (pos) m/z 395.1, 397.1.

EXAMPLE 66A

Ethyl (2-{[(2-bromophenyl)sulfonyl]amino}-1,3-thiazol-4-yl)acetate

The title compound was prepared from ethyl 2-amino-4-thiazolylacetate and 2-bromobenzenesulfonyl chloride as described in the synthetic METHOD B to give a white solid (41.9 mg) with purity >90%. MS (pos) m/z 405.1, 407.1.

EXAMPLE 67A

Ethyl (2-{[(4,5-dichloro-2-thienyl)sulfonyl]amino}-1,3-thiazol-4-yl)acetate

The title compound was prepared from ethyl 2-amino-4-thiazolylacetate and 2,3-dichlorothiophene-5-sulfonyl chloride as described in the synthetic METHOD B to give a white-yellow solid (36.9 mg) with purity >90%. MS (pos) m/z 401.1, 403.1.

EXAMPLE 68A

Ethyl [2-({[4-(phenylsulfonyl)-2-thienyl]sulfonyl}amino)-1,3-thiazol-4-yl]acetate The title compound was prepared from ethyl 2-amino-4-thiazolylacetate and 4-benzenesulfonylthiophene-2-sulfonyl chloride as described in the synthetic METHOD B to give a yellow solid (29.5 mg) with purity >90%. MS (pos) m/z 473.1.

EXAMPLE 69A

Ethyl [2-({[5-(phenylsulfonyl)-2-thienyl]sulfonyl}amino)-1,3-thiazol-4-yl]acetate The title compound was prepared from ethyl 2-amino-4-thiazolylacetate and 5-phenylthiophene-2,5-disulfonyl chloride as described in the synthetic METHOD B to give a yellow solid (18.5 mg) with purity >90%. MS (pos) m/z 473.1.

EXAMPLE 70A

Ethyl (2-{[(2,6-dichlorophenyl)sulfonyl]amino}-1,3-thiazol-4-yl)acetate

The title compound was prepared from ethyl 2-amino-4-thiazolylacetate and 2,6-dichlorobenzenesulfonyl chloride as described in the synthetic METHOD B to give a white solid (32.5 mg) with purity >90%. MS (pos) m/z 395.1, 397.1.

EXAMPLE 71A

Ethyl (2-{[(2-cyanophenyl)sulfonyl]amino}-1,3-thiazol-4-yl)acetate

The title compound was prepared from ethyl 2-amino-4-thiazolylacetate and 2-cyanobenzenesulfonyl chloride as described in the synthetic METHOD B to give a white solid (24.6 mg) with purity >90%. MS (pos) m/z 352.2.

EXAMPLE 72A

Ethyl [2-({[4-(acetylamino)-3-chlorophenyl]
sulfonyl}amino)-1,3-thiazol-4-yl]acetate The title compound was prepared from ethyl 2-amino-4-thiazolylacetate and 4-acetamido-3-chlorobenzenesulfonyl chloride as described in the synthetic METHOD B to give a white solid (16.1 mg) with purity >90%. MS (pos) m/z 418.2, 420.2.

EXAMPLE 73A

Ethyl (2-{[(5-chloro-1,3-dimethyl-1H-pyrazol-4-yl)
sulfonyl]amino}-1,3-thiazol-4-yl)acetate The title compound was prepared from ethyl 2-amino-4-thiazolylacetate and 5-chloro-1,3-dimethylpyrazole-4-sulfonyl chloride as described in the synthetic METHOD B to give a white solid (14.8 mg) with purity >90%. MS (pos) m/z 397.2, 381.2.

EXAMPLE 74A

Ethyl (2-{[(3-methoxyphenyl)sulfonyl]amino}-1,3-
thiazol-4-yl)acetate

The title compound was prepared from ethyl 2-amino-4-thiazolylacetate and 3-methoxybenzenesulfonyl chloride as described in the synthetic METHOD B to give a white solid (18.6 mg) with purity >90%. LCMS (pos) m/z 357.0.

EXAMPLE 75A

Ethyl (2-{[(4-bromo-5-chloro-2-thienyl)sulfonyl]
amino}-1,3-thiazol-4-yl)acetate The title compound was prepared from ethyl 2-amino-4-thiazolylacetate and 4-bromo-5-chlorothiophene-2-sulfonyl chloride as described in the synthetic METHOD B to give a white-yellow solid (40.9 mg) with purity >90%. MS pos) m/z 445.0, 447.0.

EXAMPLE 76A

Ethyl 2-{2-[(1-naphthylsulfonyl)amino]-1,3-thiazol-
4-yl}acetate

The title compound was prepared from ethyl 2-amino-4-thiazolylacetate and 1-naphthylsulfonyl chloride according to METHOD A, giving a crude product that was purified by flash column chromatography on silica gel eluting with 2% methanol in DCM. This gave the pure title compound (3.93 g, 89%). MS (Ionspray, [M+H]$^+$) m/z 376; Anal. Calcd. (found) for $C_{17}H_{16}N_2O_4S_2$: C, 54.2 (54.02)%; H, 4.3 (3.9)%; N, 7.4 (7.1)%.

EXAMPLE 77A

Ethyl (2-{[(2,5-dichlorophenyl)sulfonyl]amino}-1,3-
thiazol-4-yl)acetate

The title compound was prepared from ethyl 2-amino-4-thiazolylacetate and 2,5-dibenzenesulfonyl chloride according to METHOD A, giving 0.22 g (27%) of a pink solid after recrystallization from acetone ether/petroleum ether: mp 171° C.; MS (Ionspray, [M+H]$^+$) m/z 395; Anal. Calcd (found) for $C_{13}H_{12}Cl_2N_2O_4S_2$: C, 39.5 (39.7)%, H, 3.1 (2.9)%, N, 7.1 (6.8)%.

EXAMPLE 77B

Ethyl [2-({[4-(methylsulfonyl)phenyl]
sulfonyl}amino)-1,3-thiazol-4-yl]acetate

The title compound was prepared from ethyl 2-amino-4-thiazolylacetate and 4-methylsulfonylbenzenesulfonyl chloride as described in synthetic METHOD B to give a white solid (20.9 mg) with purity >90%. MS (pos) m/z 405.3.

EXAMPLE 77C

Ethyl [2-({[2-(methylsulfonyl)phenyl]
sulfonyl}amino)-1,3-thiazol-4-yl]acetate

The title compound was prepared from ethyl 2-amino-4-thiazolylacetate and 2-methylsulfonylbenzenesulfonyl chloride as described in the synthetic METHOD B to give a white solid (28.4 mg) with purity >90%. MS (pos) m/z 405.4.

EXAMPLE 77D

Ethyl (2-{[(4-bromo-2-fluorophenyl)sulfonyl]
amino}-1,3-thiazol-4-yl)acetate

The title compound was prepared from ethyl 2-amino-4-thiazolylacetate and 4-bromo-2-fluorobenzenesulfonyl chloride as described in the synthetic METHOD B to give a white solid (15.1 mg) with purity >90%. MS (pos) m/z 423.3, 425.3.

EXAMPLE 77F

Ethyl (2-{[(2,3,4-trifluorophenyl)sulfonyl]amino}-1,
3-thiazol-4-yl)acetate

The tide compound was prepared from ethyl 2-amino-4-thiazolylacetate and 2,3,4-trifluorobenzenesulfonyl chloride as described in the synthetic METHOD B to give a yellow solid (2.3 mg) with purity >90%. MS (pos) m/z 381.4.

EXAMPLE 77G

Ethyl (2-{[(7-chloro-2,1,3-benzoxadiazol-4-yl)sulfo-
nyl]amino}-1,3-thiazol-4-yl)acetate The title compound was prepared from ethyl 2-amino-4-thiazolylacetate and 4-chloro-7-chlorosulfonyl-2,1,3-benzoxadiazole as described in the synthetic METHOD B to give a yellow solid (2.5 mg) with purity >90%. MS (pos) m/z 403.4.

EXAMPLE 77H

Ethyl (2-{[(2,4,6-trifluorophenyl)sulfonyl]amino}-1,
3-thiazol-4-yl)acetate

The title compound was prepared from ethyl 2-amino-4-thiazolylacetate and 2,4,6-trifluorobenzenesulfonyl chloride as described in the synthetic METHOD B to give a yellow solid (1.0 mg) with purity >90%. MS (pos) m/z 381.4.

EXAMPLE 77I

2-Chloro-5-({[4-(2-ethoxy-2-oxoethyl)-1,3-thiazol-
2-yl]amino}sulfonyl)-4-fluorobenzoic acid The title compound was prepared from ethyl 2-amino-4-thiazolylacetate and 2-chloro-5-chlorosulfonyl-4-fluoroben-

EXAMPLE 77J

Ethyl (2-{[(5-chloro-2-thienyl)sulfonyl]amino}-1,3-thiazol-4-yl)acetate

The title compound was prepared from ethyl 2-amino-4-thiazolylacetate and 5-chlorothiophene-2-sulfonyl chloride as described in the synthetic METHOD B to give a white solid (24.3 mg) with purity >90%. MS (pos) m/z 367.1, 369.1.

EXAMPLE 77K

Ethyl (2-{[(2-chloro-4-fluorophenyl)sulfonyl]amino}-1,3-thiazol-4-yl)acetate

The title compound was prepared from ethyl 2-amino-4-thiazolylacetate and 2-chloro-4-fluorobenzenesulfonyl chloride as described in the synthetic METHOD B to give a white solid (13.9 mg) with purity >90%. MS (pos) m/z 379.2, 381.2.

EXAMPLE 77L

Ethyl [2-({[5-(3-isoxazolyl)-2-thienyl]sulfonyl}amino)-1,3-thiazol-4-yl]acetate

The title compound was prepared from ethyl 2-amino-4-thiazolylacetate and 5-isoxazol-3-ylthiophene-2-sulfonyl chloride as described in the synthetic METHOD B to give a yellow solid (15.9 mg) with purity >90%. MS (pos) m/z 400.3.

EXAMPLE 77M

Ethyl (2-{[(4-bromo-2-methylphenyl)sulfonyl]amino}-1,3-thiazol-4-yl)acetate

The tide compound was prepared from ethyl 2-amino-4-thiazolylacetate and 4-bromo-2-methylbenzenesulfonyl chloride as described in the synthetic METHOD B to give a white solid (48.2 mg) with purity >90%. MS (pos) m/z 419.2, 421.2.

EXAMPLE 77N

Ethyl (2-{[(4-phenoxyphenyl)sulfonyl]amino}-1,3-thiazol-4-yl)acetate

The title compound was prepared from ethyl 2-amino-4-thiazolylacetate and [(4-phenoxy)benzene]sulfonyl chloride as described in the synthetic METHOD B to give a white solid (33.5 mg) with purity >90%. MS (pos) m/z 419.3.

EXAMPLE 77O

Ethyl (2-({[(4-chloro-2,6-dimethylphenyl)sulfonyl]amino}-1,3-thiazol-4-yl)acetate The title compound was prepared from ethyl 2-amino-4-thiazolylacetate and 4-chloro-2,6-dimethylbenzenesulfonyl chloride as described in the synthetic METHOD B to give a white solid (27.3 mg) with purity >90%. MS (pos) m/z 389.3, 391.3.

EXAMPLE 77P

Ethyl [2-({[2-methyl-4-(trifluoromethoxy)pbenyl]sulfonyl}amino)-1,3-thiazol-4-yl]acetate The title compound was prepared from ethyl 2-amino-4-thiazolylacetate and 2-methyl-4-trifluoromethoxybenzenesulfonyl chloride as described in the synthetic METHOD B to give a yellow solid (41.7 mg) with purity >90%. MS (pos) m/z 425.3.

EXAMPLE 77Q

Ethyl [2-({[2,4-bis(trifluoromethyl)phenyl]sulfonyl}amino)-1,3-thiazol-4-yl]acetate The title compound was prepared from ethyl 2-amino-4-thiazolylacetate and 2,4-ditrifluoromethylbenzenesulfonyl chloride as described in the synthetic METHOD B to give a white solid (61.0 mg) with purity >90%. MS (pos) m/z 463.3.

EXAMPLE 78A

Ethyl 2-{2-[[(3-chloro-2-methylphenyl)sulfonyl](methyl)amino]-1,3-thiazol-4-yl}acetate Methyl iodide (0.57 g, 4.00 mmol) was added to a solution of EXAMPLE 8A (1.50 g, 4.00 mmol) and N-ethyldiisopropylamine (0.57g, 4.40 mmol) in DMF (10 mL). The mixture was stirred at room temperature over night. The solvent was evaporated and the residue was purified by flash column chromatography on silica gel eluting with DCM. The product was crystallised with DCM/petroleum ether giving 0.11 g (7%) of a white solid: MS (Ionspray, [M+H]$^+$) m/z 388; Anal. Calcd. (found) for $C_{15}H_{17}ClN_2O_4S_2$: C, 46.3 (46.5)%; H, 4.4 (4.6)%; N, 7.2 (7.2)%.

EXAMPLE 79A

Ethyl oxo(2-{[(4-propylphenyl)sulfonyl]amino}-1,3-thiazol-4-yl)acetate

The title compound was prepared from ethyl (2-amino-4-thiazolyl)glyoxylate and 4-n-propylbenzenesulfonyl chloride as described in the synthetic METHOD B to give a yellow solid (14.5 mg) with purity >90%. LCMS (pos) m/z 383.2.

EXAMPLE 80A

Ethyl (2-{[(3-chloro-2-methylphenyl)sulfonyl]amino}-1,3-thiazol-4-yl)(oxo)acetate The title compound was prepared from ethyl (2-amino-4-thiazolyl)glyoxylate and 3-chloro-2-methylbenzenesulfonyl chloride as described in the synthetic METHOD B to give a yellow solid (32.5 mg) with purity >90%. LCMS (pos) m/z 389.0.B

EXAMPLE 81A

Ethyl oxo(2-{[(2,4,6-trichlorophenyl)sulfonyl]amino}-1,3-thiazol-4-yl)acetate

The title compound was prepared from ethyl (2-amino-4-thiazolyl)glyoxylate and 2,4,6-trichlorobenzenesulfonyl chloride as described in the synthetic METHOD B to give a yellow solid (18.3 mg) with purity >80%. LCMS (pos) m/z 445.0.

EXAMPLE 82A

Ethyl {2-[([1,1'-biphenyl]-4-ylsulfonyl)amino]-1,3-thiazol-4-yl}(oxo)acetate

The title compound was prepared from ethyl (2-amino-4-thiazolyl)glyoxylate and 4-phenylbenzenesulfonyl chloride as described in the synthetic METHOD B to give a yellow solid (28.2 mg) with purity >80%. LCMS (pos) m/z 417.0.

EXAMPLE 83A

Ethyl (2-{[(2,4-dichloro-6-methylphenyl)sulfonyl]amino}-1,3-thiazol-4-yl)(oxo)acetate The title compound was prepared from ethyl (2-amino-4-thiazolyl)glyoxylate 2,4-dichloro-6-methylbenzenesulfonyl chloride as described in the synthetic METHOD B to give a yellow solid (28.9 mg) with purity >90%: LCMS (pos) m/z 423; HRMS m/z 421.9580 (calc. of mass for $C_{14}H_{12}Cl_2N_2O_5S_2$ gives 421.9565).

EXAMPLE 84A 2-(2-{[(4-Methylphenyl)sulfonyl]amino}-1,3-thiazol-4-yl)acetic acid The title compound was prepared from EXAMPLE 5A according to METHOD C, giving 0.15 g (77%) of a white solid: mp 187° C.; MS (Ionspray, [M+H]$^+$) m/z 313; Anal. Calcd (found) for $C_{12}H_{12}N_2O_4S_2$: C, 46.1 (46.1)%, H, 3.9 (3.9)%, N, 9.0 (8.9)%.

EXAMPLE 85A 2-(2-{[(2,5-Dichloro-3-thienyl)sulfonyl]amino}-1,3-thiazol-4-yl)acetic acid The title compound was prepared from EXAMPLE 6A according to METHOD C, giving 0.41 g (100%) of a pale brown solid: mp 174° C.; MS (Ionspray, [M+H]$^+$) m/z 372; Anal. Calcd (found) for $C_9H_6Cl_2N_2O_4S_3$.0.8 HCl: C, 26.9 (26.9)%, H, 1.7 (1.6)%, N, 7.0 (6.6)%.

EXAMPLE 86A (2-{[(2-Chlorophenyl)sulfonyl]amino}-1,3-thiazol-4-yl)acetic acid The title compound was prepared from EXAMPLE 7A according to METHOD C, giving 1.49 g (90%) of a pink solid after recrystallization from acetone/ether/petroleum ether: mp 176° C.; MS (Ionspray, [M+H]$^+$) m/z 333; Anal. Calcd (found) for $C_{11}H_9ClN_2O_4S_2$: C, 39.7 (39.4)%, H, 2.7 (2.6)%, N, 8.4 (8.2)%.

EXAMPLE 87A 2-(2-{[(3-Chloro-2-methylphenyl)sulfonyl]amino}-1,3-thiazol-4-yl)acetic acid The title compound was prepared from EXAMPLE 8A according to METHOD C, giving 1.89 g (100%) of an off-white solid: mp 198° C.; MS (Ionspray, [M+H]$^+$) M/z 347; Anal. Calcd (found) for $C_{12}H_{11}ClN_2O_4S_2$.0.9 HCl: C, 38.0 (38.0)%, H, 3.2 (2.6)%, N, 7.4 (7.1)%.

EXAMPLE 88A

Isopropyl 2-(2-{[(3-chloro-2-methylphenyl)sulfonyl]amino}-1,3-thiazol-4-yl)acetate EXAMPLE 87A (0.3 g, 0.9 mmol) in DCM (7 mL) was treated dropwise with oxalyl chloride (0.1 g, 0.9 mmol) and a catalytic amount of DMF. The reaction mixture was stirred for 3 h. The solvent was removed under reduced pressure and isopropanol was added to the residual off-white solid. The resulting suspension was stirred over night. Purification by flash column chromatography on silica gel eluting with methanol (1→3→5%) in DCM gave a pink oil. Analytically pure pink crystals were obtained after crystallization from acetone/petroleum ether: mp 114° C.; MS (Ionspray, [M+H]$^+$) m/z 389; Anal. Calcd (found) for $C_{15}H_{17}ClN_2O_4S_2$: C, 46.3 (46.4)%, H, 4.4 (4.2)%, N, 7.2 (7.2)%.

EXAMPLE 89A

Phenyl 2-(2-{[(3-chloro-2-methylphenyl)sulfonyl]amino}-1,3-thiazol-4-yl)acetate

Under $N_2$ atmosphere, EXAMPLE 87A (0.5 g, 1.4 mmol) and DMAP (0.3 g, 1.6 mmol) were dissolved in DCM (40 mL). The resulting red solution was chilled (0° C.) before EDCI (0.3 g, 1.6 mmol) and phenol (0.7 g, 7.2 mmol) were added. The mixture was allowed to warm to room temperature and stirred over night. The reaction mixture was washed with aqueous HCl and saturated aqueous sodium bicarbonate. The organic phase was removed and the residue purified by flash column chromatography on silica gel eluting with methanol (0→1→3%) in DCM. This gave 0.18 g (30%) of a white solid: mp 189° C.; MS (Ionspray, [M+H]$^+$) m/z 423; Anal. Calcd (found) for $C_{18}H_{15}ClN_2O_4S_2$: C, 51.1 (51.1)%, H, 3.6 (3.3)%, N, 6.6 (6.4)%.

EXAMPLE 90A

Methyl (2-{[(3-chloro-2-methylphenyl)sulfonyl]amino}-1,3-thiazol-4-yl)acetate (Note: This experimental describes the attempt to reduce the ethyl ester group to the alcohol) EXAMPLE 8 (1.2 g, 3.3 mmol) was dissolved in dry THF (10 mL). Lithium borohydride (0.2 g, 10 mmol) was added in portions under $N_2$ atmosphere at ambient temperature. The coloured suspension was stirred over night. Aqueous HCl (1M, 40 mL) and brine (40 mL) were added before extraction with ethyl acetate. Drying (sodium sulfate), and evaporation of the organic phase gave crude material that was purified by flash column chromatography on silica gel eluting with methanol (0→2→4%) in DCM. This gave 0.36 g (30%) of a yellow solid: mp 187° C.; MS (Ionspray, [M+H]$^+$) m/z 361; Anal. Calcd (found) for $C_{13}H_{13}ClN_2O_4S_2$: C, 43.3 (43.1)%, H, 3.6 (3.4)%, N, 7.8 (7.6)%.

EXAMPLE 91A

Methyl {2-[([1,1'-biphenyl]-4-ylsulfonyl)amino]-5-methyl-1,3-thiazol-4-yl}acetate The title compound was prepared from methyl 2-(2-amino-5-methyl-1,3-thiazol-4-yl)acetate and 4-biphenylsulfonyl chloride as described in the synthetic METHOD B to give a white solid (22:1 mg) with purity >90%. LCMS (pos) m/z 403.0.

EXAMPLE 92A

Methyl (2-{[(4-chlorophenyl)sulfonyl]amino}-5-methyl-1,3-thiazol-4-yl)acetate

The title compound was prepared from methyl 2-(2-amino-5-methyl-1,3-thiazol-4-yl)acetate and 4-chlorobenzenesulfonyl chloride as described in the synthetic METHOD B to give a white solid (29.2 mg) with purity >90%. LCMS (pos) m/z 361.2.

EXAMPLE 93A

Methyl (2-{[(3-chloro-2-methylphenyl)sulfonyl]amino}-5-methyl-1,3-thiazol-4-yl)acetate The title compound was prepared from methyl 2-(2-amino-5-methyl-1,3-thiazol-4-yl)acetate and 3-chloro-2-methylbenzenesulfonyl chloride as described in the synthetic METHOD B to give a white solid (23.2 mg) with purity >90%. LCMS (pos) m/z 375.2.

EXAMPLE 94A

Methyl [2-({[4-(3-chloro-2-cyanophenoxy)phenyl]sulfonyl}amino)-5-methyl-1,3-thiazol-4-yl]acetate The title compound was prepared from methyl 2-(2-amino-5-methyl-1,3-thiazol-4-yl)acetate and 4-(3-chloro-2-cyanophenoxy)benzenesulfonyl chloride as described in the synthetic METHOD B to give a yellow solid (28.3 mg) with purity >90%. LCMS (pos) m/z 478.2.

EXAMPLE 95A

Methyl (5-methyl-2-{[(4-propylphenyl)sulfonyl]amino}-1,3-thiazol-4-yl)acetate

The title compound was from prepared methyl 2-(2-amino-5-methyl-1,3-thiazol-4-yl)acetate and 4-n-propylbenzenesulfonyl chloride as described in the synthetic METHOD B to give a white solid (33.1 mg) with purity >90%. MS (pos) m/z 416.2.

EXAMPLE 96A

Methyl (5-methyl-2-{([(2,4,6-trichlorophenyl)sulfonyl]amino}-1,3-thiazol-4-yl)acetate The title compound was prepared from methyl 2-(2-amino-5-methyl-1,3-thiazol-4-yl)acetate and 2,4,6-trichlorobenzenesulfonyl chloride as described in the synthetic METHOD B to give a white solid (60.8 mg) with purity >90%: MS (pos) m/z 431.1; HRMS m/z 427.9233 (calc. of monoisotopic mass for $C_{13}H_{11}Cl_3N_2O_4S_2$ gives 427.9226).

EXAMPLE 97A

Methyl (2-{[(2,4-dichloro-6-methylphenyl)sulfonyl]amino}-5-methyl-1,3-thiazol-4-yl)acetate The title compound was prepared from methyl 2-(2-amino-5-methyl-1,3-thiazol-4-yl)acetate and 2,4-dichloro-6-methylbenzenesulfonyl chloride as described in the synthetic METHOD B to give a white solid (27.2 mg) with purity >80%. MS (pos) m/z 409.0, 411.0.

EXAMPLE 98A

N-(2-Methoxyethyl)-2-(2-{[(4-methylphenyl)sulfonyl]amino})-1,3-thiazol-4-yl)acetamide EXAMPLE 84A (0.5 g, 1.6 mmol) in DCM (15 mL) was treated dropwise with oxalyl chloride (0.3 g, 2.4 mmol). A catalytic amount of DMF was added, after which the resulting orange mixture was stirred for 2 h. The solvent was removed under reduced pressure, and the crude was suspended in 4 mL of DCM. The suspension was added dropwise to a solution of DIEA (0.62 g, 4.8 mmol) and 2-methoxyethylamine (0.24 g, 3.2 mmol) and stirred for 3 h at ambient temperature. The organic phase was washed with 2M aqueous HCl, dried (magnesium sulfate), and evaporated. The crude brown solid was recrystallized from ethyl acetate, affording 0.11 g (19%) of the pure title compound: mp 132° C.; IR (KBr) ν 3328, 1316, 1146, 1090 $cm^{-1}$; MS (Ionspray, $[M+H]^+$) m/z 370; Anal. Calcd (found) for $C_{15}H_{19}N_3O_4S_2$: C, 48.8 (48.8)%, H, 5.2 (5.2)%, N, 11.4 (11.3)%.

EXAMPLE 99A 2-(2-{[(2,5-Dichloro-3-thienyl)sulfonyl]amino}-1,3-thiazol-4-yl)-N-methylacetamide The tide compound was prepared from EXAMPLE 85A according to preparation described for EXAMPLE 98A. Recrystallisation from acetone/diethyl ether/petroleum ether gave 0.03 g (8%) of a white solid: mp 183° C.; IR (KBr) ν 3326, 1300, 1154 $cm^{-1}$; MS (Ionspray, $[M+H]^+$) m/z 385; Anal. Calcd (found) for $C_{10}H_9Cl_2N_3O_3S_3$: C, 31.1 (31.4)%, H, 2.4 (2.7)%, N, 10.9 (10.5)%.

EXAMPLE 100A

N-(1,3-Benzodioxol-5ylmethyl)-2-{2-[(1-naphthylsulfonyl)amino]-1,3-thiazol-4-yl}acetamide The title compound was prepared from EXAMPLE 76A, according to METHOD C, followed by METHOD E, giving 66 mg (16%) of the pure product. MS (Ionspray, $[M+H]^+$) m/z 482; Anal. Calcd. (found) for $C_{23}H_{19}N_3O_5S_2$.0.3 DMF: C, 57.0 (56.6)%; H, 4.2 (4.0)%; N, 9.2 (8.9)%.

EXAMPLE 100A

N-(2-Furylmethyl)-2-{2-[(1-naphthylsulfonyl)amino]-1,3-thiazol-4-yl}acetamide

The title compound was prepared from EXAMPLE 76A, according to METHOD C, followed by METHOD E, giving 98 mg (27%) of a white solid: MS (Ionspray, $[M+H]^+$) m/z 428; Anal. Calcd. (found) for $C_{20}H_{17}N_3O_4S_2$.0.1 $CH_2Cl_2$: C, 55.4 (55.3) %; H, 4.0(3.6)%; N, 9.6(9.3)%.

EXAMPLE 102A 2-(2-{[(2,4-Difluorophenyl)sulfonyl]amino}-1,3-thiazol-4-yl)-N-ethylacetamide The title compound was prepared from EXAMPLE 4A according to METHOD D Recrystallisation from acetone/ether/petroleum ether gave 0.09 g (40%) of a pink solid: mp 150° C.; IR (KBr) ν 3304, 3087, 1325, 1150 $cm^{-1}$; MS (Ionspray, $[M+H]^+$) m/z 362; Anal. Calcd (found) for $C_{13}H_{13}F_2N_3O_3S_2$: C, 43.2 (43.1)%, H, 3.6 (3.2)%, N, 11.6 (11.2)%.

EXAMPLE 103A

N-Isopropyl-2-{2-[(1-naphthylsulfonyl)amino]-1,3-thiazol-4-yl}acetamide

The title compound was prepared from EXAMPLE 76A, according to METHOD C, followed by METHOD E, giving 122 mg (36%) of the pure product: MS (Ionspray, [M+H]$^+$) m/z 390; Anal. Calcd. (found) for $C_{18}H_{19}N_3O_3S_2.0.2\text{-}CH_2Cl_2$: C, 53.8 (54.0)%; H, 4.8 (4.4)%; N, 10.3 (10.1)%.

EXAMPLE 104A

N-[2-(1H-Indol-3-yl)ethyl]-2-{2-[(1-naphthylsulfonyl)amino]-1,3-thiazol-4-yl}acetamide The title compound was prepared from EXAMPLE 76A, according to METHOD C, followed by METHOD E, giving 134 mg (32%) of the pure product: MS (Ionspray, [M+H]$^+$) m/z 391; Anal. Calcd. (found) for $C_{25}H_{22}N_4O_3S_2.0.2\ CH_2Cl_2$: C, 59.6 (59.7) %; H, 4.4(4.1)%; N, 11.0(10.7)%.

EXAMPLE 105A

N-(Cyclohexylmethyl)-2-{2-[(phenylsulfonyl)amino]-1,3-thiazol-4-yl}acetamide

The title compound was prepared from EXAMPLE 20A, according to METHOD C, followed by METHOD E, giving 134 mg (25%) pure product after recrystallisation from DCM: MS (Ionspray, [M+H]$^+$) m/z 394; Anal. Calcd. (found) for $C_{18}H_{23}N_3O_3S_2.0.3H_2O$: C, 54.2 (54.2)%; H, 6.0 (5.3)%; N, 10.5 (10.1)%.

EXAMPLE 106A 2-(2-{[(3-Chloro-2-methylphenyl)sulfonyl]amino}-1,3-thiazol-4-yl)-N-methylacetamide The title compound was prepared from EXAMPLE 8A according to METHOD D, giving 0.20 g (61%) of a pink solid: mp 165° C.; IR (KBr) ν 3334, 3085, 1318, 1142 cm$^{-1}$; MS (Ionspray, [M+H]$^+$) m/z 360; Anal. Calcd (found) for $C_{13}H_{14}ClN_3O_3S_2$: C, 43.4 (43.4)%, H, 3.9 (3.6)%, N, 11.7 (11.3)%.

EXAMPLE 107A 2-(2-{[(3-Chloro-2-methylphenyl)sulfonyl]amino}-1,3-thiazol-4-yl)-N-ethylacetamide The title compound was prepared from EXAMPLE 8A according to METHOD D, giving 0.18 g (53%) of a yellow solid: mp 96° C.; IR (KBr) ν 3327, 3098,1136 cm$^{-1}$; MS (Ionspray, [M+H]$^+$) m/z 374; Anal. Calcd (found) for $C_{14}H_{16}ClN_3O_3S_2.0.2\ H_2O$: C, 44.5 (44.4)%, H, 4.4 (3.9)%, N, 11.1 (10.7)%.

EXAMPLE 108A 2-(2-{[(3-Chloro-2-methylphenyl)sulfonyl]amino}-1,3-thiazol-4-yl)-N-phenylacetamide The title compound was prepared from EXAMPLE 87A according to METHOD E, giving 0.10 g (34%) of a pink solid after recrystallization from ethyl acetate/ether petroleum ether: mp 202° C.; IR (KBr) ν 3313, 3107, 1308, 1133 cm$^{-1}$; MS (Ionspray, [M+H]$^+$) m/z 422; Anal. Calcd (found) for $C_{18}H_{16}ClN_3O_3S_2$: C, 51.2 (50.9)%, H, 3.8 (3.6)%, N, 10.0 (9.5)%.

EXAMPLE 109A 2-(2-{[(4-Chlorophenyl)sulfonyl]amino}-1,3-thiazol-4-yl)-N-(2-furylmethyl)acetamide The title compound was prepared from EXAMPLE 2A, according to METHOD C, followed by METHOD E, giving 172 mg (35%) pure product after recrystallisation from DCM: MS (Ionspray, [M+H]$^+$) m/z 412; Anal. Calcd. (found) for $C_{16}H_{14}ClN_3O_4S_2.0.3\ H_2O$: C, 46.1 (46.1)%; H, 3.5 (3.1)%; N, 10.1 (9.8)%.

EXAMPLE 110A

N-Benzhydryl-2-(2-{[(4-chlorophenyl)sulfonyl]amino}-1,3-thiazol-4-yl)acetamide

The title compound was prepared from EXAMPLE 2A, according to METHOD C, followed by METHOD E, giving 157 mg (26%) pure product after recrystallisation from DCM: MS (Ionspray, [M+H]$^+$) m/z 498; Anal. Calcd. (found) for $C_{24}H_{20}ClN_3O_3S_2.0.6\ H_2O$: C, 56.6 (56.5)%; H, 4.2 (3.6)%; N, 8.3 (8.0)%.

EXAMPLE 111A 2-(2-{[(4-Chlorophenyl)sulfonyl]amino}-1,3-thiazol-4-yl)-N-(tetrahydro-2-furanylmethyl)acetamide The title compound was prepared from EXAMPLE 2A, according to METHOD C, followed by METHOD E, giving 92 mg (18%) pure product after recrystallisation from DCM: MS (Ionspray, [M+H]$^+$) m/z 416; Anal. Calcd. (found) for $C_{16}H_{18}ClN_3O_4S_2$: C, 46.2 (45.9)%; H, 4.3 (3.9)%; N, 10.1 (9.7)%.

EXAMPLE 112A

Ethyl 4-([2-(2-{[(4-chlorophenyl)sulfonyl]amino}-1,3-thiazol-4-yl)acetyl]amino)-1-piperidinecarboxylate The title compound was prepared from EXAMPLE 2A, according to METHOD C, followed by METHOD E, giving 281 mg (48%) pure material after recrystallization from DCM: MS (Ionspray, [M+H]$^+$) m/z 487; Anal. Calcd. (found) for $C_{19}H_{23}ClN_4O_5S_2$: C, 46.9 (46.8)%; H, 4.8 (4.6)%; N, 11.5 (11.2)%.

EXAMPLE 113A

N-Benzhydryl-2-(2-{[(3-chloro-2-methylphenyl)sulfonyl]amino}-1,3-thiazol-4-yl)acetamide The tide compound was prepared from EXAMPLE 87A according to METHOD E, giving 0.09 g (20%) of a pink solid after recrystallization from acetone/diethyl ether: mp 200° C.; MS (Ionspray, [M+H]$^+$) m/z 512.

EXAMPLE 115A 2-(2-{[(4-Chlorophenyl)sulfonyl]amino}-1,3-thiazol-4-yl)-N-phenylacetamide The title compound was prepared from EXAMPLE 2A, according to METHOD C, followed by METHOD E, giving 130 mg (26%) of pure product after recrystallization from ethanol: MS (Ionspray, [M+H]$^+$) m/z 407; Anal. Calcd. (found) for $C_{17}H_{14}ClN_3O_3S_2$: C, 50.0 (49.6)%; H, 3.5 (3.3)%; N, 10.3 (10.3)%.

EXAMPLE 116A 2-(2-{[(3-Chloro-2-methylphenyl)sulfonyl]amino}-1,3-thiazol-4-yl)acetamide A solution of EXAMPLE 8A (0.20 g, 0.53 mmol) in conc. ammonium hydroxide (6 mL) was stirred over night at room temperature. The solvent was evaporated giving a quantitative yield of the tide product: MS (Ionspray, [M+H]$^+$) m/z 345; Anal. Calcd. (found) for $C_{14}H_{16}N_2O_5S_2$: C, 42.0 (42.5)%; H, 3.5 (3.3)%; N, 11.3 (11.4)%.

EXAMPLE 117A 2-(2-{[(3-Chloro-2-methylphenyl)sulfonyl]amino}-1,3-thiazol-4-yl)-N,N-diethylacetamide The title compound was prepared according to METHOD E. The obtained product mixture was separated on a silica gel column giving the amide (53 mg, 0.13 mmol, 11%) and the decarboxylated product 3-chloro-2-methyl-N-(4-methyl-1,3-thiazol-2-yl)benzenesulfonamide (135 mg, 0.44 mmol, 39%). EXAMPLE 117A: MS (Ionspray, [M+H]$^+$) m/z 401; Anal. Calcd. (found) for $C_{16}H_{20}ClN_3O_3S_2$: C, 47.8 (47.7)%; H, 5.0 (5.4)%; N, 10.4 (10.2)%.

EXAMPLE 119A

2-{2-[([1,1'-Biphenyl]-4-ylsulfonyl)amino]-1,3-thiazol-4-yl}-N,N-diethylacetamide The title compound was prepared by coupling of INTERMEDIATE 11 and 4-biphenylsulfonyl chloride according to METHOD B: MS (Ionspray, [M−H]$^-$) m/z 428.3.

EXAMPLE 120A

N,N-diethyl-2-(2-{[(4-propylphenyl)sulfonyl]amino}-1,3-thiazol-4-yl)acetamide

The title compound was prepared by coupling of INTERMEDIATE 11 and 4-propylbenzenesulfonyl chloride according to METHOD B: MS (Ionspray, [M−H]$^-$) m/z 393.4.

EXAMPLE 121A 2-(2-{[(2,4-Dichloro-6-methylphenyl)sulfonyl]amino}-1,3-thiazol-4-yl)-N,N-diethylacetamide The title compound was prepared by coupling of INTERMEDIATE 11 and 2,4-dichloro-6-methylbenzenesulfonyl chloride according to METHOD B: MS (Ionspray, [M−H]$^-$) m/z 434.3.

EXAMPLE 122A

N,N-diethyl-2-(2-{[(2,4,6-trichlorophenyl)sulfonyl]amino}-1,3-thiazol-4-yl)acetamide The title compound was prepared by coupling of INTERMEDIATE 11 and 2,4,6-trichlorobenzenesulfonyl chloride according to METHOD B: MS (Ionspray, [M−H]$^-$) m/z 454.2.

EXAMPLE 123A

2-{2-[([1,1'-Biphenyl]-4-ylsulfonyl)amino]-1,3-thiazol-4-yl}-N,N-diisopropylacetamide The title compound was prepared by coupling of INTERMEDIATE 14 and 4-biphenylsulfonyl chloride according to METHOD B: MS (Ionspray, [M−H]$^-$) m/z 456.4.

EXAMPLE 124A

N,N-diisopropyl-2-(2-{[(4-propylphenyl)sulfonyl]amino}-1,3-thiazol-4-yl)acetamide The title compound was prepared by coupling of INTERMEDIATE 14 and 4-propylbenzenesulfonyl chloride according to METHOD B: MS (Ionspray, [M−H]$^-$) m/z 422.6.

EXAMPLE 125A 2-(2-{[(2,4-Dichloro-6-methylphenyl)sulfonyl]amino}-1,3-thiazol-4yl)-N,N-diisopropylacetamide The title compound was prepared by coupling of INTERMEDIATE 14 and 2,4-dichloro-6-methylbenzenesulfonyl chloride according to METHOD B: MS (Ionspray, [M−H]$^-$) m/z 462.2.

EXAMPLE 126A

N,N-diisopropyl-2-(2-{[(2,4,6-trichlorophenyl)sulfonyl]amino}-1,3-thiazol-4-yl)acetamide The title compound was prepared by coupling of INTERMEDIATE 14 and 2,4,6-trichlorobenzenesulfonyl chloride according to METHOD B: MS (Ionspray, [M−H]$^-$) m/z 482.3.

EXAMPLE 127A 2-(2-{[(3-Chloro-2-methylphenyl)sulfonyl]amino}-1,3-thiazol-4-yl)-N,N-diisopropylacetamide The title compound was prepared by coupling of INTERMEDIATE 14 and 3-chloro-2-methylbenzenesulfonyl chloride according to METHOD B: MS (Ionspray, [M−H]$^-$) m/z 427.9.

EXAMPLE 128A 2-(2-{[(3-Chloro-2-methylphenyl)sulfonyl]amino}-1,3-thiazol-4-yl)-N,N-dipropylacetamide The title compound was prepared by coupling of INTERMEDIATE 15 and 3-chloro-2-methylbenzenesulfonyl chloride according to METHOD B: MS (Ionspray, [M−H]$^-$) m/z 428.3.

EXAMPLE 129A

N-benzyl-2-(2-{[(3-chloro-2-methylphenyl)sulfonyl]amino}-1,3-thiazol-4-yl)-N-methylacetamide The title compound was prepared from EXAMPLE 87A according to METHOD E in 51% yield, using N-methylbenzylamine: MS (electrospray, [M+H]$^+$) m/z 450.2.

EXAMPLE 130A

N-benzyl-2-(2-{[(3-chloro-2-methylphenyl)sulfonyl]amino}-1,3-thiazol-4-yl)-N-ethylacetamide The title compound was prepared according to METHOD F, from EXAMPLE 87A. After the workup and purification by flash chromatography a pink solid (346 mg, 75%) was obtained: MS (Ionspray, [M+H]$^+$) m/z 464.0; Anal. Calcd (found) for $C_{21}H_{22}ClN_3O_3S_2$: C, 54.4 (54.2)%, H, 4.8 (4.7)%, N, 9.1 (9.1)%.

EXAMPLE 131A 2-(2-{[(3-Chloro-2-methylphenyl)sulfonyl]amino}-1,3-thiazol-4-yl)-N,N-dimethylacetamide The title compound was prepared according to METHOD D, from EXAMPLE 8A. After workup and purification by flash column chromatography a pink solid (75 mg, 38%) was obtained: mp 84-84° C.; MS (Ionspray, [M+H]$^+$) m/z 374.0; Anal. Calcd (found) for $C_{14}H_{16}ClN_3O_3S_2$: C, 45.0 (44.8)%, H, 4.3 (4.5)%, N, 11.2 (11.0)%.

EXAMPLE 132A 2-(2-{[(3-Chloro-2-methylphenyl)sulfonyl]amino}-1,3-thiazol-4yl)-N-cyclohexyl-N-methylacetamide The title compound was prepared from EXAMPLE 87A according to METHOD E in 52% yield, using N-methylcyclohexylamine: MS (electrospray, [M+H]$^+$) m/z 442.2.

EXAMPLE 132B

3-Chloro-N-{4-[2-(3,4-dihydro-2-(1H)-isoquinolinyl)-2-oxoethyl]-1,3-thiazol-2-yl}-2-methylbenzenesulfonamide The title compound was prepared from EXAMPLE 87A according to METHOD E in 29% yield, using 3,4-dihydro-2(1H)-isoquinoline: MS (electrospray, [M+H]$^+$) m/z 462.0.

EXAMPLE 133A 2-(2-{[(3-Chloro-2-methylphenyl)sulfonyl]amino}-1,3-thiazol-4-yl)-N-methyl-N-phenylacetamide The title compound was prepared from EXAMPLE 87A according to METHOD E in 57% yield, using N-methylaniline: MS (electrospray, [M+H]$^+$) m/z 436.2.

EXAMPLE 134A 2-(2-{[(3-Chloro-2-methylphenyl)sulfonyl]amino}-1,3-thiazol-4-yl)N-isopropyl-N-methylacetamide The title compound was prepared from EXAMPLE 87A according to METHOD E in 66% yield, using N-methylisopropylamine: MS (electrospray, [M+H]$^+$) m/z 402.2.

EXAMPLE 135A

2-{2-[([1,1'-Biphenyl]-4-ylsulfonyl)amino]-1,3-thiazol-4-yl}-N-isopropyl-N-methylacetamide The title compound was prepared by coupling of INTERMEDIATE 9 and 4-biphenylsulfonyl chloride according to METHOD B giving 108 mg (47%) of product: MS (electronspray, [M−H]$^-$) m/z 428.4.

EXAMPLE 136A

N-ethyl-N-methyl-2-(2-{[(2,4,6-trichlorophenyl)sulfonyl]amino}-1,3-thiazol-4-yl)acetamide The title compound was prepared by coupling of INTERMEDIATE 8 and 2,4,6-trichlorobenzenesulfonyl chloride according to METHOD B giving 180 mg (75%) of product: MS (electrospray, [M−H]$^-$) m/z 440.2.

EXAMPLE 137A 2-(2-{[(2,4-Dichloro-6-methylphenyl)sulfonyl]amino}-1,3-thiazol-4-yl)-N-ethyl-N-methylacetamide The title compound was prepared by coupling of INTERMEDIATE 8 and 2,4-dichloro-6-methylbenzenesulfonyl chloride according to METHOD B giving 27 mg (12%) of product: MS (electrospray, [M−H]$^-$) m/z 420.2.

EXAMPLE 138A

N-ethyl-N-methyl-2-(2-{[(4-propylphenyl)sulfonyl]amino}-1,3-thiazol-4-yl)acetamide The title compound was prepared by coupling of INTERMEDIATE 8 and 4-n-propylbenzenesulfonyl chloride according to METHOD B giving 115 mg (56%) of product: MS (electrospray, [M−H]$^-$) m/z 380.3.

EXAMPLE 139A

2-{2-[([1,1'-Biphenyl]-4-ylsulfonyl)amino]-1,3-thiazol-4-yl}-N-ethyl-N-methylacetamide The title compound was prepared by coupling of INTERMEDIATE 8 and 4-biphenylsulfonyl chloride according to METHOD B giving 143 mg (64%) of product: MS (electronspray, [M−H]$^-$) m/z 414.3.

EXAMPLE 140A 2-(2-{[(3-Chloro-2-methylphenyl)sulfonyl]amino}-1,3-thiazol-4-yl)-N-ethyl-N-methylacetamide The title compound was prepared from EXAMPLE 87 according to METHOD E in 63% yield, using N-methylethylamine: MS (electrospray, [M+H]$^+$) m/z 388.2.

EXAMPLE 141A 2-(2-{[(3-Chloro-2-methylphenyl)sulfonyl]amino}-1,3-thiazol-4-yl)-N-methyl-N-[(1S)-1-phenylethyl]acetamide The title compound was prepared from EXAMPLE 87A according to METHOD E in 45% yield, using (1S)-1-phenylethylamine: MS (electronspray, [M+H]$^+$) m/z 464.2.

EXAMPLE 142A

3-Chloro-2-methyl-N-{4-[2-oxo-2-(1-pyrrolidinyl)ethyl]-1,3-thiazol-2-yl}benzenesulfonamide The title compound was prepared according to METHOD G, from EXAMPLE 8A. After workup and purification by flash column chromatography a pale brown foam was obtained. This material was recrystallized from methanol to yield 139 mg (66%) of amber-coloured crystals: mp 107° C.; MS (Ionspray, [M+H]$^+$) m/z 400.0; Anal. Calcd (found) for $C_{16}H_{18}ClN_3O_3S_2 \cdot 1$ MeOH$\cdot 0.25$ H$_2$O: C, 46.8 (46.8)%, H, 5.2 (5.2)%, N, 9.6 (9.5)%.

EXAMPLE 143A

3-Chloro-2-methyl-N-{4-[2-oxo-2-(1-piperidinyl)ethyl]-1,3-thiazol-2-yl}benzenesulfonamide EXAMPLE 8A (200 mg, 0.53 mmol) was heated for 3 days in piperidine (2 mL) at 100° C. in a Heck vial. The reaction mixture was allowed to cool to room temperature and upon standing, brown crystals formed that were collected on a filter: MS (Ionspray, [M+H]$^+$) m/z 414.2.

EXAMPLE 144A

N-{4-[2-oxo-2-(1-piperidinyl)ethyl]-1,3-thiazol-2-yl}[1,1'-biphenyl]-4-sulfonamide The title compound was prepared by coupling of INTERMEDIATE 13 and 4-biphenylsulfonyl chloride according to METHOD B giving 122 mg (51%) of product: MS (electronspray, [M−H]$^−$) m/z 440.4.

EXAMPLE 145A

N-{4-[2-oxo-2-(1-piperidinyl)ethyl]-1,3-thiazol-2-yl}-4-propylbenzenesulfonamide The title compound was prepared by coupling of INTERMEDIATE 13 and 4-n-propylbenzenesulfonyl chloride according to METHOD B giving 146 mg (66%) of product: MS (electronspray, [M−H]$^−$) m/z 406.4.

EXAMPLE 146A 2,4-Dichloro-6-methyl-N-{4-[2-oxo-2-(1-piperidinyl)ethyl]-1,3-thiazol-2-yl}benzenesulfonamide The title compound was prepared by coupling of INTERMEDIATE 13 and 2,4-dichloro-6-methylbenzenesulfonyl chloride according to METHOD B giving 168 mg (69%) of product: MS (electronspray, [M−H]$^−$) m/z 446.3.

EXAMPLE 147A 2,4,6-Trichloro-N-{4-[2-oxo-2-(1-piperidinyl)ethyl]-1,3-thiazol-2-yl}benzenesulfonamide The title compound was prepared by coupling of INTERMEDIATE 13 and 2,4,6-trichlorobenzenesulfonyl chloride according to METHOD B giving 156 mg (62%) of product: MS (electronspray, [M−H]$^−$) m/z 466.3.

EXAMPLE 148A

3-Chloro-2-methyl-N-{4-[2-(4-morpholinyl)-2-oxoethyl]-1,3-thiazol-2-yl}benzenesulfonamide The title compound was prepared according to METHOD F, from EXAMPLE 87A. After the workup and purification by flash chromatography a pink foam was obtained. This material was recrystallized from methanol to give pink crystals (0.83 g, 69%): mp 208-209° C.; MS (Ionspray, [M+H]$^+$) m/z 416.0; Anal. Calcd (found) for $C_{16}H_{18}ClN_3O_4S_2$: C, 46.2 (46.0)%, H, 4.4 (4.6)%, N, 10.1 (10.0)%.

EXAMPLE 149A 2,4,6-Trichloro-N-{4-[2-(4-morpholinyl)-2-oxoethyl]-1,3-thiazol-2-yl}benzenesulfonamide The title compound was prepared by coupling of INTERMEDIATE 10 and 2,4,6-trichlorobenzenesulfonyl chloride according to the preparation of EXAMPLE 152A giving 162 mg (64%) of product: MS (electronspray, [M−H]$^−$) m/z 470.1.

EXAMPLE 150A 2,4-Dichloro-6-methyl-N-{4-[2-(4-morpholinyl)-2-oxoethyl]-1,3-thiazol-2-yl}benzenesulfonamide The title compound was prepared by coupling INTERMEDIATE 10 and 2,4-dichloro-6-methylbenzenesulfonyl chloride according to the preparation of EXAMPLE 152A giving 111 mg (46%) of product: MS (electronspray, [M−H]$^−$) m/z 448.1.

EXAMPLE 151A

N-{4-[2-(4-morpholinyl)-2-oxoethyl]-1,3-thiazol-2-yl}[1,1'-biphenyl]-4-sulfonamide INTERMEDIATE 10 (123 mg, 0.54 mmol) and DMAP (66 mg, 0.54 mmol) was mixed with TEA (0.15 mL, 1.08 mmol) and DMF (1 mL). 4-Biphenylsulfonyl chloride (137 mg, 0.54 mmol) was added. The mixture was left at room temperature overnight, then petrol ether (35 mL) was added. The oil that separated was purified by chromatography on silica gel (15 mL), eluting with DCM and 5% MeOH/DCM giving 22 mg (9%) of the title compound: MS (electronspray, [M−H]$^−$) m/z 442.2.

EXAMPLE 152A

N-{4-[2-(4-morpholinyl)-2-oxoethyl]-1,3-thiazol-2-yl}-4-propylbenzenesulfonamide INTERMEDIATE 10 (123 mg, 0.54 mmol) and DMAP (66 mg, 0.54 mmol) was mixed with pyridine (1 mL) and cooled in ice. 4-n-Propylbenzenesulfonyl chloride (118 mg, 0.54 mmol) was added. The mixture was kept at 4° C. overnight. The reaction mixture was then heated to 50° C. over 1.5 h, cooled and left at room temp for 4.5 h. The solvent was evaporated and the residue purified by flash-chromatography on silica gel with 0-5% MeOH/DCM as eluent giving 122 mg (55%) of the title compound: MS (electronspray, [M−H]⁻) m/z 408.3.

EXAMPLE 153A 2,4-Dichloro-N-{4-[2-(4-morpholinyl)-2-oxoethyl]-1,3-thiazol-2-yl}benzenesulfonamide INTERMEDIATE 10(0.227 g, 1.00 mmol) and DMAP (0.122 g, 1.00 mmol) were dissolved in DMF (2.0 mL) and diisopropylethylamine (0.258 g, 2.00 mmol) and DCM (1.5 mL). 2,4-Dichlorobenzenesulfonyl chloride (0.245 g, 1.00 mmol) in DCM (1.0 mL) was added to the mixture and the reaction stiffed over night. The reaction mixture was filtered though Hydromatrix column treated with aqueous hydrogen chloride (10 mL, 1 M) and eluted with DCM. The washings were concentrated and purified by silica chromatography using DCM/methanol (95:5) to give 177 mg (41%) of the title compound with HPLC purity >90%: MS (Ion spray, [M−H]⁻) m/z 434.2; 436.2, 438.2.

EXAMPLE 154A

4-Chloro-2,6-dimethyl-N-{4-[2-(4-morpholinyl)-2-oxoethyl]-1,3-thiazol-2-yl}benzenesulfonamide The title compound was prepared according to EXAMPLE 153A, using 4-chloro-2,6-dimethyl-benzenesulfonyl chloride to give 43 mg (10%) of product with HPLC purity >90%: MS (Ion spray, [M+H]⁺) m/z 430.0.

EXAMPLE 155A

N-{4-[2-(4-morpholinyl)-2-oxoethyl]-1,3-thiazol-2-yl}4-phenoxybenzenesulfonamide The title compound was prepared according to EXAMPLE 153A, using 4-phenoxybenzenesulfonyl chloride to give 117 mg (25%) of product with HPLC purity of 90%: MS (Ion spray, [M−H]⁻) m/z 458.3.

EXAMPLE 156A

2-Methyl-N-{4-[2-(4-morpholinyl)-2-oxoethyl]-1,3-thiazol-2-yl}-4-(trifluoromethoxy)benzenesulfonamide The title compound was prepared according to EXAMPLE 153A, using 2-methyl-4-(trifluoromethoxy)benzenesulfonyl chloride to give 129 mg (29%) of product with HPLC purity >90%: MS (Ion spray, [M−H]⁻) m/z 464.2.

EXAMPLE 157A

N-{4-[2-(4-morpholinyl)-2-oxoethyl]-1,3-thiazol-2-yl}-2,4-bis(trifluoromethyl)benzenesulfonamide The title compound was prepared according to EXAMPLE 153A, using 2,4-bis(trifluoromethyl)benzenesulfonyl chloride to give 98 mg (19%) of product with HPLC purity >90%: MS (Ion spray, [M−H]⁻) m/z 502.2.

EXAMPLE 158A

4-Bromo-2-methyl-N-{4-[2-(4-morpholinyl)-2-oxoethyl]-1,3-thiazol-2-yl}benzenesulfonamide The title compound was prepared according to EXAMPLE 153A, using 4-bromo-2-methyl-benzenesulfonyl chloride to give 73 mg (16%) of product with HPLC purity >90%: MS (Ion spray, [M+H]⁺) m/z 460.0, 462.0.

EXAMPLE 158B 4-(2-Furyl)-N-{4-[2-(4-morpholinyl)-2-oxoethyl]-1,3-thiazol-2-yl}benzenesulfonamide The title compound was prepared from furan-2-boronic acid (17 mg) as described in the synthetic METHOD L to give a beige solid (11.6 mg) with purity >80%. MS (pos) m/z 434.1.

EXAMPLE 158C

3'-Fluoro-6'-methoxy-N-{4-[2-(4-morpholinyl)-2-oxoethyl]-1,3-thiazol-2-yl})[1,1'-biphenyl]-4-sulfonamide The title compound was prepared from 5-fluoro-2-methoxyphenylboronic acid (25 mg) as described in the synthetic METHOD L to give a white solid (33.3 mg) with purity >90%: MS (pos) m/z 492.0; HRMS m/z 491.0987 (calc. of monoisotopic mass for $C_{22}H_{22}FN_3O_5S_2$ gives 491.0985).

EXAMPLE 158D 4-(5-Methyl-2-thienyl)-N-{4-[2-(4-morpholinyl)-2-oxoethyl]-1,3-thiazol-2-yl}benzenesulfonamide The title compound was prepared from 5-methylthiophene-2-boronic acid (21 mg) as described in the synthetic METHOD L to give a white solid (7.1 mg) with purity >90%. MS (pos) m/z 464.1.

EXAMPLE 158E

3'-Acetyl-N-{4-[2-(4-morpholinyl)-2-oxoethyl]-1,3-thiazol-2-yl}[1,1'-biphenyl]-4-sulfonamide The title compound was prepared from 3-acetylphenylboronic acid (25 mg) as described in the synthetic METHOD L to give a white solid (33.2 mg) with purity >90%. MS (pos) m/z 486.1.

EXAMPLE 158F

N-{4-[2-(4-Morpholinyl)-2-oxoethyl]-1,3-thiazol-2-yl}-4'-(trifluoromethoxy)[1,1'-biphenyl]-4-sulfonamide The title compound was prepared from 4-(trifluoromethoxy)benzeneboronic acid (31 mg) as described in the synthetic METHOD L to give a white solid (30.4 mg) with purity >90%. MS (pos) m/z 528.1.

EXAMPLE 158G

3',4'-Dichloro-N-{4-[2-(4-morpholinyl)-2-oxoethyl]-1,3-thiazol-2-yl}[1,1'-biphenyl]-4-sulfonamide The title compound was prepared from 3,4-dichlorophenylboronic acid (29 mg) as described in the synthetic METHOD L to give a white solid (27.3 mg) with purity >90%: MS (pos) m/z 512.0, 514.0; HRMS m/z 511.0196 (calc. of monoisotopic mass for $C_{21}H_{19}Cl_2N_3O_4S_2$ gives 511.0194).

EXAMPLE 158H 4-(1,3-Benzodioxol-5-yl)-N-{4-[2-(4-morpholinyl)-2-oxoethyl]-1,3-thiazol-2-yl}benzenesulfonamide The title compound was prepared from 3,4-methylenedioxyphenylboronic acid (25 mg) as described in the synthetic METHOD L to give a brown solid (5.2 mg) with purity >80%. MS (pos) m/z 488.1.

EXAMPLE 158I 4-(5chloro-2-thienyl)-N-{4-[2-(4-morpholinyl)-2-oxoethyl]-1,3-thiazol-2-yl}benzenesulfonamide The title compound was prepared from 5-chlorothiophene-2-boronic acid (24 mg) as described in the synthetic METHOD L to give a white solid (5.1 mg) with purity >90%. MS (pos) m/z 484.0, 486.0.

EXAMPLE 158J

N-{4-[2-(4-Morpholinyl)-2-oxoethyl]-1,3-thiazol-2-yl}-4-(4-pyridinyl)benzenesulfonamide The title compound was prepared from pyridine-4-boronic acid (18 mg) as described in the synthetic METHOD L, but at a temperature of 100° C. and with more palladium(II)acetate (4 mg) added, to give a white solid (4.0 mg) with purity >90%. MS (pos) m/z 445.0.

EXAMPLE 158K

N-{4'-[({4-[2-(4-morpholinyl)-2-oxoethyl]-1,3-thiazol-2-yl}amino)sulfonyl][1,1'-biphenyl]-3-yl}acetamide The title compound was prepared from 3-acetamidobenzeneboronic acid (27 mg) as described in the synthetic METHOD L to give a white solid (3.0 mg) with purity >90%. MS (pos) m/z 501.2.

EXAMPLE 158L

N-{4-[2-(4-Morpholinyl)-2-oxoethyl]-1,3-thiazol-2-yl}-4-(3-thienyl)benzenesulfonamide The title compound was prepared from thiophene-3-boronic acid (19 mg) as described in the synthetic METHOD L to give a beige solid (22.4 mg) with purity >90%: MS (pos) m/z 450.0; HRMS m/z 449.0543 (calc. of monoisotopic mass for $C_{19}H_{19}N_3O_4S_3$ gives 449.0538).

EXAMPLE 158M

N-{4-[2-(4-Morpholinyl)-2-oxoethyl]-1,3-thiazol-2-yl}-4-(2-thienyl)benzenesulfonamide The title compound was prepared from thiophene-2-boronic acid (19 mg) as described in the synthetic METHOD L to give a beige solid (6.1 mg) with purity >90%. MS (pos) m/z 450.1.

EXAMPLE 158N

4'-[({4-[2-(4-Morpholinyl)-2-oxoethyl]-1,3-thiazol-2-yl}amino)sulfonyl][1,1'-biphenyl]-4-carboxylic acid The title compound was prepared from 4-carboxyphenylboronic acid (25 mg) as described in the synthetic METHOD L to give a white solid (12.4 mg) with purity >80%. MS (pos) m/z 488.1.

EXAMPLE 158O

4'-(Methylsulfanyl)-N-{4-[2-(4-morpholinyl)-2-oxoethyl]-1,3-thiazol-2-yl}[1,1'-biphenyl]-4-sulfonamide The title compound was prepared from 4-(methylthio)phenylboronic acid (25 mg) as described in the synthetic METHOD L to give a beige solid (30.0 mg) with purity >90%. MS (pos) m/z 490.1.

EXAMPLE 158P

N-{4-[2-(4-Morpholinyl)-2-oxoethyl]-1,3-thiazol-2-yl}-3',5'-bis(trifluoromethyl)[1,1'-biphenyl]-4-sulfonamide The title compound was prepared from 3,5-bis(trifluoromethyl)phenylboronic acid (39 mg) as described in the synthetic METHOD L to give a beige solid (39.6 mg) with purity >90%. MS (pos) m/z 580.1.

EXAMPLE 158Q

4'-Chloro-N-{4-[2-(4-morpholinyl)-2-oxoethyl]-1,3-thiazol-2-yl}[1,1'-biphenyl]-4-sulfonamide The title compound was prepared from 4-chlorophenylboronic acid (23 mg) as described in the synthetic METHOD L to give a beige solid (31.1 mg) with purity >90%. MS (pos) m/z 478.1.

EXAMPLE 158R

N-{4-[2-(4-Morpholinyl)-2-oxoethyl]-1,3-thiazol-2-yl}-3'-nitro[1,1'-biphenyl]-4-sulfonamide The title compound was prepared from 3-nitrophenylboronic acid (25 mg) as described in the synthetic METHOD L to give a white solid (34.8 mg) with purity >90%: MS pos) m/z 489.1; HRMS m/z 488.0827 (calc. of monoisotopic mass for $C_{21}H_{20}N_4O_6S_2$ gives 488.0824).

EXAMPLE 158S 4-(1-Benzofuran-2-yl)-N-{4-[2-(4-morpholinyl)-2-oxoethyl]-1,3-thiazol-2-yl}benzenesulfonamide The title compound was prepared benzo[B]furan-2-boronic acid (24 mg) as described in the synthetic METHOD L to give a yellow solid (4.7 mg) with purity >80%. MS (pos) m/z 484.0.

EXAMPLE 158T

N-{4-[2-(4-Morpholinyl)-2-oxoethyl]-1,3-thiazol-2-yl}-4-(1-pyrrolidinyl)benzenesulfonamide The title compound was prepared from pyrrolidine (71 mg) as described in the synthetic METHOD N to give a solid (0.6 mg) with purity >90%. MS (pos) m/z 437.0.

EXAMPLE 158U 4-(4-Methyl-1-piperidinyl)-N-{4-[2-(4-morpholinyl)-2-oxoethyl]-1,3-thiazol-2-yl}benzenesulfonamide The title compound was prepared from 4-methylpiperidine (99 mg) as described in the synthetic METHOD N to give a solid (2.1 mg) with purity >80%. MS (pos) m/z 465.2.

EXAMPLE 158V

4-Anilino-N-{4-[2-(4-morpholinyl)$_2$-oxoethyl]-1,3-thiazol-2-yl}benzenesulfonamide The title compound was prepared from aniline (93 mg) as described in the synthetic METHOD N to give a solid (4.6 mg) with purity >90%. MS (pos) m/z 459.2.

EXAMPLE 158W 4-(Benzylamino)-N-{4-[2-(4-morpholinyl)-2-oxoethyl]-1,3-thiazol-2-yl}benzenesulfonamide The title compound was prepared from benzylamine (16 mg) as described in the synthetic METHOD M to give a solid (2.0 mg) with purity >80%. MS (pos) m/z 473.2.

EXAMPLE 158X

N-{4-[2-(4-Morpholinyl)-2-oxoethyl]-1,3-thiazol-2-yl}-4-[(2-thienylmethyl)amino]benzenesulfonamide The title compound was prepared from thiophene-2-methylamine (113 mg) as described in the synthetic METHOD N to give a solid (0.7 mg) with purity >90%. MS (pos) m/z 479.1.

EXAMPLE 158Y 4-(4-Morpholinyl)-N-{4-[2-(4-morpholinyl)$_2$-oxoethyl]-1,3-thiazol-2-yl}benzenesulfonamide The title compound was prepared from morpholine (13 mg) as described in the synthetic METHOD M to give a solid (8.3 mg) with purity >90%. MS (pos) m/z 453.1.

EXAMPLE 158Z 4-(4-Methyl-1-piperazinyl)-N-{4-[2-(4-morpholinyl)-2-oxoethyl]-1,3-thiazol-2-yl}benzenesulfonamide The title compound was prepared from N-methylpiperazine (15 mg) as described in the synthetic METHOD M to give a solid (3.9 mg) with purity >80%. MS (pos) m/z 466.2.

EXAMPLE 158ZA

N-{4-[2-(4-Morpholinyl)-2-oxoethyl]-1,3-thiazol-2-yl}-4-[(3-pyridinylmethyl)amino]benzenesulfonamide The title compound was prepared from 3-(aminomethyl)pyridine (108 mg) as described in the synthetic METHOD N to give a solid (0.9 mg) with purity >70%. MS (pos) m/z 474.1.

EXAMPLE 159A 2,4-Dichloro-6-methyl-N-{5-methyl-4-[2-(4-morpholinyl)$_2$-oxoethyl]-1,3-thiazol-2-yl}benzenesulfonamide The title compound was essentially prepared according METHOD B from INTERMEDIATE 16 and 2,4-dichloro-6-methylbenzenesulfonyl chloride. This procedure gave ivory crystals after recrystallization from methanol (117 mg, 60%): mp 186-187° C.; MS (Ionspray, [M+H]$^+$) m/z 464.0.

EXAMPLE 160A

N-{5-methyl-4-[2-(4-morpholinyl)-2-oxoethyl]-1,3-thiazol-2-yl}[1,1'-biphenyl]-4-sulfonamide The title compound was essentially prepared according METHOD B from INTERMEDIATE 16 and 4-biphenylsulfonyl chloride. This procedure gave an off-white solid material after column chromatography and trituration with methanol (75 mg, 39%): mp 204-206° C.; MS (Ionspray, [M+H]$^+$) m/z 458.0; Anal. Calcd (found) for $C_{22}H_{23}N_3O_4S_2$.1 $H_2O$: C, 55.6 (55.2)%, H, 5.3 (5.3)%, N, 8.8 (8.9)%.

EXAMPLE 161A 2,4,6-trichloro-N-{5-methyl-4-[2-(4-morpholinyl)-2-oxoethyl]-1,3-thiazol-2-yl}benzenesulfonamide The title compound was essentially prepared according METHOD B from INTERMEDIATE 16 and 2,4,6-trichlorobenzenesulfonyl chloride. This procedure gave ivory crystals after recrystallization from methanol (151 mg, 74%): mp 216-217° C.; MS (Ionspray, [M+H]$^+$) m/z 486.0; Anal. Calcd (found) for $C_{16}H_{16}Cl_3N_3O_4S_2$.1 $CH_3OH$: C, 39.5 (39.2)%, H, 4.0 (3.9)%, N, 8.1 (8.1)%.

EXAMPLE 162A 3-chloro-2-methyl-N-{5-methyl-4-[2-(4-morpholinyl)-2-oxoethyl]-1,3-thiazol-2-yl}benzenesulfonamide The title compound was essentially prepared according METHOD B from INTERMEDIATE 16 and 3-chloro-2-methylbenzenesulfonyl chloride. This procedure gave ivory crystals after recrystallization from methanol (105 mg, 58%): mp 194-195° C.; MS (Ionspray, [M+H]$^+$) m/z 430.2; Anal. Calcd (found) for $C_{17}H_{20}ClN_3O_4S_2 \cdot 0.5 H_2O$: C, 46.5 (46.9) %, H, 4.8 (4.6)%, N, 9.6 (9.6)%.

EXAMPLE 163A

3-Chloro-N-(4-{2-[(2R,6S)-2,6-dimethylmorpholinyl]-2-oxoethyl}-1,3-thiazol-2-yl)-2-methylbenzenesulfonamide The title compound was prepared in 190/yield from EXAMPLE 87A and cis-(2R,6S)-2,6-dimethylmorpholine according to the preparation of EXAMPLE 171A: MS (electronspray, [M–H]7) m/z 442.3.

EXAMPLE 164A

3-Chloro-2-methyl-N-(4-{2-[(1S,4S)-2-oxa-5-azabicyclo[2.2.1]hept-5-yl]-2-oxoethyl}-1,3-thiazol-2-yl)benzenesulfonamide EXAMPLE 87A (40 mg, 0.115 mmol), (1S,4S)-(+)-2-aza-5-oxabicyclo[2.2.1]heptane hydrochloride (16 mg, 0.12 mmol) and DMAP (15 mg, 0.12 mmol) were dissolved in DMF (0.3 mL). EDCI (23 mg, 0.12 mmol) was added followed by diisopropylethylamine (41 μL, 0.24 mmol). The solution was left overnight, evaporated in vacuum and the residue purified by flash-chromatography on silica gel with 2% and 5% methanol/DCM as eluent. Yield 36 mg, 73%: MS (electronspray, [M–H]$^-$) m/z 426.3.

EXAMPLE 165A

3-Chloro-2-methyl-N-{4-[2-oxo-2-(4-thiomorpholinyl)ethyl]-1,3-thiazol-2-yl}benzenesulfonamide The title compound was prepared according to METHOD G, from EXAMPLE 8A using thiomorpholine. After the workup and purification by flash chromatography a pale pink solid (150 mg, 66%) was obtained: mp 103-106° C.; MS (Ionspray, [M+H]$^+$) m/z 432.2; Anal. Calcd (found) for $C_{16}H_{18}ClN_3O_3S_3$: C, 44.5 (44.4)%, H, 4.2 (4.4)%, N, 9.7 (9.5)%.

EXAMPLE 166A

N-{4-[2-oxo-2-(4-thiomorpholinyl)ethyl-]1,3-thiazol-2-yl}[1,1'-biphenyl]-4-sulfonamide The title compound was prepared by coupling of INTERMEDIATE 12 and 4-biphenylsulfonyl chloride according to METHOD B, yielding 104 mg (42%) of the product: MS (electronspray, [M–H]$^-$) m/z 458.3.

EXAMPLE 167A

N-{4-[2-oxo-2-(4-thiomorpholinyl)ethyl]-1,3-thiazol-2-yl}-4-propylbenzenesulfonamide The title compound was prepared by coupling of INTERMEDIATE 12 and 4-n-propylbenzenesulfonyl chloride according to METHOD B, yielding 171 mg (74%) of the product: MS (electronspray, [M–H]$^-$) m/z 424.2.

EXAMPLE 168A 2,4-Dichloro-6-methyl-N-{4-[2-oxo-2-(4-thiomorpholinyl)ethyl]-1,3-thiazol-2-yl}benzenesulfonamide The title compound was prepared by coupling of INTERMEDIATE 12 and 2,4-dichloro-6-methylbenzenesulfonyl chloride according to METHOD B, yielding 145 mg (57%) of the product: MS (electronspray, [M–H]$^-$) m/z 464.3.

EXAMPLE 169A 2,4,6-Trichloro-N-{4-[2-oxo-2-(4-thiomorpholinyl)ethyl]-1,3-thiazol-2-yl}benzenesulfonamide The title compound was prepared by coupling of INTERMEDIATE 12 and 2,4,6-trichlorobenzenesulfonyl chloride according to METHOD B, yielding 114 mg (43%) of the product: MS (electronspray, [M–H]$^-$) m/z 484.1.

EXAMPLE 170A

N-{4-[2-(1,1-dioxido-4-thiomorpholinyl)-2-oxoethyl]-1,3-thiazol-2-yl}-4-propylbenzenesulfonamide EXAMPLE 167A (43 mg, 0.1 mmol) was mixed with methanol (1 mL) and cooled in ice. Oxone (potassium peroxymonosulfate, 74 mg, 0.12 mmol) dissolved in water (81 mL) was added slowly. The mixture was stirred at room temperature overnight. Methanol was evaporated, water was added and the mixture was neutralized with sodium bicarbonate and extracted with DCM. The product was purified by flash chromatography using 5% methanol/DCM as eluent. Yield 16 mg, 35%: $^1$H NMR (DMSO) δ 7.65 (d, 2H), 7.35 (d, 2H), 6.5 (s, 1H), 3.85 (m, 4H), 3.75 (s, 2H), 3.25 (m, 2H), 3.1 (m, 2H), 2.6 (t, 2H), 1.6 (m, 2H), 0.9 (t, 3H). MS-ES (neg) m/z 456.2.

EXAMPLE 171A

Tert-butyl 4-[(2-{[(3-chloro-2-methylphenyl)sulfonyl]amino}-1,3-thiazol-4-yl)acetyl]-1-piperazinecarboxylate EXAMPLE 87A (278 mg, 0.8 mmol), t-butyl 1-piperazinecarboxylate (126 mg, 1.0 mmol) and DMAP (25 mg, 0.2 mmol) were stirred in DMF (3 mL). After 3 days, the DMF was removed at the rotavapor and the residue was purified by flash chromatography on silica gel with 5% methanol/DCM as eluent yielding 111 mg (27%) of the title compound: $^1$H NMR (CDCl$_3$) δ 7.98 (d, 1H), 7.53 (d, 1H), 7.22 (t, 1H), 6.35 (bs, 1H), 3.81 (s, 2H), 3.3-3.65 (m, 9H), 2.60 (s, 3H), 1.44 (s, 9H). MS-ES (neg) m/z 513.2.

EXAMPLE 171B

N-{4-[2-(4-Acetyl-1-piperazinyl)-2-oxdethyl]-1,3-thiazol-2-yl}-3-chloro-2-methylbenzenesulfonamide This compound was prepared following the procedure for the synthesis of EXAMPLE 171A using N-acetylpiperazine. This method gave 133 mg (49%) of the title compound after purification: $^1$H NMR (DMSO) δ 7.90 (d, 1H), 7.67 (d, 1H), 7.39 (t, 1H), 6.52 (s, 1H), 3.68 (s, 2H), 3.4-3.5 (8H), 2.64 (s, 3H), 2.02 (s, 3H). MS-ES neg m/z 455.4.

EXAMPLE 172A

3-Chloro-2-methyl-N-{4-[2-(4-methyl-1-piperazinyl)-2-oxoethyl]-1,3-thiazol-2-yl}benzenesulfonamide trifluoroacetate To an ice-cold suspension of EXAMPLE 8A (2.43 g, 6.44 mmol) in DCM (60 mL) was HOBT (0.98 g, 6.44 mmol), EDCI (1.23 g, 6.44 mmol) and Et$_3$N (1.30 g, 12.89 mmol) added. The mixture was stirred for 10 minutes when 1-methylpiperazine (704 mg, 7.03 mmol) was added. The reaction was going on at room temperature over night and was then extracted with 1 M HCl containing some brine. The product solidified in the organic phase, which was separated. The solvent was evaporated and the residue was dissolved in TFA. The solution was put on top of a column and the crude material was purified by reversed phase flash chromatography on LiChroprep RP-18. The product was gradient eluting with (acetonitrile in H$_2$O/0.4% conc. HCl). Pure fractions were pooled and the solvent volume was reduced by approximately 70% A precipitate was formed which was centrifuged and the clear yellow solvent was removed. The solid was dried under vacuum at 60° C. giving a white solid (1.30 g, 2.79 mmol, 48%): Mp 245° C. dec.; MS (Ionspray, [M+H]$^+$) m/z 428; Anal. Calcd. (found) for C$_{17}$H$_{21}$ClN$_4$O$_3$S$_2$.1 HCl.0.4 H$_2$O: C, 43.2 (43.2)%; H, 4.9 (4.9)%; N, 11.8 (11.9)%.

EXAMPLE 173A

3-Chloro-2-methyl-N-{4-[2-oxo-2-(1-piperazinyl)ethyl]-1,3-thiazol-2-yl}benzenesulfonamide trifluoroacetate The title compound was prepared from EXAMPLE 171A as described for the BOC-deprotection procedure in the preparation of EXAMPLE 177A: MS-ES (neg) m/z 415.2.

EXAMPLE 174A

2-Methyl-N-{4-[2-(4-methyl-1-piperazinyl)-2-oxoethyl]-1,3-thiazol-2-yl}-4-(trifluoromethoxy)benzenesulfonamide The title compound was synthesized in two steps as described for EXAMPLE 175A, staring from ethyl [2-({[2-methyl-4-(trifluoromethoxy)phenyl]sulfonyl}amino)-1,3-thiazol-4-yl]acetate (2.80 g, 6.30 mmol) to give 116 mg (48% yield) of product with a HPLC purity of 95%: $^1$H NMR (CDCl$_3$) δ 8.03 (d, 1H), 7.05 (m, 2H), 6.28 (s, 1H), 3.70 (s, 2H), 3.55 (m, 2H), 3.46 (m, 2H), 2.50 (s, 3H), 2.38 (m, 4H), 2.25 (s, 3H).

EXAMPLE 175A 2,4-Dichloro-6-methyl-N-{4-[2-(4-methyl-1-piperazinyl)-2-oxoethyl]-1,3-thiazol-2-yl}benzenesulfonamide EXAMPLE 30A (1.91 g, 4.67 mmol) was added to a solution of potassium hydroxide (5 g, 89 mmol) in water (25 mL) and ethanol (25 mL). The reaction was stirred over night, diluted with water and washed with toluene. The water phase was adjusted with aqueous hydrogen chloride (37%) to pH 1 and the solution extracted with ethyl acetate. The combined ethyl acetate layers were dried (magnesium sulfate) and concentrated to give 1.7 g (95% yield) of (2-{[(2,4-dichloro-6-methylphenyl)-sulfonyl]amino}-1,3-thiazol-4-yl)acetic acid. ($^1$H NMR (DMSO-d$_6$) δ 7.61 (d, 1H), 7.50 (d, 1H), 6.62 (s, 1H), 3.56 (s, 2H), 2.68 (s, 3H); MS (Ion spray, [M+H]$^+$) 4M/z 381.0). The acid (0.2 g, 0.525 mmol) was coupled with 1-methyl-piperazine as in method F, to give 110 mg (45% yield) of the title compound with a HPLC purity of 95%: $^1$H NMR (CDCl$_3$) δ 7.29 (d, 1H), 7.15 (d, 1H), 6.35 (s, 1H), 3.55 (s, 2H), 3.60 (m, 2H), 3.49 (m, 2H), 2.74 (s, 3H), 2.41 (m, 4H), 2.28 (s, 3H). MS (Ion spray, [M+H]$^+$) m/z 463.0.

EXAMPLE 176A 2,4-Dichloro-N-{4-[2-(4-methyl-1-piperazinyl)-2-oxoethyl]-1,3-thiazol-2-yl}benzenesulfonamide The title compound was synthesized in two steps as described for EXAMPLE 175A, starting from EXAMPLE 32A (1.60 g, 4.05 mmol) to give 10 mg (4% yield) of product with a HPLC purity of 95%: $^1$H NMR (CDCl$_3$) δ 8.08 (d, 1H), 7.42 (d, 1H), 7.33 (dd, 1H), 6.39 (s, 1H), 3.62 (m, 2H), 3.52 (m, 2H), 3.46 (s, 2H), 2.43 (m, 4H), 2.55 (s, 3H). MS (Ion spray, [M+H]$^+$) m/z 449.0, 450.0, 451.0.

EXAMPLE 177A 3-chloro-N-(4-{2-[(2R)-2,4-dimethylpiperazinyl]-2-oxoethyl}-1,3-thiazol-2-yl)-2-methylbenzenesulfonamide EXAMPLE 87A (347, 1.0 mmol) and INTERMEDIATE 7 (240 mg, 1.2 mmol) were coupled using METHOD F, giving 260 mg (49%) of t-Butyl (3R)-4-[(2-{[(3-chloro-2-methylphenyl)sulfonyl]ainino}-1,3-thiazol-4-yl)acetyl]-3-methyl-1-piperazinecarboxylate ($^1$H NMR (CDCl$_3$) δ 7.97 (d, 1H), 7.50 (d, 1H), 7.19 (t, 1H), 6.31 (bs, 1H), 4.68, 4.28 (m, 1H), 2.62 (s, 3H), 1.44 (s, 9H), 1.19, 1.13 (d, 3H). MS-ES (neg) m/z 527.3). This intermediate was treated with TFA/DCM/water (2 mL, 10:9:1 v/v/v) and stirred for 1 h. Evaporation of the volatiles gave 231 mg (87%) of the deprotected product as the TFA salt (MS-ES (pos) m/z 429.2). This product (225 mg, 0.4 mmol) was mixed with TEA (110 µL, 0.79 mmol) and 1,2-dichloroethane (2.0 mL). 370/Formalin (65 µL, 0.86 mmol) was added, followed by sodium triacetoxyborohydride (200 mg, 0.95 mmol). The mixture was stirred overnight, 5% aqueous sodium bicarbonate was added and the product was extracted with ethyl acetate. The organic phase was dried and evaporated. The residue was passed through a LiChroprep RP-18 column (Merck) and eluted with 40% acetonitrile, 1% acetic acid/water. This procedure gave 85 mg (50%) of the title compound: MS-ES (neg) m/z 441.4.

EXAMPLE 178A 2-(2-{[(3-Chloro-2-methylphenyl)sulfonyl]amino}-1,3-thiazol-4-yl)-N-methoxy-N-methylacetamide EXAMPLE 87A (346 mg, 1.0 mmol) was coupled with O,N-dimethylhydroxylamine hydrochloride (117 mg, 1.2 mmol) using METHOD F. After work up, 382 mg of a tan brown solid was obtained that was purified by flash column chromatography eluting with DCM/methanol (20:1 v/v). Pure fractions were pooled and after evaporation of the solvents, triturated with DCM/diethylether (1:1 v/v) to give 300 mg (77%) of a light pink solid: mp 168-169° C.; MS (Ionspray, [M+H]$^+$) m/z 390; Anal. Calcd (found) for C$_{14}$H$_{16}$ClN$_3$O$_4$S$_2$.0.5 H$_2$O: C, 42.2 (41.9)%, H, 4.3 (4.2)%, N, 10.5 (10.3) %.

EXAMPLE 179A

3-Chloro-2-methyl-N-[4-(2-oxopentyl)-1,3-thiazol-2-yl]benzenesulfonamide

Under nitrogen (g) atmosphere, EXAMPLE 178A (200 mg, 0.51 mmol) was dissolved in THF (4 mL) and cooled to 0° C. n-Propylmagnesium chloride (0.52 mL, 2 M in diethyl ether) was added dropwise via a syringe through a septum. The resulting light green solution was allowed to warm to room temperature and quenched with aqueous HCl (1 M, 5 mL). Extraction with DCM (3×5 mL), drying of the organic phase (sodium sulfate) and evaporation in vacuo gave a crude yellow oil. Purification by flash chromatography on silicagel eluting with DCM/methanol (20:1 v/v) gave 10 mg of a white solid: MS (Ionspray, [M+H]$^+$) m/z 373.0; HRMS Calcd (found) for C$_{15}$H$_{17}$ClN$_2$O$_3$S$_2$ m/z 372.0361 (372.0369).

EXAMPLE 180A

4-Chloro-N-[4-(2-hydroxyethyl)-1,3-thiazol-2-yl]benzenesulfonamide

The title compound was prepared according to the preparation of EXAMPLE 181A, starting with EXAMPLE 2A. This gave a crude product that was purified by flash column chromatography on silica gel eluting with 20% acetone in DCM to yield 635 mg (36%) pure material: MS (Ionspray, [M+H]$^+$) m/z 318; Anal. Calcd. (found) for C$_{11}$H$_{11}$ClN$_2$O$_3$S$_2$: C, 41.4 (41.3)%; H, 3.5 (3.5)%; N, 8.8 (8.6)%.

EXAMPLE 181A

3-Chloro-N-[4-(2-hydroxyethyl)-1,3-thiazol-2-yl]-2-methylbenzenesulfonamide

To a solution of EXAMPLE 8A (5.00 g, 13.34 mmol) in THF (200 mL) was added lithium aluminum hydride (1.06 g, 28.02 mmol) in small portions. The temperature was kept below 0° C. during the addition, and the mixture was stirred for 45 min. at 0° C., treated with water (1 mL), conc. HCl (1 mL) and water (1 mL). Sodium sulfate was added and the solid was filtered off. The solvent was evaporated and the crude product was purified by flash column chromatography on silica gel eluting with 20% acetone in DCM to yield the title compound (2.41 g, 54%): MS (Ionspray, [M+H]$^+$) m/z 332; Anal. Calcd. (found) for C$_{12}$H$_{13}$ClN$_2$O$_3$S$_2$: C, 43.3 (46.5)%; H, 3.9 (4.0)%; N, 8.4 (8.3)%.

EXAMPLE 181B

3-Chloro-N-[4-(3-hydroxypropyl)-1,3-thiazol-2-yl]-2-methylbenzenesulfonamide

To a solution of EXAMPLE 231B (1.91 g, 4.91 mmol) in DME (10 mL) Was added lithium borohydride (180 mg, 7.86 mmol). The mixture was refluxed for 3 h and acetic acid (2 mL) was added at room temperature. When the gas development was finished, 2-ethanolamine (1 mL) was added and the mixture was refluxed for additional 40 min. The solvent was evaporated and the residue was extracted with 2 M HCl and THF. The organic phase was separated and the solvent was evaporated. The residue was crystallised from ethanol giving 1.56 g (91%) of the title compound: $^1$H NMR (DMSO) δ 1.66 (qn, 2H), 2.46 (t, 2H), 2.64 (s, 3H), 3.68 (t, 2H), 6.41 (s, 1H), 7.37 (t, 1H), 7.66 (d, 1H), 7.89 (d, 1H); MS (Ionspray, [M+H]$^+$) m/z 346.

EXAMPLE 182A

3-Chloro-N-[4-(2-ethoxyethyl)-1,3-thiazol-2-yl]-2-methylbenzenesulfonamide

Sodium hydride (95% dry, 80 mg, 3.23 mmol) was added to a stirred solution of EXAMPLE 181A (426 mg, 1.28 mmol) in tetrahydrofuran (10 mL) at room temperature. After stirring for 15 min, the mixture was treated with ethyl iodide (400 mg, 2.56 mmol). The reaction mixture was stirred for 2 h at 55° C. and then quenched with aqueous HCl (1 M, 1 mL) and water was added. The product was extracted with DCM and dried (Sodium sulfate). Evaporation of the solvent gave a residue which was purified by flash chromatography on silica gel eluting with 10% acetone in DCM giving an oil (0.25 g, 54%) which solidified on standing: MS (Ionspray, [M+H]$^+$) m/z 360; Anal. Calcd. (found) for C$_{14}$H$_{17}$ClN$_2$O$_3$S$_2$: C, 46.6 (46.5)%; H, 4.7 (4.6)%; N, 7.8 (7.8)%.

EXAMPLE 183A

3-Chloro-N-[4-(2-isopropoxyethyl)-1,3-thiazol-2-yl]-2-methylbenzenesulfonamide

Sodium hydride (95% dry, 129 mg, 5.39 mmol) was added to a stirred solution of EXAMPLE 181A (359 mg, 1.08 mmol) in THF (10 mL) at room temperature. After stirring for 15 min, the mixture was treated with 2-iodopropane (917 mg, 5.39 mmol). After two days at 50° C., additional sodium hydride (26 mg, 1.08 mmol) and 2-iodopropane (366 mg, 2.16 mmol) were added. After stirring for 1 h the reaction mixture was acidified with 2M HCl and water was added. The product was extracted with DCM and dried (sodium sulfate). Evaporation of the solvent gave a residue which was purified by flash chromatography on silica gel eluting with 4% acetone in DCM giving (15 mg, 4%) of an oil which solidified on standing: MS (Ionspray, [M+H]$^+$) m/z 374.

EXAMPLE 184A

N-{4-[2-(benzyloxy)ethyl]-1,3-thiazol-2-yl}-3-chloro-2-methylbenzenesulfonamide

Sodium hydride (95% dry, 76 mg, 3.00 mmol) was added to a stirred solution of EXAMPLE 181A (400 mg, 1.20 mmol) in THF (10 mL) at room temperature. After stirring for 15 min. the mixture was treated with benzyl bromide (226 mg, 1.32 mmol). After 2 h at 50° C. additional sodium hydride (60 mg, 2.40 mmol) and benzyl bromide (142 mg, 1.20 mmol) were added in two equal portions under a period of 2 h. The reaction was quenched by adding 1M HCl (3 mL) at room temperature. The mixture was extracted with DCM and dried (Sodium sulfate). Evaporation of the solvent gave a residue which was purified by flash chromatography on silica gel eluting with 5% acetone in DCM giving (105 mg, 0.25 mmol, 21%) which solidified on standing: MS (Ionspray, [M+H]$^+$)

m/z 322. Anal. Calcd. (found) for $C_{19}H_{19}ClN_2O_3S_2 \cdot 0.5$ $CH_2Cl_2$: C, 50.3 (50.7)%; H, 4.3 (4.1)%; N, 6.0 (5.9)%.

EXAMPLE 185A

3-Chloro-N-[4-(2-methoxyethyl)-1,3-thiazol-2-yl]-2-methylbenzenesulfonamide

The title compound was prepared from EXAMPLE 181A according to the preparation of EXAMPLE 182A, using methyl iodide. After 1.5 h at 40° C. the reaction mixture was quenched with 2M HCl (1 mL) and water was added. The mixture was extracted with DCM and dried (Sodium sulfate). Evaporation of the solvent gave a residue which was purified by flash chromatography on silica gel eluting with 5% acetone in DCM giving a colorless oil (0.25 g, 60%) which solidified on standing: MS (Ionspray, [M+H]$^+$) m/z 346. Anal. Calcd. (found) for $C_{13}H_{15}ClN_2O_3S_2$: C, 45.0 (44.8)%; H, 4.4 (4.4)%; N, 8.1 (7.9)%.

EXAMPLE 186A

3-Chloro-N-{4-[2-(2-fluoroethoxy)ethyl]-1,3-thiazol-2-yl}-2-methylbenzenesulfonamide The title compound was prepared from EXAMPLE 181A according to the preparation of EXAMPLE 182A, using 1-fluoro-2-iodoethane (6 eq). After 5 h at reflux the reaction mixture was quenched with 2M HCl and water was added. The mixture was extracted with DCM and dried (Sodium sulfate). Evaporation of the solvent gave a residue which was purified by flash chromatography on silica gel gradient eluting with 0-20% acetone in DCM giving a colorless oil (28 mg, 6%). MS (Ionspray, [M+H]$^+$) m/z 378.

EXAMPLE 187A

3-Chloro-2-methyl-N-{4-[2-(2,2,2-trifluoroethoxy)ethyl]-1,3-thiazol-2-yl}benzenesulfonamide Sodium hydride (95% dry, 253 mg, 10.00 mmol) was added to a stirred solution of 2,2,2-tirluoroethanol (1.00 g, 10.00 mmol) in THF (15 mL) at 0° C. under nitrogen atmosphere. After stirring for 15 minutes at room temperature, the temperature was lowered to −80° C. using an ethanol-dry ice bath. Trifluoromethanesulfonyl chloride (1.69 g, 10.00 mmol) dissolved in THF (5 mL) was then added in small portions, and the mixture was then left to reach room temperature over night. The reaction mixture was centrifuged and the white precipitate was separated. The solvent was diluted with THF to 25 mL (assumed concentration: 0.4 M). The prepared 2,2,2-trifluoroethyl trifluoromethanesulfonate solution (7.5 mL, 0.4 M) was added to a mixture of EXAMPLE 181A (500 mg, 1.5 mmol) and sodium hydride (95% dry, 94 mg, 3.73 mmol) in THF (10 mL) at 0° C. under nitrogen atmosphere. After stirring at 0° C. for 1.5 h an additional amount of sodium hydride (95% dry, 76 mg, 3.00 mmol) and 2,2,2-trifluoroethyl trifluoromethanesulfonate solution (7.5 mL) was added. After 1 h at 0° C. was die mixture poured on to ice and neutralized with 2.0 M HCl and extracted with DCM. Evaporation of the organic solvent gave a residue which was purified by flash chromatography on silica gel eluting with a 2-5% acetone gradient in DCM. This gave 174 mg (28%) of a white solid: MS (Ionspray, [M+H]$^+$) m/z 414.

Anal. Calcd. (found) for $C_{14}H_{14}ClF_3N_2O_3S_2$: C, 40.5 (40.5)%; H, 3.4 (3.4)%; N, 6.7 (6.7)%.

EXAMPLE 188A

3-Chloro-2-methyl-N-{4-[2-(2-pyridinylsulfanyl)ethyl]-1,3-thiazol-2-yl}benzenesulfonamide Sodium hydride (95% dry, 31 mg, 1.21 mmol) was added to a stirred solution of the bromide EXAMPLE 213A (240 mg, 0.61 mmol) and 2-mercaptopyridine (68 mg, 0.61 mmol) in tetrahydrofuran (10 mL) at 0° C. After stirring for 30 minutes at 0° C. product was slowly formed. The temperature was elevated to 40° C. and after 30 minutes, the reaction was neutralised by adding aqueous HCl (2 M) and the mixture was extracted with DCM. The organic phase was dried (sodium sulfate) and the solvent was evaporated. The crude material was purified by flash chromatography on silica gel gradient eluting with 2-5% acetone in DCM giving a solid (130 mg, 50%). MS (Ionspray, [M+H]$^+$) m/z 425; Anal. Calcd. (found) for $C_{17}H_{16}ClN_3O_2S_3$: C, 47.9 (47.9)%; H, 3.8 (3.9)%; N, 9.9 (9.9)%.

EXAMPLE 189A

3-Chloro-2-methyl-N-{4-[2-(3-pyridinyloxy)ethyl]-1,3-thiazol-2-yl}benzenesulfonamide Sodium hydride (95% dry, 32 mg, 1.27 mmol) was added to a stirred solution of bromide EXAMPLE 213A (240 mg, 0.61 mmol) and 3-hydroxypyridine (63 mg, 0.67 mmol) in tetrahydrofuran (10 mL) at 0° C. After 2 h at reflux temperature the reaction was neutralized by adding 2 M HCl and the product mixture was extracted with DCM. The organic phase was dried (Sodium sulfate) and the solvent was evaporated. The crude material was purified by flash chromatography on silica gel gradient eluting with 2-5% acetone in DCM giving the title compound as a solid (18 mg, 7%) and 3-chloro-2-methyl-N-(4-vinyl-1,3-thiazol-2-yl)benzenesulfonamide as a solid (33 mg, 17%). EXAMPLE 189A: MS (Ionspray, [M+H]$^+$) m/z 410.

EXAMPLE 189B

Methyl 2-[2-(2-{[(3-chloro-2-methylphenyl)sulfonyl]amino}-1,3-thiazol-4-yl)ethoxy]benzoate INTERMEDIATE 23 (124 mg, 0.445 mmol) and DMAP (54 mg, 0.44 mmol) were dissolved in DCM (2 mL). TEA (0.12 mL, 0.89 mmol) was added followed by 3-chloro-2-methylbenzenesulfonyl chloride (105 mg, 0.468 mmol). The solution was kept at room temperature over night and then at 4° C. for 3 days. Evaporation and chromatography on silica gel with 35% ethyl acetate/toluene gave the title product (91 mg, 44% yield): MS-ES (neg) m/z 465.5; $^1$H NMR (CDCl$_3$) δ 7.99 (m, 2H), 7.4-7.55 (m, 2H), 7.16 (m, 1H), 7.03 (t, 1H), 6.87 (d, 1H), 6.11 (s, 1H), 4.18 (t, 2H), 3.95 (s, 3H), 3.01 (t, 2H), 2.80 (s, 3H).

EXAMPLE 190A

3-Chloro-N-[5-[(dimethylamino)methyl]-4(2-ethoxyethyl)-1,3-thiazol-2-yl]-2-methylbenzenesulfonamide A solution of EXAMPLE 182A (360 mg, 1 mmol), dimethylamine hydrochloride (164 mg, 2 mmol), 37% formaldehyde (0.5 mL) in acetic acid (5 mL) was heated at 100° C. for 5.5 hrs. The solvent was evaporated. The residue was dissolved in water (5 mL). The pH of the water solution was adjusted to 9 with 2 N NaOH. The precipitate was filtered, washed with water and dried to give the product as white powder (115.4 mg, 28% yield): mp 152-153° C.; MS m/e, 420, 418 (M$^+$)

EXAMPLE 191A 2-(2-{[(3-Chloro-2-methylphenyl)sulfonyl]amino}-1,3-thiazol-4-yl)ethyl methanesulfonate EXAMPLE 181A (1.0 g, 3.0 mmol) was suspended in DCM (15 mL) and Et$_3$N (0.9 g, 8.4 mmol) was added dropwise while stirring at 0° C. Methane sulfonyl chloride (0.5 g, 4.2 mmol) was added and the coloured suspension was allowed to warm to room temperature and stirred for 4 h. Washing with aqueous HCl (1 M, 2×40 mL), drying (sodium sulfate) and evaporation of the organic phase gave crude material. Purification by preparative straight phase HPLC gave 0.7 g (54%) of an off-white solid: MS (Ionspray, [M+H]$^+$) m/z 411; Anal. Calcd (found) for C$_{13}$H$_{15}$ClN$_2$O$_5$S$_3$: C, 38.0 (37.9)%, H, 3.7 (4.0)%, N, 6.8 (6.6)%

EXAMPLE 191B 3-(2-{[(3-chloro-2-methylphenyl)sulfonyl]amino}-1,3-thiazol-4-yl)propyl methanesulfonate The title compound was essentially prepared according to the synthesis described for EXAMPLE 191A starting with EXAMPLE 181B (1.51 g, 4.36 mmol). After the workup procedure, the crude material was purified by flash chromatography on silica gel eluting with 5% acetone in DCM giving 1.00 g (54%) of an oil: $^1$H NMR (CDCl$_3$) δ 2.63 (s, 3H), 2.77 (s, 3H), 2.87 (s, 3H), 3.02 t, 2H), 3.44 (t, 2H), 6.34 (s, 1H), 7.24 (t, 1H), 7.55 (dd, 1H), 8.00 (dd, 1H); MS (Ionspray, [M+H]$^+$) m/z 423.

EXAMPLE 192A 2-(2-{[(3-Chloro-2-methylphenyl)sulfonyl]amino}-1,3-thiazol-4-yl)ethyl acetate The title compound was prepared according to METHOD J by coupling EXAMPLE 181A and acetyl chloride, giving 79 mg (70%) white foam after purification: HRMS Calcd (found) for C$_{14}$H$_{15}$ClN$_2$O$_4$S$_2$ m/z 374.0162 (374.0144).

EXAMPLE 192B 2-(2-{[(3-Chloro-2-methylphenyl)sulfonyl]amino}-1,3-thiazol-4-yl)ethyl propionate The title compound was prepared according to METHOD J by coupling EXAMPLE 181A and propionyl chloride, giving 104 mg (89%) of a white solid after purification: mp 122° C.; HRMS Calcd (found) for C$_{15}$H$_{17}$ClN$_2$O$_4$S$_2$ m/z 388.0318 (388.0307).

EXAMPLE 193A 2-(2-{[(3-Chloro-2-methylphenyl)sulfonyl]amino}-1,3-thiazol-4-yl)ethyl 2-methylpropanoate The title compound was prepared according to METHOD J by coupling EXAMPLE 181A and isobutyryl chloride, giving 58 mg (48%) of a white solid after purification: mp 118° C.; HRMS Calcd (found) for C$_{16}$H$_{19}$ClN$_2$O$_4$S$_2$ m/z 402.0475 (402.0473).

EXAMPLE 194A 2-(2-{[(3-Chloro-2-methylphenyl)sulfonyl]amino}-1,3-thiazol-4-yl)ethyl 2-furoate The title compound was prepared according to METHOD J by coupling EXAMPLE 181A and 2-furoyl chloride, giving 96 mg (75%) of a white solid after purification: HRMS Calcd (found) for C$_{17}$H$_{15}$ClN$_2$O$_5$S$_2$ m/z 426.0111 (426.0112).

EXAMPLE 195A 2-(2-{[(3-chloro-2-methylphenyl)sulfonyl]amino}-1,3-thiazol-4-yl)ethyl benzoate The title compound was prepared according to METHOD J by coupling EXAMPLE 181A and benzoyl chloride, giving 104 mg (80%) of a white foam after purification: HRMS Calcd (found) for Cl$_9$H$_{17}$ClN$_2$O$_4$S$_2$ m/z 436.0318 (436.0314).

EXAMPLE 196A 2-(2-{[(3-Chloro-2-methylphenyl)sulfonyl]amino}-1,3-thiazol-4-yl)ethyl 4-morpholinecarboxylate The title compound was prepared according to METHOD K starting from EXAMPLE 181A and using morpholine as the amine, giving 56 mg (42%) of a white solid after purification: mp 161° C.; HRMS Calcd (found) for C$_{17}$H$_{20}$ClN$_3$O$_5$S$_2$ m/z 445.0533 (445.0525).

EXAMPLE 197A 2-(2-{[(3-Chloro-2-methylphenyl)sulfonyl]amino}-1,3-thiazol-4-yl)ethyl diethylcarbamate The title compound was prepared according to METHOD K starting from EXAMPLE 181A and using N,N-diethylamine as the amine, giving 72 mg (56%) of a white solid after purification: $^1$H NMR (CDCl$_3$) δ 1.07-1.10 (m, 6H), 2.68 (s, 31), 2.99 (t, 2H), 3.21-3.27 (m, 4H), 4.33 (t, 2H), 6.15 (s, 1H), 7.22 (t, 1H), 7.53 (d, 1H), 8.02 (d, 1H), 11.17 (br s, NH).

EXAMPLE 198A 2-(2-{[(3-Chloro-2-methylphenyl)sulfonyl]amino}-1,3-thiazol-4-yl)ethyl ethylcarbamate The title compound was prepared according to METHOD K starting from EXAMPLE 181A and using N-ethylamine as the amine, giving 78 mg (64%) of a white solid after purification: HRMS Calcd (found) for C$_{15}$H$_{18}$ClN$_3$O$_4$S$_2$ m/z 403.0427 (403.0413).

EXAMPLE 199A

N-[4-(2-azidoethyl)-1,3-thiazol-2-yl]-3-chloro-2-methylbenzenesulfonamide

A mixture of EXAMPLE 191A (1.00 g, 2.43 mmol) and sodium azide (791 mg, 12.17 mmol) in ethanol (30 mL) was refluxed for 2.5 h. The solvent was evaporated and the crude material was extracted with ethyl acetate. The organic phase was dried (Sodium sulfate) and the solvent was evaporated. The crude product was purified by flash column chromatography on silica gel eluting with 2-5% acetone in DCM to yield the title product (633 mg, 1.77 mmol, 70%): MS (Ionspray, [M+H]$^+$) m/z 357.

EXAMPLE 200A

N-[4-(2-aminoethyl)-1,3-thiazol-2-yl]-3-chloro-2-methylbenzenesulfonamide

EXAMPLE 191A (1.00 g, 2.43 mmol) was stirred in 25% amoniumhydroxide (40 mL) for 1 h at 80° C. About 10 mL of the solvent was evaporated and the solid was filtered off giving 0.69 g (85%) of pure title compound: $^1$H NMR (DMSO) δ 2.63 (m, 5H), 2.99 (t, 2H), 6.21 (s, 1H), 7.24 (t, 1H), 7.49 (d, 1H), 7.85 (d, 1H); MS (Ionspray, [M+H]$^+$) m/z 331.

EXAMPLE 200B

3-Chloro-2-methyl-N-{4-[2-(methylamino)ethyl]-1,3-thiazol-2-yl}benzenesulfonamide EXAMPLE 191A (1.50g, 3.66 mmol) was stirred in 40% aqueous methylamine (12 mL) for 30 min at 80° C. Most of the solvent was evaporated, water was added and the product was extracted with DCM (150 mL) giving 1.27 g (quant.) of the title compound: $^1$H NMR (DMSO) δ 2.57 (s, 3H), 2.63 (s, 3H), 2.68 (t, 2H), 3.09 (t, 2H), 6.24 (s, 1H), 7.25 (t, 1H), 7.50 (d, 1H), 7.85 (d, 1H); MS (Ionspray, [M+H]$^+$) m/z 345.

EXAMPLE 201A

4-Chloro-N-{4-[2-(diethylamino)ethyl]-1,3-thiazol-2-yl}benzenesulfonamide hydrochloride To an ice-cold solution of EXAMPLE 180A (1.24 g, 3.90 mmol) in pyridine (15 mL) was added 4-nitrobenzenesulfonyl chloride (1.30 g, 5.85 mmol). The mixture was stirred for 2.5 h at 0° C., and then poured into a mixture of ice (50 g) and conc. HCl (40 g). The resulting precipitate was filtered and the solid washed with water giving 1.57 g. (80%) of the intermediate sulfonate 2-(2-{[(4-Chlorophenyl)sulfonyl]amino}-1,3-thiazol-4-yl)ethyl 4-nitrobenzenesulfonate. A solution of this sulfonate (600 mg, 1.19 mmol) and diethylamine (218 mg, 2.98 µmol) in DMF (10 mL) was stirred for 3 h at 50° C. The solvent was evaporated and the residue was purified by flash column chromatography on silica gel eluting with (DCM:acetone:HCOOH; 7:2:1). The product was purified again by flash column chromatography on RP silica gel gradient eluting with (1% conc. HCl in CH$_3$CN/H$_2$O) giving a white solid (40 mg, 8%): MS (Ionspray, [M+H]$^+$) m/z 300; Anal. Calcd. (found) for C$_{15}$H$_{20}$ClN$_3$O$_2$S$_2$.1 HCl: C, 43.9 (43.8)%; H, 5.1 (4.8)%; N, 10.2 (10.0)%.

EXAMPLE 202A

3-Chloro-N-{4-[2-(diethylamino)ethyl]-1,3-thiazol-2-yl}-2-methylbenzenesulfonamide hydrochloride The title compound was prepared according to the synthesis described for EXAMPLE 204A, using mesylate EXAMPLE 191A (350 mg, 0.85 mmol), diethylamine (311 mg, 4.26 mmol) and ethanol (5 mL) giving a white solid after purification (150 mg, 0.35 mmol, 41%): MS (Ionspray, [M+H]$^+$) m/z 387; Anal. Calcd. (found) for C$_{16}$H$_{22}$ClN$_3$O$_2$S$_2$.1 HCl.0.3 H$_2$O: C, 44.6 (44.6)%; H, 5.5 (5.3)%; N, 9.8 (9.8)%.

EXAMPLE 202B

3-Chloro-N-{4-[2-(1H-imidazol-1-yl)ethyl]-1,3-thiazol-2-yl}-2-methylbenzenesulfonamide dihydrate NaH (95% dry, 32 mg, 1.28 mmol) was added to a stirred solution of EXAMPLE 191A (250 mg, 0.61 mmol) and imidazole (46 mg, 0.67 mmol) in THF (10 mL) at room temperature. The mixture was stirred for 2 h at 40° C. when additional imidazole (41 mg, 0.61 mmol) and NaH (95% dry, 15 mg, 0.61 mmol) was added. The reaction was allowed to proceed for 1.5 h and was then neutralized by adding aqueous HCl (2 M). The solvent was evaporated and the resulting crude material was dissolved in TFA and purified by reversed phase flash chromatography on LiChroprep RP-18. The product was gradient eluting with (CH$_3$CN in H$_2$O/0.4% conc. HCl) to yield (80 mg, 0.21 mmol, 34%): MS (Ionspray, [M+H]$^+$) m/z 382. Anal. Calcd. (found) for C$_{15}$H$_{15}$ClN$_4$O$_2$S$_2$.2 H$_2$O: C, 43.0 (42.9)%; H, 4.6 (4.3)%; N, 13.4 (13.7)%.

EXAMPLE 203A

3-Chloro-2-methyl-N-{4-[2-(4-methyl-1-piperazinyl)ethyl]-1,3-thiazol-2-yl}benzenesulfonamide dihydrochloride The title compound was prepared according to the synthesis described for EXAMPLE 204A, using mesylate EXAMPLE 191A (300 mg, 0.73 mmol), 1-methylpiperazine (183 mg, 1.82 mmol) and ethanol (5 mL) giving a white solid after purification (168 mg, 0.34 mmol, 47%): MS (Ionspray, [M+H]$^+$) m/z 414; Anal. Calcd. (found) for C$_{17}$H$_{23}$ClN$_4$O$_2$S$_2$.2 HCl.1.5 H$_2$O: C, 39.6 (39.6)%; H, 5.5 (5.3)%; N, 10.9 (10.9)%.

EXAMPLE 204A

3-Chloro-2-methyl-N-{4-[2-(4-morpholinyl)ethyl]-1,3thiazol-2-yl}benzenesulfonamide hydrochloride Morpholine (165 mg, 1.89 mmol) was added to a stirring solution of EXAMPLE 213A (300 mg, 0.76 mmol) in ethanol (5 mL). The mixture was refluxed for 1.5 h and the solvent was evaporated. The crude material was purified by reversed phase flash chromatography on LiChroprep RP-18. The product was gradient eluting with (acetonitrile in water/0.1% conc. HCl) giving a white solid (177 mg, 53%): Mp 197-198° C.; MS (Ionspray, [M+H]$^+$) m/z 401; Anal. Calcd. (found) for C$_{16}$H$_{20}$ClN$_3$O$_3$S$_2$.1 HCl: C, 43.8 (43.5)%; H, 4.8 (4.9)%; N, 9.6 (9.5)%.

EXAMPLE 204B

3-Chloro-2-methyl-N-[4-(4-morpholinylmethyl)-1,3-thiazol-2-yl]benzenesulfonamide hydrochloride A mixture of INTERMEDIATE 19 (0.50 g, 2.70 mmol) and morpholine (1.65 g, 18.92 mmol) was stirred at room temperature over night. The solvent was evaporated and the solid residue was purified by reversed phase flash chromatography on LiChroprep RP-18. The product was eluting with (1% CH$_3$CN in H$_2$O/0.5% conc. HCl) giving approximately a 1:1 mixture of 4-(4-morpholinylmethyl)-1,3-thiazol-2-amine dihydrochloride and morpholine (1.33 g). This material was sulphonylated with 3-chloro-2-methylbenzenesulphonyl chloride according to the preparation as described for EXAMPLE 205A giving 17 mg (6%) of a solid: $^1$H NMR (DMSO) δ 2.65 (s, 3H), 3.08 (br m, 4H), 3.78 (br m, 4H), 4.13 (br s, 2H), 7.07 (s, 1H), 7.40 (t, 1H), 7.68 (d, 1H), 7.91 (d, 1H); MS (Ionspray, [M+H]$^+$) m/z 387.

EXAMPLE 205A 2,4,6-Trichloro-N-{4-[2-(4-morpholinyl)ethyl]-1,3-thiazol-2-yl}benzenesulfonamide hydrochloride To a mixture of INTERMEDIATE 17 (50 mg, 0.23 mmol) and sodium bicarbonate (39 mg, 0.47 mmol) in acetone (5 mL) was added 2,4,6-trichlorobenzenesulphonyl chloride (79 mg, 0.28 mmol) at room temperature. The reaction mixture was refluxed for 45 minutes and the solvent was evaporated. The crude material was purified by reversed phase flash chromatography on LiChroprep RP-18. The product was gradient eluting with (acetonitrile in $H_2O$/0.4% conc. HCl) giving a white solid (59 mg, 0.12 mmol, 52%): MS (Ionspray, $[M+H]^+$) m/z 372; Anal. Calcd. (found) for $C_{15}H_{16}Cl_3N_3O_3S_2$.1 HCl.7 $H_2O$: C, 35.6 (35.7)%; H, 3.7 (3.5)%; N, 8.3 (7.6)%.

EXAMPLE 206A 2,4-Dichloro-N-{4-[2-(4-morpholinyl)ethyl]-1,3-thiazol-2-yl}benzenesulfonamide hydrochloride The title compound was prepared according to the synthesis described for EXAMPLE 205A, using INTERMEDIATE 17 (100 mg, 0.47 mmol), sodium bicarbonate (79 mg, 0.94 mmol), 2,4-dichlorobenzenesulphonyl chloride (150 mg, 0.61 mmol) and acetone (10 mL) giving a white solid (88 mg, 0.19 mmol, 41%) after purification: MS (Ionspray, $[M+H]^+$) m/z 421; Anal. Calcd. (found) for $C_{15}H_{17}Cl_2N_3O_3S_2$.1 HCl.1.1 $H_2O$: C, 37.6 (37.7)%; H, 4.3 (4.5)%; N, 8.8 (8.7)%.

EXAMPLE 206B 2,4-Dichloro-6-methyl-N-{4-[2-(4-morpholinyl)ethyl]-1,3-thiazol-2-yl}benzenesulfonamide hydrochloride The title compound was prepared according to the synthesis described for EXAMPLE 205A, using INTERMEDIATE 17 (100 mg, 0.47 mmol), sodium bicarbonate (79 mg, 0.94 mmol), 2,4,-dichloro-6-methylbenzenesulphonyl chloride (158 mg, 0.61 mmol) and acetone (10 mL) giving a solid (60 mg, 0.13 mmol, 27%) after purification: MS (Ionspray, $[M+H]^+$) m/z 435. Anal. Calcd. (found) for $C_{16}H_{19}Cl_2N_3O_3S_2$.1 HCl: C, 40.6 (40.4)%; H, 4.3 (4.3)%; N, 8.9 (8.6)%.

EXAMPLE 206C

N-{4-[2-(4-Morpholinyl)ethyl]-1,3-thiazol-2-yl-}-4-propylbenzenesulfonamide hydrochloride The title compound was prepared according to the synthesis described for EXAMPLE 205A, using INTERMEDIATE 17 (100 mg, 0.47 mmol), sodium bicarbonate (79 mg, 0.94 mmol), 4-n-propylbenzenesulphonyl chloride (133 mg, 0.61 mmol) and acetone (10 mL) giving a solid (17 mg, 0.04 mmol, 8%): MS (Ionspray, $[M+H]^+$) m/z 495.

EXAMPLE 207A

3-Chloro-N-{4-[2-(ethylamino)ethyl]-1,3-thiazol-2-yl}-2-methylbenzenesulfonamide A mixture of ethylamine (3.2 mL 2M in THF) and EXAMPLE 191A (0.100 g, 0.244 mmol) in THF (2 mL) was heated for 48 h in a sealed glass tube at 60° C. The solvent was removed and the crude material was purified by silica gel chromatography eluting with 10% methanol in DCM. The product was isolated as a white solid (0.044 g, 50% yield): $^1$H NMR ($CD_3OD$) δ 7.75 (dd, 1H), 7.52 (dd, 1H), 7.23 (dt, 1H), 6.37 (s, 1H), 3.20 (t, 2H), 3.04 (q, 2H), 2.81 (t, 2H), 2.71 (d, 3H), 1.29 (t, 3H); LCMS (pos) m/z 360.0

EXAMPLE 208A

3-Chloro-N-(4-{2-[(2-hydroxyethyl)amino]ethyl}-1,3-thiazol-2-yl)-2-methylbenzenesulfonamide EXAMPLE 191A (0.100 g, 0.244 mmol) was heated together with 2-aminoethanol (0.150 g, 2.44 mmol) in THF (1.5 mL) at 60° C. for 5 h. The solvent was removed and the crude yellow oil was dissolved in methanol and eluted through a Hydromatrix Chemelute CE1003 charged with saturated aqueous sodium hydrogen carbonate (1 mL) using DCM/methanol (25 mL 1.5/1 v/v). The material was purified by silica gel chromatography eluting with 10% methanol in DCM. The title compound was isolated as a pale yellow oil (36 mg, 39% yield): $^1$H NMR ($CD_3OD$) δ 7.95 (d, 1H), 7.5 (d, 1H), 7.25 (t, 1H), 6.35 (s, 1H), 3.80 (dd, 2H), 3.21 (t, 2H), 3.08 (m, 2H), 2.82 (t, 2H), 2.72 (s, 3H). LCMS (pos) m/z 375.9

EXAMPLE 208B

3-Chloro-N-(4-{3-[(2-hydroxyethyl)amino]propyl}-1,3-thiazol-2-yl)-2-methylbenzenesulfonamide hydrochloride hydrate 2-Ethanolamine (1.43 g, 23.37 mmol) was added to EXAMPLE 191B (993 mg, 2.34 mmol) and the mixture was stirred at 60° C. for 2 h. A solid was formed. Water was added at room temperature and the mixture was centrifuged. The solvent was poured off, filtered and evaporated. The filtrate residue was flash chromatographed on RP silica gel eluting with 20% acetonitrile in $H_2O$/1% conc. HCl giving 184 mg (18%) of the title product: MS (Ionspray, $[M+H]^+$) m/z 389. Anal. Calcd. (found) for $C_{15}H_{20}ClN_3O_3S_2$.1 HCl.1.8 $H_2O$: C, 39.3 (39.3)%; H, 5.4 (5.5)%; N, 9.2 (9.3)%.

EXAMPLE 209A

N-[2-(2-{[(3-chloro-2-methylphenyl)sulfonyl]amino}-1,3-thiazol-4-yl)ethyl]-N-ethylacetamide EXAMPLE 207A (40 mg, 0.11 mmol) was dissolved in pyridine (0.3 mL). Acetyl chloride (12 mg, 0.13 mmol) was added and the reaction was stirred at ambient temperature for 1 h. DCM (25 mL) was added and the organic phase was extracted with aqueous HCl (25 mL, 2 M), and dried over sodium sulfate. Removal of the solvents in vacuo gave the title product as a white solid (46 mg, 100% yield): LCMS (pos) m/z 402.2.

EXAMPLE 210A

3-Chloro-2-methyl-N-{4-[2-(3-oxo-4-morpholinyl)ethyl]-1,3-thiazol-2-yl}benzenesulfonamide The title compound was prepared according to METHOD A from INTERMEDIATE 6 (27 mg, 0.118 mmol) and 3-chloro-2-methylbenzenesulfonyl chloride (45 mg, 0.20 mmol). The crude reaction mixture was dissolved in DCM (25 mL) and washed with aqueous HCl (2 M, 2×25 mL). The organic phase was dried (sodium sulfate), filtered and the solvent was removed in vacuo to give 50 mg of crude material. Purification on RP gel chromatography (a gradient of acetonitrile in water, 25-50% with 0.1% TFA) gave a pale yellow solid (29 mg, 46% ): LCMS (pos) m/z 416.1.

EXAMPLE 210B

3-Chloro-N-{4-[2-(2-hydroxy-3-oxo-4-morpholinyl) ethyl]-1,3-thiazol-2-yl}-2-methylbenzenesulfonamide To a slurry of EXAMPLE 208A (0.759 g, 2.02 mmol) in ethyl acetate (6 mL) and saturated sodium carbonate (6 mL) at 0° C., 2,2-dichloroacetic acid chloride was added neat in portions (15×40 µl 3 eq.). The mixture was stirred for 1.5 h at room temperature. The reaction mixture was then extracted with ethyl acetate (3×40 mL), washed with brine (40 mL), and dried over magnesium sulfate. The solvent was evaporated and 1.10 g of crude N-acetylated product was isolated as yellow oil (70% pure by HPLC). The crude 2,2-Dichloro-N-[2-(2-{[(3-chloro-2-methylphenyl)sulfonyl]amino}-1,3-thiazol-4-yl)ethyl]-N-(2-hydroxyethyl)acetamide (1.00 g, 2.05 mmol) was dissolved in THF (27 mL) and water (27 mL). The solution was cooled to 0° C. and the pH was adjusted to 14-15 with aqueous KOH (50%). After 20 h, the reaction mixture was neutralized with aqueous HCl (1 M, 12 mL). The reaction mixture was extracted with ethyl acetate (3×25 mL), and the combined organic phases was dried over magnesium sulfate. Removal of solvent and purification by silica gel chromatography (gradient of 2-4% methanol in DCM) gave the title compound as a white solid (20 mg): HRMS calcd (found) for $C_{16}H_{18}ClN_3O_5S_2$ m/z 431.0376 (431.0380).

EXAMPLE 210C 2,4-Dichloro-N-{4-[2-(3-oxo-4-morpholinyl)ethyl]-1,3-thiazol-2-yl}benzenesulfonamide INTERMEDIATE 6 (264 mg, 1.0 mmol) and DMAP (122 mg, 1.0 mmol) was mixed with DCM (2.5 mL) and $Et_3N$ (0.28 mL, 2.0 mmol). 2,4-Dichlorobenzenesulfonyl chloride (270 mg, 1.1 mmol) was added. The resulting solution was left overnight at room temperature. An additional 98 mg (0.4 mmol) of the sulfonyl chloride was added and the solution was again left overnight. The solvent was evaporated and aqueous sodium carbonate (1 M, 20 mL) was added and the solution was extracted with diethyl ether (20+10 mL). The aqueous phase was neutralized with HCl and the precipitate was filtered off. The product was purified by flash-chromatography on silica gel using 5% methanol/DCM as eluent. Yield 265 mg, 61%: $^1$H NMR (DMSO) δ 8.01 (d, 1H), 7.8 (d, 1H), 7.59 (dd, 1H), 6.57 (s, 1H), 3.95 (s, 2H), 3.76 (t, 2H), 3.53 (t, 2H), 3.26 (t, 2H), 2.68 (t, 2H); MS-ES (neg) m/z 434.3.

EXAMPLE 210D 2,4-Dichloro-6methyl-N-{4-[2-(3-oxo-4-morpholinyl)ethyl]-1,3-thiazol-2-yl}benzenesulfonamide The title compound was prepared according to method described for EXAMPLE 210C. Yield 142 mg, 32%: $^1$H NMR (DMSO) δ 7.59 (d, 1H), 7.48 (d, 1H), 6.54 (s, 1H), 3.95 (s, 2H), 3.76 (t, 2H), 3.52 (t, 2H), 3.25 (t, 2H), 2.67 (s, 3H), 2.67 (2H); MS-ES (neg) m/z 448.3.

EXAMPLE 210E 2,4,6-Trichloro-N-{4-[2-(3-oxo-4-morpholinyl) ethyl]-1,3-thiazol-2-yl}benzenesulfonamide The title compound was prepared according to method described for EXAMPLE 210C. Yield 228 mg, 48%: $^1$H NMR (DMSO) δ 7.80 (s, 2H), 6.60 (s, 1H), 3.96 (s, 2H), 3.76 (t, 2H), 3.53 (t, 2H), 3.26 (t, 2H); MS-ES (neg) m/z 470.3.

EXAMPLE 210F 4,5-Dichloro-N-{4-[2-(3-oxo-4-morpholinyl)ethyl]-1,3-thiazol-2-yl}-2-thiophenesulfonamide The title compound was prepared according to method described for EXAMPLE 210C. Yield 136 mg, 77%: $^1$H NMR (DMSO) δ 7.61 (s, 1H), 6.67 (s, 1H), 3.94 (s, 2H), 3.77 (t 2H), 3.54 (t, 2H), 3.27 (t, 2H), 2.70 (t, 2H); MS-ES (pos) m/z 442.

EXAMPLE 210G

N-{4-[2-(3-Oxo-4-morpholinyl)ethyl]-1,3-thiazol-2-yl}-4-phenoxybenzenesulfonamide The title compound was prepared according to method described for EXAMPLE 210C. Yield 142 mg, 77%: $^1$H NMR (DMSO) δ 7.76 (d, 2H), 7.44 (t, 2H), 7.22 (t, 1H), 7.0-7.15 (m, 4H), 6.51 (s, 1H), 3.95 (s, 2H), 3.76 (t, 2H), 3.51 (t, 2H), 3.25 (t, 2H), 2.65 (t, 2H); MS-ES (pos) m/z 460.

EXAMPLE 210H

3-Fluoro-N-{4-[2-(3-oxo-4-morpholinyl)ethyl]-1,3-thiazol-2-yl}benzenesulfonamide The title compound was prepared according to method described for EXAMPLE 210C. Yield 128 mg, 83%: $^1$H NMR (DMSO) δ 7.39-7.67 (m, 4H), 6.55 (s, 1H), 3.94. (s, 2H), 3.75 (t, 2H), 3.52 (t, 2H), 3.25 (t, 2H), 2.66 (t, 2H); MS-EI m/z 385.

EXAMPLE 210I

N-{4-[2-(3-Oxo-4-morpholinyl)ethyl]-1,3-thiazol-2-yl}-5-(2-pyridinyl)-2-thiophenesulfonamide The title compound was prepared according to method described for EXAMPLE 210C. Yield 74 mg, 41%: $^1$H NMR (DMSO) δ 8.54 (d, 1H), 7.98 (d, 1H), 7.87 (m, 1H), 7.76 (d, 1H), 7.54 (d, 1H), 7.35 (m, 1H), 6.61 (s, 1H), 3.95 (s, 2H), 3.75 (t, 2H), 3.52 (t, 2H), 3.25 (t, 2H), 2.68 (S 2H); MS-ES (pos) m/z 451.

EXAMPLE 210J

N-{2-Chloro-4-[({4-[2-(3-oxo-4-morpholinyl)ethyl]-1,3-thiazol-2-yl}amino)sulfonyl]phenyl}acetamide The title compound was prepared according to method described for EXAMPLE 210C. Yield 62 mg, 34%: $^1$H NMR (DMSO) δ 12.85 (bs, 1H), 9.70 (s, 1H), 7.98 (d, 1H), 7.77 (s, 1H), 7.70 (d, 1H), 6.54 (s, 1H), 3.95 (s, 2H), 3.75 (t, 2H), 3.51 (t, 2H), 3.25 (t, 2H), 2.66 (t, 2H), 2.12 (s, 3H); MS-ES (pos) m/z 459.

EXAMPLE 210K

3-Chloro-2-methyl-N-{4-[(3-oxo-4-morpholinyl)methyl]-1,3-thiazol-2-yl}benzenesulfonamide A mixture of INTERMEDIATE 21 (100 mg, 0.49 mmol), 3-chloro-2-methylbenzenesulphonyl chloride (337 mg, 1.50 mmol) and sodium bicarbonate (126 mg, 1.50 mmol) was heated neat until it melted and the heating was continued for 10 min. At room temperature the solid was extracted with ethyl acetate. The organic phase was dried (sodium sulfate), filtered and the solvent was evaporated. The residue was purified by flash chromatography on silica gel eluting with 30% acetone in DCM giving (84 mg, 43%) solid material: MS (Ionspray, [M+H]$^+$) m/z 401; Anal. Calcd. (found) for $C_{15}H_{16}ClN_3O_4S_2$: C, 44.8 (44.8)%; H, 4.0 (4.3)%; N, 10.4 (9.9)%.

EXAMPLE 210L

3-Chloro-2-methyl-N-{4-[3-(3-oxo-4-morpholinyl)propyl]-1,3-thiazol-2-yl}benzenesulfonamide To a solution of EXAMPLE 208B (187 mg, 0.44 mmol) in H$_2$O (2 mL)/THF (1 mL) was chloroacetyl chloride (110 mg, 0.97 mmol) in THF (3 mL) dropwise added under a period of 40 min. The temperature was kept at 8° C. and 2 M KOH was added continuously to adjust the pH to around 6-8. Aqueous potassium hydroxide (6 M, 0.38 mL, 1.41 mmol) was added and the mixture was stirred at room temperature for 20 min. The pH was adjusted to 8 and the mixture was extracted with ethyl acetate. The organic phase was separated and the solvent was evaporated. The residue was flash chromatographed on silica gel eluting with 30% acetone in DCM, yielding 98 mg (52%) of the title compound: MS (Ionspray, [M+H]$^+$) m/z 429. Anal. Calcd. (found) for $C_{17}H_{20}ClN_3O_4S_2$: C, 47.5 (47.4)%; H, 4.7 (4.9)%; N, 9.8 (9.5)%.

EXAMPLE 210M

3-Chloro-N,2-dimethyl-N-{4-[2-(3-oxo-4-morpholinyl)ethyl]-1,3-thiazol-2-yl}benzenesulfonamide Iodomethane (34 mg, 0.24 mmol) was added to a solution of EXAMPLE 210A (100 mg, 0.24 mmol) and N-ethyldiisopropylamine (31 mg, 0.24 mmol) in DMF (3 mL). The mixture was stirred at room temperature for 2 h and was then extracted with ethyl acetate. The organic phase was dried over sodium sulphate, filtered and the solvent was evaporated giving a solid. The solid was boiled in ethanol and was then filtered off giving 38 mg (37%) of the title compound: $^1$H NMR (DMSO) δ 2.65 (s, 3H), 2.83 (t, 2H), 3.34 (t, 3H), 3.50 (s, 3H), 3.54 (t, 2H), 3.78 (t, 2H), 3.93 (s, 2H), 6.63 (s, 1H), 7.37 (t, 1H), 7.66 (d, 1H), 7.90 (d, 1H); MS (Ionspray, [M+H]$^+$) m/z 429.

EXAMPLE 210N

3-Chloro-2-methyl-N-{4-[2-(2-methyl-3-oxo-4-morpholinyl)ethyl]-1,3-thiazol-2-yl}benzenesulfonamide EXAMPLE 208 (0.250 g, 0.665 mmol) was stirred in THF (3 mL) and water (2 mL) at 5° C. 2-Chloropropionic acid chloride was added neat (10×16 μL) while the pH was adjusted to approximately 8 with aqueous potassium hydroxide (50%). Upon completion of the acylation (monitored by HPLC), the pH was adjusted to 14-15 with aqueous KOH to effect the ring closure. The reaction mixture was extracted with ethyl acetate (3×25 mL), and the combined organic phases was dried over magnesium sulfate. Removal of solvent and purification by silica gel chromatography (gradient of 2-4% methanol in DCM) gave the product as a white solid (0.120 g, 41% yield): HRMS calcd (found) for $C_{17}H_{20}ClN_3O_4S_2$ m/z 429.0584 (429.0581).

EXAMPLE 210O

N-[2-(2-{[(3-Chloro-2-methylphenyl)sulfonyl]amino}-1,3-thiazol-4-yl)ethyl]acetamide The synthesis was performed using METHOD A, starting from EXAMPLE 200A (100 mg, 0.30 mmol), acetic acid anhydride (37 mg, 0.36 mmol) and pyridine (3 mL) giving 85 mg (76%) of the title compound after purification: MS (Ionspray, [M+H]$^+$) m/z 373; Anal. Calcd. (found) for $C_{14}H_{16}ClN_3O_3S_2$: C, 45.0 (44.3)%; H, 4.3 (4.4)%; N, 11.2 (11.0)%.

EXAMPLE 210Q

3-Chloro-2-methyl-N-{4-[2-(3-oxo-1,4-oxazepan-4-yl)ethyl]-1,3-thiazol-2-yl}benzenesulfonamide INTERMEDIATE 22 (0.133 g, 0.389 mmol) was dissolved in DCM:TFA (1:1; 9 mL) and stirred for 25 min. The solvent was evaporated and the oil (0.250 g) was dissolved in DCM (25 mL) and washed with aqueous NaOH (2 M, 2 mL). The organic phase was dried over magnesium sulphate and concentration in vacuo gave an oil that was taken up in DCM (3 mL). DMAP (45 mg, 0.35 mmol, 1.6 eq) and 3-chloro-2-methylbenzenesulfonyl chloride (0.094 g, 0.44 mmol, 2 eq.) were added. The reaction mixture was stirred overnight. The solvent was removed in vacuo and the residue was purified on silica gel by chromatography (gradient of 1% to 2% methanol in DCM) affording the title compound as a white solid (27 mg, 28% yield): HRMS calcd (found) for $C_{17}H_{20}ClN_3O_4S_2$ m/z 429.0662 (429.0568).

EXAMPLE 210R

3-Chloro-2-methyl-N-{4-[2-(2-oxo-1-pyrrolidinyl)ethyl]-1,3-thiazol-2-yl}benzenesulfonamide A mixture of EXAMPLE 200A (200 mg, 0.60 mmol), ethyl 4-bromobutyrate (118 mg, 0.60 mmol), DIEA (156 mg, 1.20) and potassium iodide (10 mg, 0.06 mmol) in ethanol (5 mL)/DMSO (2 mL) was refluxed overnight, allowed to cool to room temperature, and extracted with ethyl acetate. The organic phase was separated, dried over sodium sulphate, filtered and the solvent was evaporated. The residue was purified by flash chromatography on silica gel eluting with 20% acetone in DCM giving 18 mg (7%) of solid material: $^1$H NMR (CDCl$_3$) δ 2.00 (qn, 2H), 2.38 (t, 2H), 2.65 (s, 3H), 2.88 (t, 2H), 3.40 (t, 2H), 3.58 (t, 2H), 6.24 (s, 1H), 7.22 (t, 1H), 7.52 (dd, 1H), 8.01 (dd, 1H); MS (Ionspray, [M+H]$^+$) m/z 399.

EXAMPLE 210S

3-Chloro-2-methyl-N-{4-[2-(2-oxo-1-imidazolidinyl)ethyl]-1,3-thiazol-2-yl}benzenesulfonamide EXAMPLE 191A (6.5 g, 15.8 mmol) in THF (6 mL) was added dropwise to 1,2-ethanediamine (25 mL) at 5° C. The mixture was stirred at ambient temperature for 1 h and was then concentrated in vacuo. The residue was dissolved in MeOH (10 mL) and added dropwise to water (400 mL) at 0° C. The pale orange yellow precipitate was filtered off and dried (5.0 g, 84% yield) and used in the next step without further purification. The crude intermediate (0.381 g, 1.01 mmol) was stirred in THF (8 mL) at 0° C. and bis(trichloromethyl) carbonate (0.340 g, 1.1 mmol) in THF (2 mL) was added. The mixture was cooled to −10° C. and triethylamine (0.268 g, 2.5 mmol) in THF (3 mL) at −10° C. was added slowly. The mixture was stirred at 0° C. for 1.5h, and then allowed to warm to room temperature. Stirring continued for 40 min. Water (5 mL) was added and the resulting mixture was extracted with ethyl acetate (3×20 mL). The combined organic phases were dried (magnesium sulfate) and removed in vacuo giving a residue that was purified by reverse phase HPLC. This procedure gave 9 mg of the title compound as a white solid: HRMS calcd (found) for $C_{15}H_{17}ClN_4O_2S_2$ m/z 400.0431 (400.0414)

EXAMPLE 210T

3-Chloro-2-methyl-N-{4-[2-(2-oxo-1,3-oxazolidin-3-yl)ethyl]-1,3-thiazol-2-yl}benzenesulfonamide To a solution of EXAMPLE 208A (0.490 g, 1.45 mmol) in THF (6 mL) at 0° C. N,N'-carbonyl diimidazole (0.194 g, 1.2 mmol) was added. The reaction mixture was cooled to −10° C. and triethylamine (0.400 g, 4 mmol) in THF (3 mL) at −10° C. was added slowly. Ethyl acetate (50 mL) was added and the resulting solution was washed with 0.25 M HCL (2×15 mL), brine (30 mL) and dried over magnesium sulfate. After removal of the solvent the crude material was purified by reversed phase HPLC to give the product as white solid (0.080 g, 14% yield): HRMS calcd (found) for $C_{15}H_{16}ClN_3O_4S_2$ m/z 401.0271 (401.0260).

EXAMPLE 210U

N-[2-(2-{[(3-Chloro-2-methylphenyl)sulfonyl] amino}-1,3-thiazol-4-yl)ethyl]-N-(2-hydroxyethyl)-2-furamide A mixture of EXAMPLE 208A (131 mg, 0.3 mmol), aqueous sodium carbonate (10%, 2 mL) in THF (5 mL) was treated with furoyl chloride (117 mg, 0.9 mmol) in THF (1 mL) at 0° C. The reaction mixture was allowed to warm to room temperature and stirred over night. Ethyl acetate (20 mL) was added and the mixture was washed with water, dried (sodium sulfate) and evaporated to give an oily residue. Purification by flash column chromatography on silica gel eluting with ethyl acetate t methanol mixtures gave 51 mg (36%) of the title compound: $^1$H NMR (DMSO) δ 2.66 (s, 3H), 2.78 (t, 2H), 3.52-3.61 (m, 4H), 3.74 (t 2H), 6.45 (s, 1H), 6.52 (dd, 1H), 6.90 (d, 1H), 7.36 (t, 1H), 7.63 (dd, 1H), 7.69 (br s, 1H), 7.91 (dd, 1H), 12.62 (br s, NH).

EXAMPLE 210UA

N-[2-(2-{[(3-chloro-2-methylphenyl)sulfonyl] amino}-1,3-thiazol-4-yl)ethyl]-N-methylcyclopropanecarboxamide The synthesis was performed using synthetic METHOD A at room temperature, with EXAMPLE 200B (200 mg, 0.58 mmol), cyclopropanecarbonyl chloride (63 mg, 0.61 mmol) and pyridine (2 mL) giving 125 mg (52%) of the title compound of purification: MS (Ionspray, [M+H]$^+$) m/z 414; Anal. Calcd. (found) for $C_{17}H_{20}ClN_3O_3S_2$.0.5 $H_2O$: C, 48.4 (48.5)%; H, 5.0 (5.2)%; N, 9.9 (9.6)%.

EXAMPLE 210V

3-Chloro-2-methyl-N-{4-[2-(4-methyl-2-oxo-1-piperazinyl)ethyl]-1,3-thiazol-2-yl}benzenesulfonamide hydrochloride A mixture of EXAMPLE 191A (600 mg, 1.46 mmol), N-BOC-ethylenediamine (469 mg, 2.93 mmol) and DIEA (189 mg, 1.46 mmol) was refluxed in ethanol (10 mL) for 3 h. The solvent was evaporated and the residue was flash chromatographed on $SiO_2$ eluting with 10% methanol in DCM affording 265 mg (38%) intermediate tert-butyl 2-{[2-(2-{[(3-chloro-2-methylphenyl)sulfonyl]amino}-1,3-thiazol-4-yl)ethyl]amino}ethylcarbamate. This material (255 mg, 0.54 mmol) was dissolved in DCM (4 mL), followed by the addition of DMAP (163 mg, 1.21 mmol). Chloroacetyl chloride (134 mg, 1.18 mmol) dissolved in DCM (2 mL) was added, and the mixture was stirred for 1 h at room temperature followed by a wash with aqueous HCl (2 M). The remaining organic phase was dried over sodium sulphate, filtered and evaporated in vacuo. The residue was taken up in ethyl acetate (25 mL), and at 0° C. HCl gas was bubbled trough under a period of 3 minutes. The mixture was stirred for 10 minutes and the solvent was evaporated giving 284 mg of N-(2-aminoethyl)-2-chloro-N-[2-(2-{[(3-chloro-2-methylphenyl)sulfonyl]amino}-1,3-thiazol-4-yl)ethyl]acetamide hydrochloride. This material (280 mg, 0.57 mmol) and sodium bicarbonate (169 mg, 2.01 mmol) were refluxed in ethanol (30 mL) for 2 h. The solvent was evaporated and the residue was flash chromatographed on RP silica gel gradient eluting with (acetonitrile in $H_2O$/1% conc. HCl) giving 113 mg (47%) of 3-chloro-2-methyl-N-{4-[2-(2-oxo-1-piperazinyl) ethyl]-1,3-thiazol-2-yl}benzenesulfonamide hydrochloride.

To a solution of this material (113 mg, 0.27 mmol), 37% aqueous formaldehyde (38 uL, 1.36 mmol), 5M HCl/methanol. (22 uL, 0.11 mmol) in methanol (10 mL) was added sodium cyanaborohydride (24 mg, 0.38 mmol). The mixture was stirred at room temperature for 1 h. The solvent was evaporated and the residue was flash chromatographed on RP silica gel gradient eluting with (acetonitrile in $H_2O$/1% conc. HCl) giving 69 mg (59%) of the title compound: MS (Ionspray, [M+H]$^+$) m/z 428. Anal. Calcd. (found) for $C_{17}H_{21}ClN_4O_3S_2$.1 HCl: C, 43.9 (43.5)%; H, 5.2 (4.9)%; N, 12.0 (11.9)%.

EXAMPLE 210W

3-Chloro-2-methyl-N-(4-{2-[(methylsulfonyl)amino] ethyl}-1,3-thiazol-2-yl)benzenesulfonamide The synthesis was performed using METHOD A, with EXAMPLE 200A (100 mg, 0.30 mmol), methanesulphonyl chloride (42 mg, 0.36 mmol) and pyridine (3 mL) giving 85 mg (69%) of the title compound after purification: MS (Ionspray, [M+H]$^+$) m/z 409; Anal. Calcd. (found) for $C_{13}H_{16}ClN_3O_4S_3$: C, 38.1 (38.5)%; H, 3.9 (4.1)%; N, 10.2 (9.9)%.

EXAMPLE 210X

3-Chloro-2-methyl-N-(4-{2-[methyl(methylsulfonyl) amino]ethyl}-1,3-thiazol-2-yl)benzenesulfonamide The synthesis was performed according to METHOD A at room temperature, with EXAMPLE 200B (81 mg, 0.23 mmol), methanesulphonyl chloride (60 mg, 0.52 mmol) and pyridine (2 mL) giving 31 mg (28%) of the title compound: $^1$H NMR (CDCl$_3$) δ 2.63 (s, 3H), 2.77 (s, 3H), 2.87 (s, 3H), 3.02 t, 2H), 3.44 (t, 2H), 6.34 (s, 1H), 7.24 (t, 1H), 7.55 (dd, 1H), 8.00 (dd, 1H); MS (Ionspray, [M+H]$^+$) m/z 423.

EXAMPLE 210Y

3-Chloro-2-methyl-N-[4-(2-{[(trifluoromethyl)sulfonyl]amino}ethyl)-1,3-thiazol-2-yl]benzenesulfonamide Trifluoromethanesulphonic anhydride (128 mg, 0.45 mmol) dissolved in DCM (1 mL) was added to a solution of EXAMPLE 200A (150 mg, 0.45 mmol) in DCM (15 mL) and TEA (46 mg, 0.45 mmol) at room temperature. The mixture was stirred for 1 h and the solvent was evaporated. The crude material was purified by flash chromatography on silica gel eluting with 10% acetone in DCM giving 100 mg (48%) of a solid material: MS (Ionspray, [M+H]$^+$) m/z 463. Anal. Calcd. (found) for $C_{13}H_{13}ClF_3N_3O_4S_3$: C, 33.7 (34.0)%; H, 2.8 (2.9)%; N, 9.1 (9.0)%.

EXAMPLE 210Z

3-Chloro-2-methyl-N-[4-(2-{methyl[(trifluoromethyl)sulfonyl]amino}ethyl)-1,3-thiazol-2-yl]benzenesulfonamide Trifluoromethanesulphonic anhydride (123 mg, 0.43 mmol) dissolved in DCM (1 mL) was added to a solution of EXAMPLE 200B (150 mg, 0.43 mmol) in DCM (25 mL) and TEA (44 mg, 0.43 mmol) at room temperature. The mixture was stirred overnight and the solvent was evaporated. The crude material was purified by flash chromatography on silica gel eluting with 10% acetone in DCM giving 110 mg (53%) of solid material: MS (Ionspray, [M+H]$^+$) m/z 477. Anal. Calcd. (found) for $C_{14}H_{15}ClF_3N_3O_4S_3$: C, 35.2 (35.3)%; H, 3.2 (3.1)%; N, 8.8 (8.5)%.

EXAMPLE 210ZA

N-[2-(2-{[(3-Chloro-2-methylphenyl)sulfonyl]amino}-1,3-thiazol-4-yl)ethyl]-1-methyl-1H-imidazole-4-sulfonamide A suspension of EXAMPLE 200A (200 mg, 0.60 mmol), 1-methylimidazole-4-sulphonyl chloride (109 mg, 0.60 mmol), TEA (61 mg, 0.60 mmol) in DCM (10 mL) was refluxed for 1 h. The reaction mixture was allowed to cool to room temperature and the solid was filtered off giving 161 mg (58%) of pure title compound: MS (Ionspray, [M+H]$^+$) m/z 476; Anal. Calcd. (found) for $C_{16}H_{18}ClN_5O_4S_3$: C, 40.4 (40.2)%; H, 3.8 (3.8)%; N, 14.7 (14.6)%.

EXAMPLE 210ZB

3-Chloro-N-(4-{2-[[(3-chloro-2-methylphenyl)sulfonyl](methyl)amino]ethyl}-1,3-thiazol-2-yl)-2-methylbenzenesulfonamide The synthesis was performed using METHOD A at room temperature, with EXAMPLE 200B (150 mg, 0.43 mmol), 3-chloro-2-methylbenzenesulphonyl chloride (117 mg, 0.52 mmol) and pyridine (2 mL) giving 91 mg (39%) of the title compound after purification: MS (Ionspray, [M+H]$^+$) m/z 533; Anal. Calcd. (found) for $C_{20}H_{21}Cl_2N_3O_4S_3$: C, 45.0 (45.4)%; H, 4.0 (4.1)%; N, 7.9 (7.7)%.

EXAMPLE 213A

N-[4-(2-bromoethyl)-1,3-thiazol-2-yl]-3 chloro-2-methylbenzenesulfonamide

An ice-cold mixture of EXAMPLE 181A (2.03 g, 6.10 mmol), triphenylphosphine (4.80 g, 18.31 mmol) and carbontetrabromide (6.07 g, 18.31 mmol) in DMF (30 mL) was stirred for 1.5 h, and was then poured into water. The mixture was extracted with DCM, dried (sodium sulfate) and the solvent was evaporated. The crude material was twice purified by flash chromatography on silica gel gradient eluting with 0-4% acetone in DCM giving N-[4-(2-bromoethyl)-1,3-thiazol-2-yl]-3-chloro-2-methylbenzenesulfonamide as a solid (990 mg, 41%). MS (Ionspray, [M+H]$^+$) m/z 394; Anal. Calcd. (found) for $C_{12}H_{12}BrClN_2O_2S_2$: C, 36.4 (36.6)%; H, 3.1 (3.3)%; N, 7.1 (7.2)%.

EXAMPLE 214A

3-Chloro-N-[4-(2-chloroethyl)-1,3-thiazol-2-yl]-2-methylbenzenesulfonamide

A mixture of EXAMPLE 181A (100 mg, 0.30 mmol), triphenylphosphine (158 mg, 0.60 mmol) and carbontetrachloride (116 mg, 0.75 mmol) in DMF (2 mL) was stirred over night, and was then poured into water. The mixture was extracted with EtOAc, dried (Sodium sulfate) and the solvent was evaporated. The crude material was purified by flash chromatography on silica gel gradient eluting with 2-4% acetone in DCM giving a solid (25 mg, 24%). $^1$H NMR (CDCl$_3$) δ 2.64 (s, 3H), 3.17 (t, 2H), 3.77 (t, 2H), 6.30 (s, 1H), 7.24 (m, 2H), 7.56 (d, 1H), 8.02 (d, 1H); MS (Ionspray, [M+H]$^+$) m/z 350.

EXAMPLE 223A

3-Chloro-2-methyl-N-{4-[(5-methyl-1,3,4-oxadiazol-2-yl)methyl]-1,3-thiazol-2-yl}benzenesulfonamide EXAMPLE 87A (367 mg, 1.06 mmol) was coupled with N-acetyl hydrazine (94 mg, 1.24 mmol) using METHOD F. After purification, 330 mg (94%) of the intermediate hydrazide was obtained (mp 112° C.). This hydrazide (49 mg, 0.12 mmol) was suspended in acetonitrile (dry, 1 mL) in a Heck vial and treated with phosphorus oxychloride (100 μL, 0.593 mmol). The vial was sealed and heated at 80° C. on an oil bath for 2 h. Water (3 mL) was added and extractive work up with ethyl acetate, drying (sodium sulfate), filtration and evaporation of the volatiles at the rotavapor gave a pale brown oil that was crystallized from methanol. Pale brown crystals were obtained (17 mg, 36%): MS (Ionspray, [M+H]$^+$) m/z 385.

EXAMPLE 231B

Ethyl 3-(2-{[(3-chloro-2-methylphenyl)sulfonyl]amino}-1,3-thiazol-4-yl)propanoate Thiourea (4.86 g, 64 mmol) was dissolved in ethanol (60 mL) at 60° C. Methyl levulinate (4.16 g, 32 mmol) and iodine (8.11 g, 32 mmol) were added and the temperature was elevated to reflux. The mixture was stirred for 6 h and the solvent was evaporated. Ethyl acetate, water and sodium bicarbonate solution was added and mixture was extracted. The organic phase was dried (sodium sulphate), filtered and the solvent was evaporated giving 6 g crude product. The crude was flash cromatographed on SiO$_2$ eluting with 5% methanol in DCM giving ethyl 3-(2-amino-1,3-thiazol-4-yl)propanoate (1.33 g, 7.14 mmol, 11%). This material (1.23 g, 6.14 mmol) was sulphonylated with 3-chloro-2-methylbenzenesulphonyl chloride (1.79 g, 7.98 mmol) in pyridine (5 mL) according to METHOD A giving 1.91 g (80%) of the title product: MS (Ionspray, [M+H]⁺) m/z 388. Anal. Calcd. (found) for $C_{15}H_{17}ClN_2O_4S_2$: C, 46.3 (46.3)%; H, 4.4 (4.5)%; N, 7.2 (7.0)%.

Various embodiments of the present invention have been described above but a person skilled in the art realizes further minor alterations which would fall into the scope of the present invention. The breadth and scope of the present invention should not be limited by any of the above-described exemplary embodiments, but should be defined only in accordance with the following claims and their equivalents.

The invention claimed is:

1. A compound selected from the group consisting of:

Ethyl 2-(2-{[(2,5-dichloro-3-thienyl)sulfonyl]amino}-1,3-thiazol-4-yl)acetate,

Ethyl (2-{[(2-chlorophenyl)sulfonyl]amino}-1,3-thiazol-4-yl)acetate,

Ethyl 2-(2-{[(3-chloro-2-methylphenyl)sulfonyl]amino}-1,3-thiazol-4-yl)acetate,

Ethyl 2-{2-[([1,1'-biphenyl]-4-ylsulfonyl)amino]-1,3-thiazol-4-yl}acetate,

Ethyl 2-(2-{[(3-bromophenyl)sulfonyl]amino}-1,3-thiazol-4-yl)acetate,

Ethyl (2-{[(4-nitrophenyl)sulfonyl]amino}-1,3-thiazol-4-yl)acetate,

Ethyl (2-{[(4-methoxyphenyl)sulfonyl]amino}-1,3-thiazol-4-yl)acetate,

Ethyl (2-{[(3-chlorophenyl)sulfonyl]amino}-1,3-thiazol-4-yl)acetate,

Ethyl (2-{[(4-fluorophenyl)sulfonyl]amino}-1,3-thiazol-4-yl)acetate,

Ethyl (2-{[(3-fluorophenyl)sulfonyl]amino}-1,3-thiazol-4-yl)acetate,

Ethyl [2-({[3-({[4-(2-ethoxy-2-oxoethyl)-1,3-thiazol-2-yl]amino}carbonyl)phenyl]sulfonyl}amino)-1,3-thiazol-4-yl]acetate, Ethyl [2-({[4-({[4-(2-ethoxy-2-oxoethyl)-1,3-thiazol-2-yl]amino}carbonyl)phenyl]sulfonyl}amino)-1,3-thiazol-4-yl]acetate, Ethyl [2-({[2-(trifluoromethyl)phenyl]sulfonyl}amino)-1,3-thiazol-4-yl]acetate, Ethyl [2-({[3-(trifluoromethyl)phenyl]sulfonyl}amino)-1,3-thiazol-4-yl]acetate, Ethyl [2-({[4-(trifluoromethyl)phenyl]sulfonyl}amino)-1,3-thiazol-4-yl]acetate, Ethyl 2-(2-{[(4-bromophenyl)sulfonyl]amino}-1,3-thiazol-4-yl)acetate, Ethyl (2-{[(2-nitrophenyl)sulfonyl]amino}-1,3-thiazol-4-yl)acetate, Ethyl (2-{[(2,4-dichloro-6-methylphenyl)sulfonyl]amino}-1,3-thiazol-4-yl)acetate, Ethyl (2-{[(2,4,6-trichlorophenyl)sulfonyl]amino}-1,3-thiazol-4-yl)acetate, Ethyl (2-{[(2,4-dichlorophenyl)sulfonyl]amino}-1,3-thiazol-4-yl)acetate, Ethyl (2-{[(5-fluoro-2-methylphenyl)sulfonyl]amino}-1,3-thiazol-4-yl)acetate, Ethyl (2-{[(2-methoxy-4-methylphenyl)sulfonyl]amino}-1,3-thiazol-4-yl)acetate, Ethyl (2-{[(3,5-dichlorophenyl)sulfonyl]amino}-1,3-thiazol-4-yl)acetate, Ethyl [2-({[4-(3-chloro-2-cyanophenoxy)phenyl]sulfonyl}amino)-1,3-thiazol-4-yl]acetate, Ethyl (2-{[(3,4-dichlorophenyl)sulfonyl]amino}-1,3-thiazol-4-yl)acetate, Ethyl (2-{[(4-butoxyphenyl)sulfonyl]amino}-1,3-thiazol-4-yl)acetate, Ethyl (2-{[(4-chloro-2-methylphenyl)sulfonyl]amino}-1,3-thiazol-4-yl)acetate, Ethyl {2-[(8-quinolinylsulfonyl)amino]-1,3-thiazol-4-yl}acetate, Ethyl (2-{[(3,4-dimethoxyphenyl)sulfonyl]amino}-1,3-thiazol-4-yl)acetate, Ethyl (2-{[(4-iodophenyl)sulfonyl]amino}-1,3-thiazol-4-yl)acetate, Ethyl (2-{[(3-chloro-4-methylphenyl)sulfonyl]amino}-1,3-thiazol-4-yl)acetate, Ethyl [2-({[5-(dimethylamino)-1-naphthyl]sulfonyl}amino)-1,3-thiazol-4-yl]acetate, Ethyl (2-{[(1-methyl-1H-imidazol-4-yl)sulfonyl]amino}-1,3-thiazol-4-yl)acetate, Ethyl (2-{[(5-bromo-2-methoxyphenyl)sulfonyl]amino}-1,3-thiazol-4-yl)acetate, Ethyl (2-{[(2,5-dimethoxyphenyl)sulfonyl]amino}-1,3-thiazol-4-yl)acetate, Ethyl {2-[(2-naphthylsulfonyl)amino]-1,3-thiazol-4-yl}acetate, Ethyl (2-{[(3-bromo-5-chloro-2-thienyl)sulfonyl]amino}-1,3-thiazol-4-yl)acetate, Ethyl {2-[({5-[(benzoylamino)methyl]-2-thienyl}sulfonyl)amino]-1,3-thiazol-4-yl}acetate, Ethyl {2-[({5-[1-methyl-5-(trifluoromethyl)-1H-pyrazol-3-yl]-2-thienyl}sulfonyl)amino]-1,3-thiazol-4-yl}acetate, Ethyl (2-{[(4-cyanophenyl)sulfonyl]amino}-1,3-thiazol-4-yl)acetate, Ethyl {2-[({5-[2-(methylsulfanyl)-4-pyrimidinyl]-2-thienyl}sulfonyl)amino]-1,3-thiazol-4yl}acetate, Ethyl (2-{[(3-cyanophenyl)sulfonyl]amino}-1,3-thiazol-4-yl)acetate, Ethyl (2-{[(2,4,5-trichlorophenyl)sulfonyl]amino}-1,3-thiazol-4-yl)acetate, Ethyl [2-({[(E)-2-phenylethenyl]sulfonyl}amino)-1,3-thiazol-4-yl]acetate, Ethyl (2-{[(2,3,4-trichlorophenyl)sulfonyl]amino}-1,3-thiazol-4-yl)acetate, Ethyl (2-{[(4-bromo-2,5-difluorophenyl)sulfonyl]amino}-1,3-thiazol-4-yl)acetate, Ethyl [2-({[4-(trifluoromethoxy)phenyl]sulfonyl}amino)-1,3-thiazol-4-yl]acetate, Ethyl (2-{[(2,3-dichlorophenyl)sulfonyl]amino}-1,3-thiazol-4-yl)acetate, Ethyl (2-{[(2-bromophenyl)sulfonyl]amino}-1,3-thiazol-4-yl)acetate, Ethyl (2-{[(4,5-dichloro-2-thienyl)sulfonyl]amino}-1,3-thiazol-4-yl)acetate, Ethyl [2-({[4-(phenylsulfonyl)-2-thienyl]sulfonyl}amino)-1,3-thiazol-4-yl]acetate, Ethyl [2-({[5-phenylsulfonyl)-2-thienyl]sulfonyl}amino)-1,3-thiazol-4-yl]acetate, Ethyl (2-{[(2,6-dichlorophenyl)sulfonyl]amino}-1,3-thiazol-4-yl)acetate, Ethyl (2-{[(2-cyanophenyl)sulfonyl]amino}-1,3-thiazol-4-yl)acetate, Ethyl [2-({[4-(acetylamino)-3-chlorophenyl]sulfonyl}amino)-1,3-thiazol-4-yl]acetate, Ethyl (2-{[(5-chloro-1,3-dimethyl-1H-pyrazol-4-yl)sulfonyl]amino}-1,3-thiazol-4-yl)acetate, Ethyl (2-{[3-methoxyphenyl)sulfonyl]amino}-1,3-thiazol-4-yl)acetate, Ethyl (2-{[(4-bromo-5-chloro-2-thienyl)sulfonyl]amino}-1,3-thiazol-4-yl)acetate, Ethyl 2-{2-[(1-naphthylsulfonyl)amino]-1,3-thiazol-4-yl}acetate, Ethyl (2-{[(2,5-dichlorophenyl)sulfonyl]amino}-1,3-thiazol-4-yl)acetate,
Ethyl [2-({[4-(methylsulfonyl)phenyl]sulfonyl}amino)-1,3-thiazol-4-yl]acetate,
Ethyl [2-({[2-(methylsulfonyl)phenyl]sulfonyl}amino)-1,3-thiazol-4-yl]acetate,
Ethyl (2-{[(4-bromo-2-fluorophenyl)sulfonyl]amino}-1,3-thiazol-4-yl)acetate,
Ethyl (2-{[(2,3,4-trifluorophenyl)sulfonyl]amino}-1,3-thiazol-4-yl)acetate,
Ethyl (2-{[(7-chloro-2,1,3-benzoxadiazol-4-yl)sulfonyl]amino}-1,3-thiazol-4-yl)acetate,
Ethyl (2-{[(2,4,6-trifluorophenyl)sulfonyl]amino}-1,3-thiazol-4-yl)acetate,
2-Chloro-5-({[4-(2-ethoxy-2-oxoethyl)-1,3-thiazol-2-yl]amino}sulfonyl)-4-fluorobenzoic acid,
Ethyl (2-{[(5-chloro-2-thienyl)sulfonyl]amino}-1,3-thiazol-4-yl)acetate,
Ethyl (2-{[(2-chloro-4-fluorophenyl)sulfonyl]amino}-1,3-thiazol-4-yl)acetate,
Ethyl [2-({[5-(3-isoxazolyl)-2-thienyl]sulfonyl}amino)-1,3-thiazol-4-yl]acetate,
Ethyl (2-{[(4-bromo-2-methylphenyl)sulfonyl]amino}-1,3-thiazol-4-yl)acetate,
Ethyl (2-{[(4-phenoxyphenyl)sulfonyl]amino}-1,3-thiazol-4-yl)acetate,
Ethyl (2-{[(4-chloro-2,6-dimethylphenyl)sulfonyl]amino}-1,3-thiazol-4-yl)acetate,
Ethyl [2-({[2-methyl-4-(trifluoromethoxy)phenyl]sulfonyl}amino)-1,3-thiazol-4-yl]acetate,
Ethyl [2-({[2,4-bis(trifluoromethyl)phenyl]sulfonyl}amino)-1,3-thiazol-4-yl]acetate,
Ethyl 2-{2-[[(3-chloro-2-methylphenyl)sulfonyl](methyl)amino]-1,3-thiazol-4-yl}acetate,
Ethyl (2-{[(3-chloro-2-methylphenyl)sulfonyl]amino}-1,3-thiazol-4-yl)(oxo)acetate,
Ethyl oxo(2-{[(2,4,6-trichlorophenyl)sulfonyl]amino}-1,3-thiazol-4-yl)acetate,
Ethyl {2-[([1,1'-biphenyl]-4-ylsulfonyl)amino]-1,3-thiazol-4-yl}(oxo)acetate,
Ethyl (2-{[(2,4-dichloro-6-methylphenyl)sulfonyl]amino}-1,3-thiazol-4-yl)(oxo)acetate,
2-(2-{[(2,5-Dichloro-3-thienyl)sulfonyl]amino}-1,3-thiazol-4-yl)acetic acid,
(2-{[(2-Chlorophenyl)sulfonyl]amino}-1,3-thiazol-4-yl)acetic acid,
2-(2-{[(3-Chloro-2-methylphenyl)sulfonyl]amino}-1,3-thiazol-4-yl)acetic acid,
Isopropyl 2-(2-{[(3-chloro-2-methylphenyl)sulfonyl]amino}-1,3-thiazol-4-yl)acetate,
Phenyl 2-(2-{[(3-chloro-2-methylphenyl)sulfonyl]amino}-1,3-thiazol-4-yl)acetate,
Methyl (2-{[(3-chloro-2-methylphenyl)sulfonyl]amino}-1,3-thiazol-4-yl)acetate,
Methyl {2-[([1,1'-biphenyl]-4-ylsulfonyl)amino]-5-methyl-1,3-thiazol-4-yl}acetate,
Methyl (2-{[(4-chlorophenyl)sulfonyl]amino}-5-methyl-1,3-thiazol-4-yl)acetate,
Methyl (2-{[(3-chloro-2-methylphenyl)sulfonyl]amino}-5-methyl-1,3-thiazol-4-yl)acetate,
Methyl [2-({[4-(3-chloro-2-cyanophenoxy)phenyl]sulfonyl}amino)-5-methyl-1,3-thiazol-4-yl]acetate,
Methyl (5-methyl-2-{[(2,4,6-trichlorophenyl)sulfonyl]amino}-1,3-thiazol-4-yl)acetate,
Methyl (2-{[(2,4-dichloro-6-methylphenyl)sulfonyl]amino}-5-methyl-1,3-thiazol-4-yl)acetate, 2-(2-{[(2,5-Dichloro-3-thienyl)sulfonyl]amino}-1,3-thiazol-4-yl)-N-methylacetamide,
N-(1,3-Benzodioxol-5-ylmethyl)-2-{2-[(1-naphthylsulfonyl)amino]-1,3-thiazol-4-yl}acetamide,
N-(2-Furylmethyl)-2-{2-[(1-naphthylsulfonyl)amino]-1,3-thiazol-4-yl}acetamide,
2-(2-{[(2,4-Difluorophenyl)sulfonyl]amino}-1,3-thiazol-4-yl)-N-ethylacetamide,
N-Isopropyl-2-{2-[(1-naphthylsulfonyl)amino]-1,3-thiazol-4-yl}acetamide,
N-[2-(1H-Indol-3-yl)ethyl]-2-{2-[(1-naphthylsulfonyl)amino]-1,3-thiazol-4-yl}acetamide,
N-(Cyclohexylmethyl)-2-{2-[(phenylsulfonyl)amino]-1,3-thiazol-4-yl}acetamide,
2-(2-{[(3-Chloro-2-methylphenyl)sulfonyl]amino}-1,3-thiazol-4-yl)-N-methylacetamide,
2-(2-{[(3-Chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N-phenylacetamide,
2-(2-{[(4-Chlorophenyl)sulfonyl]amino}-1,3-thiazol-4-yl)-N-(2-furylmethyl)acetamide,
N-Benzhydryl-2-(2-{[(4-chlorophenyl)sulfonyl]amino}-1,3-thiazol-4-yl)acetamide,
2-(2-{[(4-Chlorophenyl)sulfonyl]amino}-1,3-thiazol-4-yl)-N-(tetrahydro-2-furanylmethyl)acetamide,
Ethyl 4-{[2-(2-{[(4-chlorophenyl)sulfonyl]amino}-1,3-thiazol-4-yl)acetyl]amino}-1-piperidinecarboxylate,
N-Benzhydryl-2-(2-{[(3-chloro-2-methylphenyl)sulfonyl]amino}-1,3-thiazol-4-yl)acetamide,
2-(2-{[(4-Chlorophenyl)sulfonyl]amino}-1,3-thiazol-4-yl)-N-phenylacetamide,
2-(2-{[(3-Chloro-2-methylphenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diethylacetamide,
2-{2-[([1,1'-Biphenyl]-4-ylsulfonyl)amino]-1,3-thiazol-4-yl}-N,N-diethylacetamide,
2-(2-{[(2,4-Dichloro-6-methylphenyl)sulfonyl]amino}-1,3-thiazol-4-yl)-N,N-diethylacetamide,
N,N-diethyl-2-(2-{[(2,4,6-trichlorophenyl)sulfonyl]amino}-1,3-thiazol-4-yl)acetamide,
2-{2-[([1,1'-Biphenyl]-4-ylsulfonyl)amino]-1,3-thiazol-4-yl}-N,N-diisopropylacetamide,
2-(2-{[(2,4-Dichloro-6-methylphenyl)sulfonyl]amino}-1,3-thiazol-4-yl)-N,N-diisopropylacetamide,
N,N-diisopropyl-2-(2-{[(2,4,6-trichlorophenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diisopropylacetamide,
2-(2-{[(3-Chloro-2-methylphenyl)sulfonyl]amino}-1,3-thiazol-4-yl)-N,N-dipropylacetamide,
N-benzyl-2-(2-{[(3-chloro-2-methylphenyl)sulfonyl]amino}-1,3-thiazol-4-yl)-N-methylacetamide,
N-benzyl-2-(2-{[(3-chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N,N-dimethylacetamide,
2-(2-{[(3-chloro-2-methylphenyl)sulfonyl]amino}-1,3-thiazol-4-yl)-N-cyclohexyl-N-methylacetamide,
3-Chloro-N-{4-[2-(3,4-dihydro-2(1H)-isoquinolinyl)-2-oxoethyl]-1,3-thiazol-2-yl}-2-methylbenzenesulfonamide,
2-(2-{[(3-Chloro-2-methylphenyl)sulfonyl]amino}-1,3-thiazol-4-yl)-N-methyl-N-phenylacetamide,
2-(2-{[(3-Chloro-2-methylphenyl)sulfonyl]amino}-1,3-thiazol-4-yl)-N-isopropyl-N-methylacetamide, 2-{2-[([1,1'-Biphenyl]-4-ylsulfonyl)amino]-1,3-thiazol-4-yl}-N-isopropyl-N-methylacetamide,
N-ethyl-N-methyl-2-(2-{[(2,4,6-trichlorophenyl)sulfonyl]amino}-1,3-thiazol-4-yl)acetamide,
2-(2-{[(2,4-Dichloro-6-methylphenyl)sulfonyl]amino}-1,3-thiazol-4-yl)-N-ethyl-N-methylacetamide,
2-{2-[([1,1'-Biphenyl]-4-ylsulfonyl)amino]-1,3-thiazol-4-yl}-N-ethyl-N-methylacetamide,
2-(2-{[(3-Chloro-2-methylphenyl)sulfonyl]amino}-1,3-thiazol-4-yl)-N-ethyl-N-methylacetamide,
2-(2-{[(3-Chloro-2-methylphenyl)sulfonyl]amino}-1,3-thiazol-4-yl)-N-methyl-N-[(1S)-1-phenylethyl]acetamide,
3-Chloro-2-methyl-N-{4-[2-oxo-2-(1-pyrrolidinyl)ethyl]-1,3-thiazol-2-yl}benzenesulfonamide,
3-Chloro-2-methyl-N-{4-[2-oxo-2-(1-piperidinyl)ethyl]-1,3-thiazol-2-yl}benzenesulfonamide,
N-{4-[2-oxo-2-(1-piperidinyl)ethyl]-1,3-thiazol-2-yl}[1,1'-biphenyl]-4-sulfonamide,
2,4-Dichloro-6-methyl-N-{4-[2-oxo-2-(1-piperidinyl)ethyl]-1,3-thiazol-2-yl}benzenesulfonamide,
2,4,6-Trichloro-N-{4-[2-oxo-2-(1-piperidinyl)ethyl]-1,3-thiazol-2-yl}benzenesulfonamide,
3-Chloro-2-methyl-N-{4-[2-(4-morpholinyl)-2-oxoethyl]-1,3-thiazol-2-yl}benzenesulfonamide,
2,4,6-Trichloro-N-{4-[2-(4-morpholinyl)-2-oxoethyl]-1,3-thiazol-2-yl}benzenesulfonamide,
2,4-Dichloro-6-methyl-N-{4-[2-(4-morpholinyl)-2-oxoethyl]-1,3-thiazol-2-yl}benzenesulfonamide,
N-{4-[2-(4-morpholinyl)-2-oxoethyl]-1,3-thiazol-2-yl}[1,1'-biphenyl]-4-sulfonamide,
2,4-Dichloro-N-{4-[2-(4-morpholinyl)-2-oxoethyl]-1,3-thiazol-2-yl}benzenesulfonamide,
4-Chloro-2,6-dimethyl-N-{4-[2-(4-morpholinyl)-2-oxoethyl]-1,3-thiazol-2-yl}benzenesulfonamide,
N-{4-[2-(4-morpholinyl)-2-oxoethyl]-1,3-thiazol-2-yl}-4-phenoxybenzenesulfonamide,
2-Methyl-N-{4-[2-(4-morpholinyl)-2-oxoethyl]-1,3-thiazol-2-yl}-4-(trifluoromethoxy)benzenesulfonamide,
N-{4-[2-(4-morpholinyl)-2-oxoethyl]-1,3-thiazol-2-yl}-2,4-bis(trifluoromethyl)benzenesulfonamide,
4-Bromo-2-methyl-N-{4-[2-(4-morpholinyl)-2-oxoethyl]-1,3-thiazol-2-yl}benzenesulfonamide,
4-(2-Furyl)-N-{4-[2-(4-morpholinyl)-2-oxoethyl]-1,3-thiazol-2-yl}benzenesulfonamide,
3'-Fluoro-6'-methoxy-N-{4-[2-(4-morpholinyl)-2-oxoethyl]-1,3-thiazol-2-yl}[1,1'-biphenyl]-4-sulfonamide,
4-(5-Methyl-2-thienyl)-N-{4-[2-(4-morpholinyl)-2-oxoethyl]-1,3-thiazol-2-yl}benzenesulfonamide,
3'-Acetyl-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-4'-(trifluoromethoxy)[1,1'-biphenyl]-4-sulfonamide,
3'4'-Dichloro-N-{4-[2-(4-morpholinyl)-2-oxoethyl]-1,3-thiazol-2-yl}[1,1'-biphenyl]-4-sulfonamide,
4-(1,3-Benzodioxol-5-yl)-N-{4-[2-(4-morpholinyl)-2-oxoethyl]-1,3-thiazol-2-yl}benzenesulfonamide,
4-(5-chloro-2-thienyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(4-pyridinyl)benzenesulfonamide,
N-{4'-[({4-[2-(4-morpholinyl)-2-oxoethyl]-1,3-thiazol-2-yl}amino)sulfonyl][1,1'-biphenyl]-3-yl}acetamide,
N-{4-[2-(4-Morpholinyl)-2-oxoethyl]-1,3-thiazol-2-yl}-4-(3-thienyl)benzenesulfonamide,
N-{4-[2-(4-Morpholinyl)-2-oxoethyl]-1,3-thiazol-2-yl}-4-(2-thienyl)benzenesulfonamide,
4'-[({4-[2-(4-Morpholinyl)-2-oxoethyl]-1,3-thiazol-2-yl}amino)sulfonyl][1,1'-biphenyl]-4-carboxylic acid,
4'-(Methylsulfanyl)-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3'5'-bis(trifluoromethyl)[1,1'-biphenyl]-4-sulfonamide,
4'-Chloro-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3'-nitro[1,1'-biphenyl]-4-sulfonamide,
4-(1-Benzofuran-2-yl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(1-pyrrolidinyl)benzenesulfonamide,
4-(4-Methyl-1-piperidinyl)-N-{4-[2-(4-morpholinyl)-2-oxoethyl]-1,3-thiazol-2-yl}benzenesulfonamide,
4-Anilino-N-{4-[2-(4-morpholinyl)-2-oxoethyl]-1,3-thiazol-2-yl}benzenesulfonamide,
4-(Benzylamino)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(2-thienylmethyl)amino]benzenesulfonamide,
4-(4-Morpholinyl)-N-{4-[2-(4-morpholinyl)-2-oxoethyl]-1,3-thiazol-2-yl}benzenesulfonamide,
4-(4-Methyl-1-piperazinyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(3-pyridinylmethyl)amino]benzenesulfonamide,
2,4-Dichloro-6-methyl-N-{5-methyl-4-[2-(4-morpholinyl)-2-oxoethyl]-1,3-thiazol-2-yl}benzenesulfonamide,
N-{5-methyl-4-[2-(4-morpholinyl)-2-oxoethyl]-1,3-thiazol-2-yl}[1,1'-biphenyl]-4-sulfonamide,
2,4,6-trichloro-N-{5-methyl-4-[2-(4-morpholinyl)-2-oxoethyl]-1,3-thiazol-2-yl}benzenesulfonamide,
3-chloro-2-methyl-N-{5-methyl-4-[2-(4-morpholinyl)-2-oxoethyl]-1,3-thiazol-2-yl}benzenesulfonamide,
3-Chloro-N-(4-{2-[(2R,6S)-2,6-dimethylmorpholinyl]-2-oxoethyl}-1,3-thiazol-2-yl)-2-methylbenzenesulfonamide,
3-Chloro-2-methyl-N-(4-{2-[(1S,4S)-2-oxa-5-azabicyclo[2.2.1]hept-5-yl]-2-oxoethyl}-1,3-thiazol-2-yl)benzenesulfonamide,
3-Chloro-2-methyl-N-{4-[2-oxo-2-(4-thiomorpholinyl)ethyl]-1,3-thiazol-2-yl}benzenesulfonamide,
N-{4-[2-oxo-2-(4-thiomorpholinyl)ethyl]-1,3-thiazol-2-yl}[1,1'-biphenyl]-4-sulfonamide,
2,4-Dichloro-6-methyl-N-{4-[2-oxo-2-(4-thiomorpholinyl)ethyl]-1,3-thiazol-2-yl}benzenesulfonamide,
2,4,6-Trichloro-N-{4-[2-oxo-2-(4-thiomorpholinyl)ethyl]-1,3-thiazol-2-yl}benzenesulfonamide,
Tert-butyl 4-[(2-{[(3-chloro-2-methylphenyl)sulfonyl]amino}-1,3-thiazol-4-1)acetyl]-1-piperazinecarboxylate,
N-{4-[2-(4-Acetyl-1-piperazinyl)-2-oxoethyl]-1,3-thiazol-2-yl}-3-chloro-2-methylbenzenesulfonamide,
3-Chloro-2-methyl-N-{4-[2-(4-methyl-1-piperazinyl)-2-oxoethyl]-1,3-thiazol-2-yl}benzenesulfonamide trifluoroacetate,
3-Chloro-2-methyl-N-{4-[2-oxo-2-(1-piperazinyl)ethyl]-1,3-thiazol-2-yl}benzenesulfonamide trifluoroacetate,
2-Methyl-N-{4-[2-(4-methyl-1-piperazinyl)-2-oxoethyl]-1,3-thiazol-2-yl}-4-(trifluoromethoxy)benzenesulfonamide,
2,4-Dichloro-6-methyl-N-{4-[2-(4-methyl-1-piperazinyl)-2-oxoethyl]-1,3-thiazol-2-yl}benzenesulfonamide, 2,4-Dichloro-N-{4-[2-(4-methyl-1-piperazinyl)-2-oxoethyl]-1,3-thiazol-2-yl}benzenesulfonamide,
3-chloro-N-(4-{2-[(2R)-2,4-dimethylpiperazinyl]-2-oxoethyl}-1,3-thiazol-2-yl)-2-methylbenzenesulfonamide,
2-(2-{[(3-Chloro-2-methylphenyl)sulfonyl]amino}-1,3-thiazol-4-yl)-N-methoxy-N-methylacetamide,
3-Chloro-2-methyl-N-[4-(2-oxopentyl)-1,3-thiazol-2-yl]benzenesulfonamide,
4-Chloro-N-[4-(2-hydroxyethyl)-1,3-thiazol-2-yl]benzenesulfonamide,
3-Chloro-N-[4-(2-hydroxyethyl)-1,3-thiazol-2-yl]-2-methylbenzenesulfonamide,
3-Chloro-N-[4-(3-hydroxypropyl)-1,3-thiazol-2-yl]-2-methylbenzenesulfonamide,
3-Chloro-N-[4-(2-ethoxyethyl)-1,3-thiazol-2-yl]-2-methylbenzenesulfonamide,
3-Chloro-N-[4-(2-isopropoxyethyl)-1,3-thiazol-2-yl]-2-methylbenzenesulfonamide,
N-{4-[2-(benzyloxy)ethyl]-1,3-thiazol-2-yl}-3-chloro-2-methylbenzenesulfonamide,
3-Chloro-N-[4-(2-methoxyethyl)-1,3-thiazol-2-yl]-2-methylbenzenesulfonamide,
3-Chloro-N-{4-[2-(2-fluoroethoxy)ethyl]-1,3-thiazol-2-yl}-2-methylbenzenesulfonamide,
3-Chloro-2-methyl-N-{4-[2-(2,2,2-trifluoroethoxy)ethyl]-1,3-thiazol-2-yl}benzenesulfonamide,
3-Chloro-2-methyl-N-{4-[2-(2-pyridinylsulfanyl)ethyl]-1,3-thiazol-2-yl}benzenesulfonamide,
3-Chloro-2-methyl-N-{4-[2-(3-pyridinyloxy)ethyl]-1,3-thiazol-2-yl}benzenesulfonamide,
Methyl 2-[2-(2-{[(3-chloro-2-methylphenyl)sulfonyl]amino}-1,3-thiazol-4-yl)ethoxy]benzoate,
2-(2-{[(3-Chloro-2-methylphenyl)sulfonyl]amino}-1,3-thiazol-4-yl)ethyl methanesulfonate,
3-(2-{[(3-chloro-2-methylphenyl)sulfonyl]amino}-1,3-thiazol-4-yl)propyl methanesulfonate,
2-(2-{[(3-Chloro-2-methylphenyl)sulfonyl]amino}-1,3-thiazol-4-yl)ethyl acetate,
2-(2-{[(3-Chloro-2-methylphenyl)sulfonyl]amino}-1,3-thiazol-4-yl)ethyl propionate,
2-(2-{[(3-Chloro-2-methylphenyl)sulfonyl]amino}-1,3-thiazol-4-yl)ethyl 2-methylpropanoate,
2-(2-{[(3-Chloro-2-methylphenyl)sulfonyl]amino}-1,3-thiazol-4-yl)ethyl 2-furoate,
2-(2-{[(3-chloro-2-methylphenyl)sulfonyl]amino}-1,3-thiazol-4-yl)ethyl benzoate,
2-(2-{[(3-Chloro-2-methylphenyl)sulfonyl]amino}-1,3-thiazol-4-yl)ethyl 4-morpholinecarboxylate,
2-(2-{[(3-Chloro-2-methylphenyl)sulfonyl]amino}-1,3-thiazol-4-yl)ethyl diethylcarbamate,
2-(2-{[(3-Chloro-2-methylphenyl)sulfonyl]amino}-1,3-thiazol-4-yl)ethyl ethylcarbamate,
N-[4-(2-azidoethyl)-1,3-thiazol-2-yl]-3-chloro-2-methylbenzenesulfonamide,
N-[4-(2-aminoethyl)-1,3-thiazol-2-yl]-3-chloro-2-methylbenzenesulfonamide,
3-Chloro-2-methyl-N-{4-[2-(methylamino)ethyl]-1,3-thiazol-2-yl}benzenesulfonamide,
4-Chloro-N-{4-[2-(diethylamino)ethyl]-1,3-thiazol-2-yl}benzenesulfonamide hydrochloride,
3-Chloro-N-{4-[2-(diethylamino)ethyl]-1,3-thiazol-2-yl}-2-methylbenzenesulfonamide hydrochloride,
3-Chloro-N-{4-[2-(1H-imidazol-1-yl)ethyl]-1,3-thiazol-2-yl}-2-methylbenzenesulfonamide dihydrate,
3-Chloro-2-methyl-N-{4-[2-(4-methyl-1-piperazinyl)ethyl]-1,3-thiazol-2-yl}benzenesulfonamide dihydrochloride,
3-Chloro-2-methyl-N-{4-[2-(4-morpholinyl)ethyl]-1,3-thiazol-2-yl}benzenesulfonamide hydrochloride,
3-Chloro-2-methyl-N-[4-(4-morpholinylmethyl)-1,3-thiazol-2-yl]benzenesulfonamide hydrochloride,
2,4,6-Trichloro-N-{4-[2-(4-morpholinyl)ethyl]-1,3-thiazol-2-yl}benzenesulfonamide hydrochloride,
2,4-Dichloro-N-{4-[2-(4-morpholinyl)ethyl]-1,3-thiazol-2-yl}benzenesulfonamide hydrochloride,
2,4-Dichloro-6-methyl-N-{4-[2-(4-morpholinyl)ethyl]-1,3-thiazol-2-yl}benzenesulfonamide hydrochloride,
3-Chloro-N-{4-[2-(ethylamino)ethyl]-1,3-thiazol-2-yl}-2-methylbenzenesulfonamide,
3-Chloro-N-(4-{2-[(2-hydroxyethyl)amino]ethyl}-1,3-thiazol-2-yl)-2-methylbenzenesulfonamide,
3-Chloro-N-(4-{3-[(2-hydroxyethyl)amino]propyl}-1,3-thiazol-2-yl)-2-methylbenzenesulfonamide hydrochloride hydrate,
N-[2-(2-{[(3-chloro-2-methylphenyl)sulfonyl]amino}-1,3-thiazol-4-yl)ethyl]-N-ethylacetamide,
3-Chloro-2-methyl-N-{4-[2-(3-oxo-4-morpholinyl)ethyl]-1,3-thiazol-2-yl}benzenesulfonamide,
3-Chloro-N-{4-[2-(2-hydroxy-3-oxo-4-morpholinyl)ethyl]-1,3-thiazol-2-yl}-2-methylbenzenesulfonamide,
2,4-Dichloro-N-{4-[2-(3-oxo-4-morpholinyl)ethyl]-1,3-thiazol-2-yl}benzenesulfonamide,
2,4-Dichloro-6-methyl-N-{4-[2-(3-oxo-4-morpholinyl)ethyl]-1,3-thiazol-2-yl}benzenesulfonamide,
2,4,6-Trichloro-N-{4-[2-(3-oxo-4-morpholinyl)ethyl]-1,3-thiazol-2-yl}benzenesulfonamide,
4,5-Dichloro-N-{4-[2-(3-oxo-4-morpholinyl)ethyl]-1,3-thiazol-2-yl}-2-thiophenesulfonamide,
N-{4-[2-(3-Oxo-4-morpholinyl)ethyl]-1,3-thiazol-2-yl}-4-phenoxybenzenesulfonamide,
3-Fluoro-N-{4-[2-(3-oxo-4-morpholinyl)ethyl]-1,3-thiazol-2-yl}benzenesulfonamide,
N-{4-[2-(3-Oxo-4-morpholinyl)ethyl]-1,3-thiazol-2-yl}-5-(2-pyridinyl)-2-thiophenesulfonamide,
N-{2-Chloro-4-[({4-[2-(3-oxo-4-morpholinyl)ethyl]-1,3-thiazol-2-yl}amino) sulfonyl]phenyl}acetamide,
3-Chloro-2-methyl-N-{4-[(3-oxo-4-morpholinyl)methyl]-1,3-thiazol-2-yl}benzenesulfonamide,
3-Chloro-2-methyl-N-{4-[3-(3-oxo-4-morpholinyl)propyl]-1,3-thiazol-2-yl}benzenesulfonamide,
3-Chloro-N,2-dimethyl-N-{4-[2-(3-oxo-4-morpholinyl)ethyl]-1,3-thiazol-2-yl}benzenesulfonamide,
3-Chloro-2-methyl-N-{4-[2-(2-methyl-3-oxo-4-morpholinyl)ethyl]-1,3-thiazol-2-yl}benzenesulfonamide,
N-[2-(2-{[(3-Chloro-2-methylphenyl)sulfonyl]amino}-1,3-thiazol-4-yl)ethyl]acetamide,
3-Chloro-2-methyl-N-{4-[2-(3-oxo-1,4-oxazepan-4-yl)ethyl]-1,3-thiazol-2-yl}benzenesulfonamide,
3-Chloro-2-methyl-N-{4-[2-(2-oxo-1-pyrrolidinyl)ethyl]-1,3-thiazol-2-yl}benzenesulfonamide,
3-Chloro-2-methyl-N-{4-[2-(2-oxo-1-imidazolidinyl)ethyl]-1,3-thiazol-2-yl}benzenesulfonamide,
3-Chloro-2-methyl-N-{4-[2-(2-oxo-1,3-oxazolidin-3-yl)ethyl]-1,3-thiazol-2-yl}benzenesulfonamide,
N-[2-(2-{[(3-Chloro-2-methylphenyl)sulfonyl]amino}-1,3-thiazol-4-yl)ethyl]-N-(2-hydroxyethyl)-2-furamide,
N-[2-(2-{[(3-chloro-2-methylphenyl)sulfonyl]amino}-1,3-thiazol-4-yl)ethyl]-N-methylcyclopropanecarboxamide,
3-Chloro-2-methyl-N-{4-[2-(4-methyl-2-oxo-1-piperazinyl)ethyl]-1,3-thiazol-2-yl}benzenesulfonamide hydrochloride,
3-Chloro-2-methyl-N-(4-{2-[(methylsulfonyl)amino]ethyl}-1,3-thiazol-2-yl)benzenesulfonamide, 3-Chloro-2-methyl-N-(4-{2-[methyl(methylsulfonyl) amino]ethyl}-1,3-thiazol-2-yl)benzenesulfonamide, 3-Chloro-2-methyl-N-[4-(2-{[(trifluoromethyl)sulfonyl] amino}ethyl)-1,3-thiazol-2-yl]benzenesulfonamide, 3-Chloro-2-methyl-N-[4-(2-{methyl[(trifluoromethyl)sulfonyl]amino}ethyl)-1,3-thiazol-2-yl]benzenesulfonamide, N-[2-(2-{[(3-Chloro-2-methylphenyl)sulfonyl]amino}-1,3-thiazol-4-yl)ethyl]-1-methyl-1H-imidazole-4-sulfonamide, 3-Chloro-N-(4-{2-[[(3-chloro-2-methylphenyl)sulfonyl](methyl)amino]ethyl}-1,3-thiazol-2-yl)-2-methylbenzenesulfonamide, N-[4-(2-bromoethyl)-1,3-thiazol-2-yl]-3-chloro-2-methylbenzenesulfonamide, 3-Chloro-N-[4-(2-chloroethyl)-1,3-thiazol-2-yl]-2-methylbenzenesulfonamide, 3-Chloro-2-methyl-N-{4-[(5-methyl-1,3,4-oxadiazol-2-yl)methyl]-1,3-thiazol-2-yl}benzenesulfonamide, and Ethyl 3-(2-{[(3-chloro-2-methylphenyl)sulfonyl]amino}-1,3-thiazol-4-yl)propanoate.

2. A method for the treatment of diabetes, syndrome X, obesity, glaucoma, hyperlipidemia, hyperglycemia and hyperinsulinemia, said method comprising administering to a mammal in need of such treatment an effective amount of a compound selected from the group consisting of:

Ethyl (2-{[(2,4-dichloro-5-methylphenyl)sulfonyl]amino}-1,3-thiazol-4-yl)acetate, Ethyl 2-(2-[[(4-chlorophenyl)sulfonyl]amino]-1,3-thiazole-4-yl)acetate, Ethyl 2-(2-{[(4-chloro-2,5-dimethylphenyl)sulfonyl]amino}-1,3-thiazol-4-yl)acetate, Ethyl 2-(2-{[(2,4-difluorophenyl)sulfonyl]amino}-1,3-thiazol-4-yl)acetate, Ethyl 2-(2-{[(2,5-dichloro-3-thienyl)sulfonyl]amino}-1,3-thiazol-4-yl)acetate, Ethyl (2-{[(2-chlorophenyl)sulfonyl]amino}-1,3-thiazol-4-yl)acetate, Ethyl 2-(2-{[(3-chloro-2-methylphenyl)sulfonyl]amino}-1,3-thiazol-4-yl)acetate, Ethyl 2-{2-[([1,1'-biphenyl]-4-ylsulfonyl)amino]-1,3-thiazol-4-yl}acetate, Ethyl 2-(2-{[(3-bromophenyl)sulfonyl]amino}-1,3-thiazol-4-yl)acetate, Ethyl (2-{[(4-nitrophenyl)sulfonyl]amino}-1,3-thiazol-4-yl)acetate, Ethyl (2-{[(4-methoxyphenyl)sulfonyl]amino}-1,3-thiazol-4-yl)acetate, Ethyl (2-{[(3-nitrophenyl)sulfonyl]amino}-1,3-thiazol-4-yl)acetate, Ethyl (2-{[(3-chlorophenyl)sulfonyl]amino}-1,3-thiazol-4-yl)acetate, Ethyl (2-{[(4-fluorophenyl)sulfonyl]amino}-1,3-thiazol-4-yl)acetate, Ethyl (2-{[(3-fluorophenyl)sulfonyl]amino}-1,3-thiazol-4-yl)acetate, Ethyl {2-[phenylsulfonyl)amino]-1,3-thiazol-4-yl}acetate, Ethyl [2-({[3-({[4-(2-ethoxy-2-oxoethyl)-1,3-thiazol-2-yl]amino}carbonyl)phenyl]sulfonyl}amino)-1,3-thiazol-4-yl]acetate, Ethyl [2-({[4-({[4-(2-ethoxy-2-oxoethyl)-1,3-thiazol-2-yl]amino}carbonyl)phenyl]sulfonyl}amino)-1,3-thiazol-4-yl]acetate, Ethyl [2-({[2-(trifluoromethyl)phenyl]sulfonyl}amino)-1,3-thiazol-4-yl]acetate, Ethyl [2-({[3-(trifluoromethyl)phenyl]sulfonyl}amino)-1,3-thiazol-4-yl]acetate, Ethyl [2-({[4-(trifluoromethyl)phenyl]sulfonyl}amino)-1,3-thiazol-4-yl]acetate, Ethyl 2-(2-{[(4-bromophenyl)sulfonyl]amino}-1,3-thiazol-4-yl)acetate, Ethyl (2-{[(2-nitrophenyl)sulfonyl]amino}-1,3-thiazol-4-yl)acetate, Ethyl (2-{[(2,4-dichloro-6-methylphenyl)sulfonyl]amino}-1,3-thiazol-4-yl)acetate, Ethyl (2-{[(2,4,6-trichlorophenyl)sulfonyl]amino}-1,3-thiazol-4-yl)acetate, Ethyl (2-{[(2,4-dichlorophenyl)sulfonyl]amino}-1,3-thiazol-4-yl)acetate, Ethyl (2-{[(5-fluoro-2-methylphenyl)sulfonyl]amino}-1,3-thiazol-4-yl)acetate, Ethyl (2-{[(2-methoxy-4-methylphenyl)sulfonyl]amino}-1,3-thiazol-4-yl)acetate, Ethyl (2-{[(3,5-dichlorophenyl)sulfonyl]amino}-1,3-thiazol-4-yl)acetate, Ethyl [2-({[4-(3-chloro-2-cyanophenoxy)phenyl]sulfonyl}amino)-1,3-thiazol-4-yl]acetate, Ethyl (2-{[(3,4-dichlorophenyl)sulfonyl]amino}-1,3-thiazol-4-yl)acetate, Ethyl (2-{[(4-butoxyphenyl)sulfonyl]amino}-1,3-thiazol-4-yl)acetate, Ethyl (2-{[(4-chloro-2-methylphenyl)sulfonyl]amino}-1,3-thiazol-4-yl)acetate, Ethyl [2-({[4-(acetylamino)phenyl]sulfonyl}amino)-1,3-thiazol-4-yl]acetate, Ethyl {2-[(8-quinolinylsulfonyl)amino]-1,3-thiazol-4-yl}acetate, Ethyl (2-{[(3,4-dimethoxyphenyl)sulfonyl]amino}-1,3-thiazol-4-yl)acetate, Ethyl (2-{[(4-iodophenyl)sulfonyl]amino}-1,3-thiazol-4-yl)acetate, Ethyl (2-{[(3-chloro-4-methylphenyl)sulfonyl]amino}-1,3-thiazol-4-yl)acetate, Ethyl [2-({[5-(dimethylamino)-1-naphthyl]sulfonyl}amino)-1,3-thiazol-4-yl]acetate, Ethyl (2-{[(1-methyl-1H-imidazol-4-yl)sulfonyl]amino}-1,3-thiazol-4-yl)acetate, Ethyl (2-{[(5-bromo-2-methoxyphenyl)sulfonyl]amino}-1,3-thiazol-4-yl)acetate, Ethyl (2-{[(2,5-dimethoxyphenyl)sulfonyl]amino}-1,3-thiazol-4-yl)acetate, Ethyl {2-[(2-naphthylsulfonyl)amino]-1,3-thiazol-4-yl}acetate, Ethyl (2-{[(3-bromo-5-chloro-2-thienyl)sulfonyl]amino}-1,3-thiazol-4-yl)acetate, Ethyl {2-[({5-[(benzoylamino)methyl]-2-thienyl}sulfonyl)amino]-1,3-thiazol-4-yl}acetate, Ethyl {2-[({5-[1-methyl-5-(trifluoromethyl)-1H-pyrazol-3-yl]-2-thienyl}sulfonyl)amino]-1,3-thiazol-4-yl}acetate, Ethyl (2-{[(4-cyanophenyl)sulfonyl]amino}-1,3-thiazol-4-yl)acetate, Ethyl {2-[({5-[2-(methylsulfanyl)-4-pyrimidinyl]-2-thienyl}sulfonyl)amino]1,3-thiazol-4-yl}acetate, Ethyl (2-{[(3-cyanophenyl)sulfonyl]amino}-1,3-thiazol-4-yl)acetate, Ethyl (2-{[(2,4,5-trichlorophenyl)sulfonyl]amino}-1,3-thiazol-4-yl)acetate, Ethyl [2-({[(E)-2-phenylethenyl]sulfonyl}amino)-1,3-thiazol-4-yl]acetate, Ethyl (2-{[(2,3,4-trichlorophenyl)sulfonyl]amino}-1,3-thiazol-4-yl)acetate, Ethyl (2-{[(4-bromo-2,5-difluorophenyl)sulfonyl] amino}-1,3-thiazol-4-yl)acetate,
Ethyl [2-({[4-(trifluoromethoxy)phenyl]sulfonyl}amino)-1,3-thiazol-4-yl]acetate,
Ethyl (2-{[(2,3-dichlorophenyl)sulfonyl]amino}-1,3-thiazol-4-yl)acetate,
Ethyl (2-{[(2-bromophenyl)sulfonyl]amino}-1,3-thiazol-4-yl)acetate,
Ethyl (2-{[(4,5-dichloro-2-thienyl)sulfonyl]amino}-1,3-thiazol-4-yl)acetate,
Ethyl [2-({[4-(phenylsulfonyl)-2-thienyl]sulfonyl}amino)-1,3-thiazol-4-yl]acetate,
Ethyl [2-({[5-(phenylsulfonyl)-2-thienyl]sulfonyl}amino)-1,3-thiazol-4-yl]acetate,
Ethyl (2-{[(2,6-dichlorophenyl)sulfonyl]amino}-1,3-thiazol-4-yl)acetate,
Ethyl (2-{[(2-cyanophenyl)sulfonyl]amino}-1,3-thiazol-4-yl)acetate,
Ethyl [2-({[4-(acetylamino)-3-chlorophenyl]sulfonyl}amino)-1,3-thiazol-4-yl]acetate,
Ethyl (2-{[(5-chloro-1,3-dimethyl-1H-pyrazol-4-yl)sulfonyl]amino}-1,3-thiazol-4-yl)acetate,
Ethyl (2-{[(3-methoxyphenyl)sulfonyl]amino}-1,3-thiazol-4-yl)acetate,
Ethyl (2-{[(4-bromo-5-chloro-2-thienyl)sulfonyl]amino}-1,3-thiazol-4-yl)acetate,
Ethyl 2-{2-[(1-naphthylsulfonyl)amino]-1,3-thiazol-4-yl}acetate,
Ethyl (2-{[(2,5-dichlorophenyl)sulfonyl]amino}-1,3-thiazol-4-yl)acetate,
Ethyl [2-({[4-(methylsulfonyl)phenyl]sulfonyl}amino)-1,3-thiazol-4-yl]acetate,
Ethyl [2-({[2-(methylsulfonyl)phenyl]sulfonyl}amino)-1,3-thiazol-4-yl]acetate,
Ethyl (2-{[(4-bromo-2-fluorophenyl)sulfonyl]amino}-1,3-thiazol-4-yl)acetate,
Ethyl (2-{[(2,3,4-trifluorophenyl)sulfonyl]amino}-1,3-thiazol-4-yl)acetate,
Ethyl (2-{[(7-chloro-2,1,3-benzoxadiazol-4-yl)sulfonyl]amino}-1,3-thiazol-4-yl)acetate,
Ethyl (2-{[(2,4,6-trifluorophenyl)sulfonyl]amino}-1,3-thiazol-4-yl)acetate, 2-Chloro-5-({[4-(2-ethoxy-2-oxoethyl)-1,3-thiazol-2-yl]amino}sulfonyl)-4-fluorobenzoic acid,
Ethyl (2-{[(5-chloro-2-thienyl)sulfonyl]amino}-1,3-thiazol-4-yl)acetate,
Ethyl (2-{[(2-chloro-4-fluorophenyl)sulfonyl]amino}-1,3-thiazol-4-yl)acetate,
Ethyl [2-({[5-(3-isoxazolyl)-2-thienyl]sulfonyl}amino)-1,3-thiazol-4-yl]acetate,
Ethyl (2-{[(4-bromo-2-methylphenyl)sulfonyl]amino}-1,3-thiazol-4-yl)acetate,
Ethyl (2-{[(4-phenoxyphenyl)sulfonyl]amino}-1,3-thiazol-4-yl)acetate,
Ethyl (2-{[(4-chloro-2,6-dimethylphenyl)sulfonyl]amino}-1,3-thiazol-4-yl)acetate,
Ethyl [2-({[2-methyl-4-(trifluoromethoxy)phenyl]sulfonyl}amino)-1,3-thiazol-4-yl]acetate,
Ethyl [2-({[2,4-bis(trifluoromethyl)phenyl]sulfonyl}amino)-1,3-thiazol-4-yl]acetate,
Ethyl 2-{2-[[(3-chloro-2-methylphenyl)sulfonyl](methyl)amino]-1,3-thiazol-4-yl}acetate,
Ethyl (2-{[(3-chloro-2-methylphenyl)sulfonyl]amino}-1,3-thiazol-4-yl)(oxo)acetate,
Ethyl oxo(2-{[(2,4,6-trichlorophenyl)sulfonyl]amino}-1,3-thiazol-4-yl)acetate,
Ethyl {2-[([1,1'-biphenyl]-4-ylsulfonyl)amino]-1,3-thiazol-4-yl}(oxo)acetate,
Ethyl (2-{[(2,4-dichloro-6-methylphenyl)sulfonyl]amino}-1,3-thiazol-4-yl)(oxo)acetate,
2-(2-{[(2,5-Dichloro-3-thienyl)sulfonyl]amino}-1,3-thiazol-4-yl)acetic acid,
(2-{[(2-Chlorophenyl)sulfonyl]amino}-1,3-thiazol-4-yl)acetic acid,
2-(2-{[(3-Chloro-2-methylphenyl)sulfonyl]amino}-1,3-thiazol-4-yl)acetic acid,
Isopropyl 2-(2-{[(3-chloro-2-methylphenyl)sulfonyl]amino}-1,3-thiazol-4-yl)acetate,
Phenyl 2-(2-{[(3-chloro-2-methylphenyl)sulfonyl]amino}-1,3-thiazol-4-yl)acetate,
Methyl (2-{[(3-chloro-2-methylphenyl)sulfonyl]amino}-1,3-thiazol-4-yl)acetate,
Methyl {2-[([1,1'-biphenyl]-4-ylsulfonyl)amino]-5-methyl-1,3-thiazol-4-yl}acetate,
Methyl (2-{[(4-chlorophenyl)sulfonyl]amino}-5-methyl-1,3-thiazol-4-yl)acetate,
Methyl (2-{[(3-chloro-2-methylphenyl)sulfonyl]amino}-5-methyl-1,3-thiazol-4-yl)acetate,
Methyl [2-({[4-(3-chloro-2-cyanophenoxy)phenyl]sulfonyl}amino)-5-methyl-1,3-thiazol-4-yl]acetate,
Methyl (5-methyl-2-{[(2,4,6-trichlorophenyl)sulfonyl]amino}-1,3-thiazol-4-yl)acetate,
Methyl (2-{[(2,4-dichloro-6-methylphenyl)sulfonyl]amino}-5-methyl-1,3-thiazol-4-yl)acetate,
2-(2-{[(2,5-Dichloro-3-thienyl)sulfonyl]amino}-1,3-thiazol-4-yl)-N-methylacetamide,
N-(1,3-Benzodioxol-5-ylmethyl)-2-{2-[(1-naphthylsulfonyl)amino]-1,3-thiazol-4-yl}acetamide,
N-(2-Furylmethyl)-2-{2-[(1-naphthylsulfonyl)amino]-1,3-thiazol-4-yl}acetamide,
2-(2-{[(2,4-Difluorophenyl)sulfonyl]amino}-1,3-thiazol-4-yl)-N-ethylacetamide,
N-Isopropyl-2-{2-[(1-naphthylsulfonyl)amino]-1,3-thiazol-4-yl}acetamide,
N-[2-(1H-Indol-3-yl)ethyl]-2-{2-[(1-naphthylsulfonyl)amino]-1,3-thiazol-4-yl}acetamide,
N-(Cyclohexylmethyl)-2-{2-[(phenylsulfonyl)amino]-1,3-thiazol-4-yl}acetamide,
2-(2-{[(3-Chloro-2-methylphenyl)sulfonyl]amino}-1,3-thiazol-4-yl)-N-methylacetamide,
2-(2-{[(3-Chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N-phenylacetamide,
2-(2-{[(4-Chlorophenyl)sulfonyl]amino}-1,3-thiazol-4-yl)-N-(2-furylmethyl)acetamide,
N-Benzhydryl-2-(2-{[(4-chlorophenyl)sulfonyl]amino}-1,3-thiazol-4-yl)acetamide,
2-(2-{[(4-Chlorophenyl)sulfonyl]amino}-1,3-thiazol-4-yl)-N-(tetrahydro-2-furanylmethyl)acetamide,
Ethyl 4-{[2-(2-{[(4-chlorophenyl)sulfonyl]amino}-1,3-thiazol-4-yl)acetyl]amino}-1-piperidinecarboxylate,
N-Benzhydryl-2-(2-{[(3-chloro-2-methylphenyl)sulfonyl]amino}-1,3-thiazol-4-yl)acetamide,
2-(2-{[(4-Chlorophenyl)sulfonyl]amino}-1,3-thiazol-4-yl)-N-phenylacetamide,
2-(2-{[(3-Chloro-2-methylphenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diethylacetamide,
2-{2-[([1,1'-Biphenyl]-4-ylsulfonyl)amino]-1,3-thiazol-4-yl}-N,N-diethylacetamide, 2-(2-{[(2,4-Dichloro-6-methylphenyl)sulfonyl]amino}-1,3-thiazol-4-yl)-N,N-diethylacetamide,
N,N-diethyl-2-(2-{[(2,4,6-trichlorophenyl)sulfonyl]amino}-1,3-thiazol-4-yl)acetamide,
2-{2-[([1,1'-Biphenyl]-4-ylsulfonyl)amino]-1,3-thiazol-4-yl}-N,N-diisopropylacetamide,
2-(2-{[(2,4-Dichloro-6-methylphenyl)sulfonyl]amino}-1,3-thiazol-4-yl)-N,N-diisopropylacetamide,
N,N-diisopropyl-2-(2-{[(2,4,6-trichlorophenyl)sulfonyl]amino}-1,3-thiazol-4-yl)acetamide,
2-(2-{[(3-Chloro-2-methylphenyl)sulfonyl]amino}-1,3-thiazol-4-yl)-N,N-diisopropylacetamide,
2-(2-{[(3-Chloro-2-methylphenyl)sulfonyl]amino}-1,3-thiazol-4-yl)-N,N-dipropylacetamide,
N-benzyl-2-(2-{[(3-chloro-2-methylphenyl)sulfonyl]amino}-1,3-thiazol-4-yl)-N-methylacetamide,
N-benzyl-2-(2-{[(3-chloro-2-methylphenyl)sulfonyl]amino}-1,3-thiazol-4-yl)-N-ethylacetamide,
2-(2-{[(3-Chloro-2-methylphenyl)sulfonyl]amino}-1,3-thiazol-4-yl)-N,N-dimethylacetamide,
2-(2-{[(3-chloro-2-methylphenyl)sulfonyl]amino}-1,3-thiazol-4-yl)-N-cyclohexyl-N-methylacetamide,
3-Chloro-N-{4-[2-(3,4-dihydro-2(1H)-isoquinolinyl)-2-oxoethyl]-1,3-thiazol-2-yl}-2-methylbenzenesulfonamide,
2-(2-{[(3-Chloro-2-methylphenyl)sulfonyl]amino}-1,3-thiazol-4-yl)-N-methyl-N-phenylacetamide,
2-(2-{[(3-Chloro-2-methylphenyl)sulfonyl]amino}-1,3-thiazol-4-yl)-N-isopropyl-N-methylacetamide,
2-{2-[([1,1'-Biphenyl]-4-ylsulfonyl)amino]-1,3-thiazol-4-yl}-N-isopropyl-N-methylacetamide,
N-ethyl-N-methyl-2-(2-{[(2,4,6-trichlorophenyl)sulfonyl]amino}-1,3-thiazol-4-yl)acetamide, 2-(2-{[(2,4-Dichloro-6-methylphenyl)sulfonyl]amino}-1,3-thiazol-4-yl)-N-ethyl-N-methylacetamide,
2-{2-[([1,1'-Biphenyl]-4-ylsulfonyl)amino]-1,3-thiazol-4-yl}-N-ethyl-N-methylacetamide,
2-(2-{[(3-Chloro-2-methylphenyl)sulfonyl]amino}-1,3-thiazol-4-yl)-N-ethyl-N-methylacetamide,
2-(2-{[(3-Chloro-2-methylphenyl)sulfonyl]amino}-1,3-thiazol-4-yl)-N-methyl-N-[(1S)-1-phenylethyl]acetamide,
3-Chloro-2-methyl-N-{4-[2-oxo-2-(1-pyrrolidinyl)ethyl]-1,3-thiazol-2-yl}benzenesulfonamide,
3-Chloro-2-methyl-N-{4-[2-oxo-2-(1-piperidinyl)ethyl]-1,3-thiazol-2-yl}benzenesulfonamide,
N-{4-[2-oxo-2-(1-piperidinyl)ethyl]-1,3-thiazol-2-yl}[1,1'-biphenyl]-4-sulfonamide,
N-{4-[2-oxo-2-(1-piperidinyl)ethyl]-1,3-thiazol-2-yl}-4-propylbenzenesulfonamide,
2,4-Dichloro-6-methyl-N-{4-[2-oxo-2-(1-piperidinyl)ethyl]-1,3-thiazol-2-yl}benzenesulfonamide,
2,4,6-Trichloro-N-{4-[2-oxo-2-(1-piperidinyl)ethyl]-1,3-thiazol-2-yl}benzenesulfonamide,
3-Chloro-2-methyl-N-{4-[2-(4-morpholinyl)-2-oxoethyl]-1,3-thiazol-2-yl}benzenesulfonamide,
2,4,6-Trichloro-N-{4-[2-(4-morpholinyl)-2-oxoethyl]-1,3-thiazol-2-yl}benzenesulfonamide,
2,4-Dichloro-6-methyl-N-{4-[2-(4-morpholinyl)-2-oxoethyl]-1,3-thiazol-2-yl}benzenesulfonamide,
N-{4-[2-(4-morpholinyl)-2-oxoethyl]-1,3-thiazol-2-yl}[1,1'-biphenyl]-4-sulfonamide, 2,4-Dichloro-N-{4-[2-(4-morpholinyl)-2-oxoethyl]-1,3-thiazol-2-yl}benzenesulfonamide,
4-Chloro-2,6-dimethyl-N-{4-[2-(4-morpholinyl)-2-oxoethyl]-1,3-thiazol-2-yl}benzenesulfonamide,
N-{4-[2-(4-morpholinyl)-2-oxoethyl]-1,3-thiazol-2-yl}-4-phenoxybenzenesulfonamide,
2-Methyl-N-{4-[2-(4-morpholinyl)-2-oxoethyl]-1,3-thiazol-2-yl}-4-(trifluoromethoxy)benzenesulfonamide,
N-{4-[2-(4-morpholinyl)-2-oxoethyl]-1,3-thiazol-2-yl}-2,4-bis(trifluoromethyl)benzenesulfonamide,
4-Bromo-2-methyl-N-{4-[2-(4-morpholinyl)-2-oxoethyl]-1,3-thiazol-2-yl}benzenesulfonamide,
4-(2-Furyl)-N-{4-[2-(4-morpholinyl)-2-oxoethyl]-1,3-thiazol-2-yl}benzenesulfonamide,
3'-Fluoro-6'-methoxy-N-{4-[2-(4-morpholinyl)-2-oxoethyl]-1,3-thiazol-2-yl}[1,1'-biphenyl]-4-sulfonamide,
4-(5-Methyl-2-thienyl)-N-{4-[2-(4-morpholinyl)-2-oxoethyl]-1,3-thiazol-2-yl}benzenesulfonamide,
3'-Acetyl-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-4'-(trifluoromethoxy)[1,1'-biphenyl]-4-sulfonamide,
3'4'-Dichloro-N-{4-[2-(4-morpholinyl)-2-oxoethyl]-1,3-thiazol-2-yl}[1,1'-biphenyl]-4-sulfonamide,
4-(1,3-Benzodioxol-5-yl)-N-{4-[2-(4-morpholinyl)-2-oxoethyl]-1,3-thiazol-2-yl}benzenesulfonamide,
4-(5-chloro-2-thienyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(4-pyridinyl)benzenesulfonamide,
N-{4'-[({4-[2-(4-morpholinyl)-2-oxoethyl]-1,3-thiazol-2-yl}amino)sulfonyl][1,1'-biphenyl]-3-yl}acetamide,
N-{4-[2-(4-Morpholinyl)-2-oxoethyl]-1,3-thiazol-2-y1}-4-(3-thienyl)benzenesulfonamide,
N-{4-[2-(4-Morpholinyl)-2-oxoethyl]-1,3-thiazol-2-yl}-4-(2-thienyl)benzenesulfonamide,
4'-[({4-[2-(4-Morpholinyl)-2-oxoethyl]-1,3-thiazol-2-yl}amino)sulfonyl][1,1'-biphenyl]-4-carboxylic acid,
4'-(Methylsulfanyl)-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3'5'-bis(trifluoromethyl)[1,1'-biphenyl]-4-sulfonamide,
4'-Chloro-N-{4-[2-(4-morpholinyl)-2-oxoethyl]-1,3-thiazol-2-yl}[1,1'-biphenyl]-4-sulfonamide,
N-{4-[2-(4-Morpholinyl)-2-oxoethyl]-1,3-thiazol-2-yl}-3'-nitro[1,1'-biphenyl]-4-sulfonamide,
4-(1-Benzofuran-2-yl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-(1-pyrrolidinyl)benzenesulfonamide,
4-(4-Methyl-1-piperidinyl)-N-{4-[2-(4-morpholinyl)-2-oxoethyl]-1,3-thiazol-2-yl}benzenesulfonamide,
4-Anilino-N-{4-[2-(4-morpholinyl)-2-oxoethyl]-1,3-thiazol-2-yl}benzenesulfonamide,
4-(Benzylamino)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(2-thienylmethyl)amino]benzenesulfonamide,
4-(4-Morpholinyl)-N-{4-[2-(4-morpholinyl)-2-oxoethyl]-1,3-thiazol-2-yl}benzenesulfonamide,
4-(4-Methyl-1-piperazinyl)-N-{4-[2-(4-morpholinyl)-2-oxoethyl]-1,3-thiazol-2-yl}benzenesulfonamide,
N-{4-[2-(4-Morpholinyl)-2-oxoethyl]-1,3-thiazol-2-yl}-4-[(3-pyridinylmethyl)amino]benzenesulfonamide,
2,4-Dichloro-6-methyl-N-{5-methyl-4-[2-(4-morpholinyl)-2-oxoethyl]-1,3-thiazol-2-yl}benzenesulfonamide,
N-{5-methyl-4-[2-(4-morpholinyl)-2-oxoethyl]-1,3-thiazol-2-yl}[1,1'-biphenyl]-4-sulfonamide,
2,4,6-trichloro-N-{5-methyl-4-[2-(4-morpholinyl)-2-oxoethyl]-1,3-thiazol-2-yl}benzenesulfonamide, 3-chloro-2-methyl-N-{5-methyl-4-[2-(4-morpholinyl)-2-oxoethyl]-1,3-thiazol-2-yl}benzenesulfonamide,
3-Chloro-N-(4-{2-[(2R,6S)-2,6-dimethylmorpholinyl]-2-oxoethyl}-1,3-thiazol-2-yl)-2-methylbenzenesulfonamide,
3-Chloro-2-methyl-N-(4-{2-[(1S,4S)-2-oxa-5-azabicyclo[2.2.1]hept-5-yl]-2-oxoethyl}-1,3-thiazol-2-yl)benzenesulfonamide,
3-Chloro-2-methyl-N-{4-[2-oxo-2-(4-thiomorpholinyl)ethyl]-1,3-thiazol-2-yl}benzenesulfonamide,
N-{4-[2-oxo-2-(4-thiomorpholinyl)ethyl]-1,3-thiazol-2-yl}[1,1'-biphenyl]-4-sulfonamide, 2,4-Dichloro-6-methyl-N-{4-[2-oxo-2-(4-thiomorpholinyl)ethyl]-1,3-thiazol-2-yl}benzenesulfonamide,
2,4,6-Trichloro-N-{4-[2-oxo-2-(4-thiomorpholinyl)ethyl]-1,3-thiazol-2-yl}benzenesulfonamide,
Tert-butyl 4-[(2-{[(3-chloro-2-methylphenyl)sulfonyl]amino}-1,3-thiazol-4-yl)acetyl]-1-piperazinecarboxylate,
N-{4-[2-(4-Acetyl-1-piperazinyl)-2-oxoethyl]-1,3-thiazol-2-yl}-3-chloro-2-methylbenzenesulfonamide,
3-Chloro-2-methyl-N-{4-[2-(4-methyl-1-piperazinyl)-2-oxoethyl]-1,3-thiazol-2-yl}benzenesulfonamide trifluoroacetate,
3-Chloro-2-methyl-N-{4-[2-oxo-2-(1-piperazinyl)ethyl]-1,3-thiazol-2-yl}benzenesulfonamide trifluoroacetate,
2-Methyl-N-{4-[2-(4-methyl-1-piperazinyl)-2-oxoethyl]-1,3-thiazol-2-yl}-4-(trifluoromethoxy)benzenesulfonamide,
2,4-Dichloro-6-methyl-N-{4-[2-(4-methyl-1-piperazinyl)-2-oxoethyl]-1,3-thiazol-2-yl}benzenesulfonamide,2,4-Dichloro-N-{4-[2-(4-methyl-1-piperazinyl)-2-oxoethyl]-1,3-thiazol-2-yl}benzenesulfonamide,
3-chloro-N-(4-{2-[(2R)-2,4-dimethylpiperazinyl]-2-oxoethyl}-1,3-thiazol-2-yl)-2-methylbenzenesulfonamide,
2-(2-{[(3-Chloro-2-methylphenyl)sulfonyl]amino}-1,3-thiazol-4-yl)-N-methoxy-N-methylacetamide,
3-Chloro-2-methyl-N-[4-(2-oxopentyl)-1,3-thiazol-2-yl]benzenesulfonamide,
4-Chloro-N-[4-(2-hydroxyethyl)-1,3-thiazol-2-yl]benzenesulfonamide,
3-Chloro-N-[4-(2-hydroxyethyl)-1,3-thiazol-2-yl]-2-methylbenzenesulfonamide,
3-Chloro-N-[4-(3-hydroxypropyl)-1,3-thiazol-2-yl]-2-methylbenzenesulfonamide,
3-Chloro-N-[4-(2-ethoxyethyl)-1,3-thiazol-2-yl]-2-methylbenzenesulfonamide,
3-Chloro-N-[4-(2-isopropoxyethyl)-1,3-thiazol-2-yl]-2-methylbenzenesulfonamide,
N-{4-[2-(benzyloxy)ethyl]-1,3-thiazol-2-yl}-3-chloro-2-methylbenzenesulfonamide,
3-Chloro-N-[4-(2-methoxyethyl)-1,3-thiazol-2-yl]-2-methylbenzenesulfonamide,
3-Chloro-N-{4-[2-(2-fluoroethoxy)ethyl]-1,3-thiazol-2-yl}-2-methylbenzenesulfonamide,
3-Chloro-2-methyl-N-{4-[2-(2,2,2-trifluoroethoxy)ethyl]-1,3-thiazol-2-yl}benzenesulfonamide,
3-Chloro-2-methyl-N-{4-[2-(2-pyridinylsulfanyl)ethyl]-1,3-thiazol-2-yl}benzenesulfonamide,
3-Chloro-2-methyl-N-{4-[2-(3-pyridinyloxy)ethyl]-1,3-thiazol-2-yl}benzenesulfonamide,
Methyl 2-[2-(2-{[(3-chloro-2-methylphenyl)sulfonyl]amino}-1,3-thiazol-4-yl)ethoxy]benzoate,
2-(2-{[(3-Chloro-2-methylphenyl)sulfonyl]amino}-1,3-thiazol-4-yl)ethyl methanesulfonate,
3-(2-{[(3-chloro-2-methylphenyl)sulfonyl]amino}-1,3-thiazol-4-yl)propyl methanesulfonate,
2-(2-{[(3-Chloro-2-methylphenyl)sulfonyl]amino}-1,3-thiazol-4-yl)ethyl acetate,
2-(2-{[(3-Chloro-2-methylphenyl)sulfonyl]amino}-1,3-thiazol-4-yl)ethyl propionate,
2-(2-{[(3-Chloro-2-methylphenyl)sulfonyl]amino}-1,3-thiazol-4-yl)ethyl 2-methylpropanoate,
2-(2-{[(3-Chloro-2-methylphenyl)sulfonyl]amino}-1,3-thiazol-4-yl)ethyl 2-furoate,
2-(2-{[(3-chloro-2-methylphenyl)sulfonyl]amino}-1,3-thiazol-4-yl)ethyl benzoate,
2-(2-{[(3-Chloro-2-methylphenyl)sulfonyl]amino}-1,3-thiazol-4-yl)ethyl 4-morpholinecarboxylate,
2-(2-{[(3-Chloro-2-methylphenyl)sulfonyl]amino}-1,3-thiazol-4-yl)ethyl diethylcarbamate,
2-(2-{[(3-Chloro-2-methylphenyl)sulfonyl]amino}-1,3-thiazol-4-yl)ethyl ethylcarbamate,
N-[4-(2-azidoethyl)-1,3-thiazol-2-yl]-3-chloro-2-methylbenzenesulfonamide,
N-[4-(2-aminoethyl)-1,3-thiazol-2-yl]-3-chloro-2-methylbenzenesulfonamide,
3-Chloro-2-methyl-N-{4-[2-(methylamino)ethyl]-1,3-thiazol-2-yl}benzenesulfonamide,
4-Chloro-N-{4-[2-(diethylamino)ethyl]-1,3-thiazol-2-yl}benzenesulfonamide hydrochloride,
3-Chloro-N-{4-[2-(diethylamino)ethyl]-1,3-thiazol-2-yl}-2-methylbenzenesulfonamide hydrochloride,
3-Chloro-N-{4-[2-(1H-imidazol-1-yl)ethyl]-1,3-thiazol-2-yl}-2-methylbenzenesulfonamide dihydrate,
3-Chloro-2-methyl-N-{4-[2-(4-methyl-1-piperazinyl)ethyl]-1,3-thiazol-2-yl}benzenesulfonamide dihydrochloride,
3-Chloro-2-methyl-N-{4-[2-(4-morpholinyl)ethyl]-1,3-thiazol-2-yl}benzenesulfonamide hydrochloride,
3-Chloro-2-methyl-N-[4-(4-morpholinylmethyl)-1,3-thiazol-2-yl]benzenesulfonamide hydrochloride,
2,4,6-Trichloro-N-{4-[2-(4-morpholinyl)ethyl]-1,3-thiazol-2-yl}benzenesulfonamide hydrochloride,
2,4-Dichloro-N-{4-[2-(4-morpholinyl)ethyl]-1,3-thiazol-2-yl}benzenesulfonamide hydrochloride,
2,4-Dichloro-6-methyl-N-{4-[2-(4-morpholinyl)ethyl]-1,3-thiazol-2-yl}benzenesulfonamide hydrochloride,
3-Chloro-N-{4-[2-(ethylamino)ethyl]-1,3-thiazol-2-yl}-2-methylbenzenesulfonamide,
3-Chloro-N-(4-{2-[(2-hydroxyethyl)amino]ethyl}-1,3-thiazol-2-yl)-2-methylbenzenesulfonamide,
3-Chloro-N-(4-{3-[(2-hydroxyethyl)amino]propyl}-1,3-thiazol-2-yl)-2-methylbenzenesulfonamide hydrochloride hydrate,
N-[2-(2-{[(3-chloro-2-methylphenyl)sulfonyl]amino}-1,3-thiazol-4-yl)ethyl]-N-ethylacetamide,
3-Chloro-2-methyl-N-{4-[2-(3-oxo-4-morpholinyl)ethyl]-1,3-thiazol-2-yl}benzenesulfonamide,
3-Chloro-N-{4-[2-(2-hydroxy-3-oxo-4-morpholinyl)ethyl]-1,3-thiazol-2-yl}-2-methylbenzenesulfonamide,
2,4-Dichloro-N-{4-[2-(3-oxo-4-morpholinyl)ethyl]-1,3-thiazol-2-yl}benzenesulfonamide,
2,4-Dichloro-6-methyl-N-{4-[2-(3-oxo-4-morpholinyl)ethyl]-1,3-thiazol-2-yl}benzenesulfonamide,
2,4,6-Trichloro-N-{4-[2-(3-oxo-4-morpholinyl)ethyl]-1,3-thiazol-2-yl}benzenesulfonamide,
4,5-Dichloro-N-{4-[2-(3-oxo-4-morpholinyl)ethyl]-1,3-thiazol-2-yl}-2-thiophenesulfonamide,
N-{4-[2-(3-Oxo-4-morpholinyl)ethyl]-1,3-thiazol-2-yl}-4-phenoxybenzenesulfonamide, 3-Fluoro-N-{4-[2-(3-oxo-4-morpholinyl)ethyl]-1,3-thiazol-2-yl}benzenesulfonamide,
N-{4-[2-(3-Oxo-4-morpholinyl)ethyl]-1,3-thiazol-2-yl}-5-(2-pyridinyl)-2-thiophenesulfonamide,
N-{2-Chloro-4-[({4-[2-(3-oxo-4-morpholinyl)ethyl]-1,3-thiazol-2-yl}amino)sulfonyl]phenyl}acetamide,
3-Chloro-2-methyl-N-{4-[(3-oxo-4-morpholinyl)methyl]-1,3-thiazol-2-yl}benzenesulfonamide,
3-Chloro-2-methyl-N-{4-[3-(3-oxo-4-morpholinyl)propyl]-1,3-thiazol-2-yl}benzenesulfonamide,
3-Chloro-N,2-dimethyl-N-{4-[2-(3-oxo-4-morpholinyl)ethyl]-1,3-thiazol-2-yl}benzenesulfonamide,
3-Chloro-2-methyl-N-{4-[2-(2-methyl-3-oxo-4-morpholinyl)ethyl]-1,3-thiazol-2-yl}benzenesulfonamide,
N-[2-(2-{[(3-Chloro-2-methylphenyl)sulfonyl]amino}-1,3-thiazol-4-yl)ethyl]acetamide,
3-Chloro-2-methyl-N-{4-[2-(3-oxo-1,4-oxazepan-4-yl)ethyl]-1,3-thiazol-2-yl}benzene sulfonamide,
3-Chloro-2-methyl-N-{4-[2-(2-oxo-1-pyrrolidinyl)ethyl]-1,3-thiazol-2-yl}benzenesulfonamide,
3-Chloro-2-methyl-N-{4-[2-(2-oxo-1-imidazolidinyl)ethyl]-1,3-thiazol-2-yl}benzenesulfonamide,
3-Chloro-2-methyl-N-{4-[2-(2-oxo-1,3-oxazolidin-3-yl)ethyl]-1,3-thiazol-2-yl}benzenesulfonamide,
N-[2-(2-{[(3-Chloro-2-methylphenyl)sulfonyl]amino}-1,3-thiazol-4-yl)ethyl]-N-(2-hydroxyethyl)-2-furamide,
N-[2-(2-{[(3-chloro-2-methylphenyl)sulfonyl]amino}-1,3-thiazol-4-yl)ethyl]-N -methylcyclopropanecarboxamide,
3-Chloro-2-methyl-N-{4-[2-(4-methyl-2-oxo-1-piperazinyl)ethyl]-1,3-thiazol-2-yl}benzenesulfonamide hydrochloride,
3-Chloro-2-methyl-N-(4-{2-[(methylsulfonyl)amino]ethyl}-1,3-thiazol-2-yl)benzenesulfonamide,
3-Chloro-2-methyl-N-(4-{2-[methyl(methylsulfonyl)amino]ethyl}-1,3-thiazol-2-yl)benzenesulfonamide,
3-Chloro-2-methyl-N-[4-(2-{[(trifluoromethyl)sulfonyl]amino}ethyl)-1,3-thiazol-2-yl]benzenesulfonamide,
3-Chloro-2-methyl-N-[4-(2-{methyl[(trifluoromethyl)sulfonyl]amino}ethyl)-1,3-thiazol-2-yl]benzenesulfonamide,f
N-[2-(2-{[(3-Chloro-2-methylphenyl)sulfonyl]amino}-1,3-thiazol-4-yl)ethyl]-1-methyl-1H-imidazole-4-sulfonamide,
3-Chloro-N-(4-{2-[[(3-chloro-2-methylphenyl)sulfonyl](methyl)amino]ethyl}-1,3-thiazol-2-yl)-2-methylbenzenesulfonamide,
N-[4-(2-bromoethyl)-1,3-thiazol-2-yl]-3-chloro-2-methylbenzenesulfonamide,
3-Chloro-N-[4-(2-chloroethyl)-1,3-thiazol-2-yl]-2-methylbenzenesulfonamide,
3-Chloro-2-methyl-N-{4-[(5-methyl-1,3,4-oxadiazol-2-yl)methyl]-1,3-thiazol-2-yl}benzenesulfonamide,
Ethyl 3-(2-{[(3-chloro-2-methylphenyl)sulfonyl]amino}-1,3-thiazol-4-yl)propanoate.

3. A pharmaceutical composition comprising at least one compound as recited in claim 1, and a pharmaceutically acceptable carrier.

* * * * *